United States Patent [19]
Batchelor et al.

[11] Patent Number: 5,874,424
[45] Date of Patent: Feb. 23, 1999

[54] INHIBITORS OF INTERLEUKIN-1β CONVERTING ENZYME

[75] Inventors: Mark James Batchelor, Cumnor Hill; David Bebbington, Pewsey, both of United Kingdom; Guy W. Bemis, Arlington, Mass.; Wolf Herman Fridman, Paris, France; Roger John Gillespie, Oaksey; Julian M. C. Golec, Ashbury, both of United Kingdom; David J. Lauffer, Stow; David J. Livingston, Newtonville, both of Mass.; Saroop Singh Matharu, Cricklade, United Kingdom; Michael D. Mullican, Needham; Mark A. Murcko, Holliston, both of Mass.; Robert Murdoch, Highworth, United Kingdom; Robert E. Zelle, Stow, Mass.

[73] Assignee: Vertex Pharmaceuticals Incorporated, Cambridge, Mass.

[21] Appl. No.: 598,332

[22] Filed: Feb. 8, 1996

Related U.S. Application Data

[63] Continuation-in-part of Ser. No. 575,641, Dec. 20, 1995.
[51] Int. Cl.[6] .................... A61K 31/55; C07D 243/02
[52] U.S. Cl. .................... 514/221; 514/211; 514/220; 540/491; 540/495; 540/500; 540/501
[58] Field of Search .................... 540/500; 514/221

[56] References Cited

U.S. PATENT DOCUMENTS

| | | | |
|---|---|---|---|
| 4,276,298 | 6/1981 | Jones et al. | 424/270 |
| 4,369,183 | 1/1983 | Jones et al. | 424/263 |
| 4,499,295 | 2/1985 | Mueller et al. | 560/53 |
| 4,551,279 | 11/1985 | Mueller et al. | 260/404 |
| 4,584,397 | 4/1986 | Mueller et al. | 560/75 |
| 4,968,607 | 11/1990 | Dower et al. | 435/69.1 |
| 5,008,245 | 4/1991 | Digenis et al. | 514/18 |
| 5,055,451 | 10/1991 | Krantz et al. | 514/19 |
| 5,081,228 | 1/1992 | Dower et al. | 530/35.1 |
| 5,158,936 | 10/1992 | Krantz et al. | 514/19 |
| 5,180,812 | 1/1993 | Dower et al. | 530/351 |
| 5,374,623 | 12/1994 | Zimmerman et al. | 514/17 |
| 5,411,985 | 5/1995 | Bills et al. | 514/460 |
| 5,416,013 | 5/1995 | Black et al. | 435/226 |
| 5,430,128 | 7/1995 | Chapman et al. | 530/330 |
| 5,434,248 | 7/1995 | Chapman et al. | 530/330 |
| 5,462,939 | 10/1995 | Dolle et al. | 514/231.5 |
| 5,486,623 | 1/1996 | Zimmerman et al. | 549/417 |
| 5,498,616 | 3/1996 | Mallamo et al. | 514/300 |
| 5,498,695 | 3/1996 | Daumy et al. | 530/331 |
| 5,552,400 | 9/1996 | Dolle et al. | 514/221 |
| 5,565,430 | 10/1996 | Dolle et al. | 514/19 |
| 5,716,929 | 2/1998 | Bemis et al. | 514/18 |

FOREIGN PATENT DOCUMENTS

| | | |
|---|---|---|
| A-64514/94 | 12/1994 | Australia . |
| A-0 275 101 | 7/1988 | European Pat. Off. . |
| A-0 410 411 | 1/1991 | European Pat. Off. . |
| A-0 417 721 | 3/1991 | European Pat. Off. . |
| A-0 479 489 | 4/1992 | European Pat. Off. . |
| A-0 504 938 | 9/1992 | European Pat. Off. . |
| A-0 519 748 | 12/1992 | European Pat. Off. . |
| A-0 525 420 | 2/1993 | European Pat. Off. . |
| A-0 528 487 | 2/1993 | European Pat. Off. . |
| A-0 529 713 | 3/1993 | European Pat. Off. . |
| A-0 533 226 | 3/1993 | European Pat. Off. . |
| A-0 533 350 | 3/1993 | European Pat. Off. . |
| A-0 618 223 | 10/1994 | European Pat. Off. . |
| A-0 623 606 | 11/1994 | European Pat. Off. . |
| A-0 628 550 | 12/1994 | European Pat. Off. . |
| A-0 644 197 | 3/1995 | European Pat. Off. . |
| A-0 644 198 | 3/1995 | European Pat. Off. . |
| WO 90/13549 | 11/1990 | WIPO . |
| WO 91/15577 | 10/1991 | WIPO . |
| WO 93/05071 | 3/1993 | WIPO . |
| WO 93/09135 | 5/1993 | WIPO . |
| WO 93/14777 | 8/1993 | WIPO . |
| WO 93/16710 | 9/1993 | WIPO . |
| WO 93/25683 | 12/1993 | WIPO . |
| WO 93/25685 | 12/1993 | WIPO . |

(List continued on next page.)

OTHER PUBLICATIONS

M. Ator, "Peptide and Non–peptide Inhibitors of Interleukin–1β Converting Enzyme", *Cambridge Healthtech Institute* ( *Inflammatory Cytokine Antagonists Targets, Strategies, and Indication*), (1994).

M.A. Ator and R.E. Dolle, "Interleukin–1β Converting Enzyme: Biology and the Chemistry of Inhibitors", *Curr. Pharm. Design*, 1, pp. 191–210 (1995).

M. Baringa, "Death Gives Birth to the Nervous System. But How?", *Science*, 259, pp. 762–763 (1993).

P. Bender & J. Lee, "Pharmacological Modulation of Interleukin–1", *Annu. Rep. Med. Chem.*, 25, pp. 185–193 (1989).

R. Black et al., "Activation of Interleukin–1β by a Co–induced Protease", *FEBS Lett.*, 247, pp. 386–390 (1989).

(List continued on next page.)

*Primary Examiner*—Richard L. Raymond
*Attorney, Agent, or Firm*—Fish & Neave; James F. Haley, Jr.; Lisa A. Dixon

[57] ABSTRACT

The present invention relates to novel classes of compounds which are inhibitors of interleukin-1β converting enzyme. The ICE inhibitors of this invention are characterized by specific structural and physicochemical features. This invention also relates to pharmaceutical compositions comprising these compounds. The compounds and pharmaceutical compositions of this invention are particularly well suited for inhibiting ICE activity and consequently, may be advantageously used as agents against an IL-1 mediated disease, an apoptosis mediated disease, AML, CML, melanoma, myeloma, Kaposi's sarcoma, graft vs host disease, rheumatoid arthritis, inflammatory bowel disorder, psoriasis, osteoarthritis, myeloma, apoptosis, sepsis, rheumatoid arthritis, asthma, Alzheimer's disease, Parkinson's disease, and ischemic heart disease diseases. This invention also relates to methods for inhibiting ICE activity and methods for treating interleukin-1 mediated diseases using the compounds and compositions of this invention.

7 Claims, 33 Drawing Sheets

FOREIGN PATENT DOCUMENTS

| | | |
|---|---|---|
| WO 93/25694 | 12/1993 | WIPO. |
| WO 94/00154 | 1/1994 | WIPO. |
| WO 94/03480 | 2/1994 | WIPO. |
| WO 95/00160 | 1/1995 | WIPO. |
| WO 95/05192 | 2/1995 | WIPO. |
| WO 95/16706 | 6/1995 | WIPO. |
| WO 95/26958 | 10/1995 | WIPO. |
| WO 95/29672 | 11/1995 | WIPO. |
| WO 95/33751 | 12/1995 | WIPO. |
| WO 96/03982 | 2/1996 | WIPO. |

OTHER PUBLICATIONS

J. Breitner et al., "Inverse Association of Anti–inflammatory Treatments and Alzheimer's Disease: Initial Results of a Co–twin Control Study", Neurology, 44, pp. 227–232 (1994).

F. Casano et al., "The Structure and Complete Nucleotide Sequence of the Murine Gene Encoding Interleukin–1β Converting Enzyme (ICE)", Genomics, 20, pp. 474–481 (1994).

D. Cerretti et al., "Molecular Cloning of the Interleukin–1β Converting Enzyme", Science, 256, pp. 97–100 (1992).

K. Chapman, "Synthesis of a Potent, Reversible Inhibitor of Interleukin–1β Converting Enzyme", Bioorg. Med. Chem. Lett., 2, pp. 613–618 (1992).

C. Dinarello, "Role of Interleukin–1 in Infectious Diseases", Immunol. Rev., 127, pp. 119–146 (1992).

C. Dinarello et al., "Anticytokine Strategies in the Treatment of the Systemic Inflammatory Response Syndrome", J. Am. Med. Assoc., 269, pp. 1829–1835 (1993).

R. Dolle et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme–Peptide Inhibitor Binding", J. Med. Chem., 37, pp. 3863–3865 (1994).

R. Dolle et al., "Aspartyl α–((Diphenylphosphinyl)oxy)methyl Ketones as Novel Inhibitors of Interleukin–1β Converting Enzyme. Utility of the Diphenylphosphinic Acid Leaving Group for the Inhibition of Cysteine Proteases", J. Med. Chem., 38, pp. 220–222 (1995).

R. Dolle et al., "$P_1$ Aspartate–Based Peptide α–((2,6–Dichlorobenzoyl)oxy)methyl Ketones as Potent Time–Dependent Inhibitors of Interleukin–1β–Converting Enzyme" J. Med. Chem., 37, pp. 563–564 (1994).

P. Edwards et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and the Ac–Ala–Pro–Val–2–Benzoxazole", J. Am. Chem. Soc., 114, pp. 1854–1863 (1992).

T. Fan et al., "Stimulation of Angiogenesis by Substance P and Interleukin–1 in the Rat and Its Inhibition by $NK_1$ or Interleukin–1 Receptor Antagonists", Br. J. Pharmacol., 110, pp. 43–49 (1993).

I. Fauszt et al., "Inhibition of Interleukin–1β Converting Enzyme by Peptide Derivatives", Proc. of the 13th Am. Peptide Symp., Jun. 20–25, 1993, Hodges, R.S. and Smith, J.A., Eds., Peptides, pp. 589–591 (1994).

D.S. Fletcher, et al., "A Synthetic Inhibitor of Interleukin–1β Converting Enzyme Prevents Endotoxin–Induced Interleukin–1β Production In Vitro and In Vivo," J. Interfer. Cytokine Res., 15, pp. 243–248 (1995).

V. Gagliardini et al., "Prevention of Vertebrate Neuronal Death by the crmA Gene", Science, 263, pp. 826–828 (1994).

T. Geiger et al., "Neutralization of Interleukin–1β Activity in vivo with a Monoclonal Antibody Alleviates Collagen–induced Arthritis in DBA/1 Mice and Prevents the Associated Acute–phase Response", Clin. Exp. Rheumatol., 11, pp. 515–522 (1993).

T. Graybill et al., "The Preparation and Evaluation of Peptidic Aspartyl Hemiacetals as Reversible Inhibitors of ICE", Am. Chem. Soc. Abs. (206th Natl. Mtg.), MEDI 235 (1993).

T. Graybill et al., "Preparation and evaluation of peptidic aspartyl hemiacetals as reversible inhibitors of interleukin–1β converting enzyme (ICE)", Int. J. Peptide Protein Res., 44, pp. 173–182 (1994).

T. Graybill et al., "Synthesis and Evaluation of Diacylhydrazines as Inhibitors of the Interleukin–1β Converting Enzyme (ICE)", Bioorg. Med. Chem. Lett., 5, pp. 1197–1202 (1995).

W. Griffin et al., "Brain Interleukin 1 and S–100 Immunoreactivity are Elevated in Down Syndrome and Alzheimer Disease", Proc. Natl. Acad. Sci. USA, 86, pp. 7611–7615 (1989).

C. Hammerberg et al., "Interleukin–1 Receptor Antagonist in Normal and Psoriatic Epidermis", J. Clin. Invest., 90, pp. 571–583 (1992).

S. Hanessian et al., "Design and Synthesis of a Prototype Model Antagonist of Tachykinin NK–2 Receptor", Biorg. Med. Chem. Lett., 3, pp. 2689–2692 (1993).

E. Harris, "Rheumatoid Arthritis: Pathophysiology and Implications for Therapy", N. Eng. J. Med., 322, pp. 1277–1289 (1990).

A. Howard et al., "High–Level Production and Characterization of Functional Human Interleukin–1β Converting Enzyme in Baculovirus and E. coli Expression System", J. Cell. Biochem. Suppl., 17B, p. 146 (1993).

A. Howard et al., "Human Interleukin–1β Converting Enzyme: A Mutational Analysis of Proenzyme Activation", J. Cell. Biochem. Suppl., 17B, p. 113 (1993).

A. Howard et al., "IL–1–Converting Enzyme Requires Aspartic Acid Residues for Processing of the IL–1β Precursor at Two Distinct Sites and Does Not Cleave 31–kDa IL–1α", J. Immunol., 147, pp. 2964–2969 (1991).

I. Kamphuis et al., "Thiol Proteases: Comparative Studies Based on the High–resolution Structures of Papain and Actinidin, and on Amino Acid Sequence Information for Cathepsins B and H, and Stem Bromelain", J. Mol. Biol., 182, pp. 317–329 (1985).

M. Kostura et al., "Identification of a Monocyte Specific Pre–Interleukin 1β Convertase Activity", Proc. Natl. Acad. Sci. USA, 86, pp. 5227–5231 (1989).

K. Kuida et al., "Altered Cytokine Export and Apoptosis in Mice Deficient in Interleukin–1β Converting Enzyme", Science, 267, pp. 2000–2003 (1995).

P. Li et al., "Mice Deficient in IL–1β–Converting Enzyme are Defective in Production of Mature IL–1β and Resistant to Endotoxic Shock", Cell, 80, pp. 401–411 (1995).

C. Lipinski, "Bioisosterism in Drug Design", Annu. Rep. Med. Chem., 21, pp. 283–291 (1986).

G. Lonnemann et al., "Differences in the Synthesis and Kinetics of Release of Interleukin 1α, Interleukin 1β and Tumor Necrosis Factor from Human Mononuclear Cells", Eur. J. Immunol., 19, pp. 1531–1536 (1989).

A. MacKenzie et al., "An Inhibitor of the Interleukin–1β–Processing Enzyme Blocks IL–1 Release and Reduces Pyrexia and Acute Inflammation", *Inflammation Research Association (7th Internat. Conf.)*, W42 (1994).

T. Mandrup–Poulsen et al., "Involvement of Interleukin 1 and Interleukin 1 Antagonist in Pancreatic β–Cell Destruction in Insulin–dependent Diabetes Mellitus", *Cytokine*, 5, pp. 185–191 (1993).

C. March et al., "Cloning, Sequence and Expression of Two Distinct Human Interleukin–1 Complementary DNAs", *Nature*, 315, pp. 641–647 (1985).

J. Marx, "Cell Death Studies Yield Cancer Clues", *Science*, 259, pp. 760–761 (1993).

D. Miller et al., "The IL–1β Converting Enzyme as a Therapeutic Target", *Ann. N. Y. Acad. Sci.*, 696, pp. 133–148 (1993).

B. Miller et al., "Inhibition of Mature IL–1β Production in Murine Macrophages and a Murine Model of Inflammation by WIN 67694, an Inhibitor of IL–1β Converting Enzyme", *J. Immunol.*, 154, pp. 1331–1338 (1995).

M. Miura et al., "Induction of Apoptosis in Fibroblasts by IL–1β–Converting Enzyme, a Mammalian Homolog of the C.elegans Cell Death Gene ced–3", *Cell*, 75, pp. 653–660 (1993).

A. Mjalli et al., "Phenylalkyl Ketones as Potent Reversible Inhibitors of Interleukin–1β Converting Enzyme", *Bioorg. Med. Chem. Lett.*, 3, pp. 2689–2692 (1993).

A. Mjalli et al., "Activated Ketones as Potent Reversible Inhibitors of Interleukin–1β Converting Enzyme", *Bioorg. Med. Chem. Lett.*, 4, pp. 1965–1968 (1994).

S. Molineaux et al., "Interleukin 1β (IL–1β) Processing in Murine Macrophages Requires a Structurally Conserved Homologue of Human IL–1β Converting Enzyme", *Proc. Natl. Acad. Sci. USA*, 90, pp. 1809–1813 (1993).

B. Mosley et al., "Determination of the Minimum Polypeptide Lengths of the Functionally Active Sites of Human Interleukins 1α and 1β", *Proc. Natl. Acad. Sci. USA*, 84, pp. 4572–4576 (1987).

M. Mullican et al., "The Synthesis and Evaluation of Peptidyl Aspartyl Aldehydes as Inhibitors of ICE", *Bioorg. Med. Chem. Lett.*, 4, pp. 2359–2364 (1994).

C. Nalin, "Apoptosis Research Enters the ICE Age", *Structure*, 3, pp. 143–145 (1995).

M. Nett et al., "Molecular Cloning of the Murine IL–1β Converting Enzyme cDNA", *J. Immunol.*, 149, pp. 3254–3259 (1992).

M. Nett–Fiordalisi et al., "Characterization and Activation of the Murine Interleukin–1β (IL–1β) Converting Enzyme", *J. Cell. Biochem. Suppl.*, 17B, p. 117 (1993).

I. Noronha et al., "In situ Production of TNF–α, IL–1β and IL–2R in ANCA–positive Glomerulonephritis", *Kidney Int.*, 43, pp. 682–692 (1993).

K. Ohlsson et al., "Interleukin–1 Receptor Antagonist Reduces Mortality from Endotoxin Shock", *Nature*, 348, pp. 550–552 (1990).

J. Oppenheim et al., "There is More than One Interleukin 1", *Immunol. Today*, 7, pp. 45–55 (1986).

M. Pennington & N. Thornberry, "Synthesis of a Fluorogenic Interleukin–1β Converting Enzyme Substrate Based on Resonance Energy Transfer", *Pept. Res.*, 7, pp. 72–76 (1994).

L. Polgár, "On the Mode of Activation of the Catalytically Essential Sulfhydryl Group of Papain", *Eur. J. Biochem.*, 33, pp. 104–109 (1973).

C. Prasad et al., "$P_1$ Aspartate–Based Peptide α–Arylacyloxy– and α–Aryloxymethyl Ketones as Potent Time–Dependent Inhibitors of Interleukin 1β Converting Enzyme", *Am. Chem. Soc. Abs.* (*24th Med. Chem. Symp.*), 66 (1994).

C. Ray et al., "Viral Inhibition of Inflammation: Cowpox Virus Encodes an Inhibitor of the Interleukin–1β Convering Enzyme", *Cell*, 69, pp. 597–604 (1992).

L. Reiter, "Peptidic p–Nitroanilide Substrates of Interleukin–1β–Converting Enzyme", *Int. J. Pept. Protein Res.*, 43, pp. 87–96 (1994).

L. Revesz et al., "Synthesis of P1 Aspartate–Based Peptide Acyloxymethyl and Fluoromethyl Ketones as Inhibitors of Interleukin–1β–Converting Enzyme", *Tetrahedron Lett.*, 35, pp. 9693–9696 (1994).

R. Robinson amd K. Donahue, "Synthesis of a Peptidyl Difluoro Ketone Bearing the Aspartic Acid Side Chain: An Inhibitor of Interleukin–1β Converting Enzyme", *J. Org. Chem.*, 57, pp. 7309–7314 (1992).

M. Salvatore et al., "L–741,494, A Fungal Metabolite that is an Inhibitor of Interleukin–1β Converting Enzyme", *J. Nat. Prods.*, 57, pp. 755–760 (1994).

J. Sandberg et al., "Treatment with an Interleukin–1 Receptor Antagonist Protein Prolongs Mouse Islet Allograft Survival", *Diabetes*, 42, pp. 1845–1851 (1993).

S. Schmidt et al., "Synthesis and Evaluation of Aspartyl α–Chloro–, α–Aryloxy–, and α–Arylacyloxymethyl Ketones as Inhibitors of Interleukin–1β Converting Enzyme", *Am. Chem. Soc. Abs.* (*208th Natl. Mtg.*), MEDI 4 (1994).

B. Shivers et al., "Molecular Cloning of Rat Interleukin–1β–Converting Enzyme: Distribution and Regulation", *J. Cell. Biochem. Suppl.*, 17B, p. 119 (1993).

I. Singer et al., "Interleukin 1β is Localized in the Cytoplasmic Ground Substance but is Largely Absent from the Golgi Apparatus and Plasma Membranes of Stimulated Human Monocytes", *J. Exp. Med.*, 167, pp. 389–407 (1988).

P. Sleath et al., "Substrate Specificity of the Protease that Processes Human Interleukin–1β", *J. Biol. Chem.*, 265, pp. 14526–14528 (1990).

A.F. Spatola, *Chemistry and Biochemistry of Amino Acids, Peptides and Proteins*, vol. 7, B. Weinstein, ed., Marcel Dekker Inc., ch. 5, pp. 267–281 (1983).

N. Thornberry et al., "A Novel Heterodimeric Cysteine Protease is Required for Interleukin–1β Processing in Monocytes", *Nature*, 356, pp. 768–774 (1992).

N. Thornberry et al., "Inactivation of Interleukin–1β Converting Enzyme by Peptide (Acyloxy)methyl Ketones", *Biochemistry*, 33, pp. 3934–3940 (1994).

J. Uhl et al., "Secretion of Human Monocyte Mature IL–1β: Optimization of Culture Conditions and Inhibition by ICE Inhibitors", *Inflammation Research Association (7th Internat. Conf.)*, W41 (1994).

N.P.C. Walker et al., "Crystal Structure of the Cysteine Protease Interleukin–1β–Converting Enzyme: A $(p20/p10)_2$ Homodimer", *Cell,* 78, pp. 343–352 (1994).

P. Warner, et al., "Pyridone HLE Inhibitors: Variation of the 3 and 5 Substituents", *Royal Soc. Chem. Abs.* (*7th RSC–SCI Med. Chem. Symp.*), P23 (1993).

K.P. Wilson et al., "Structure and Mechanism of Interleukin–1β Converting Enzyme", *Nature,* 370, pp. 270–275 (1994).

P. Wooley et al., "The Effect of an Interleukin–1 Receptor Antagonist Protein on Type II Collagen–induced Arthritis and Antigen–induced Arthritis in Mice", *Arthritis Rheum.,* 36, pp. 1305–1314 (1993).

J. Yuan et al., "The C.elegans Cell Death Gene ced–3 Encodes a Protein Similar to Mammalian Interleukin–1β–Converting Enzyme", *Cell,* 75, pp. 641–652 (1993).

FIGURE 1

| Compound | Structure | MF | MW | HPLC RT min (method) Purity | MS (M+H)+ | Synthetic Method |
|---|---|---|---|---|---|---|
| 214e | 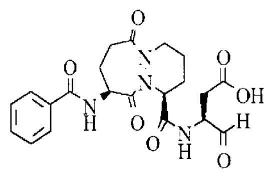 | C21H24N4O7 | 444.45 | 6.67 (2) 98% | 445 | 2 |
| 404 | 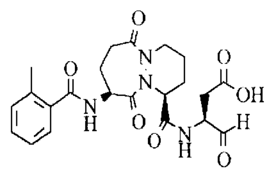 | C22H26N4O7 | 458.48 | 6.66 (2) 97% | 459 | 2 |
| 405 | 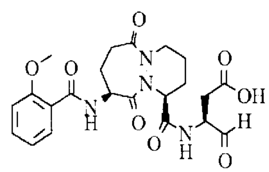 | C22H26N4O8 | 474.47 | 8.2 (1) 98% | 475 | 2 |
| 406 | 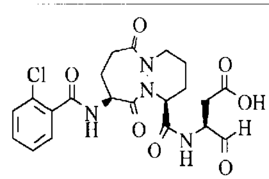 | C21H23ClN4O7 | 478.89 | 6.33 (1) 98% | 479 | 2 |

FIGURE 1 (cont.)

| Compound | Structure | MF | MW | HPLC RT min (method) Purity | MS (M+H)+ | Synthetic Method |
|---|---|---|---|---|---|---|
| 407 | 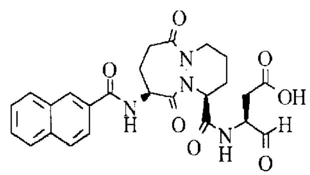 | C25H26N4O7 | 494.51 | 9.90 (1) 98% | 495 | 2 |
| 408 | 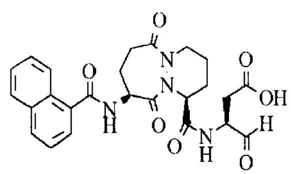 | C25H26N4O7 | 494.51 | 9.0 (1) 98% | 495 | 2 |
| 409 | 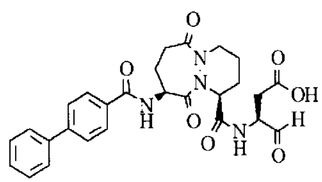 | C27H28N4O7 | 520.55 | 11.14 (1) 98% | 521 | 2 |
| 410 | 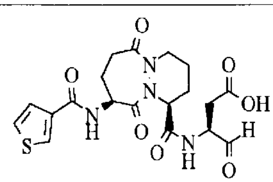 | C19H22N4O7S | 450.47 | 4.87 (1) 98% | 451 | 1 |

FIGURE 1 (cont.)

| Compound | Structure | MF | MW | HPLC RT min (method) Purity | MS (M+H)+ | Synthetic Method |
|---|---|---|---|---|---|---|
| 411 | 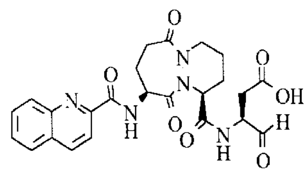 | C24H25N5O7 | 495.50 | 10.7 (1) 98% | 496 | 1 |
| 412 | 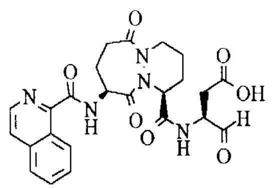 | C24H25N5O7 | 495.50 | 8.57 (1) 98% | 496 | 1 |
| 413 | 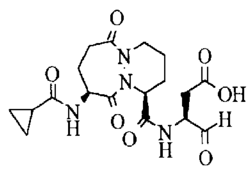 | C18H24N4O7 | 408.41 | 7.21 (2) 98% | 409 | 1 |
| 415 | 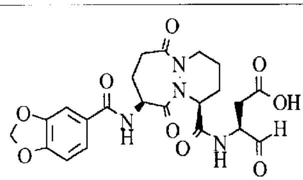 | C22H24N4O9 | 488.46 | 7.58 (1) 98% | 489 | 1 |

FIGURE 1 (cont.)

| Compound | Structure | MF | MW | HPLC RT min (method) Purity | MS (M+H)+ | Synthetic Method |
|---|---|---|---|---|---|---|
| 416 | 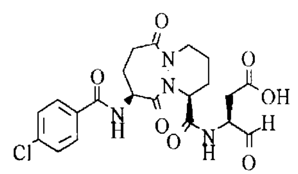 | C21H23ClN4O7 | 478.89 | 9.66 (1) 98% | 479 | 1 |
| 417 | 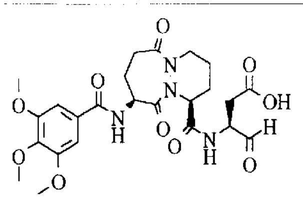 | C24H30N4O10 | 534.53 | 8.12 (1) 535 | 535 | 1 |
| 418 | 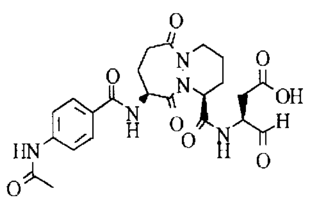 | C23H27N5O8 | 501.50 | 5.93 (1) 98% | 502 | 1A |
| 419 | 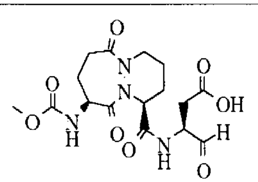 | C16H22N4O8 | 398.38 | 6.84 (2) 98% | 399 | 2 |

FIGURE 1 (cont.)

| Compound | Structure | MF | MW | HPLC RT min (method) Purity | MS (M+H)+ | Synthetic Method |
|---|---|---|---|---|---|---|
| 420 | 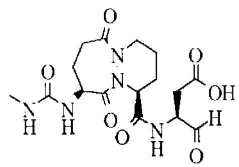 | C16H23N5O7 | 397.39 | 5.25 (2) 98% | 398 | 4 |
| 421 | 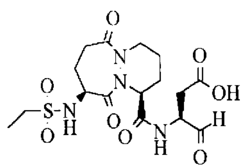 | C16H24N4O8S | 432.46 | 7.13 (2) 98% | 433 | 3 |
| 422 | 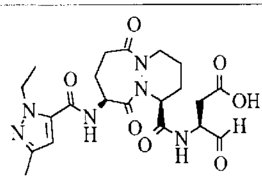 | C21H28N6O7 | 476.49 | 6.89 (1) 98% | 477 | 1 |
| 423 | 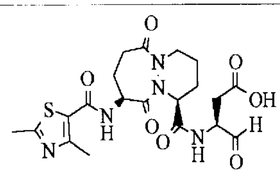 | C20H25N5O7S | 479.52 | 5.62 (1) 98% | 480 | 1 |

FIGURE 1 (cont.)

| Compound | Structure | MF | MW | HPLC RT min (method) Purity | MS (M+H)+ | Synthetic Method |
|---|---|---|---|---|---|---|
| 424 | 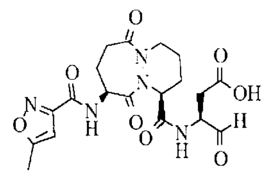 | C19H23N5O8 | 449.42 | 6.28 (1) 450 | 450 | 1 |
| 425 | 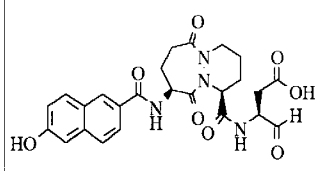 | C25H26N4O8 | 510.51 | 8.25 (1) 98% | 511 | 1 |
| 426 | 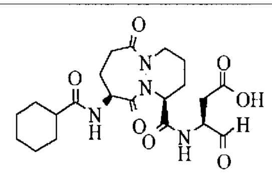 | C21H30N4O7 | 450.50 | 8.0 (1) 98% | 451 | 2 |
| 427 | 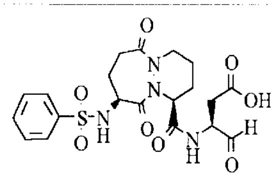 | C20H24N4O8S | 480.50 | 7.87 (1) 98% | 481 | 3 |

FIGURE 1 (cont.)

| Compound | Structure | MF | MW | HPLC RT min (method) Purity | MS (M+H)+ | Synthetic Method |
|---|---|---|---|---|---|---|
| 428 | 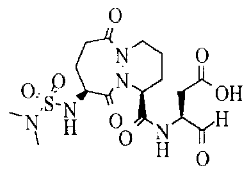 | C16H25N5O8S | 447.47 | 5.13 (1) 98% | 448 | 3 |
| 429 | 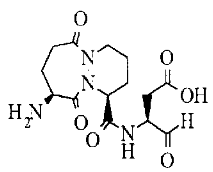 | C14H20N4O6 | 340.34 | 3.19 (3) 98% | 341 | |
| 430 | 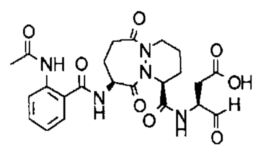 | C23H27N5O8 | 501.50 | 5.53 (1) 98% | 502 | 1A |
| 431 | 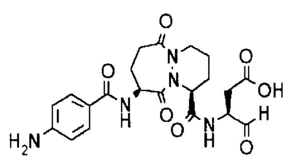 | C21H25N5O7 | 459.46 | 6.66 (2) 98% | 460 | 1 |

FIGURE 1 (cont.)

| Compound | Structure | MF | MW | HPLC RT min (method) Purity | MS (M+H)+ | Synthetic Method |
|---|---|---|---|---|---|---|
| 432 | 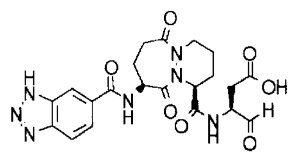 | C21H23N7O7 | 485.46 | 5.59 (1) 98% | 486 | 1 |
| 433 | 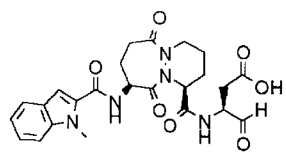 | C24H27N5O7 | 497.51 | 11.07 (1) 97% | 498 | 1 |
| 434 | 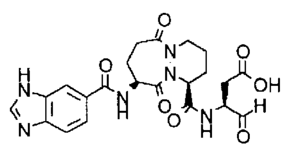 | C22H24N6O7 | 484.47 | 4.43 (1) 98% | 485 | 1 |
| 435 | 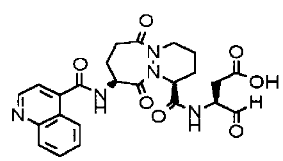 | C24H25N5O7 | 495.50 | 5.10 (1) 98% | 496 | 1 |

FIGURE 1 (cont.)

| Compound | Structure | MF | MW | HPLC RT min (method) Purity | MS (M+H)+ | Synthetic Method |
|---|---|---|---|---|---|---|
| 436 | 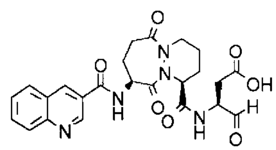 | C24H25N5O7 | 495.50 | 8.20 (4) 98% | 496 | 1 |
| 437 | 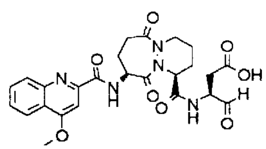 | C25H27N5O8 | 525.52 | 12.78 (5) 98% | 526 | 1 |
| 438 | 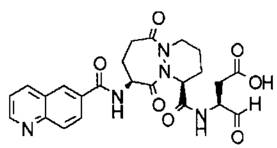 | C24H25N5O7 | 495.50 | 4.85 (1) 98% | 496 | 1 |
| 439 | 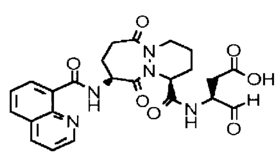 | C24H25N5O7 | 495.50 | 8.70 (5) 98% | 496 | 1 |

FIGURE 1 (cont.)

| Compound | Structure | MF | MW | HPLC RT min (method) Purity | MS (M+H)+ | Synthetic Method |
|---|---|---|---|---|---|---|
| 440 | 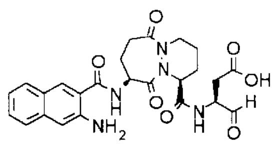 | C25H27N5O7 | 509.52 | 9.96 (5) 98% | 510 | 1 |
| 441 | 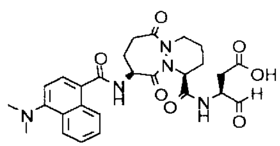 | C27H31N5O7 | 537.58 | 6.15 (1) 98% | 538 | 1 |
| 442 | 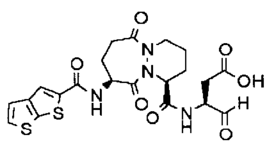 | C21H22N4O7S2 | 506.56 | 10.10 (1) 98% | 507 | 1 |
| 443 | 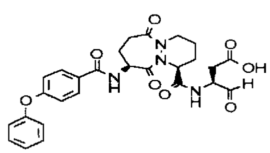 | C27H28N4O8 | 536.55 | 13.12 (1) 98% | 537 | 1 |

FIGURE 1 (cont.)

| Compound | Structure | MF | MW | HPLC RT min (method) Purity | MS (M+H)+ | Synthetic Method |
|---|---|---|---|---|---|---|
| 444 | 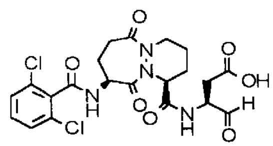 | C21H22Cl2N4O7 | 513.34 | 9.96 (5) 98% | 510 | 1 |
| 445 | 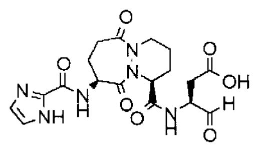 | C18H22N6O7 | 434.41 | 5.72 (1) 98% | 435 | 5 |
| 446 | 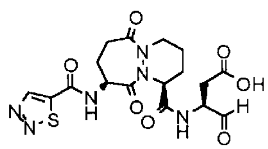 | C17H20N6O7S | 452.45 | 5.00 (1) 98% | 453 | 1 |
| 447 | 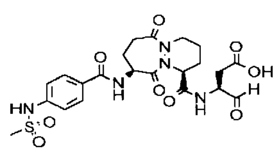 | C22H27N5O9S | 537.55 | 6.32 (1) 98% | 538 | 1B |

FIGURE 1 (cont.)

| Compound | Structure | MF | MW | HPLC RT min (method) Purity | MS (M+H)+ | Synthetic Method |
|---|---|---|---|---|---|---|
| 448 | 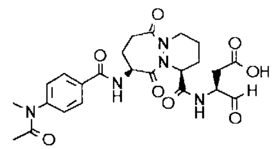 | C24H29N5O8 | 515.53 | 6.36 (1) 98% | 516 | 1A |
| 449 | 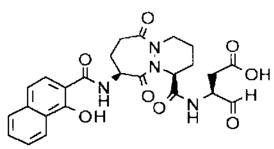 | C25H26N4O8 | 510.51 | 13.86 (1) 98% | 511 | 1 |
| 450 | 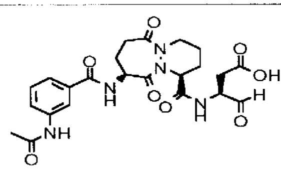 | C23H27N5O8 | 501.50 | 6.10 (1) 98% | 502 | 1A |
| 451 | 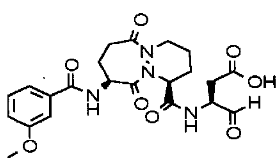 | C22H26N4O8 | 474.47 | 8.02 (1) 98% | 475 | 2 |

FIGURE 1 (cont.)

| Compound | Structure | MF | MW | HPLC RT min (method) Purity | MS (M+H)+ | Synthetic Method |
|---|---|---|---|---|---|---|
| 452 | 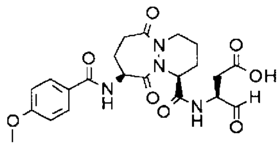 | C22H26N4O8 | 474.47 | 7.77 (1) 98% | 475 | 2 |
| 453 | 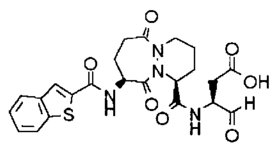 | C23H24N4O7S | 500.53 | 11.11 (1) 98% | 501 | 2 |
| 454 | 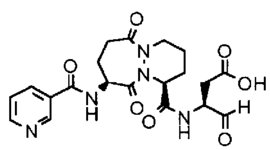 | C20H23N5O7 | 445.44 | 6.24 (2) 98% | 446 | 2 |
| 455 | 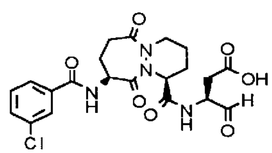 | C21H23ClN4O7 | 478.89 | 9.45 (1) 98% | 479 | 2 |

FIGURE 1 (cont.)

| Compound | Structure | MF | MW | HPLC RT min (method) Purity | MS (M+H)+ | Synthetic Method |
|---|---|---|---|---|---|---|
| 456 | 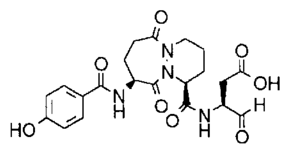 | C21H24N4O8 | 460.45 | 5.58 (1) 98% | (M+Na) 483 | 1 |
| 457 | 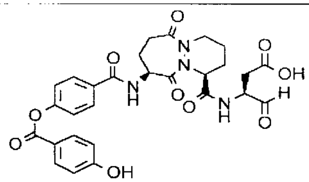 | C28H28N4O10 | 580.56 | 10.42 (1) 98% | (M+Na) 603 | 1 |
| 458 | 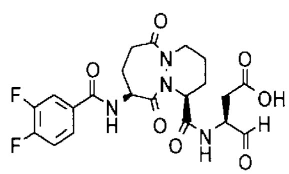 | C21H22F2N4O7 | 480.43 | 8.65 (1) 98% | 481.1 | 1 |
| 459 | 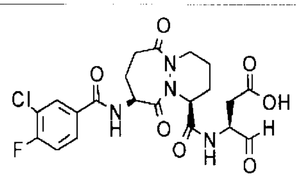 | C21H22ClFN4O7 | 496.88 | 10.11 (1) 98% | 498.3 | 1 |

FIGURE 1 (cont.)

| Compound | Structure | MF | MW | HPLC RT min (method) Purity | MS (M+H)+ | Synthetic Method |
|---|---|---|---|---|---|---|
| 460 | 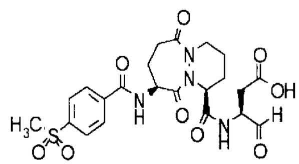 | C22H26N4O9S | 522.54 | 6.16 (1) 98% | 523.6 | 1 |
| 461 | 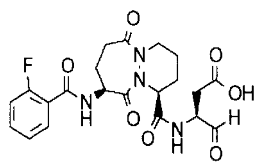 | C21H23FN4O7 | 462.44 | 7.41 (1) 98% | 463.3 | 1 |
| 462 | 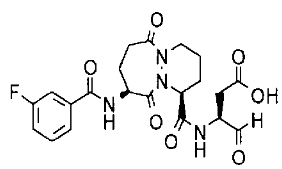 | C21H23FN4O7 | 462.44 | 7.71 (1) 98% | 463.3 | 1 |
| 463 | 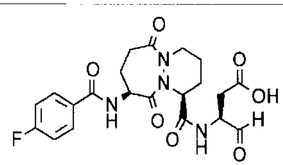 | C21H23FN4O7 | 462.44 | 7.64 (1) 98% | 464 | 1 |

FIGURE 1 (cont.)

| Compound | Structure | MF | MW | HPLC RT min (method) Purity | MS (M+H)+ | Synthetic Method |
|---|---|---|---|---|---|---|
| 464 | 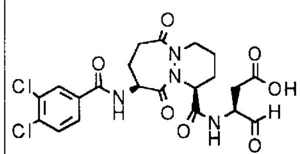 | C21H22Cl2N4O7 | 513.34 | 11.59 (1) 98% | 414.5 | 1 |
| 465 | 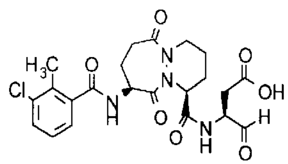 | C22H25ClN4O7 | 492.92 | 9.65 (1) 98% | 493.9 | 1 |
| 466 | 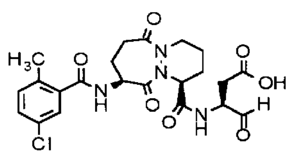 | C22H25ClN4O7 | 492.92 | 9.63 (1) 98% | 493.9 | 1 |
| 467 | 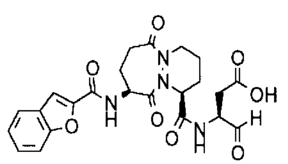 | C23H24N4O8 | 484.47 | 9.73 (1) 98% | 485.8 | 1 |

FIGURE 1 (cont.)

| Compound | Structure | MF | MW | HPLC RT min (method) Purity | MS (M+H)+ | Synthetic Method |
|---|---|---|---|---|---|---|
| 468 | 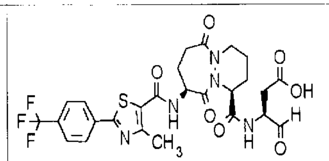 | C26H26F3N5O7S | 609.59 | 14.84 (1) 98% | 609.7 | 1 |
| 470 | 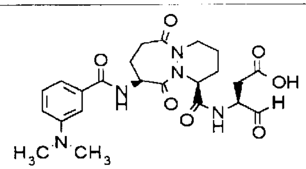 | C23H29N5O7 | 487.52 | 4.57 (1) 98% | 489.5 | 1 |
| 471 | 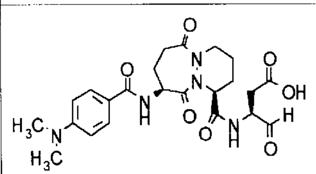 | C23H29N5O7 | 487.52 | 5.74 (1) 98% | 488.2 | 1 |
| 472 | 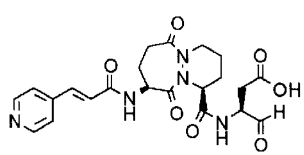 | C22H25N5O7 | 471.47 | 4.00 (1) 98% | 474 | 1 |

FIGURE 1 (cont.)

| Compound | Structure | MF | MW | HPLC RT min (method) Purity | MS (M+H)+ | Synthetic Method |
|---|---|---|---|---|---|---|
| 473 | 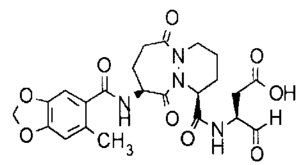 | C23H26N4O9 | 502.49 | 7.65 (1) 98% | 503.6 | 1 |
| 474 | 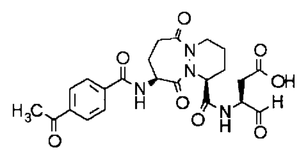 | C23H26N4O8 | 486.49 | 7.16 (1) 98% | 488.1 | 1 |
| 475 | 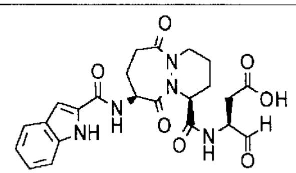 | C23H25N5O7 | 483.49 | 9.77 (1) 97% | 485.1 | 1 |
| 476 | 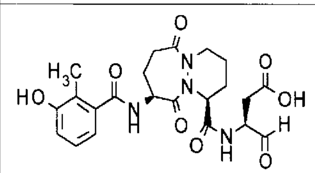 | C22H26N4O8 | 474.47 | 5.25 (1) 98% | 475.8 | 1 |

FIGURE 1 (cont.)

| Compound | Structure | MF | MW | HPLC RT min (method) Purity | MS (M+H)+ | Synthetic Method |
|---|---|---|---|---|---|---|
| 477 | 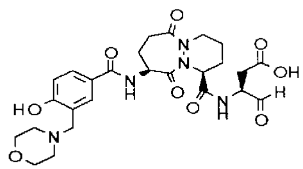 | C26H33N5O9 | 559.58 | 4.76 (1) 95% | 561.8 | 1 |
| 478 | 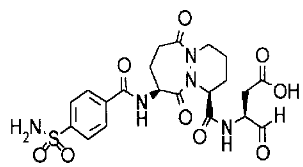 | C21H25N5O9S | 523.53 | 5.25 (1) 98% | 524.3 | 1 |
| 479 | 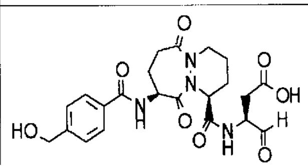 | C22H26N4O8 | 474.47 | 5.35 (1) 98% | 475.8 | 1 |
| 480 | 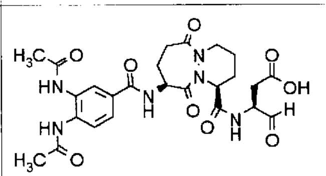 | C25H30N6O9 | 558.55 | 5.11 (1) 98% | 559.3 | 1A |

FIGURE 1 (cont.)

| Compound | Structure | MF | MW | HPLC RT min (method) Purity | MS (M+H)+ | Synthetic Method |
|---|---|---|---|---|---|---|
| 481 | 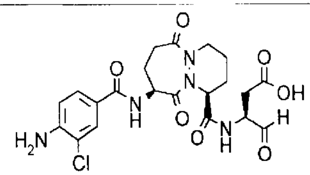 | C21H24ClN5O7 | 493.91 | 7.10 (1) 98% | 495.1 | 1 |
| 482 | 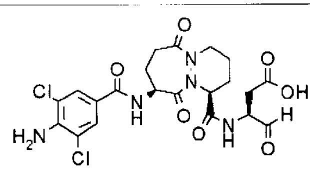 | C21H23Cl2N5O7 | 528.35 | 9.05 (1) 98% | 529.8 | 1 |
| 483 | 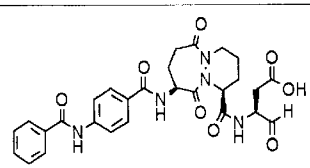 | C28H29N5O8 | 563.57 | 10.01 (1) 98% | 565.6 | 1,2 |
| 484 | 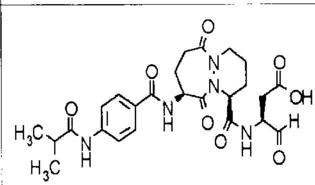 | C25H31N5O8 | 529.55 | 7.88 (1) 98% | 531 | 1,2 |

FIGURE 1 (cont.)

| Compound | Structure | MF | MW | HPlC RT min (method) Purity | MS (M+H)+ | Synthetic Method |
|---|---|---|---|---|---|---|
| 485 | 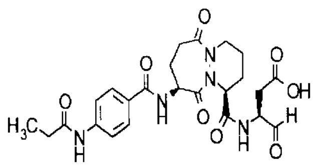 | C24H29N5O8 | 515.53 | 7.00 (1) 98% | 517.6 | 1,2 |
| 486 | 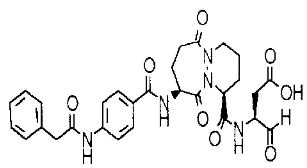 | C29H31N5O8 | 577.60 | 10.43 (1) 98% | 579.4 | 1,2 |
| 487 | 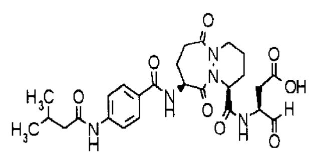 | C26H33N5O8 | 543.58 | 9.30 (1) 98% | 545.7 | 1,2 |
| 488 | 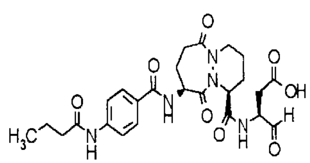 | C25H31N5O8 | 529.55 | 8.13 (1) 98% | 531.1 | 1,2 |

FIGURE 1 (cont.)

| Compound | Structure | MF | MW | HPLC RT min (method) Purity | MS (M+H)+ | Synthetic Method |
|---|---|---|---|---|---|---|
| 489 | 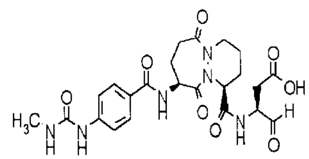 | C23H28N6O8 | 516.52 | 5.89 (1) 98% | 517.8 | 1,4 |
| 490 | 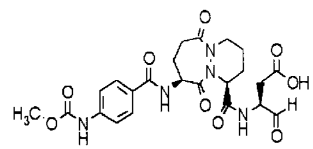 | C23H27N5O9 | 517.50 | 7.27 (1) 98% | (M+Na) 540.8 | 1,2 |
| 491 | 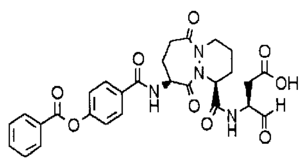 | C28H28N4O9 | 564.56 | 12.9 (1) 98% | 565.3 | 1 |
| 493 | 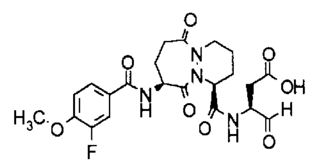 | C22H25FN4O8 | 492.46 | 8.31 (1) 98% | 493.9 | 1 |

FIGURE 1 (cont.)

| Compound | Structure | MF | MW | HPLC RT min (method) Purity | MS (M+H)+ | Synthetic Method |
|---|---|---|---|---|---|---|
| 494 | 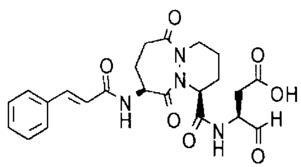 | C23H26N4O7 | 470.49 | 9.34 (1) 98% | 471.2 | 2 |
| 495 | 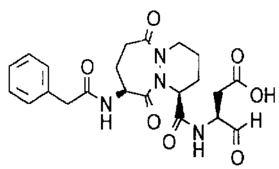 | C22H26N4O7 | 458.48 | 7.24 (1) 98% | 459.9 | 2 |
| 496 | 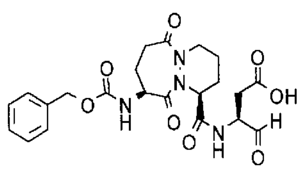 | C22H26N4O8 | 474.47 | 9.47 (1) 98% | 475.7 | 2 |
| 497 | 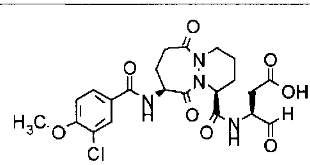 | C22H25ClN4O8 | 508.92 | 9.58 (1) 98% | 509.5 | 1 |

FIGURE 1 (cont.)

| Compound | Structure | MF | MW | HPLC RT min (method) Purity | MS (M+H)+ | Synthetic Method |
|---|---|---|---|---|---|---|
| 498 | 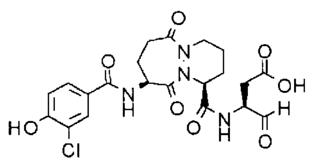 | C21H23ClN4O8 | 494.89 | 7.18 (1) 98% | 495.1 | 1 |
| 499 | 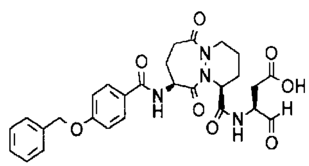 | C28H30N4O8 | 550.57 | 13.27 (1) 98% | 552 | 1 |

FIGURE 2

| Compound | Structure | MF | MW | HPLC RT min (method) Purity | MS (M+H)+ | Synthetic Method |
|---|---|---|---|---|---|---|
| 619 | 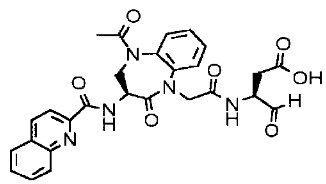 | C27H25N5O7 | 531.53 | 11.71 (1) 98% | 532 | 1 |
| 620 | 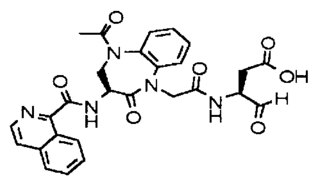 | C27H25N5O7 | 531.53 | 10.44 (1) 98% | 532 | 1 |
| 621 | 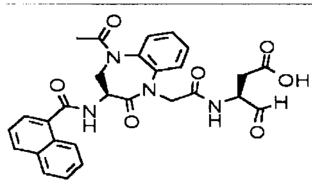 | C28H26N4O7 | 530.54 | 11.57 (1) 98% | (M+Na)+ 553 | 2 |
| 622 | 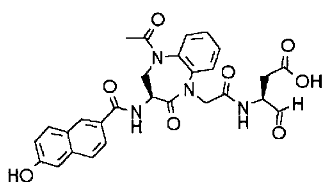 | C28H26N4O8 | 546.54 | 10.19 (1) 98% | (M+Na)+ 569 | 1 |

FIGURE 2 (cont.)

| Compound | Structure | MF | MW | HPLC RT min (method) Purity | MS (M+H)+ | Synthetic Method |
|---|---|---|---|---|---|---|
| 623 | 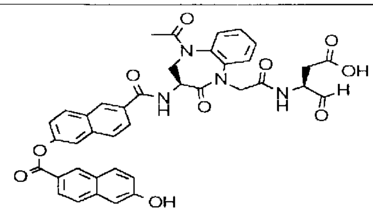 | C39H32N4O10 | 716.71 | 15.8 (1) 09% | (M-) 716 | 1 |
| 624 | 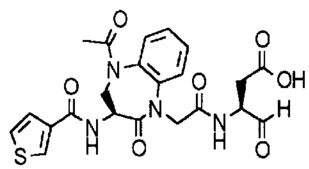 | C22H22N4O7S | 486.51 | 8.39 (1) 98% | 487 | 1 |
| 625 | 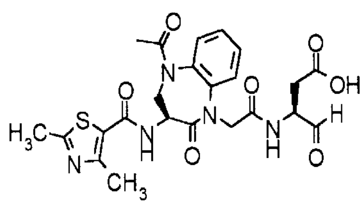 | C23H25N5O7S | 515.55 | 7.60 (1) 98% | 516 | 1 |
| 626 | 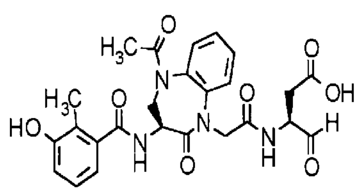 | C25H26N4O8 | 510.51 | 7.58 (1) 98% | 511 | 1 |

FIGURE 2 (cont.)

| Compound | Structure | MF | MW | HPLC RT min (method) Purity | MS (M+H)+ | Synthetic Method |
|---|---|---|---|---|---|---|
| 627 | 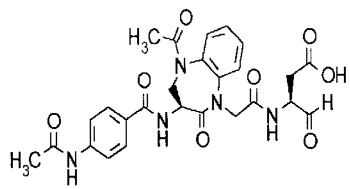 | C26H27N5O8 | 537.53 | 7.96 (1) 98% | 538 | 1A |
| 628 | 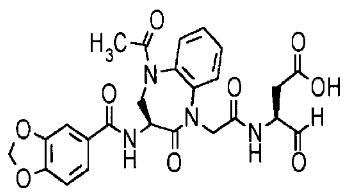 | C25H24N4O9 | 524.49 | 9.50 (1) 98% | 525 | 1 |
| 629 | 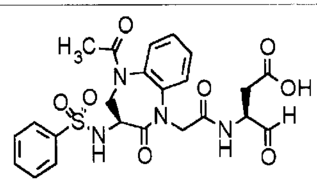 | C23H24N4O8S | 516.53 | 9.85 (1) 98% | 517 | 3 |
| 630 | 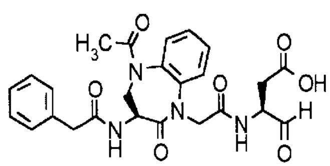 | C25H26N4O7 | 494.51 | 9.25 (1) 98% | 495 | 2 |

| Compound | Structure | MF | MW | HPLC RT min (method) Purity | MS (M+H)+ | Synthetic Method |
|---|---|---|---|---|---|---|
| 631 | 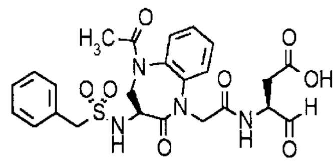 | C24H26N4O8S | 530.56 | 10.19 (1) 98% | 531 | 3 |
| 632 | 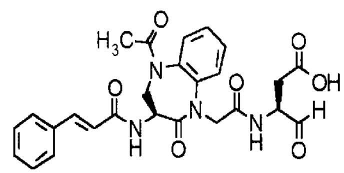 | C26H26N4O7 | 506.52 | 10.99 (1) 98% | 507 | 2 |
| 633 | 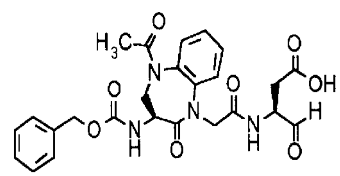 | C25H26N4O8 | 510.51 | 11.48 (1) 98% | 511 | 2 |
| 634 | 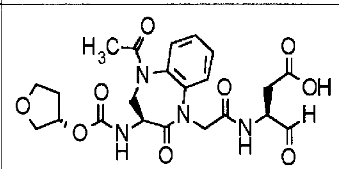 | C22H26N4O9 | 490.47 | 6.87 (1) 98% | 491 | 2 |

FIGURE 2 (cont.)

| Compound | Structure | MF | MW | HPLC RT min (method) Purity | MS (M+H)+ | Synthetic Method |
|---|---|---|---|---|---|---|
| 635 | (structure) | C25H24N4O8 | 508.49 | 10.03 (1) 98% | 509 | 1 |

INHIBITORS OF INTERLEUKIN-1β CONVERTING ENZYME

This application is a continuation in part of U.S. application Ser. No. 08/575,641, filed Dec. 20, 1995.

TECHNICAL FIELD OF THE INVENTION

The present invention relates to novel classes of compounds which are inhibitors of interleukin-1β converting enzyme ("ICE"). This invention also relates to pharmaceutical compositions comprising these compounds. The compounds and pharmaceutical compositions of this invention are particularly well suited for inhibiting ICE activity and consequently, may be advantageously used as agents against interleukin-1- ("IL-1") and apoptosis-mediated diseases, including inflammatory diseases, autoimmune diseases, proliferative disorders, infectious diseases, and degenerative diseases. This invention also relates to methods for inhibiting ICE activity and methods for treating interleukin-1 and apoptosis-mediated diseases using the compounds and compositions of this invention.

BACKGROUND OF THE INVENTION

Interleukin 1 ("IL-1") is a major proinflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today*, 7, pp. 45–56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., *Arthritis Rheum* 26, 975, (1983); Pettipher, E. J. et al., *Proc. Natl. Acad. Sci. USA* 71, 295 (1986); Arend, W. P. and Dayer, J. M., *Arthritis Rheum* 38, 151 (1995). IL-1 is also a highly potent bone resorption agent. Jandiski, J. J.,*J. Oral Path* 17, 145 (1988); Dewhirst, F. E. et al., *J. Immunol.* 8, 2562 1985). It is alternately referred to as "osteoclast activating factor" in destructive bone diseases such as osteoarthritis and multiple myeloma. Bataille, R. et al., *Int. J. Clin. Lab. Res.* 21(4), 283 (1992). In certain proliferative disorders, such as acute myelogenous leukemia and multiple myeloma, IL-1 can promote tumor cell growth and adhesion. Bani, M. R.,*J. Natl. Cancer Inst.* 83, 123 (1991); Vidal-Vanaclocha, F., *Cancer Res.* 54, 2667 (1994). In these disorders, IL-1 also stimulates production of other cytokines such as IL-6, which can modulate tumor development (Tartour et al., *Cancer Res.* 54, 6243 (1994). IL-1 is predominantly produced by peripheral blood monocytes as part of the inflammatory response and exists in two distinct agonist forms, IL-1α and IL-1β. Mosely, B. S. et al., *Proc. Nat. Acad. Sci.*, 84, pp. 4572–4576 (1987); Lonnemann, G. et al., *Eur. J. Immunol.*, 19, pp. 1531–1536 (1989).

IL-1β is synthesized as a biologically inactive precursor, pIL-1β. pIL-1β lacks a conventional leader sequence and is not processed by a signal peptidase. March, C. J., *Nature*, 315, pp. 641–647 (1985). Instead, pIL-1β is cleaved by interleukin-1β converting enzyme ("ICE") between Asp-116 and Ala-117 to produce the biologically active C-terminal fragment found in human serum and synovial fluid. Sleath, P. R., et al., *J. Biol. Chem.*, 265, pp. 14526–14528 (1992); A. D. Howard et al., *J. Immunol.*, 147, pp. 2964–2969 (1991). ICE is a cysteine protease localized primarily in monocytes. It converts precursor IL-1β to the mature form. Black, R. A. et al., *FEBS Lett.*, 247, pp. 386–390 (1989); Kostura, M. J. et al., *Proc. Natl. Acad. Sci. USA*, 86, pp. 5227–5231 (1989). Processing by ICE is also necessary for the transport of mature IL-1β through the cell membrane.

ICE, or its homologs, also appears to be involved in the regulation of programmed cell death or apoptosis. Yuan, J. et al., *Cell*, 75, pp. 641–652 (1993); Miura, M. et al., *Cell*, 75, pp. 653–660 (1993); Nett-Fiordalisi, M. A. et al.,*J. Cell Biochem.*, 17B, p. 117 (1993). In particular, ICE or ICE homologs are thought to be associated with the regulation of apoptosis in neurodegenerative diseases, such as Alzheimer's and Parkinson's disease. Marx, J. and M. Baringa, *Science*, 259, pp. 760–762 (1993); Gagliardini, V. et al., *Science*, 263, pp. 826–828 (1994). Therapeutic applications for inhibition of apoptosis may include treatment of Alzheimer's disease, Parkinson's disease, stroke, myocardial infarction, spinal atrophy, and aging.

ICE has been demonstrated to mediate apoptosis (programmed cell death) in certain tissue types. Steller, H., *Science*, 267, p. 1445 (1995); Whyte, M. and Evan, G., *Nature*, 376, p. 17 (1995); Martin, S. J. and Green, D. R., *Cell*, 82, p. 349 (1995); Alnemri, E. S., et al.,*J. Biol. Chem.*, 270, p. 4312 (1995); Yuan, J. *Curr. Opin. Cell Biol.*, 7, p. 211 (1995). A transgenic mouse with a disruption of the ICE gene is deficient in Fas-mediated apoptosis (Kuida, K. et al., *Science* 267, 2000 (1995)). This activity of ICE is distinct from its role as the processing enzyme for pro-IL1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp. 768–774 (1992). The ICE proenzyme has been divided into several functional domains: a prodomain (p14), a p22/20 subunit, a polypeptide linker and a p10 subunit. Thornberry et al., supra; Casano et al., *Genomics*, 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al.,*Ann. N.Y. Acad. Sci.*, 696, pp. 133–148 (1993); Molineaux, S. M. et al., *Proc. Nat. Acad, Sci.*, 90, pp. 1809–1813 (1993). The three-dimensional structure of ICE has been determined at atomic resolution by X-ray crystallography. Wilson, K. P., et al., *Nature*, 370, pp. 270–275 (1994). The active enzyme exists as a tetramer of two p20 and two p10 subunits.

Additionally, there exist human homologs of ICE with sequence similarities in the active site regions of the enzymes. Such homologs include TX (or $ICE_{rel-II}$ or ICH-2) (Faucheu, et al., *EMBO J.*, 14, p. 1914 (1995); Kamens J., et al.,*J. Biol. Chem.*, 270, p. 15250 (1995); Nicholson et al., *J. Biol. Chem.*, 270 15870 (1995)), TY (or $ICE_{rel-III}$) (Nicholson et al., *J. Biol. Chem.*, 270, p. 15870 (1995); ICH-1 (or Nedd-2) (Wang, L. et al., *Cell*, 78, p. 739 (1994)), MCH-2, (Fernandes-Alnemri, T. et al., *Cancer Res.*, 55, p. 2737 (1995), CPP32 (or YAMA or apopain) (Fernandes-Alnemri, T. et al., *J. Biol. Chem.*, 269, p. 30761 (1994);

Nicholson, D. W. et al., *Nature*, 376, p. 37 (1995)), and CMH-1 (or MCH-3) (Lippke, et al., *J. Biol. Chem.*, (1996); Fernandes-Alnemri, T. et al., *Cancer Res.*, (1995)). Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines. Lazebnik et al., *Nature*, 371, p. 346 (1994). The compounds described herein are also capable of inhibiting one or more homologs of ICE (see example). Therefore, these compounds may be used to inhibit apoptosis in tissue types that contain ICE homologs, but which do not contain active ICE or produce mature IL-1-β.

ICE inhibitors represent a class of compounds useful for the control of inflammation or apoptosis or both. Peptide and peptidyl inhibitors of ICE have been described. PCT patent applications WO 91/15577; WO 93/05071; WO 93/09135; WO 93/14777 and WO 93/16710; and European patent application 0 547 699. Such peptidyl inhibitors of ICE has been observed to block the production of mature IL-1β in a mouse model of inflammation (vide infra) and to suppress growth of leukemia cells in vitro (Estrov et al., *Blood* 84, 380a (1994)). However, due to their peptidic nature, such inhibitors are typically characterized by undesirable pharmacologic properties, such as poor cellular penetration and cellular activity, poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92–126. This has hampered their development into effective drugs.

Accordingly, the need exists for compounds that can effectively inhibit the action of ICE in vivo, for use as agents for preventing and treating chronic and acute forms of IL-1-mediated diseases, apoptosis-mediated diseases, as well as inflammatory, autoimmune, proliferative, infectious, or degenerative diseases.

SUMMARY OF THE INVENTION

The present invention provides novel classes of compounds, and pharmaceutically acceptable derivatives thereof, that are useful as inhibitors of ICE. These compounds can be used alone or in combination with other therapeutic or prophylactic agents, such as antibiotics, immunomodulators or other anti-inflammatory agents, for the treatment or prophylaxis of diseases mediated by IL-1 or by apoptosis. According to a preferred embodiment, the compounds of this invention are capable of binding to the active site of ICE and inhibiting the activity of that enzyme. Additionally, they have improved cellular potency, improved pharmacokinetics, and/or improved oral bioavailability compared to peptidyl ICE inhibitors.

It is a principal object of this invention to provide novel classes of compounds which are inhibitors of ICE represented by formulas:

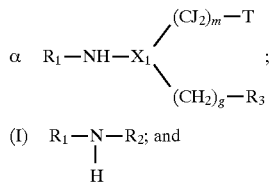

(I) $R_1 - \underset{H}{N} - R_2$; and

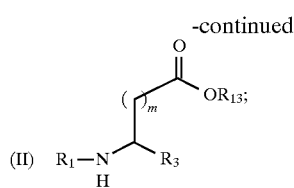

(II) $R_1 - \underset{H}{N} - R_3$ wherein the various substituents are described herein.

BRIEF DESCRIPTION OF THE DRAWINGS

FIGS. 1 and 2 lists the structure, molecular formula, molecular weight, HPLC analytical data, mass spectral data, and synthetic method of preparation for selected compounds of this invention.

Figure 2:
Figure 2:
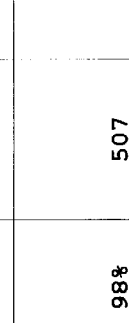
Figure 2:
Figure 2:
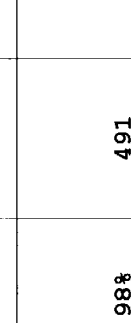

| ABBREVIATIONS AND DEFINITIONS | |
|---|---|
| Abbreviations | |
| Designation | Reagent or Fragment |
| Ala | alanine |
| Arg | arginine |
| Asn | asparagine |
| Asp | aspartic acid |
| Cys | cysteine |
| Gln | glutamine |
| Glu | glutamic acid |
| Gly | glycine |
| His | histidine |
| Ile | isoleucine |
| Leu | leucine |
| Lys | lysine |
| Met | methionine |
| Phe | phenylalanine |
| Pro | proline |
| Ser | serine |
| Thr | threonine |
| Trp | tryptophan |
| Tyr | tyrosine |
| Val | valine |
| Ac₂O | acetic anhydride |
| n-Bu | normal-butyl |
| DMF | dimethylformamide |
| DIEA | N,N-diisopropylethylamine |
| EDC | 1-(3-Dimethylaminopropyl)-3-ethylcarbodiimide hydrochloride |
| Et₂O | diethyl ether |
| EtOAc | ethyl acetate |
| Fmoc | 9-fluorenylmethyoxycarbonyl |
| HBTU | O-benzotriazol-1-yl-N,N,N',N'-tetramethyluronium hexafluorophosphate |
| HOBT | 1-hydroxybenzotriazole hydrate |

ABBREVIATIONS AND DEFINITIONS
Abbreviations

| Designation | Reagent or Fragment |
|---|---|
| MeOH | methanol |
| TFA | trifluoroacetic acid |

Definitions

The following terms are employed herein:

The term "active site" refers to any or all of the following sites in ICE: the substrate binding site, the site where an inhibitor binds and the site where the cleavage of substrate occurs.

The term "heterocycle" or "heterocyclic" refers to a stable mono- or polycyclic compound which may optionally contain one or two double bonds or may optionally contain one or more aromatic rings. Each heterocycle consists of carbon atoms and from one to four heteroatoms independently selected from a group including nitrogen, oxygen, and sulfur. As used herein, the terms "nitrogen heteroatoms" and "sulphur heteroatoms" include any oxidized form of nitrogen or sulfur and the quaternized form of any basic nitrogen. Heterocycles defined above include, for example, pyrimidinyl, tetrahydroquinolyl, tetrahydroisoquinonlinyl, purinyl, pyrimidyl, indolinyl, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranyl, thiamorpholinyl sulfone, benzoxazolyl, oxopiperidinyl, oxopyrrolidinyl, oxazepinyl, azepinyl, isoxazolyl, tetrahydropyranyl, tetrahydrofuranyl, thiadiazolyl, benzodioxolyl, benzothienyl, tetrahydrothiophenyl and sulfolanyl. Further heterocycles are described in A. R. Katritzky and C. W. Rees, eds., *Comprehensive Heterocyclic Chemistry: The Structure, Reactions, Synthesis and Use of Heterocyclic Compounds*, Vol. 1–8, Pergamon Press, NY (1984).

The term "cycloalkyl" refers to a mono- or polycyclic group which contains 3 to 15 carbons and may optionally contain one or two double bonds. Examples include cyclohexyl, adamantyl and norbornyl.

The term "aryl" refers to a mono- or polycyclic group which contains 6, 10, 12, or 14 carbons in which at least one ring is aromatic. Examples include phenyl, naphthyl, and tetrahydronaphthalene.

The term "heteroaromatic" refers to a mono- or polycyclic group which contains 1 to 15 carbon atoms and from 1 to 4 heteroatoms, each of which is selected independently from a group including sulphur, nitrogen and oxygen, and which additionally contains from 1 to 3 five or six membered rings, at least one of which is aromatic.

The term "alpha-amino acid" (α-amino acid) refers to both the naturally occurring amino acids and other "non-protein" α-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of "non-protein" alpha-amino acids include hydroxylysine, homoserine, homotyrosine, homophenylalanine, citrulline, kynurenine, 4-aminophenylalanine, 3-(2-naphthyl)-alanine, 3-(1-naphthyl)-alanine, methionine sulfone, t-butyl-alanine, t-butylglycine, 4-hydroxyphenylglycine, aminoalanine, phenylglycine, vinylalanine, propargyl-glycine, 1,2,4-triazolo-3-alanine, 4,4,4-trifluoro-threonine, thyronine, 6-hydroxytryptophan, 5-hydro-xytryptophan, 3-hydroxykynurenine, 3-aminotyrosine, trifuoromethylalanine, 2-thienylalanine, (2-(4-pyridyl)ethyl) cysteine, 3,4-dimethoxy-phenylalanine, 3-(2-thiazolyl) alanine, ibotenic acid, 1-amino-1-cyclopentanecarboxylic acid, 1-amino-1-cyclohexanecarboxylic acid, quisqualic acid, trifuoromethylphenylalanine, 4-trifluoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxyproline, isonipectotic acid, homoproline, cyclohexylglycine, α-amino-n-butyric acid, cyclohexylalanine, aminophenylbutyric acid, phenylalanines substituted at the ortho, meta, or para position of the phenyl moiety with one or two of the following: a $(C_1-C_4)$ alkyl, a $(C_1-C_4)$ alkoxy, halogen or nitro groups or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitrotyrosine, ε-alkyl lysine, and delta-alkyl ornithine. Any of these α-amino acids may be substituted with a methyl group at the alpha position, a halogen at any aromatic residue on the α-amino side chain, or an appropriate protective group at the O, N, or S atoms of the side chain residues. Appropriate protective groups are disclosed in "Protective Groups In Organic Synthesis," T. W. Greene and P. G. M. Wuts, J. Wiley & Sons, NY, N.Y., 1991.

The term "substitute" refers to the replacement of a hydrogen atom in a compound with a substituent group. In the present invention, those hydrogen atoms which form a part of a hydrogen bonding moiety which is capable of forming a hydrogen bond with the carbonyl oxygen of Arg-341 of ICE or the carbonyl oxygen of Ser-339 of ICE are excluded from substitution. These excluded hydrogen atoms include those which comprise an —NH— group which is alpha to a —CO— group and are depicted as —NH— rather than an X group or some other designation in the following diagrams: (a) through (t), (v) through (z).

The term "straight chain" refers to a contiguous unbranching string of covalently bound atoms. The straight chain may be substituted, but these substituents are not a part of the straight chain.

The term "$K_i$" refers to a numerical measure of the effectiveness of a compound in inhibiting the activity of a target enzyme such as ICE. Lower values of $K_i$ reflect higher effectiveness. The $K_i$ value is a derived by fitting experimentally determined rate data to standard enzyme kinetic equations (see I. H. Segel, *Enzyme Kinetics*, Wiley-Interscience, 1975).

The term "patient" as used in this application refers to any mammal, especially humans.

The term "pharmaceutically effective amount" refers to an amount effective in treating or ameliorating an IL-1- or apoptosis-mediated disease in a patient. The term "prophylactically effective amount" refers to an amount effective in preventing or substantially lessening IL-1- or apoptosis-mediated diseases in a patient.

The term "pharmaceutically acceptable carrier or adjuvant" refers to a non-toxic carrier or adjuvant that may be administered to a patient, together with a compound of this invention, and which does not destroy the pharmacological activity thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-ICE active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N—$(C_{1-4}$ alkyl$)_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The ICE inhibitors of this invention may contain one or more "asymmetric" carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. Although specific compounds and scaffolds exemplified in this application may be depicted in a particular stereochemical configuration, compounds and scaffolds having either the opposite stereochemistry at any given chiral center or mixtures thereof are also envisioned.

The ICE inhibitors of this invention may comprise ring structures which may optionally be substituted at carbon, nitrogen or other atoms by various substituents. Such ring structures may be singly or multiply substituted. Preferably, the ring structures contain between 0 and 3 substituents. When multiply substituted, each substituent may be picked independently of any other substituent as long as the combination of substituents results in the formation of a stable compound.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

DETAILED DESCRIPTION OF THE INVENTION

In order that the invention herein described may be more fully understood, the following detailed description is set forth.

The ICE inhibitors of one embodiment (A) of this invention are those of formula α:

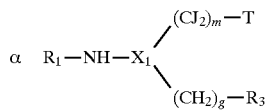

wherein:

$X_1$ is —CH;

g is 0 or 1;

each J is independently selected from the group consisting of —H, —OH, and —F, provided that when a first and second J are bound to a C and said first J is —OH, said second J is —H;

m 0, 1, or 2;

T is —OH, —CO—$CO_2H$, —$CO_2H$, or any bioisosteric replacement for —$CO_2H$;

$R_1$ is selected from the group consisting of the following formulae, in which any ring may optionally be singly or multiply substituted at any carbon by $Q_1$, at any nitrogen by $R_5$, or at any atom by =O, —OH, —$CO_2H$, or halogen; any saturated ring may optionally be unsaturated at one or two bonds; and wherein $R_1$ (e) and $R_1$ (y) are optionally benzofused;

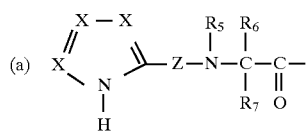

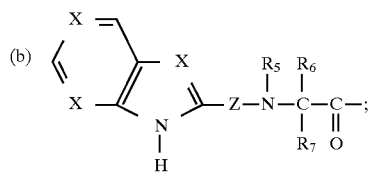

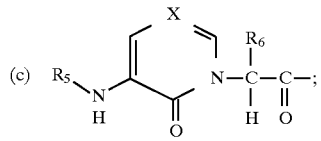

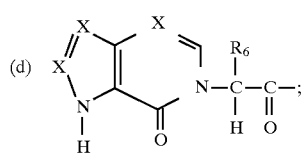

(e) 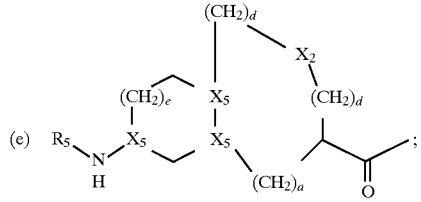
(f) 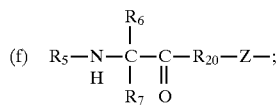
(g) 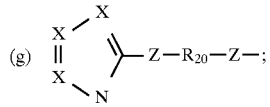
(h) 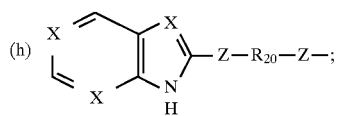
(i) 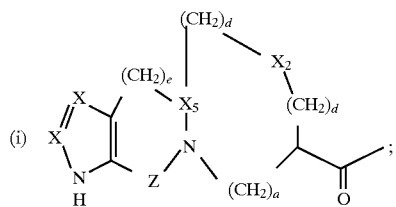
(j) 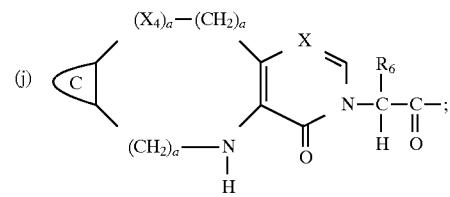
(k) 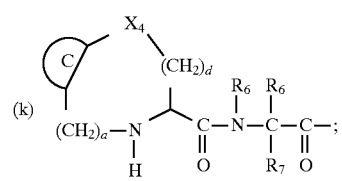
(l) 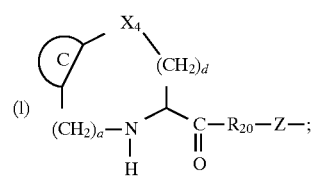
(m) 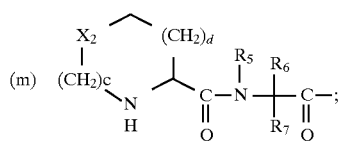
(n) 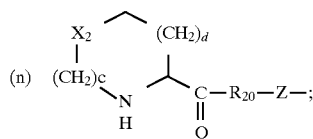
(o) 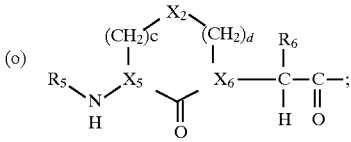
(p) 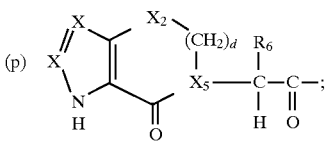
(q) 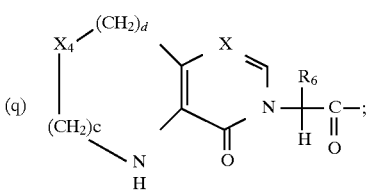
(r) 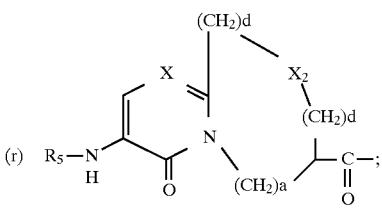
(s) 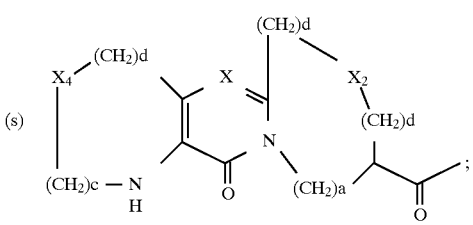
(t) 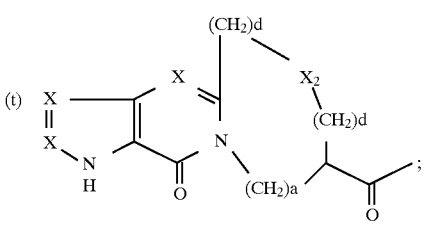
(v) 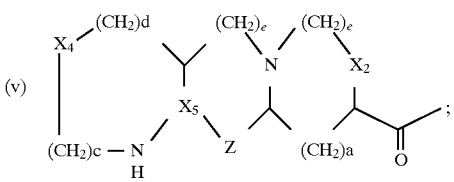
(w) 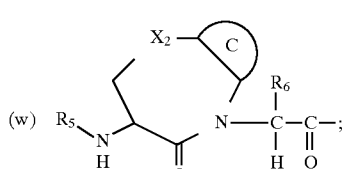

(x) 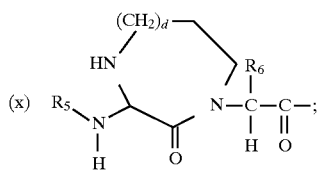

(y) 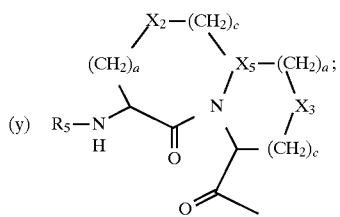

$R_{20}$ is selected from the group consisting of:

(aa1) 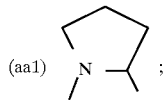

(aa2) 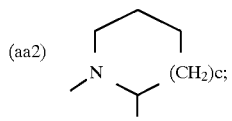

(aa3) 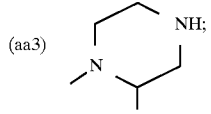

(aa4) 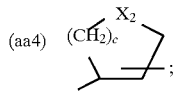

(aa5) 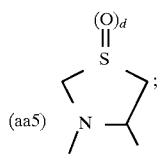

(bb) 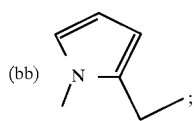

(cc) 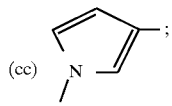

(dd) 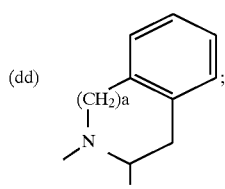

(ee) 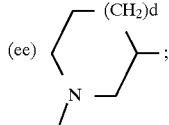

(ff) 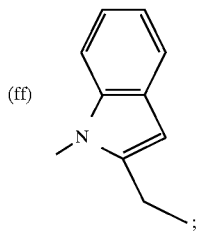

(gg) 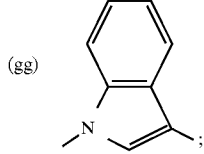

(gga) 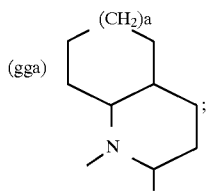

(ggb) 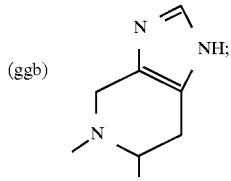

and (ggc) 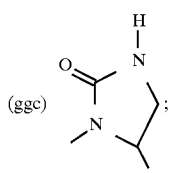

wherein each ring C is independently chosen from the group consisting of benzo, pyrido, thieno, pyrrolo, furano, thiazolo, isothiazolo, oxazolo, isoxazolo, pyrimido, imidazolo, cyclopentyl and cyclohexyl;

$R_3$ is:
 —CN,
 —CH=CH—$R_9$,
 —CH=N—O—$R_9$,
 —(CH$_2$)$_{1-3}$—T$_1$—$R_9$,
 —CJ$_2$—$R_9$,
 —CO—$R_{13}$, or

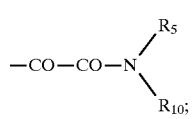

each $R_4$ is independently selected from the group consisting of:

—H,
—$Ar_1$,
—$R_9$,
—$T_1$—$R_9$, and
—$(CH_2)_{1,2,3}$—$T_1$—$R_9$;

each $T_1$ is independently selected from the group consisting of:
CH=CH—,
—O—,
—S—,
—SO—,
—$SO_2$—,
—$NR_{10}$—,
—$NR_{10}$—CO—,
—CO—,
—O—CO—,
—CO—O—,
—CO—$NR_{10}$—,
—O—CO—$NR_{10}$—,
—$NR_{10}$—CO—O—,
—$NR_{10}$—CO—$NR_{10}$—,
—$SO_2$—$NR_{10}$—,
—$NR_{10}$—$SO_2$—, and
—$NR_{10}$—$SO_2$—$NR_{10}$—;

each $R_5$ is independently selected from the group consisting of:
—H,
—$Ar_1$,
—CO—$Ar_1$,
—$SO_2$—$Ar_1$,
—CO—$NH_2$,
—$SO_2$—$NH_2$,
—$R_9$,
—CO—$R_9$,
—CO—O—$R_9$,
—$SO_2$—$R_9$, —CO—N(Ar$_1$)(R$_{10}$), —SO$_2$—N(Ar$_1$)(R$_{10}$), —CO—N(R$_9$)(R$_{10}$), and

—SO$_2$—N(R$_9$)(R$_{10}$);

$R_6$ and $R_7$ taken together form a saturated 4–8 member carbocyclic ring or heterocyclic ring containing —O—, —S—, or —NH—; or $R_7$ is —H and $R_6$ is
—H
—$Ar_1$,
—$R_9$,
—$(CH_2)_{1,2,3}$—$T_1$—$R_9$, or
an α-amino acid side chain residue;

each $R_9$ is a $C_{1-6}$ straight or branched alkyl group optionally singly or multiply substituted with —OH, —F, or =O and optionally substituted with one or two $Ar_1$ groups;

each $R_{10}$ is independently selected from the group consisting of —H or a $C_{1-6}$ straight or branched alkyl group;

each $R_{13}$ is independently selected from the group consisting of —$Ar_2$, —$R_4$ and

—N(R$_5$)—OH;

each $Ar_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —$SO_2$—, =N—, and —NH—, said heterocycle group optionally containing one or more double bonds, said heterocycle group optionally comprising one or more aromatic rings, and said cyclic group optionally being singly or multiply substituted with —$NH_2$, —$CO_2H$, —Cl, —F, —Br, —I, —$NO_2$, —CN, =O, —OH, —perfluoro $C_{1-3}$ alkyl, a dioxolane ring (O—CH$_2$—O), or —$Q_1$;

each $Ar_2$ is independently selected from the following group, in which any ring may optionally be singly or multiply substituted by —$Q_1$ and —$Q_2$:

(hh) benzofused five-membered ring with Y and X heteroatoms;

(ii) five-membered ring with Y and X;

(jj) five-membered ring with N, Y, and X; and (kk) five-membered ring with N, X, and Y;

each $Q_1$ is independently selected from the group consisting of:
—Ar,
—O—$Ar_1$
—$R_9$,
—$T_1$—$R_9$, and
—$(CH_2)_{1,2,3}$—$T_1$—$R_9$;

each $Q_2$ is independently selected from the group consisting of —OH, —$NH_2$, —$CO_2H$, —Cl, —F, —Br, —I, —$NO_2$, —CN, —$CF_3$, and

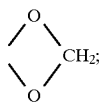

provided that when —Ar$_1$ is substituted with a Q$_1$ group which comprises one or more additional —Ar$_1$ groups, said additional —Ar$_1$ groups are rot substituted with Q$_1$;

each X is independently selected from the group consisting of =N—, and =CH—;

each X$_2$ is independently selected from the group consisting of —O—, —CH$_2$—, —NH—, —S—, —SO—, and —SO$_2$—;

each X$_3$ is independently selected from the group consisting of —CH$_2$—, —S—, —SO—, and —SO$_2$—;

each X$_4$ is independently selected from the group consisting of —CH$_2$— and —NH—;

each X$_5$ is independently selected from the group consisting of

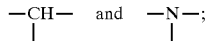

X$_6$ is —CH— or —N—;

each Y is independently selected from the group consisting of —O—, —S—, and —NH;

each Z is independently CO or SO$_2$;

each a is independently 0 or 1;

each c is independently 1 or 2;

each d is independently 0, 1, or 2; and each e is independently 0, 1, 2, or 3; provided that when
R$_1$ is (f),
R$_6$ is an α-amino acid side chain residue, and
R$_7$ is —H,
then (aa1) and (aa2) must be substituted with Q$_1$;
also provided that when
R$_1$ is (o),
g is 0,
J is —H,
m is 1,
R$_6$ is an α-amino acid side chain residue,
R$_7$ is —H,
X$_2$ is —CH$_2$—,
X$_5$ is

X$_6$ is

and

R$_3$ is

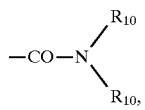

or —CO—R$_{13}$, when
R$_{13}$ is:
—CH$_2$—O—CO—Ar$_1$,
—CH$_2$—S—CO—Ar$_1$,
—CH$_2$—O—Ar$_1$,
—CH$_2$—S—Ar$_1$, or
—R$_4$ when —R$_4$ is —H;
then the ring of the R$_1$(o) group must be substituted with Q$_1$ or benzofused; and
provided that when
R$_1$ is (w),
g is 0,
J is —H,
m is 1,
T is —CO$_2$H,
X$_2$ is O,
R$_5$ is benzyloxycarbonyl, and
ring C is benzo,
then R$_3$ cannot be —CO—R$_{13}$ when:
R$_{13}$ is —CH$_2$—O—Ar$_1$ and
Ar$_1$ is 1-phenyl-3-trifluoromethylpyrazole-5-yl wherein the phenyl is optionally substituted with a chlorine atom;
or when
R$_{13}$ is —CH$_2$—O—CO—Ar$_1$, wherein
Ar$_1$ is 2,6-dichlorophenyl.

Preferred compounds of embodiment A employ formula α, wherein R$_1$ is (w):

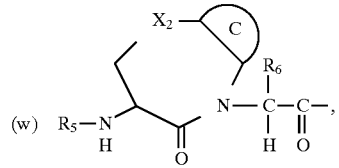

wherein the other substituents are as described above.

Other preferred compounds of embodiment A employ formula α, wherein R$_1$ is (y):

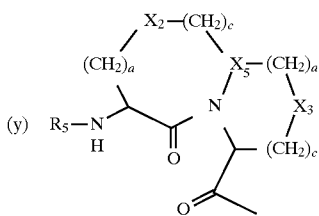

wherein the other substituents are as described above.

More preferred compounds of embodiment A employ formula α, wherein:
X$_1$ is —CH;
g is 0;
J is —H;
m is 0 or 1 and T is —CO—CO$_2$H, or any bioisosteric replacement for —CO$_2$H, or m is 1 and T is —CO$_2$H;

R$_1$ is selected from the group consisting of the following formulae, in which any ring may optionally be singly or multiply substituted at any carbon by Q$_1$, at any nitrogen by R$_5$, or at any atom by =O, —OH, —CO$_2$H, or halogen, and wherein (e) is optionally benzofused:

(a) 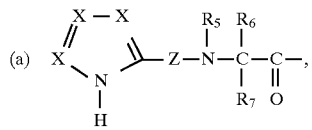

(b) 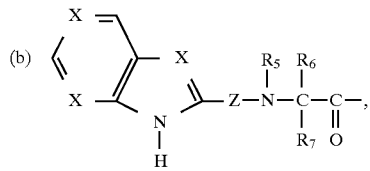

(c) 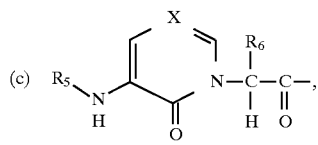

(e) 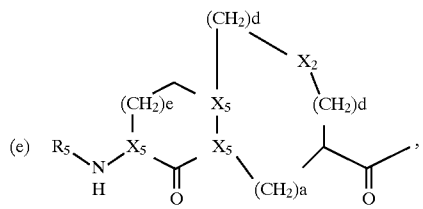

(f) 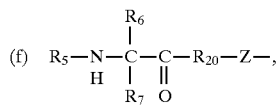

(g) 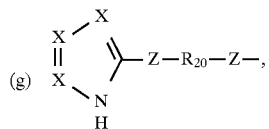

(h) 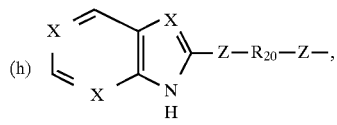

(o) 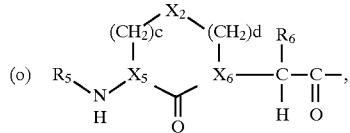

(r) 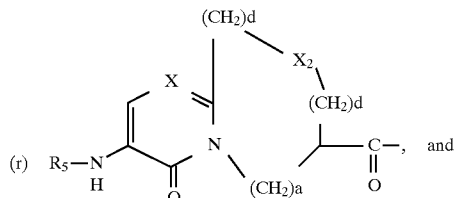

(w) 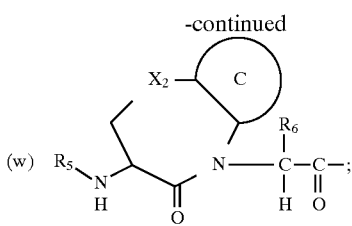

R$_{20}$ is:

(aa1) 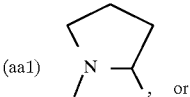, or (aa2) 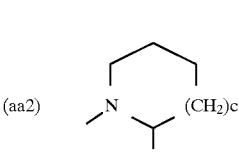

and c is 1;

ring C is benzo optionally substituted with —C$_{1-3}$ alkyl, —O—C$_{1-3}$ alkyl, —Cl, —F or —CF$_3$;

when R$_1$ is (a) or (b), R$_5$ is preferably —H, and when R$_1$ is (c), (e), (f), (o), (r), (w), (x) or (y), R$_5$ is preferably:
 —CO—Ar$_1$
 —SO$_2$—Ar$_1$,
 —CO—NH$_2$,
 —CO—NH—Ar$_1$
 —CO—R$_9$,
 —CO—O—R$_9$,
 —SO$_2$—R$_9$, or
 —CO—NH—R$_9$, R$_7$ is —H and R$_6$ is:
 —H,
 —R$_9$, or
 —Ar$_1$;

R$_9$ is a C$_{1-6}$ straight or branched alkyl group optionally substituted with =O and optionally substituted with —Ar$_1$;

R$_{10}$ is —H or a —C$_{1-3}$ straight or branched alkyl group;

Ar$_1$ is phenyl, naphthyl, pyridyl, benzothiazolyl, thienyl, benzothienyl, benzoxazolyl, 2-indanyl, or indolyl optionally substituted with —O—C$_{1-3}$ alkyl, —NH—C$_{1-3}$ alkyl, —N—(C$_{1-3}$ alkyl)$_2$, —Cl, —F, —CF$_3$, —C$_{1-3}$ alkyl, or

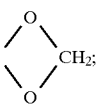

Q$_1$ is R$_9$ or —(CH$_2$)$_{0,1,2}$—T$_1$—(CH$_2$)$_{0,1,2}$—Ar$_1$, wherein T$_1$ is —O— or —S—;

each X is independently selected from the group consisting of =N—, and =CH—;

each X$_2$ is independently selected from the group consisting of —O—, —CH$_2$—, —NH—, —S—, —SO—, and —SO$_2$—;

each X$_5$ is independently selected from the group consisting of

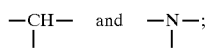

$X_6$ is

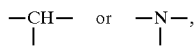

provided that when:

$R_1$ is (o), $X_2$ is

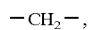

$X_5$ is

and $X_6$ is

then the ring of the $R_1$(o) group must be substituted with $Q_1$ or benzofused; and Z is C=O.

Most preferably, compounds of this more preferred embodiment are those wherein the $R_1$ group is:

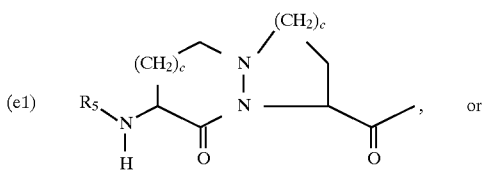

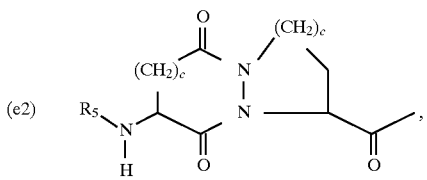

and c is 2; or

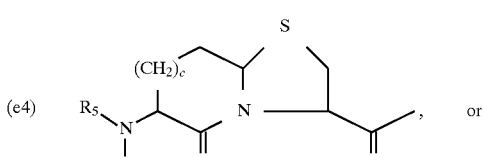

-continued

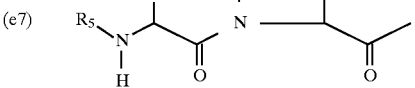

which is optionally benzofused, and c is 1 or 2;

provided that when $R_1$ is (e4), g is 0,

J is —H, m is 1,

T is —$CO_2H$, $R_5$ is benzyloxycarbonyl, and c is 1, then $R_3$ cannot be —CO—$R_{13}$ when $R_{13}$ is —$CH_2$—O—$Ar_1$ and $Ar_1$ is 1-phenyl-3-trifluoromethyl-pyrazole-5-yl, wherein the phenyl is optionally substituted with a chlorine atom; or when $R_{13}$ is —$CH_2$—O—CO—$Ar_1$, wherein $Ar_1$ is 2,6-dichlorophenyl, and when the 2-position of the scaffold ring is substituted with para-fluoro-phenyl; and also provided that when $R_1$ is (e7), g is 0, J is —H, m is 1, T is —$CO_2H$ or —CO—NH—OH, $R_5$ is a protective group for the N atom of an amino acid side chain residue, and each c is 1, then $R_3$ cannot be —CO—$R_{13}$ when $R_{13}$ is:

—$CH_2$—O—CO—$Ar_1$,

—$CH_2$—S—CO—$Ar_1$,

—$CH_2$—O—$Ar_1$, or

—$CH_2$—S—$Ar_1$.

The most preferred compounds of this embodiment are those wherein:

$R_1$ is:

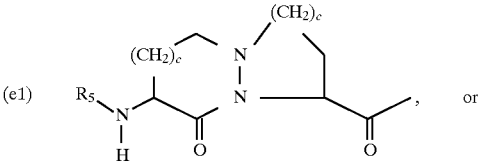

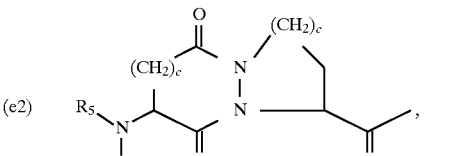

and c is 2;

m is 1;

T is —$CO_2H$; and $R_3$ is —CO—$R_{13}$.

Other most preferred compounds of this embodiment are those wherein:

$R_1$ is:

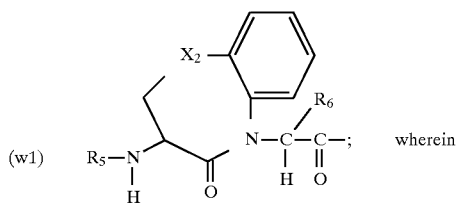

(w1) wherein $X_2$ is:
- —O—,
- —S—,
- —SO$_2$—, or
- —NH—;

optionally substituted with $R_5$ or $Q_1$ at $X_2$ when $X_2$ is —NH—; and ring C is benzo substituted with —C$_{1-3}$ alkyl, —O—C$_{1-3}$ alkyl, —Cl, —F or —CF$_3$.

The ICE inhibitors of another embodiment (B) of this invention are those of formula (I):

  (I)

wherein:

$R_1$ is selected from the group consisting of the following formulae:

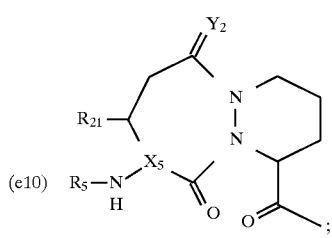
(e10)

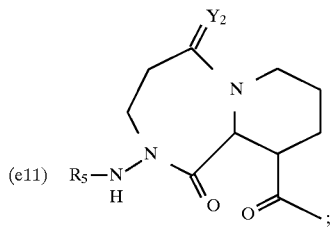
(e11)

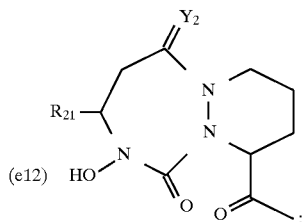
(e12)

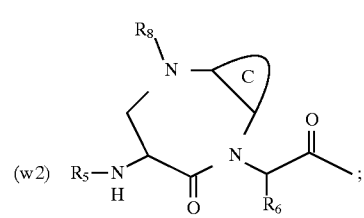
(w2)

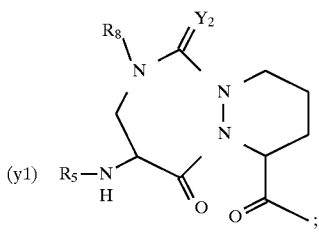
(y1)

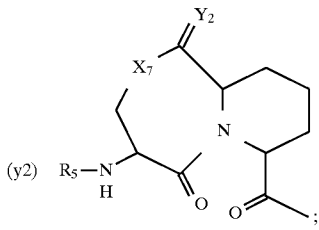
(y2)

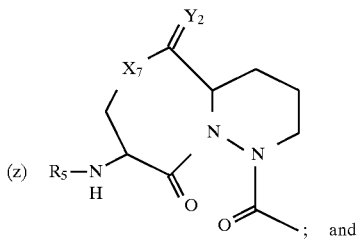
(z) ; and ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_2$ is:

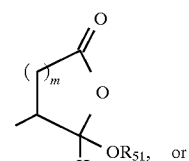
(a)  , or

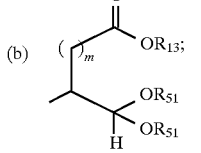
(b)

m is 1 or 2;

$R_5$ is selected from the group consisting of:
- —C(O)—R$_{10}$,
- —C(O)O—R$_9$,

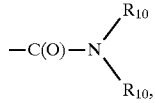

- —S(O)$_2$—R$_9$,
- —C(O)—CH$_2$—O—R$_9$,
- —C(O)C(O)—R$_{10}$,
- —R$_9$,
- —H, and
- —C(O)C(O)—OR$_{10}$;

$X_5$ is

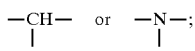

$Y_2$ is $H_2$ or O;
$X_7$ is —N($R_8$)— or —O—;
$R_6$ is selected from the group consisting of —H and —$CH_3$;
$R_8$ is selected from the group consisting of:
- —C(O)—$R_{10}$,
- —C(O)O—$R_9$,
- —C(O)—N(H)—$R_{10}$,
- —S(O)$_2$—$R_9$,
- —S(O)$_2$—NH—$R_{10}$,
- —C(O)—$CH_2$—$OR_{10}$,
- —C(O)C(O)—$R_{10}$;
- —C(O)—$CH_2$N($R_{10}$)($R_{10}$),
- —C(O)—$CH_2$C(O)—O—$R_9$,
- —C(O)—$CH_2$C(O)—$R_9$,
- —H, and
- —C(O)—C(O)—$OR_{10}$;

each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;

each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;

$R_{13}$ is selected from the group consisting of H, $Ar_3$, and a $C_{1-6}$ straight or branched alkyl group optionally substituted with $Ar_3$, —$CONH_2$, —$OR_5$, —OH, —$OR_9$, or —$CO_2$H;

each $R_{51}$ is independently selected from the group consisting of $R_9$, —C(O)—$R_9$, —C(O)—N(H)—$R_9$, or each $R_{51}$ taken together forms a saturated 4–8 member carbocyclic ring or heterocyclic ring containing —O—, —S—, or —NH—;

each $R_{21}$ is independently selected from the group consisting of —H or a —$C_{1-6}$ straight or branched alkyl group;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, =N—, and —NH—, said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —$NH_2$, —$CO_2$H, —Cl, —F, —Br, —I, —$NO_2$, —CN, =O, —OH, —perfluoro $C_{1-3}$ alkyl, $R_5$, —$OR_5$, —$NHR_5$, $OR_9$, —$NHR_9$, $R_9$, —C(O)—$R_{10}$, and

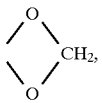

provided that when —$Ar_3$ is substituted with a $Q_1$ group which comprises one or more additional —$Ar_3$ groups, said additional —$Ar_3$ groups are not substituted with another —$Ar_3$.

Preferably, $R_5$ is selected from the group consisting of:
- —C(O)—$R_{10}$,
- —C(O)O—$R_9$, and
- —C(O)—NH—$R_{10}$.

Alternatively, $R_5$ is selected from the group consisting of:
- —S(O)$_2$—$R_9$,
- S(O)$_2$—NH—$R_{10}$,
- —C(O)—C(O)—$R_{10}$,
- —$R_9$, and
- —C(O)—C(O)—$OR_{10}$.

More preferably:

m is 1;

$R_{13}$ is H or a —$C_{1-4}$ straight or branched alkyl group optionally substituted with —$Ar_3$, —OH, —$OR_9$, or —$CO_2$H, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by —$Q_1$;

$Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —$OR_5$ wherein $R_5$ is —C(O)—$R_{10}$, —$OR_9$, —$NHR_9$, and

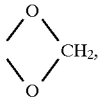

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

The ICE inhibitors of another embodiment (C) of this invention are those of formula (II):

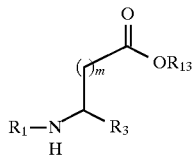

wherein:

m is 1 or 2;

$R_1$ is selected from the group consisting of the following formulae:

(e10) 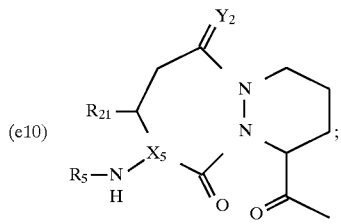

(e11) 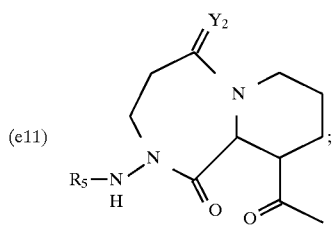

(e12) 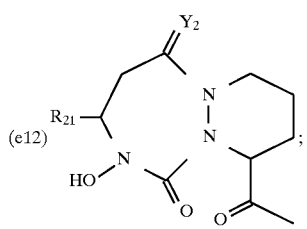

(w2) 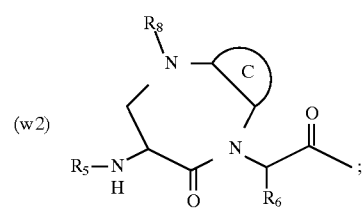

(y1) 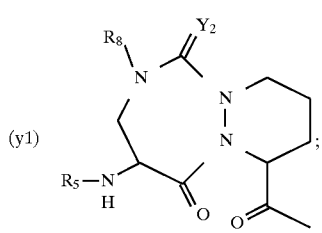

(y2) 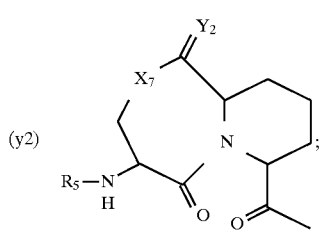

(z) 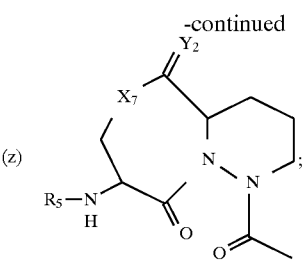

and ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is selected from the group consisting of:
—CN,
—C(O)—H,
—C(O)—CH$_2$—T$_1$—R$_{11}$,
—C(O)—CH$_2$—F,
—C=N—O—R$_9$, and
—CO—Ar$_2$;

$R_5$ is selected from the group consisting of:
—C(O)—R$_{10}$,
—C(O)O—R$_9$,

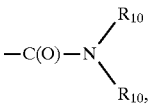

—S(O)$_2$—R$_9$,
—C(O)—CH$_2$—O—R$_9$,
—C(O)C(O)—R$_{10}$,
—R$_9$,
—H, and
—C(O)C(O)—OR$_{10}$, $X_5$ is —CH— or —N—;

$Y_2$ is H$_2$ or O;
$X_7$ is —N(R$_8$)— or —O—;

each $T_1$ is independently selected from the group consisting of —O—, —S—, —S(O)—, and —S(O)$_2$—;

$R_6$ is selected from the group consisting of —H and —CH$_3$;

$R_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$)(R$_{10}$),
—C(O)—CH$_2$C(O)—O—R$_9$,
—C(O)—CH$_2$C(O)—R$_9$,
—H, and
—C(O)—C(O)—OR$_{10}$;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;

each $R_{11}$ is independently selected from the group consisting of:
 $Ar_4$,
 —$(CH_2)_{1-3}$—$Ar_4$,
 —H, and
 —C(O)—$Ar_4$;

$R_{13}$ is selected from the group consisting of H, $Ar_3$, and a $C_{1-6}$ straight or branched alkyl group optionally substituted with $Ar_3$, —$CONH_2$, —$OR_5$, —OH, —$OR_9$, or —$CO_2H$;

—$OR_{13}$ is optionally —N(H)—OH;

each $R_{21}$ is independently selected from the group consisting of —H or a —$C_{1-6}$ straight or branched alkyl group;

$Ar_2$ is independently selected from the following group, in which any ring may optionally be singly or multiply substituted by —$Q_1$:

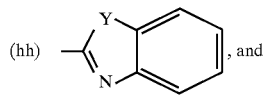

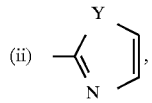

wherein each Y is independently selected from the group consisting of O and S;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, =N—, and —NH—, —$N(R_5)$—, and —$N(R_9)$— said heterocycle group optionally containing one or more double bonds, said heterocycle group optionally comprising one or more aromatic rings, and said cyclic group optionally being singly or multiply substituted by —$Q_1$;

each $Ar_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, $SO_2$, =N—, —NH—, —$N(R_5)$—, and —$N(R_9)$— said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —$NH_2$, —$CO_2H$, —Cl, —F, —Br, —I, —$NO_2$, —CN, =O, —OH, —perfluoro $C_{1-3}$ alkyl, $R_5$, —$OR_5$, —$NHR_5$, $OR_9$, $NHR_9$, —$NHR_9$, $R_9$, —C(O)—$R_{10}$, and

provided that when —$Ar_3$ is substituted with a $Q_1$ group which comprises one or more additional —$Ar_3$ groups, said additional —$Ar_3$ groups are not substituted with another —$Ar_3$.

Preferred compounds of this embodiment include, but are not limited to:

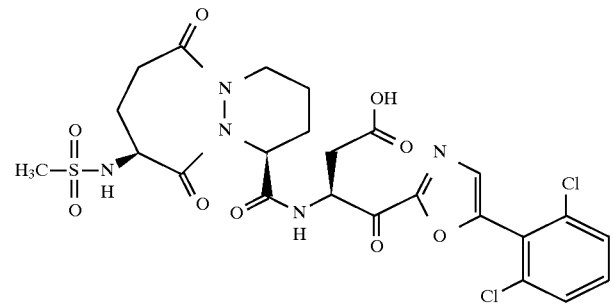

220b

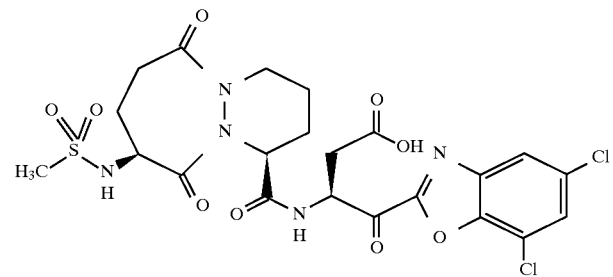

223b

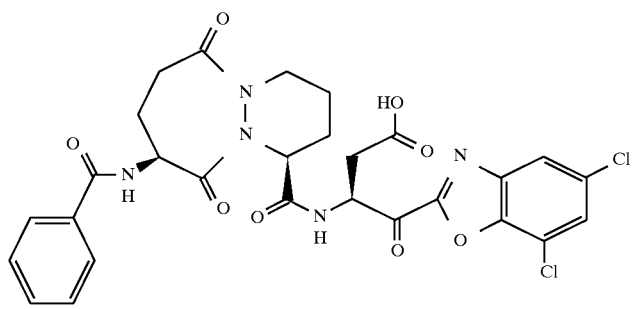
223e
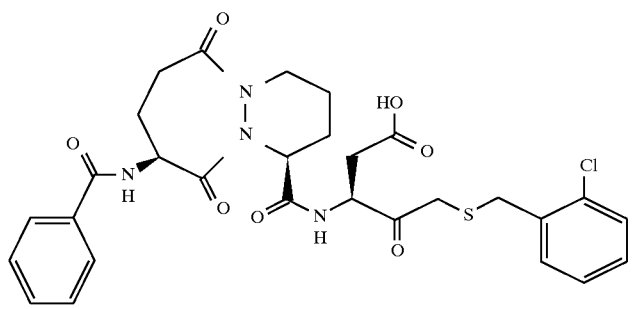
226e
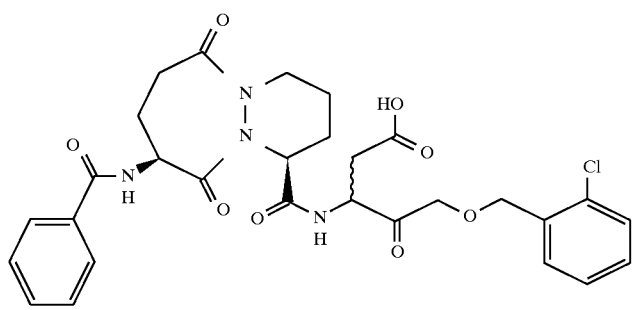
227e
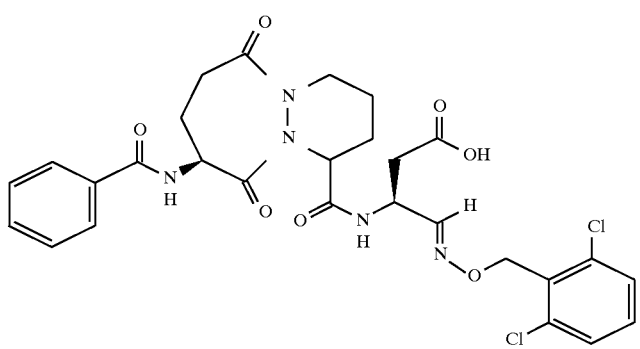
307a
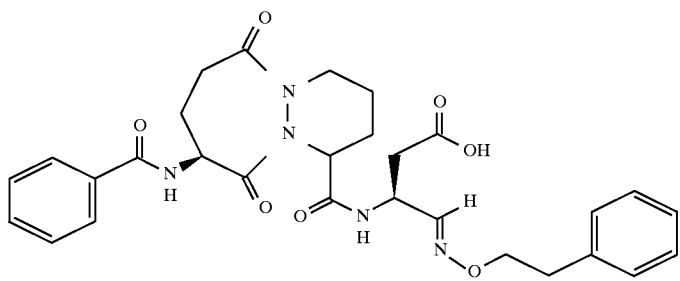
307b -continued
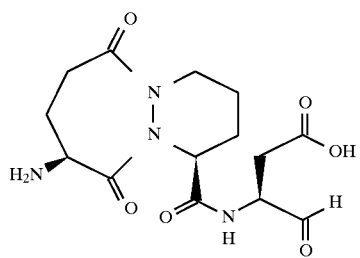
429
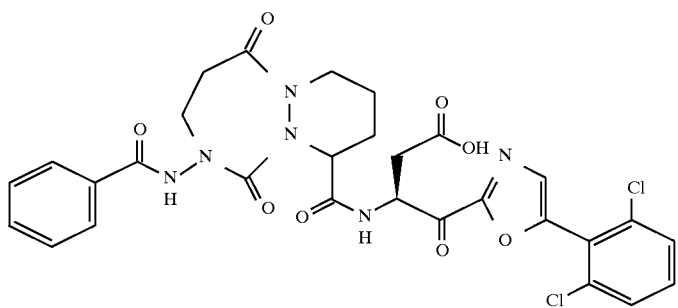
820b
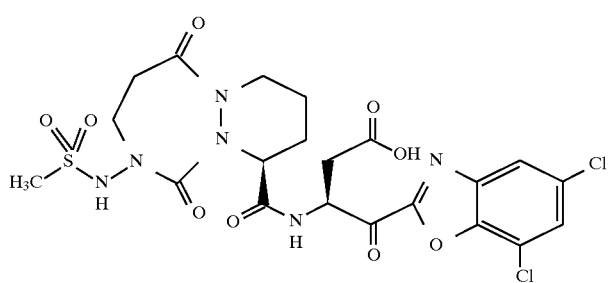
823b
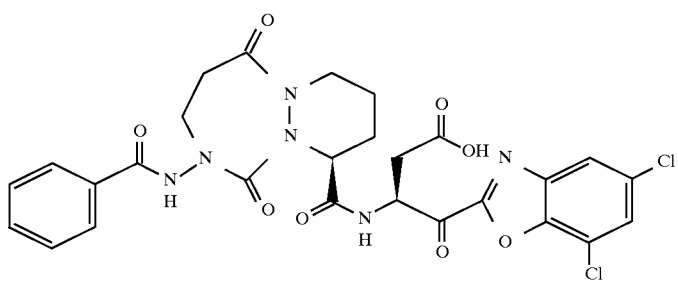
823e
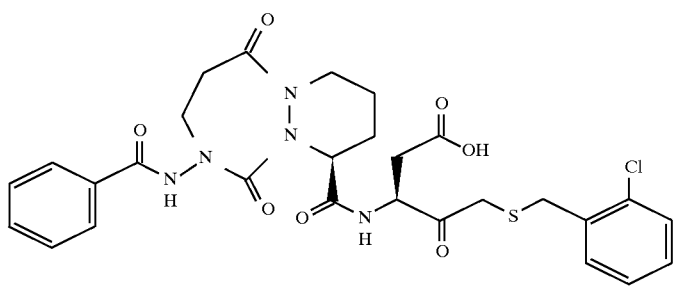
826e

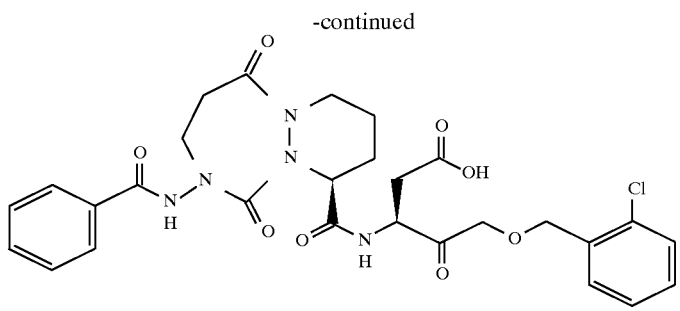

827e

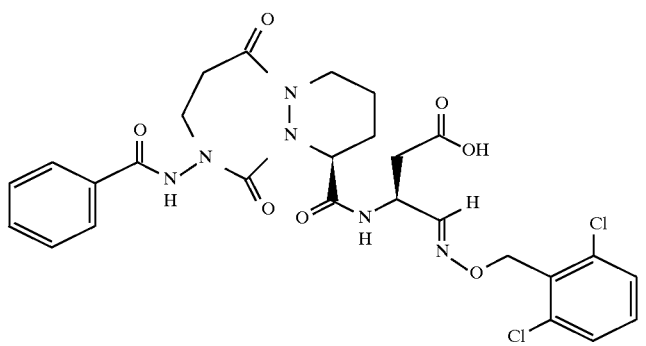

907a

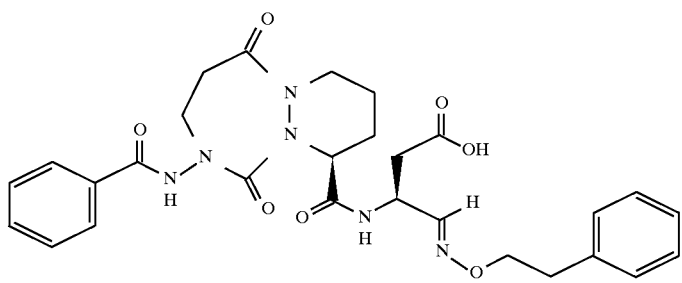

907b

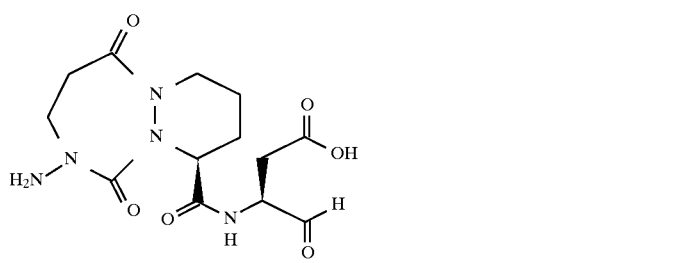

1029

Preferred compounds of embodiment C employ formula (II), wherein $R_1$ is (e11) and the other substituents are as defined above.

Other preferred compounds of embodiment C employ formula (II), wherein $R_1$ is (e12) and the other substituents are as defined above.

Other preferred compounds of embodiment C employ formula (II) wherein $R_1$ is (y1) and the other substituents are as defined above.

Other preferred compounds of embodiment C employ formula (II) wherein $R_1$ is (y2) and the other substituents are as defined above.

Other preferred compounds of embodiment C of employ formula (II) wherein $R_1$ is (z) and the other substituents are as defined above.

Other preferred compound of embodiment C employ formula (II) wherein $R_1$ is (w2) and the other substituents are as defined above.

More preferably, $R_1$ is (w2) and
m is 1;

ring C is benzo, pyrido, or thieno;

$R_3$ is selected from the group consisting of —C(O)—H, —C(O)—$Ar_2$, and —C(O)$CH_2$—$T_1$—$R_{11}$;

$R_5$ is selected from the group consisting of:
—C(O)—$R_{10}$, wherein $R_{10}$ is —$Ar_3$;
—C(O)O—$R_9$, wherein $R_9$ is —$CH_2$—$Ar_3$;
—C(O)C(O)—$R_{10}$, wherein $R_{10}$ is —$CH_2Ar_3$;
—$R_9$, wherein $R_9$ is a $C_{1-2}$ alkyl group substituted with —$Ar_3$; and
—C(O)C(O)—$OR_{10}$, wherein $R_{10}$ is —$CH_2Ar_3$;

$T_1$ is O or S;

$R_6$ is H;

$R_8$ is selected from the group consisting —C(O)—$R_{10}$, —C(O)—$CH_2$—$OR_{10}$, and —C(O)$CH_2$—$N(R_{10})(R_{10})$, wherein $R_{10}$ is H, $CH_3$, or —$CH_2CH_3$;

$R_{11}$ is selected from the group consisting of —$Ar_4$, —$(CH_2)_{1-3}$—$Ar_4$, and —C(O)—$Ar_4$;

$R_{13}$ is H or a —$C_{1-4}$ straight or branched alkyl group optionally substituted with —$Ar_3$, —OH, —$OR_9$, or —CO₂H, wherein the $R_9$ is a —$C_{1-4}$ branched or straight alkyl group, wherein $Ar_3$ is morpholinyl or phenyl, wherein the phenyl is optionally substituted with $Q_1$;

$Ar_2$ is (hh);

Y is O;

$Ar_3$ is phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl;

$Ar_4$ is phenyl, tetrazolyl, naphthyl, pyridinyl, oxazolyl, pyrimidinyl, or indolyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)₂—$R_9$, —$OR_5$ wherein $R_5$ is —C(O)—$R_{10}$, —$OR_9$, —$NHR_9$, and

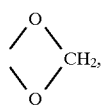

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$. Copy2

Preferred compounds of this embodiment include, but are not limited to:

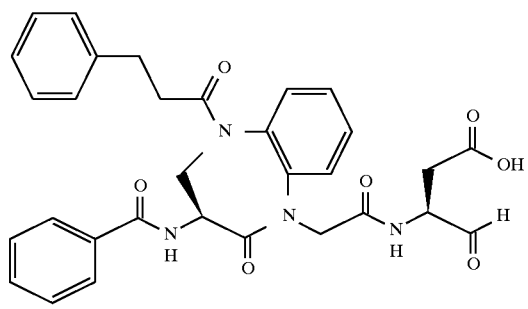

605a

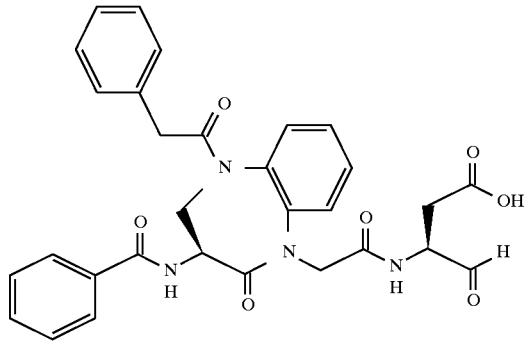

605b

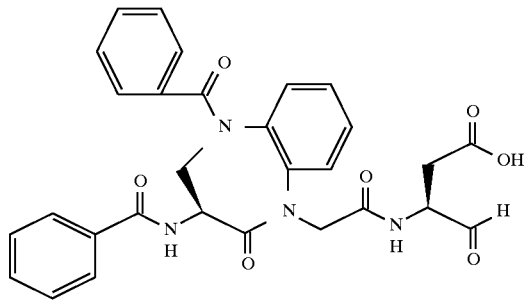

605c

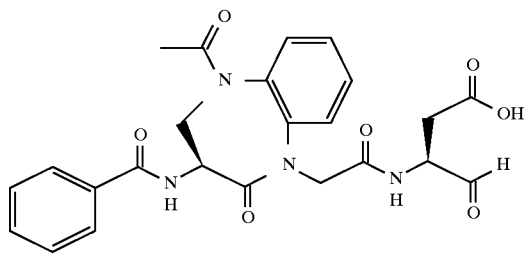

605d

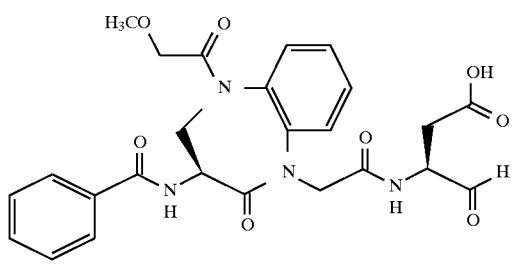
605e
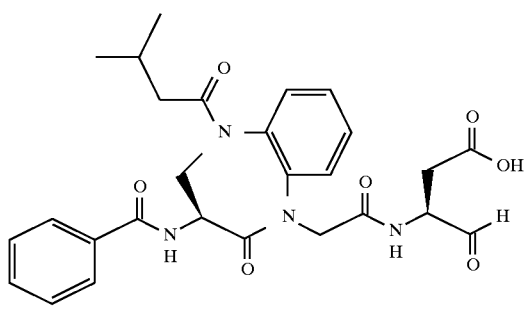
605f
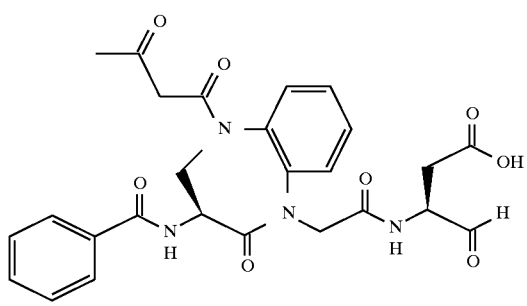
605g
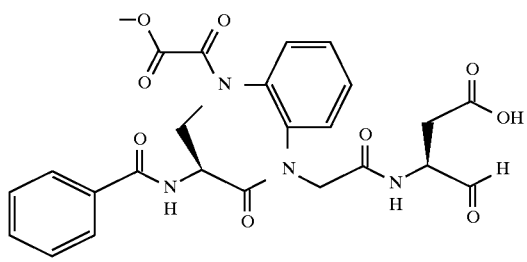
605h
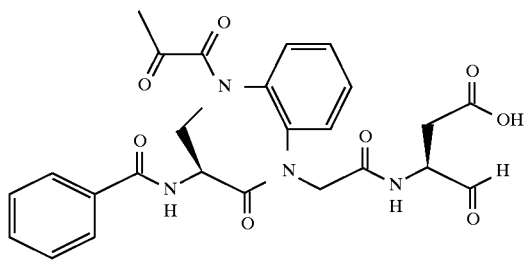
605i
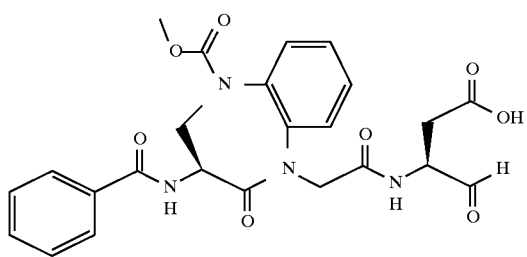
605j

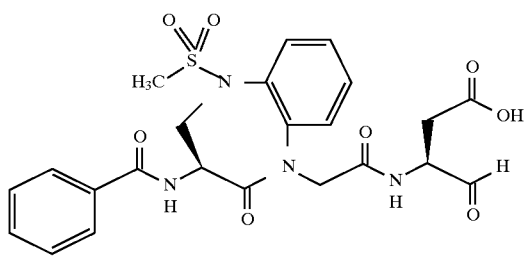
605m
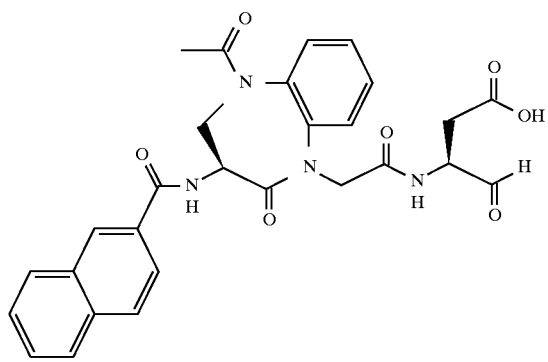
605n
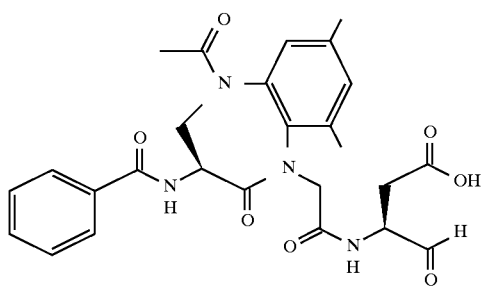
605o
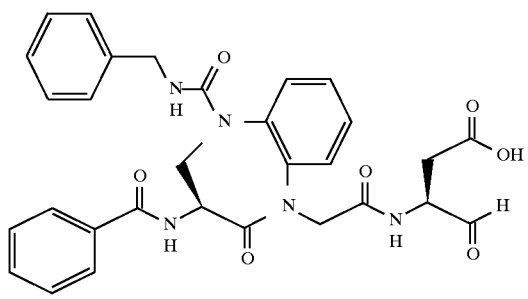
605p
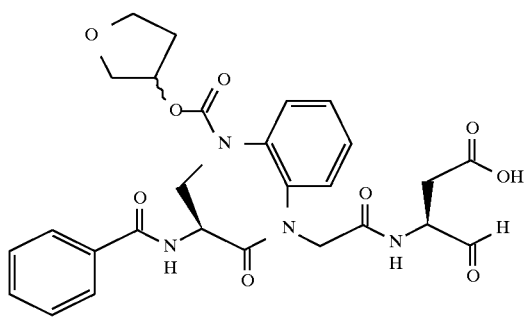
605q 605s
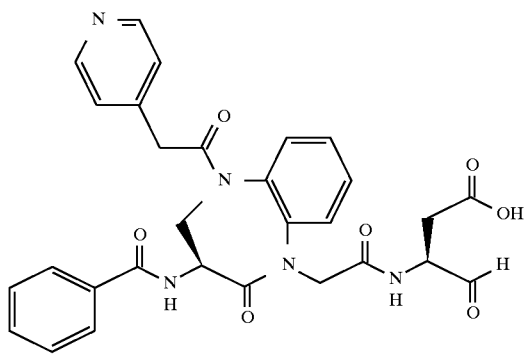
605t
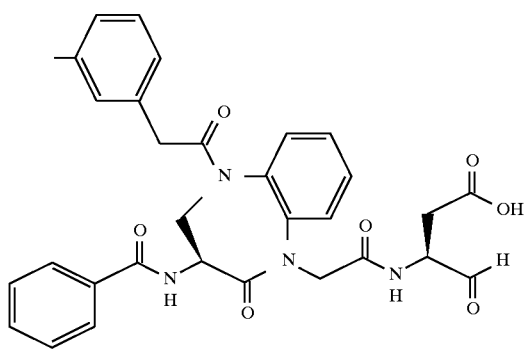
605v
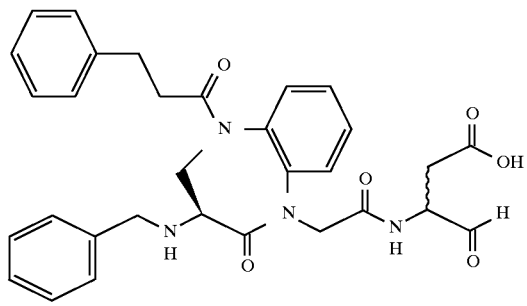
609a
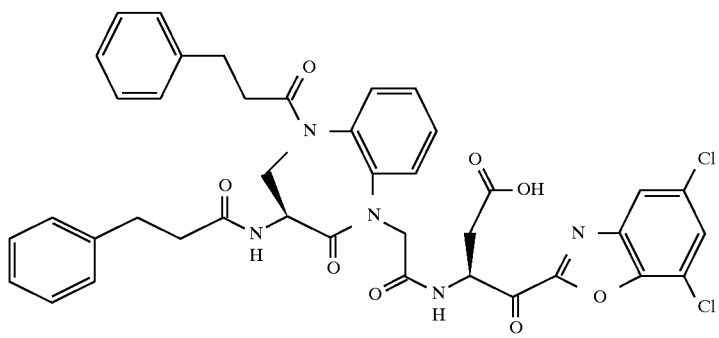
609b
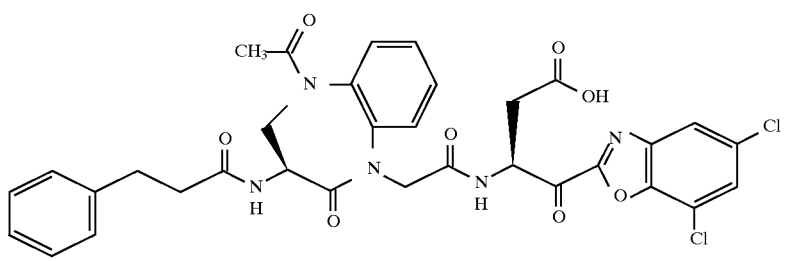

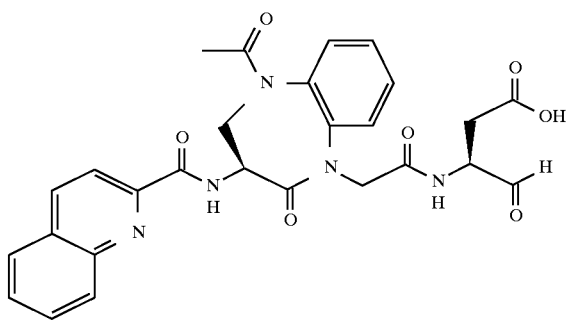
619
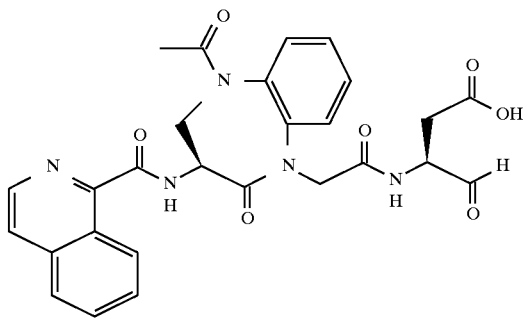
620
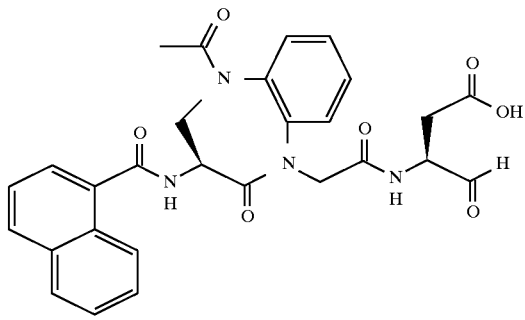
621
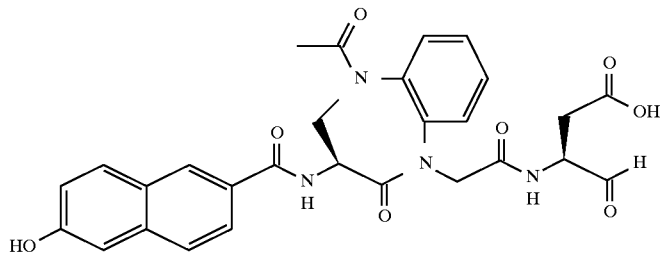
622
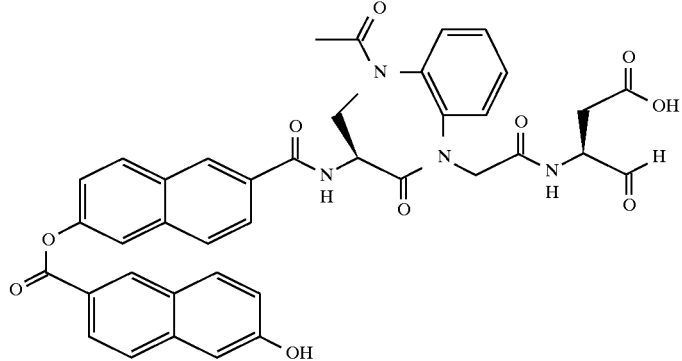
623

-continued
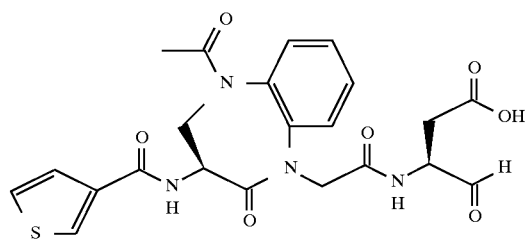
624
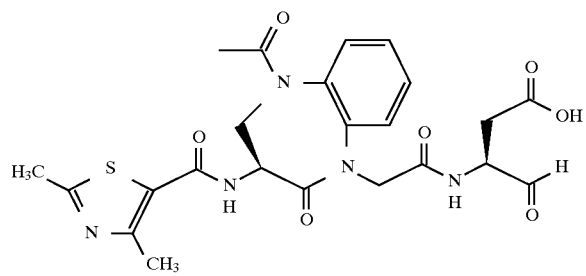
625
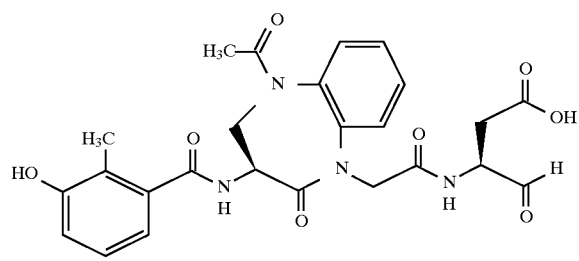
626
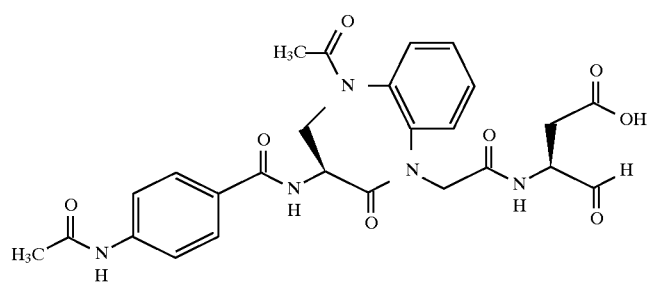
627
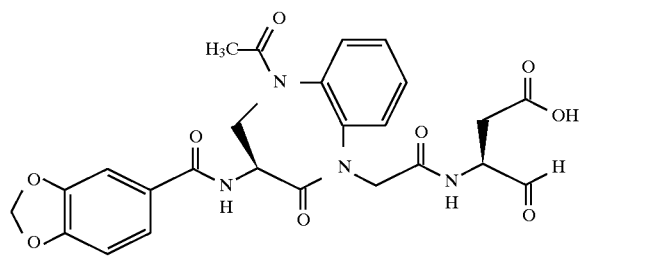
628
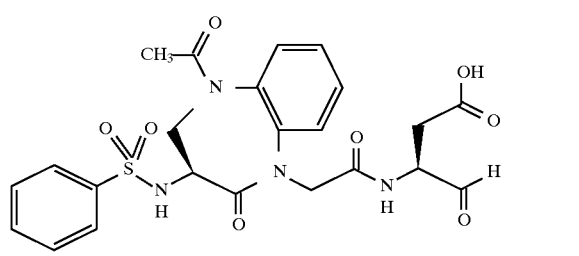
629

-continued

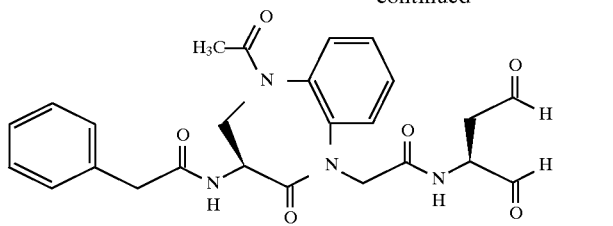
630

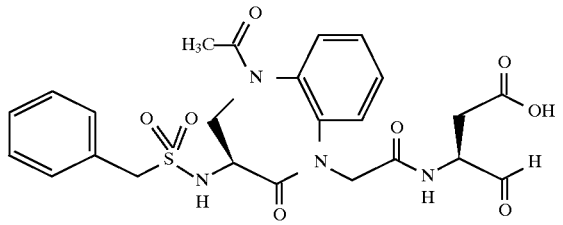
631

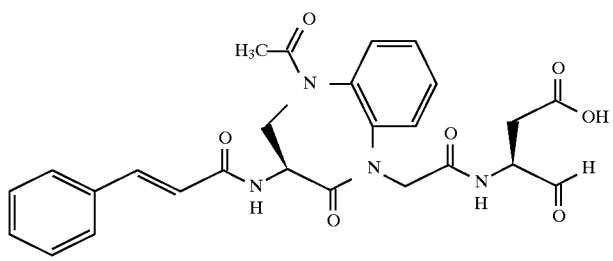
632

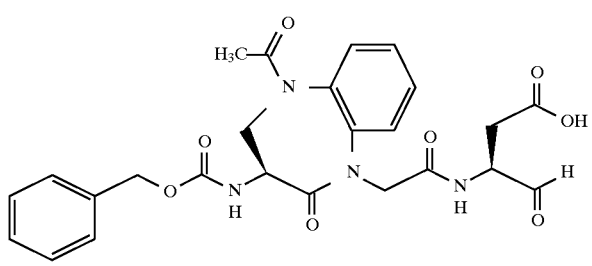
633

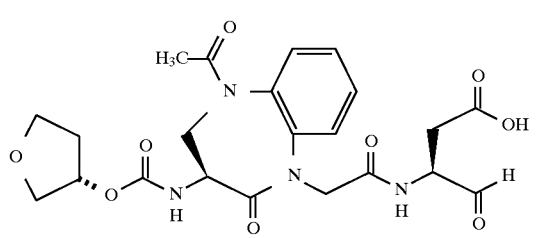
634

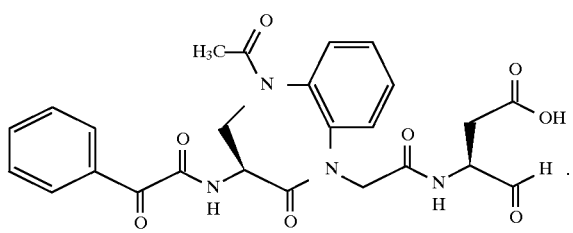
635

Other preferred compounds of embodiment C employ formula (II) wherein $R_1$ is (e10), $X_5$ is CH, and the other substituents are as defined above.

More preferred compounds of embodiment C employ formula (II) wherein $R_1$ is (e10), $X_5$ is CH, $R_3$ is CO—$Ar_2$, and the other substituents are as defined above.

Other more preferred compounds of embodiment C employ formula (II) wherein $R_1$ is (e10), $X_5$ is CH, $R_3$ is —C(O)—$CH_2$—$T_1$—$R_{11}$, $R_{11}$ is —$(CH_2)_{1-3}$—$Ar_4$, and the other substituents are as defined above.

Other more preferred compounds of embodiment C employ formula (II) wherein $R_1$ is (e10) and $X_5$ is CH and
$R_3$ is —C(O)—$CH_2$—$T_1$—$R_{11}$;
$T_1$ is O; and
$R_{11}$ is —C(O)—$Ar_4$,
and the other substituents are as defined above.

More preferably, in these more preferred compounds, $R_5$ is selected from the group consisting of:

—C(O)—$R_{10}$,
—C(O)O—$R_9$, and
—C(O)—NH—$R_{10}$.

Alternatively, in these more preferred compounds, $R_5$ is selected from the group consisting of:

—S(O)$_2$—$R_9$,
S(O)$_2$—NH—$R_{10}$,
—C(O)—C(O)—$R_{10}$,
—$R_9$, and
—C(O)—C(O)—O$R_{10}$.

Most preferably, in these more preferred compounds, m is 1;

$T_1$ is O or S;

$R_{13}$ is H or a —$C_{1-4}$ straight or branched alkyl group optionally substituted with —Ar$_3$, —OH, —OR$_9$, or —CO$_2$H, wherein the $R_9$ is a —$C_{1-4}$ branched or straight alkyl group, wherein Ar$_3$ is morpholinyl or phenyl, wherein the phenyl is optionally substituted with $Q_1$;

$R_{21}$ is —H or —CH$_3$;

$R_{51}$ is a $C_{1-6}$ straight or branched alkyl group optionally substituted with Ar$_3$, wherein Ar$_3$ is phenyl, optionally substituted by —$Q_1$;

Ar$_2$ is (hh);

Y is O, and

Ar$_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

Ar$_4$ is phenyl, tetrazolyl, pyridinyl, oxazolyl, naphthyl, pyrimidinyl, or thienyl;

each $Q_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —NHR$_9$, and

wherein each $R_9$ and $R_{10}$ are independently a —$C_{1-6}$ straight or branched alkyl group optionally substituted with Ar$_3$ wherein Ar$_3$ is phenyl;

provided that when —Ar$_3$ is substituted with a $Q_1$ group which comprises one or more additional —Ar$_3$ groups, said additional —Ar$_3$ groups are not substituted with another —Ar$_3$.

Other more preferred compounds of embodiment C employ formula (II) wherein $R_1$ is (e10), $X_5$ is CH, $R_3$ is —C(O)—H, and the other substituents are as defined above.

More preferably, in these more preferred compounds, $R_5$ is selected from the group consisting of:

—C(O)—$R_{10}$,
—C(O)O—$R_9$, and
—C(O)—NH—$R_{10}$.

Alternatively, in these more preferred compounds, $R_5$ is selected from the group consisting of:

—S(O)$_2$—$R_9$,
—S(O)$_2$—NH—$R_{10}$,
—C(O)—C(O)—$R_{10}$,
—$R_9$, and
—C(O)—C(O)—O$R_{10}$.

Most preferably, in these more preferred compounds, m is 1;

$T_1$ is O or S;

$R_{13}$ is H or a —$C_{1-4}$ straight or branched alkyl group optionally substituted with —Ar$_3$, —OH, —OR$_9$, or —CO$_2$H, wherein the $R_9$ is a —$C_{1-4}$ branched or straight alkyl group, wherein Ar$_3$ is morpholinyl or phenyl, wherein the phenyl is optionally substituted with $Q_1$;

$R_{21}$ is —H or —CH$_3$;

$R_{51}$ is a $C_{1-6}$ straight or branched alkyl group optionally substituted with Ar$_3$, wherein Ar$_3$ is phenyl, optionally substituted by —$Q_1$;

Ar$_2$ is (hh);

Y is O, and

Ar$_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

Ar$_4$ is phenyl, tetrazolyl, pyridinyl, oxazolyl, naphthyl, pyrimidinyl, or thienyl;

each $Q_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R, is —C(O)—R$_{10}$, —OR$_9$, —NHR$_9$, and

wherein each $R_9$ and $R_{10}$ are independently a —$C_{1-6}$ straight or branched alkyl group optionally substituted with Ar$_3$ wherein Ar$_3$ is phenyl;

provided that when —Ar$_3$ is substituted with a $Q_1$ group which comprises one or more additional —Ar$_3$ groups, said additional —Ar$_3$ groups are not substituted with another —Ar$_3$.

Other more preferred compounds of embodiment C employ formula (II) wherein $R_1$ is (e10) and $X_5$ is CH, $R_3$ is —CO—CH$_2$—T$_1$—R$_{11}$, and $R_{11}$ is —Ar$_4$, and the other substituents are as defined above.

More preferably, in these more preferred compounds, $R_5$ is selected from the group consisting of:

—C(O)—$R_{10}$,
—C(O)O—$R_9$, and
—C(O)—NH—$R_{10}$.

Alternatively, in these more preferred compounds, $R_5$ is selected from the group consisting of:

—S(O)$_2$—$R_9$,
—S(O)$_2$—NH—$R_{10}$,
—C(O)—C(O)—$R_{10}$,
—$R_9$, and
—C(O)—C(O)—O$R_{10}$.

Most preferably, in these more preferred compounds, m is 1;

$T_1$ is O or S;

$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by —$Q_1$;

$Ar_2$ is (hh);

Y is O, and $Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

$Ar_4$ is phenyl, tetrazolyl, pyridinyl, oxazolyl, naphthyl, pyrimidinyl, or thienyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

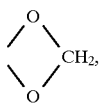

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other preferred compounds of embodiment C employ formula (II) wherein $R_1$ is (e10), $X_5$ is N, and the other substituents are as defined above.

More preferred compounds of embodiment C, employ formula (II) wherein $R_1$ is (e10), $X_5$ is N, $R_3$ is CO—$Ar_2$, and the other substituents are as defined above.

Other more preferred compounds of embodiment C, employ formula (II) wherein $R_1$ is (e10), $X_5$ is N, $R_3$ is —C(O)—$CH_2$—$T_1$—$R_{11}$, $R_{11}$ is —$(CH_2)_{1-3}$—$Ar_4$, and the other substituents are as defined above.

Other more preferred compounds of embodiment C, employ formula (II) wherein $R_1$ is (e10) and $X_5$ is N and:

$R_3$ is —C(O)—$CH_2$—$T_1$—$R_{11}$;

$T_1$ is O; and $R_{11}$ is —C(O)—$Ar_4$, and the other substituents are as defined above.

More preferably, in these more preferred compounds, $R_5$ is selected from the group consisting of:

—C(O)—$R_{10}$,

—C(O)O—$R_9$, and

—C(O)—NH—$R_{10}$.

Alternatively, in these more preferred compounds, $R_5$ is selected from the group consisting of:

—$S(O)_2$—$R_9$,

—$S(O)_2$—NH—$R_{10}$,

—C(O)—C(O)—$R_{10}$,

—$R_9$, and

—C(O)—C(O)—$R_{10}$.

Most preferably, in these more preferred compounds, $R_5$ is selected from the group consisting of:

—$S(O)_2$—$R_9$,

—$S(O)_2$—NH—$R_{10}$,

—C(O)—C(O)—$R_{10}$,

—$R_9$, and

—C(O)—C(O)—$OR_{10}$.

m is 1;

$T_1$ is O or S;

$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by —$Q_1$;

$Ar_2$ is (hh);

Y is O, and $Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

$Ar_4$ is phenyl, tetrazolyl, pyridinyl, oxazolyl, naphthyl, pyrimidinyl, or thienyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

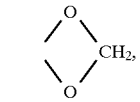

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment C, employ formula (II) wherein $R_1$ is (e10), $X_5$ is N, $R_3$ is —C(O)—H, and the other substituents are as defined above.

More preferably, in these more preferred compounds, $R_5$ is selected from the group consisting of:

—C(O)—$R_{10}$,

—C(O)O—$R_9$, and

—C(O)—NH—$R_{10}$.

Alternatively, in these more preferred compounds, $R_5$ is selected from the group consisting of:

—$S(O)_2$—$R_9$,

—$S(O)_2$—NH—$R_{10}$,

—C(O)—C(O)—$R_{10}$,

—$R_9$, and

—C(O)—C(O)—$OR_{10}$.

Most preferably, in these more preferred compounds, m is 1;

$T_1$ is O or S;

$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by —$Q_1$;

$Ar_2$ is (hh);

Y is O, and $Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

$Ar_4$ is phenyl, tetrazolyl, pyridinyl, oxazolyl, naphthyl, pyrimidinyl, or thienyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

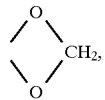

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment C, employ formula (II) wherein $R_1$ is (e10), $X_5$ is N, $R_3$ is —CO—$CH_2$—$T_1$—$R_{11}$, $R_{11}$ is —$Ar_4$, and the other substituents are as defined above.

More preferably, in these more preferred compounds, $R_5$ is selected from the group consisting of:

—C(O)—$R_{10}$,

—C(O)O—$R_9$, and

—C(O)—NH—$R_{10}$.

Alternatively, in these more preferred compounds, $R_5$ is selected from the group consisting of:

—$S(O)_2$—$R_9$,

—$S(O)_2$—NH—$R_{10}$,

—C(O)—C(O)—$R_{10}$,

—$R_9$, and

—C(O)—C(O)—$OR_{10}$.

Most preferably, in these more preferred compounds m is 1;

$T_1$ is O or S;

$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by —$Q_1$;

$Ar_2$ is (hh);

Y is O, and $Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

$Ar_4$ is phenyl, tetrazolyl, pyridinyl, oxazolyl, naphthyl, pyrimidinyl, or thienyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

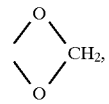

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$. Copy3

Preferred compounds of embodiment B include, but are not limited to:

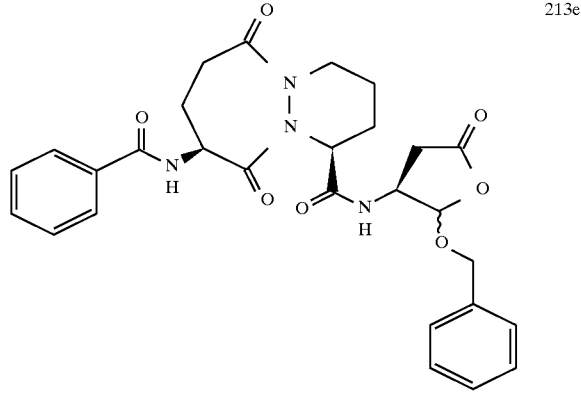

213e

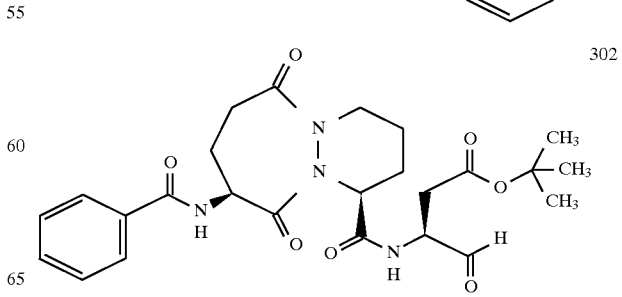

302

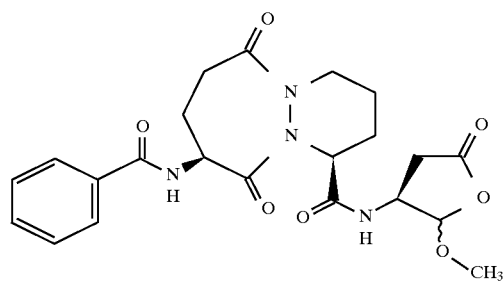
304a
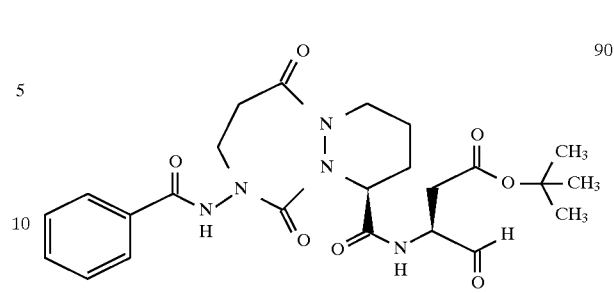
902
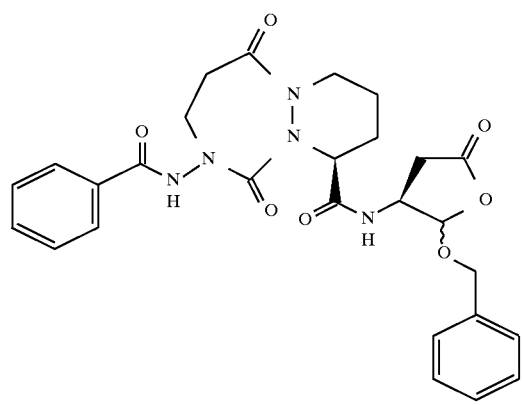
813e
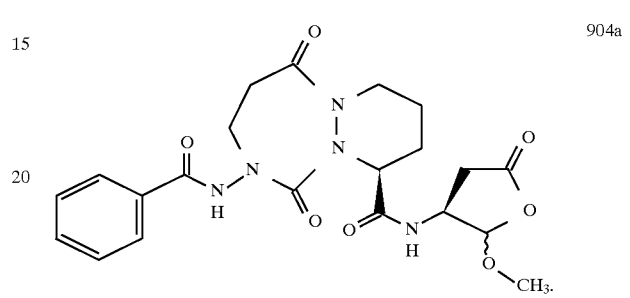
904a
Preferred compounds of embodiment C include, but are not limited to:
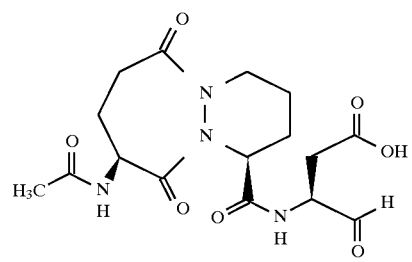
214c
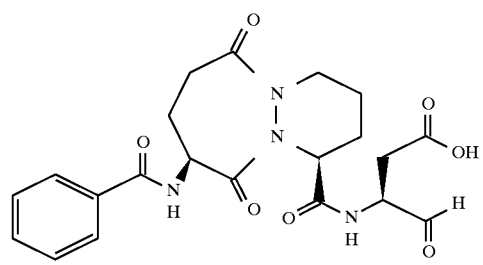
214e
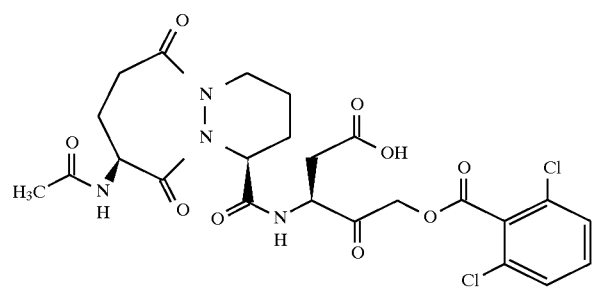
217c -continued
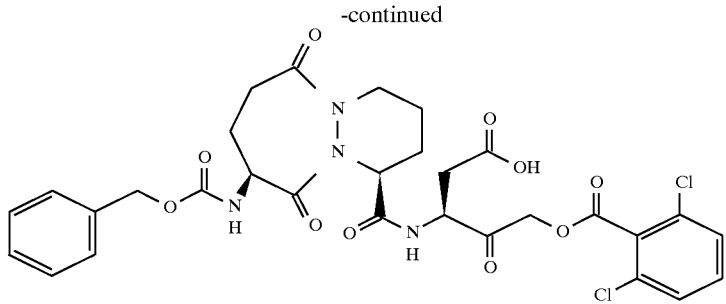
217d
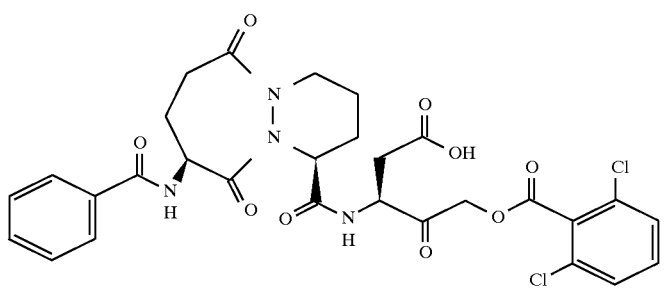
217e
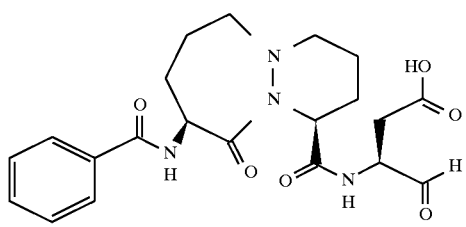
246
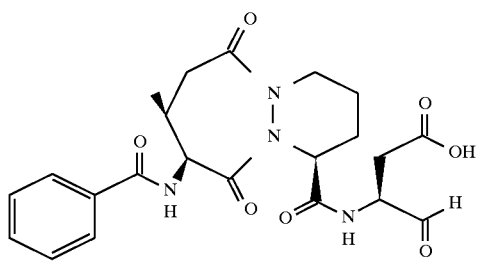
257
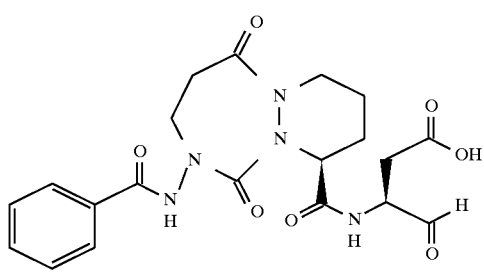
265
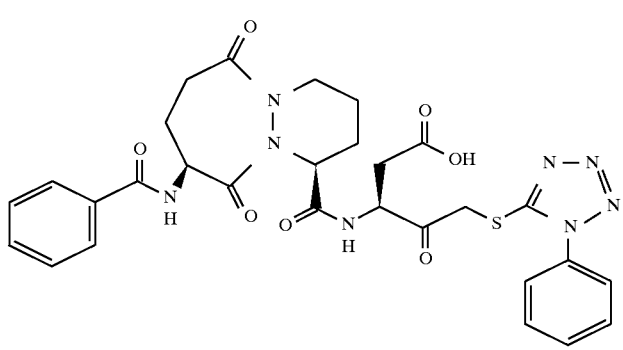
280

281
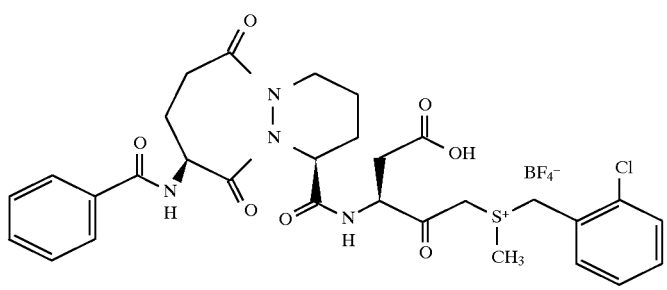
282
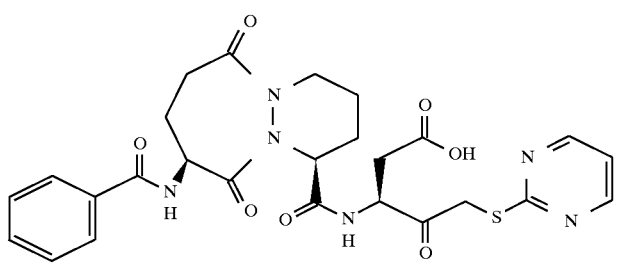
283
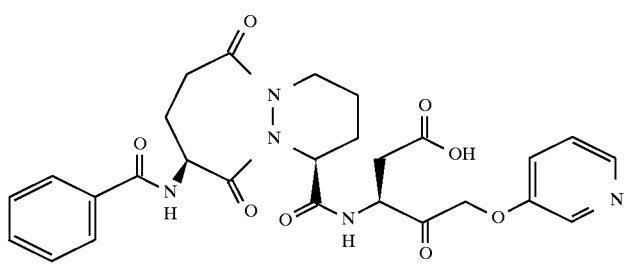
284
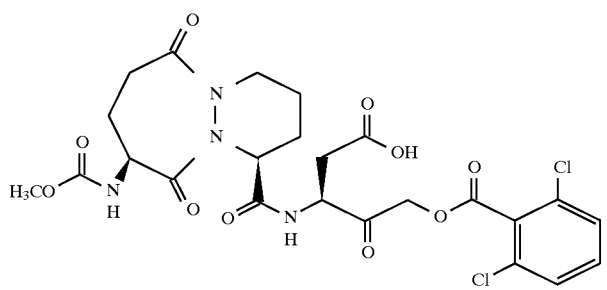
285
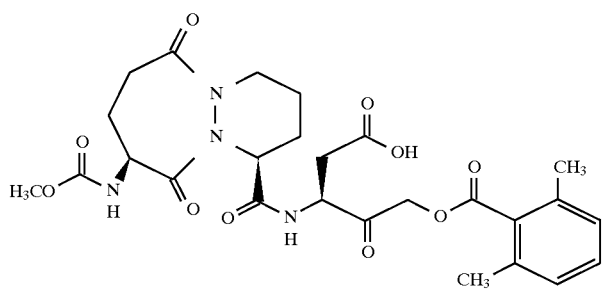

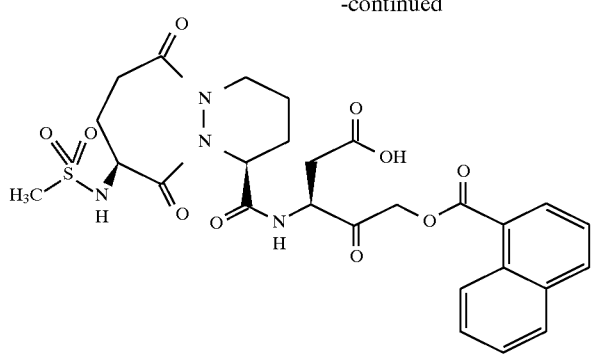
286
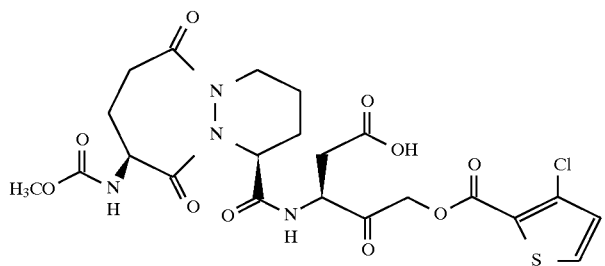
287
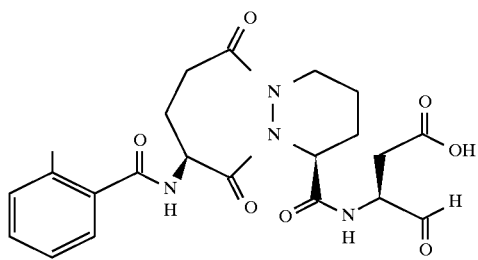
404
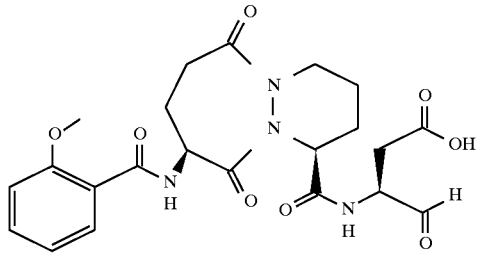
405
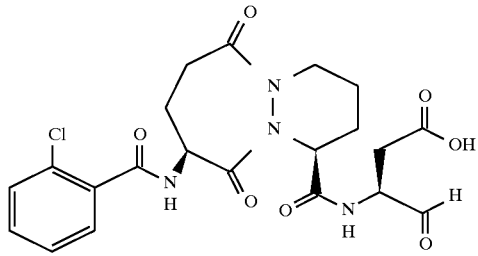
406
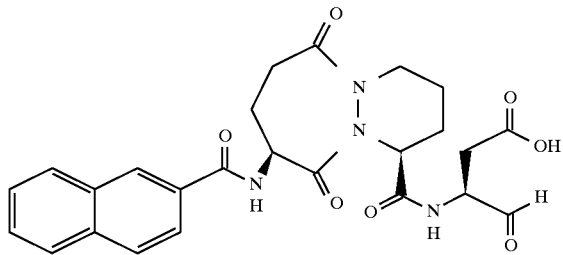
407

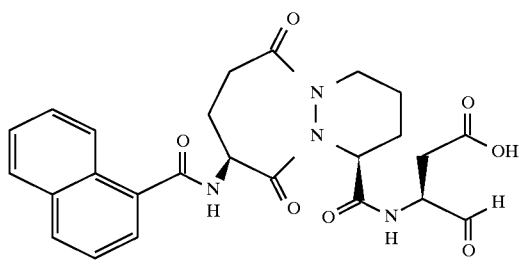
408
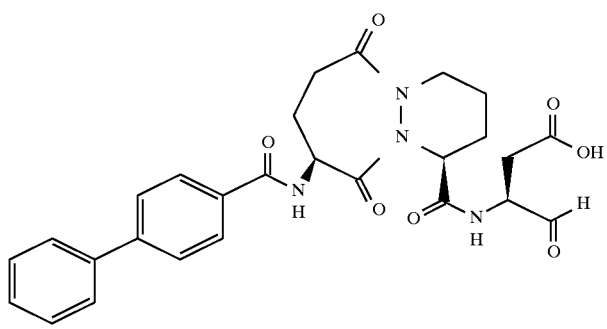
409
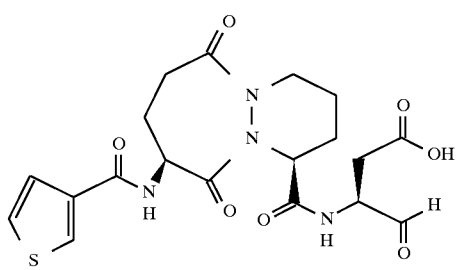
410
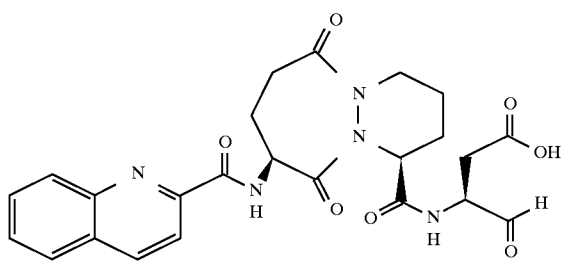
411
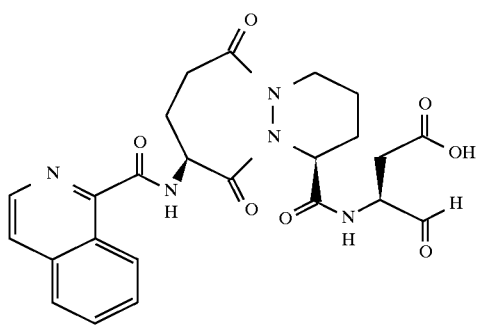
412

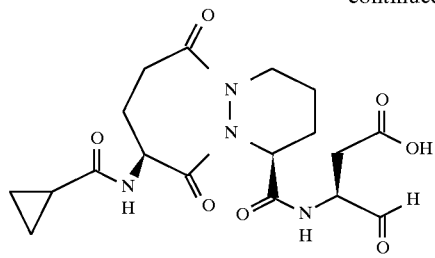
413
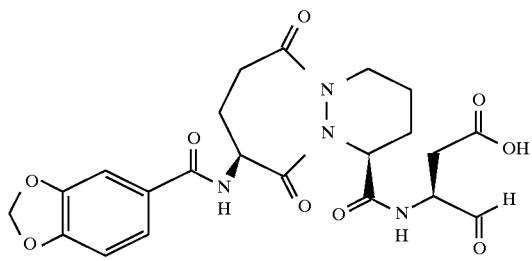
415
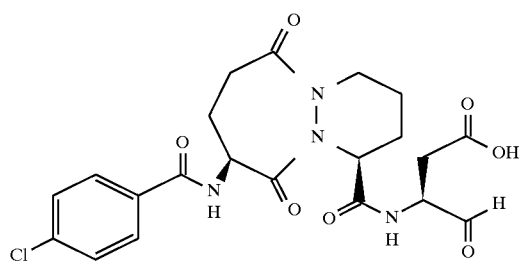
416
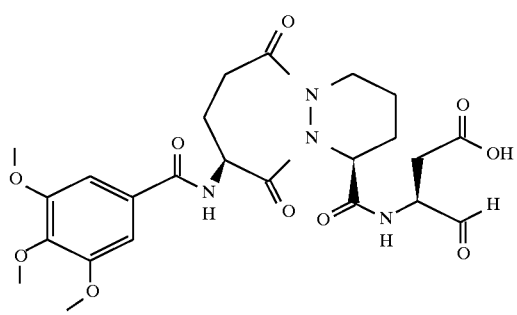
417
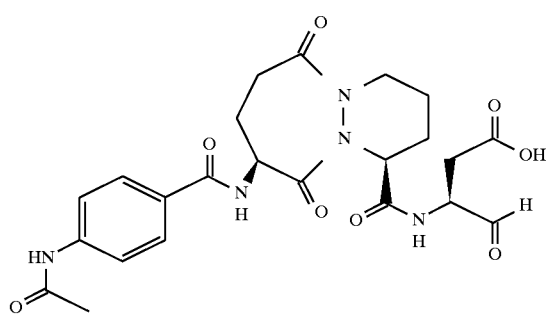
418
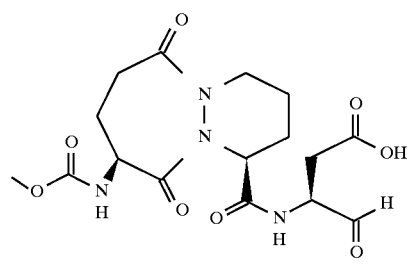
419

420
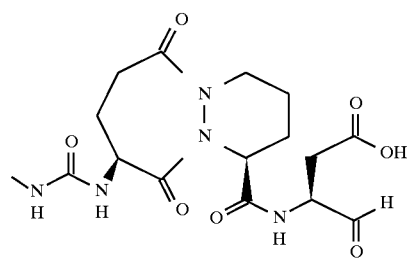
422
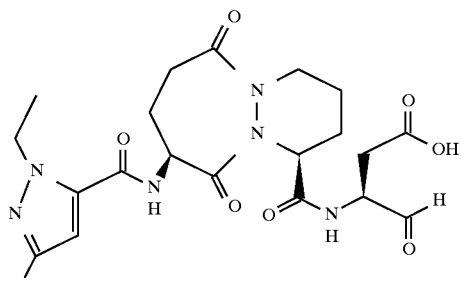
423
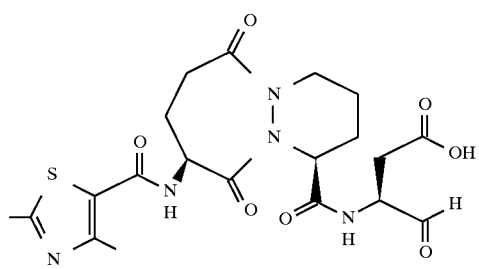
424
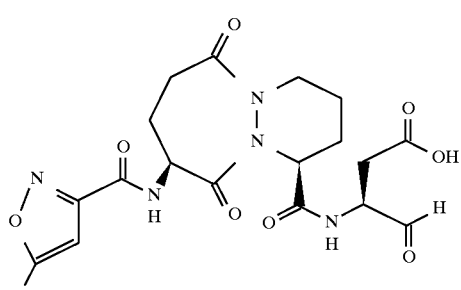
425
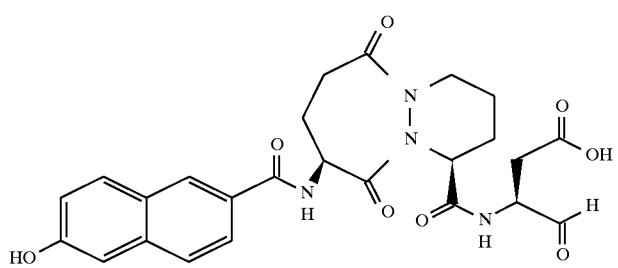
426
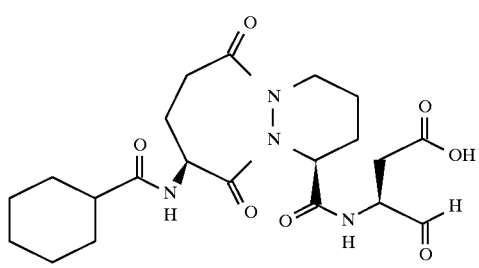

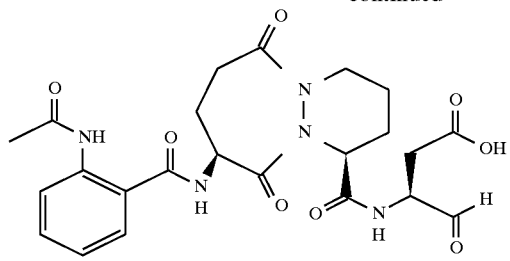
430
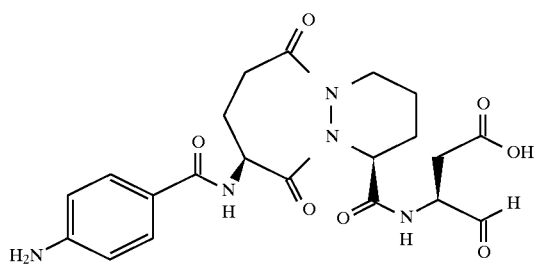
431
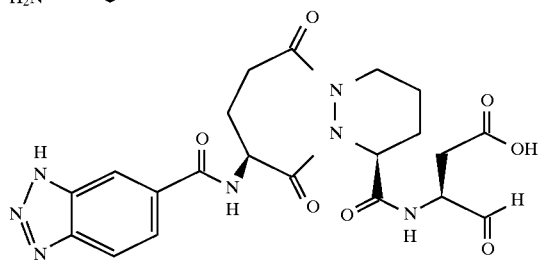
432
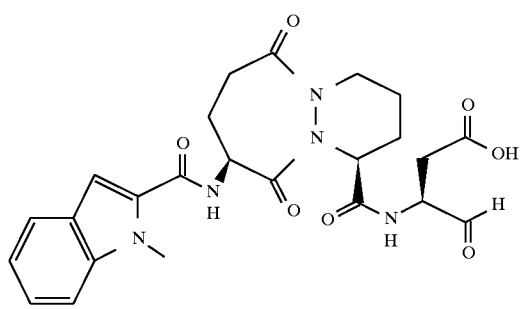
433
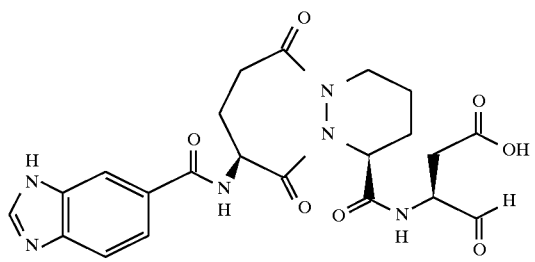
434
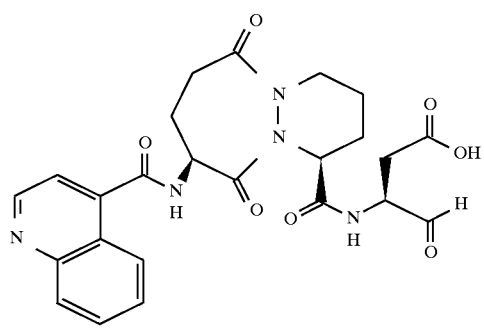
435

436
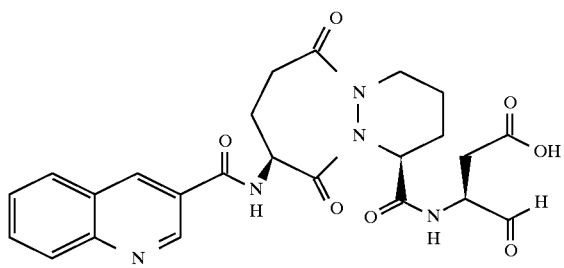
437
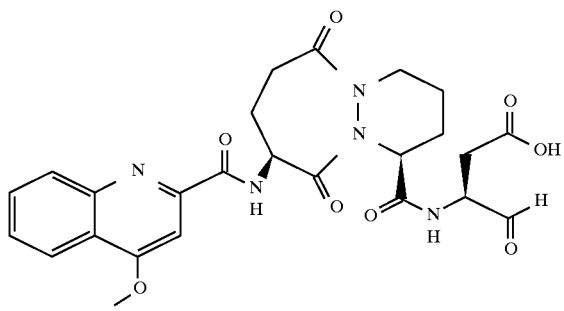
438
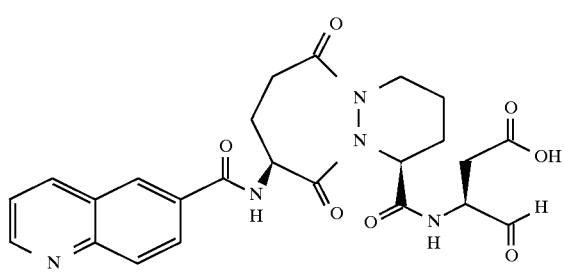
439
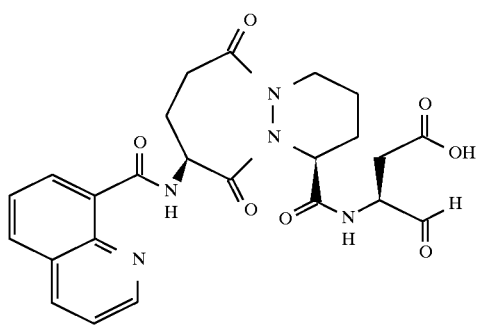
440
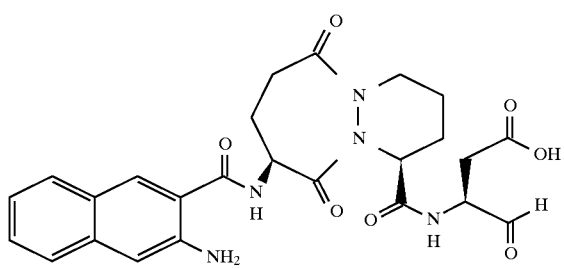

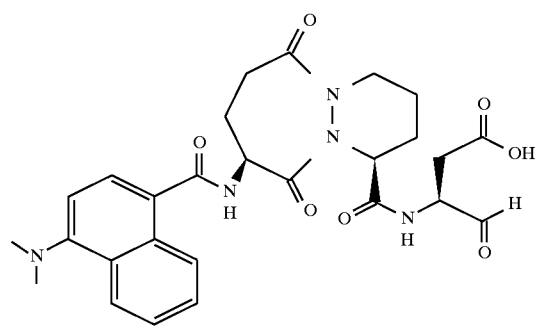
441
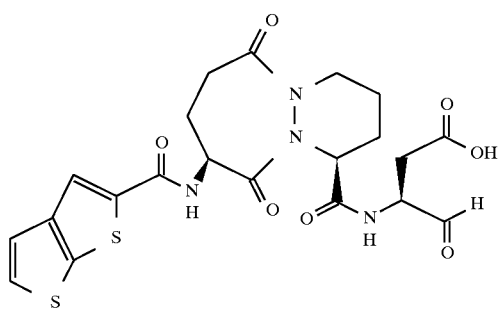
442
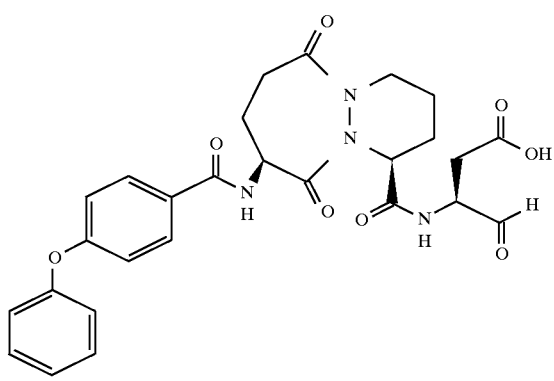
443
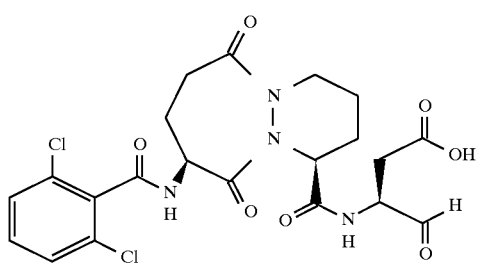
444
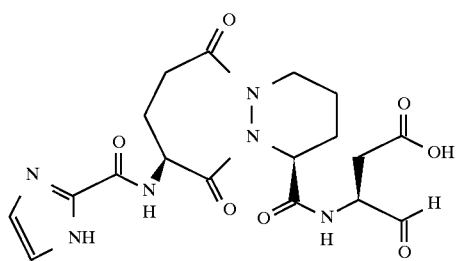
445

446
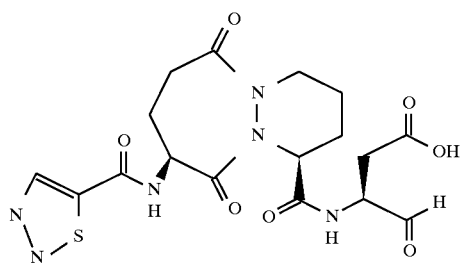
447
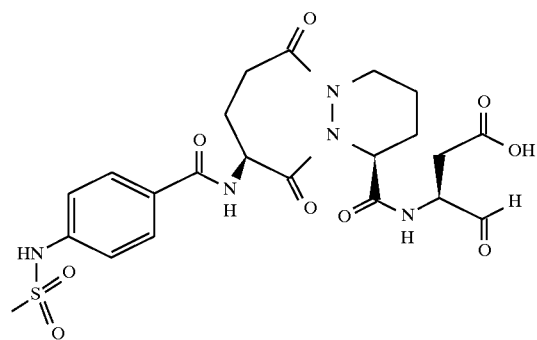
448
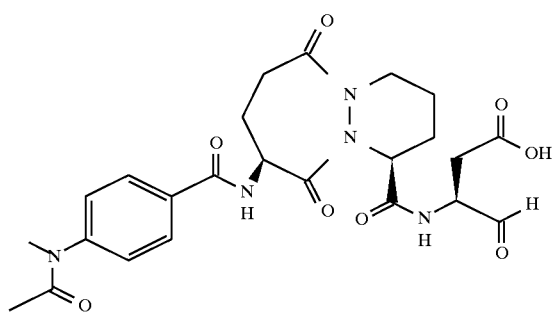
449
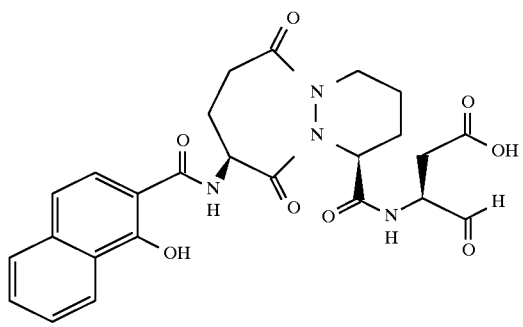
450
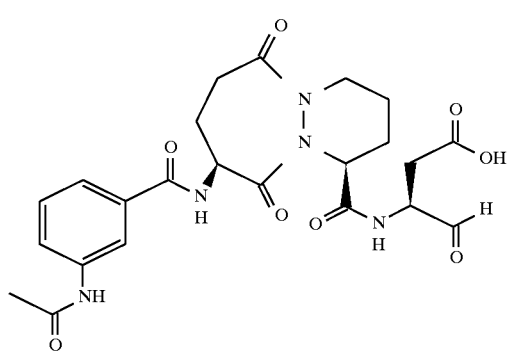

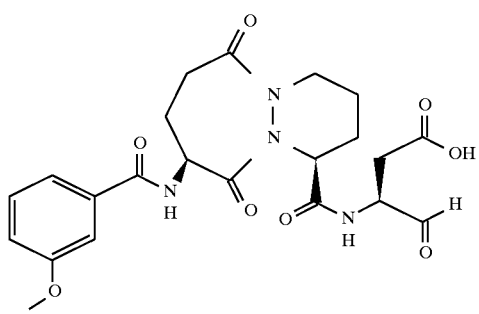
451
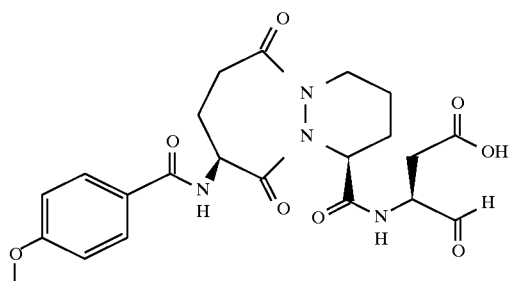
452
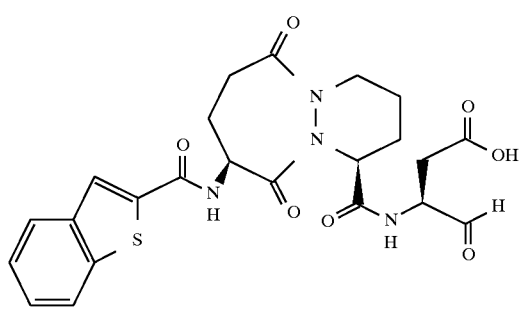
453
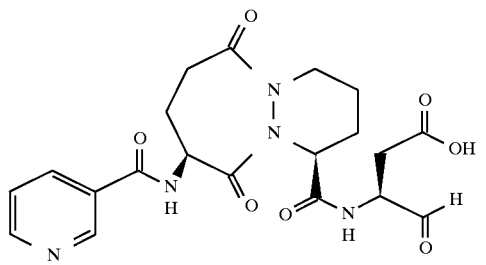
454
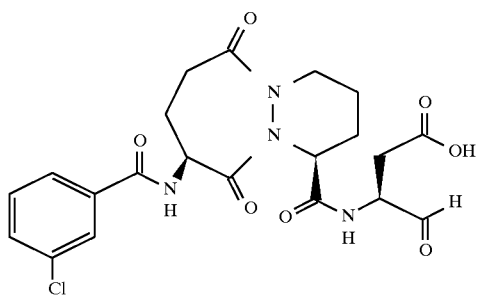
455

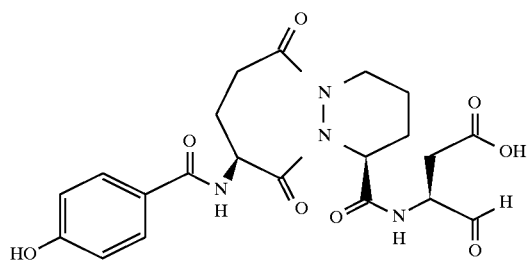
456
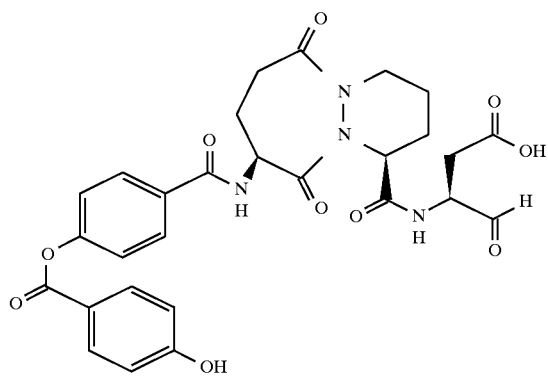
457
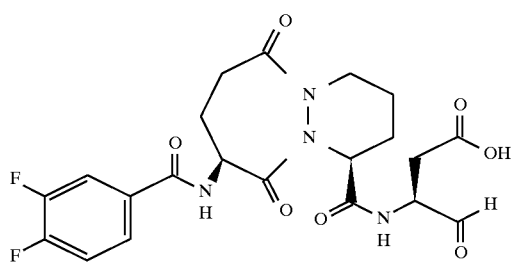
458
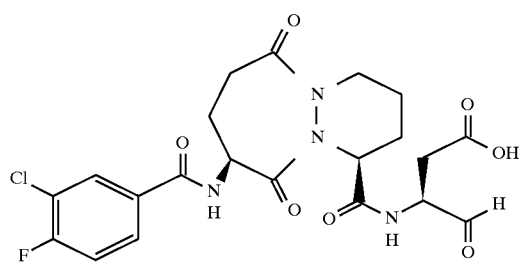
459
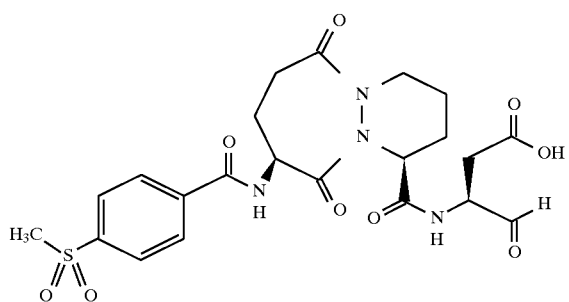
460

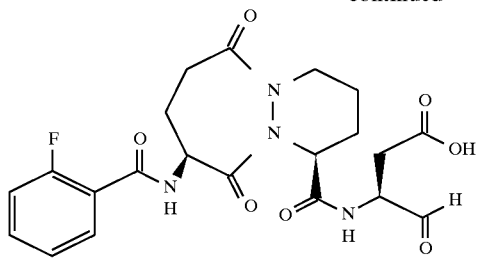
461
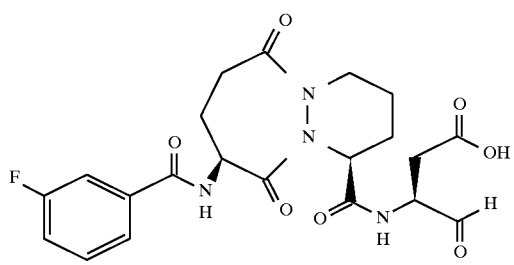
462
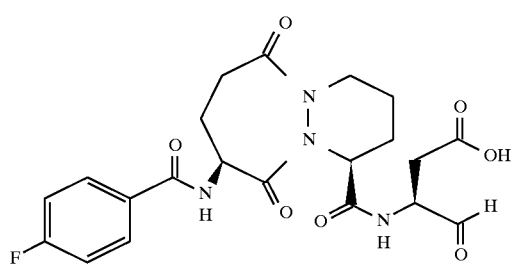
463
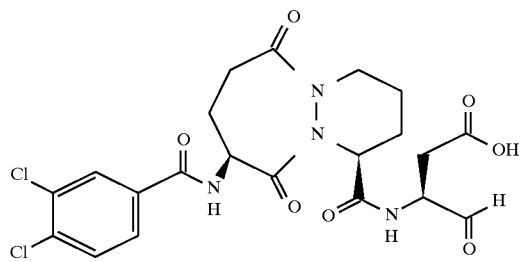
464
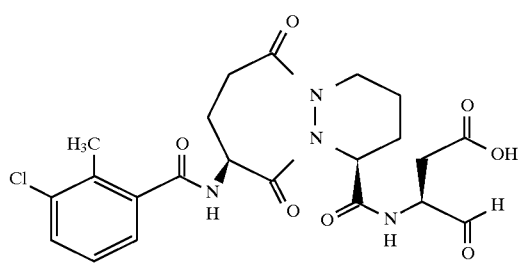
465
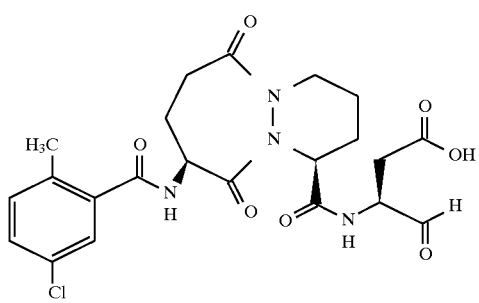
466

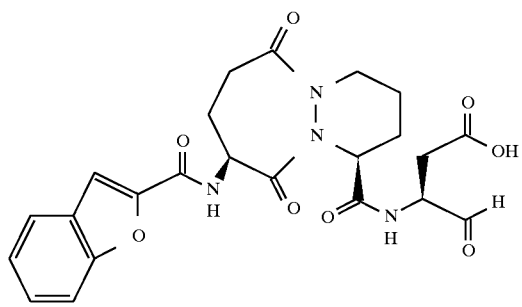
467
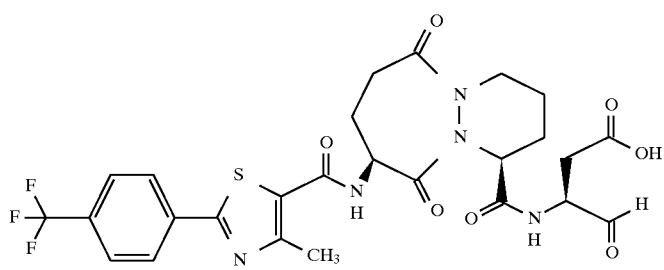
468
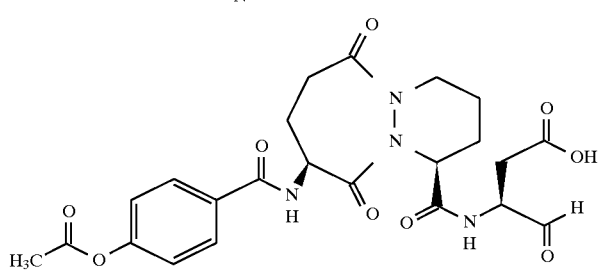
469
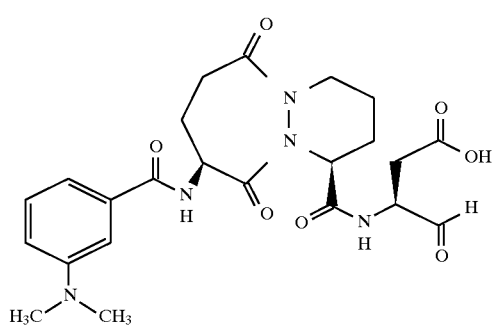
470
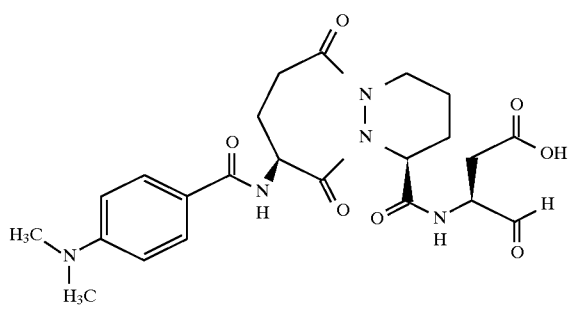
471

472
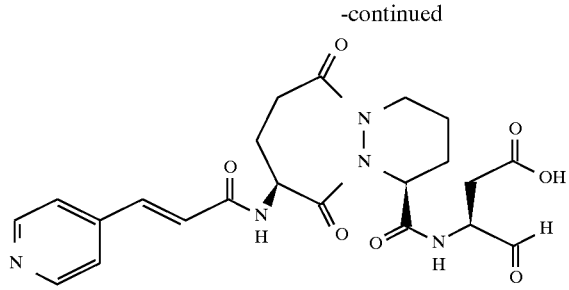
473
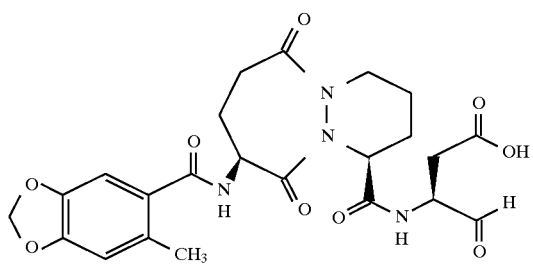
474
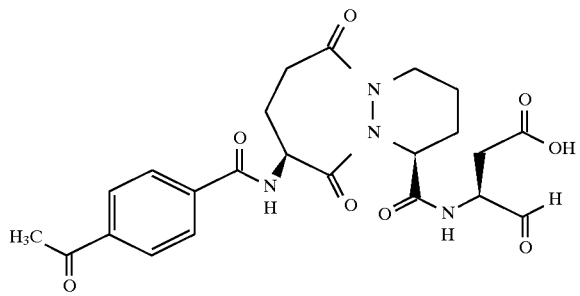
475
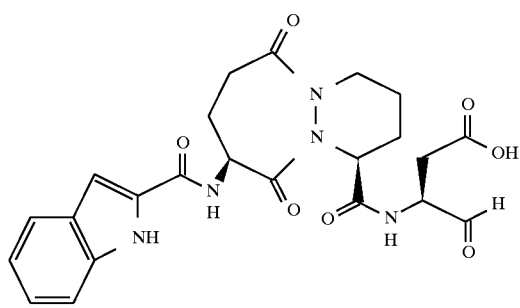
476
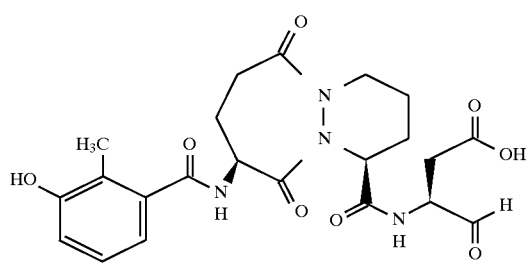

477
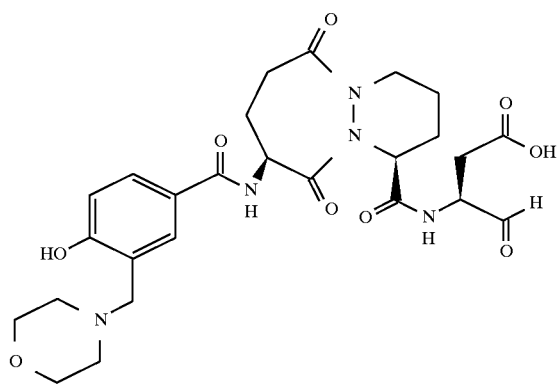
478
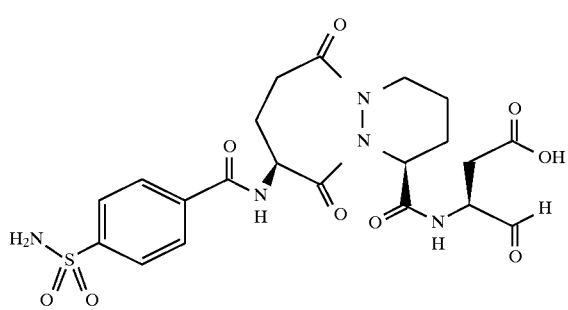
479
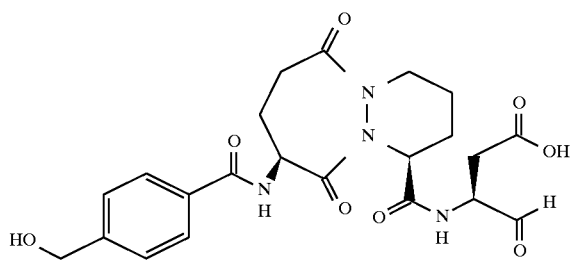
480
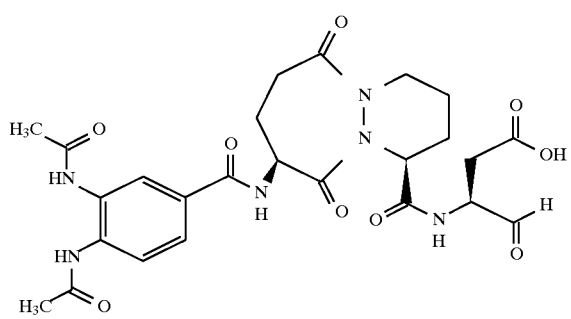
481
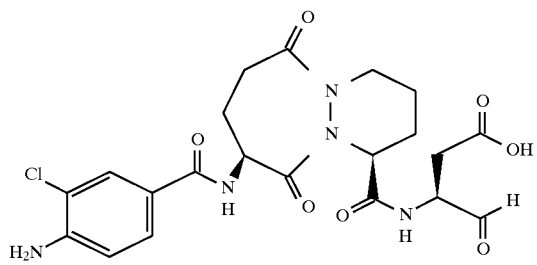

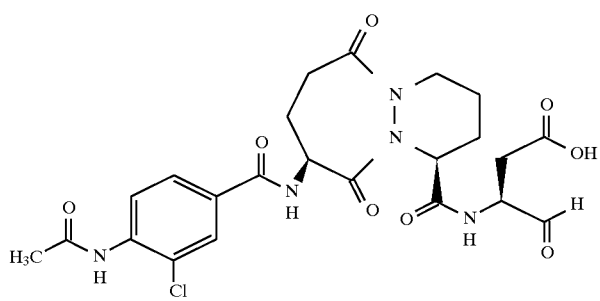
481s
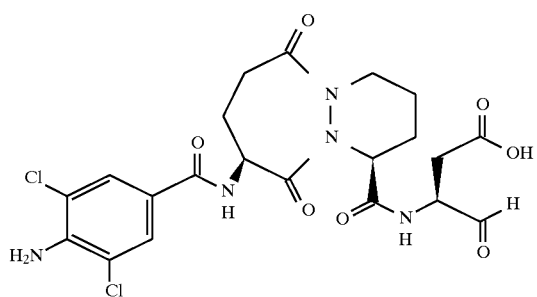
482
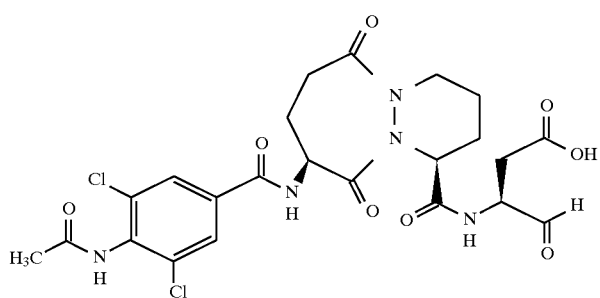
482s
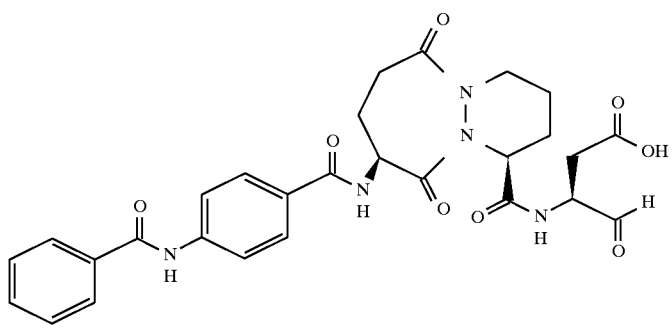
483
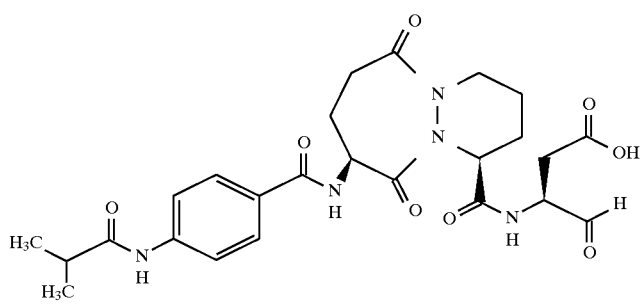
484

485
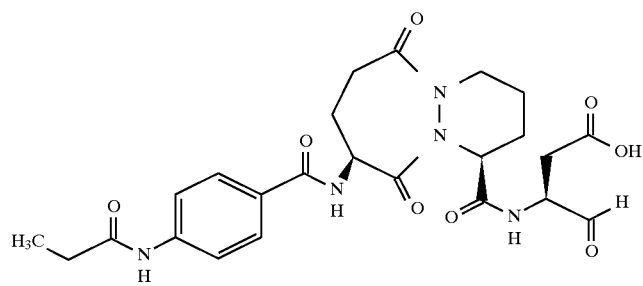
486
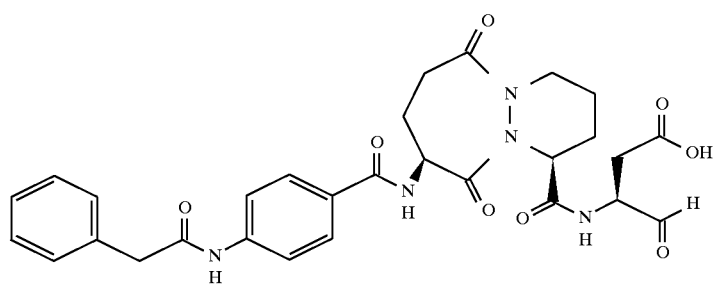
487
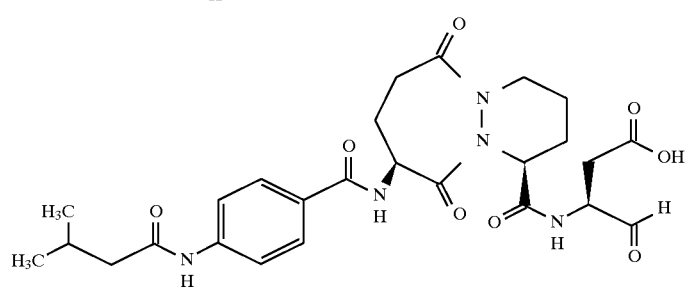
488
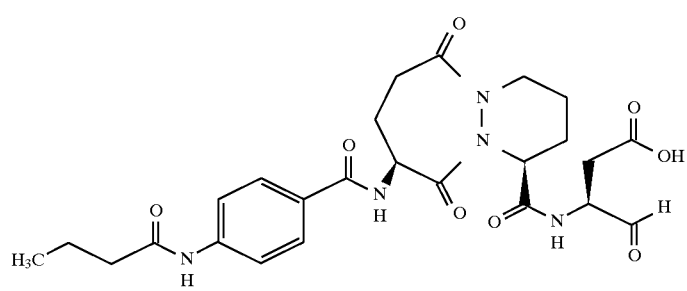
489
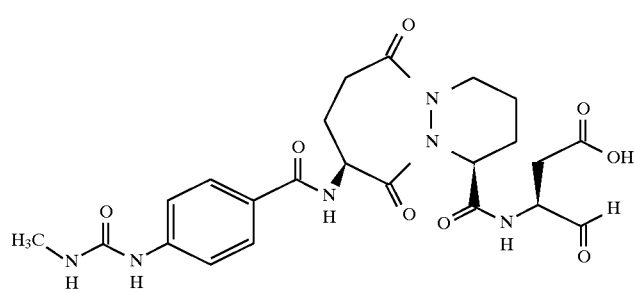

490
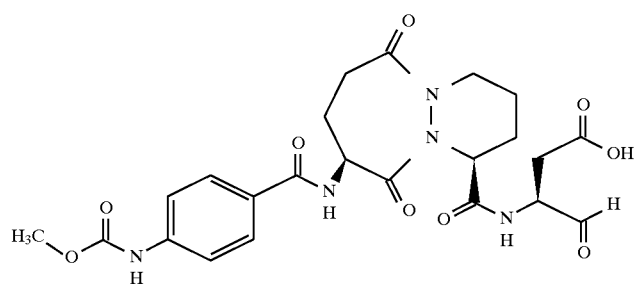
491
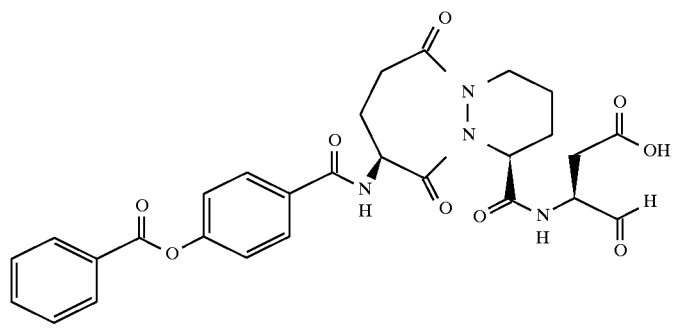
493
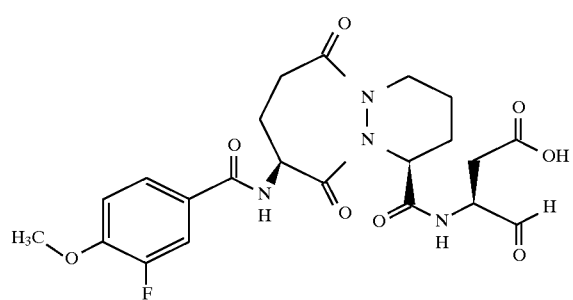
494
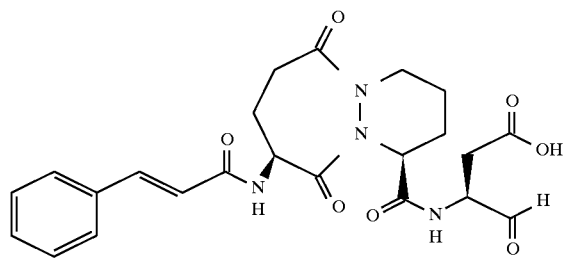
495
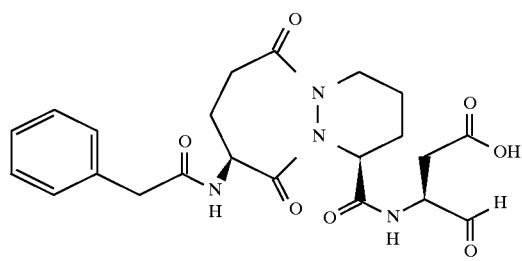

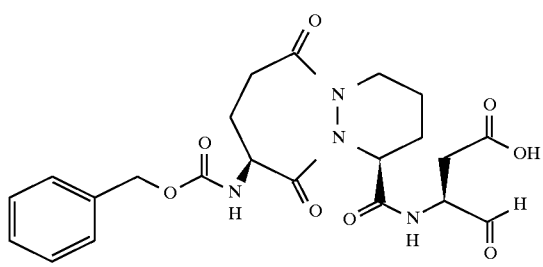
496
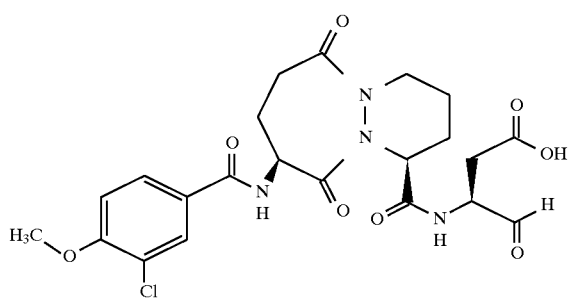
497
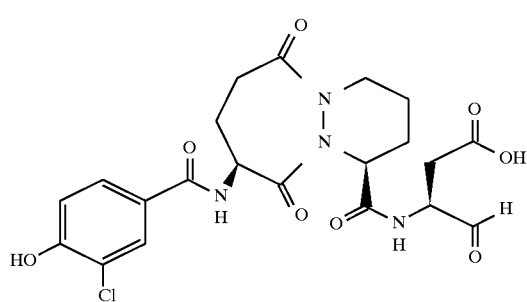
498
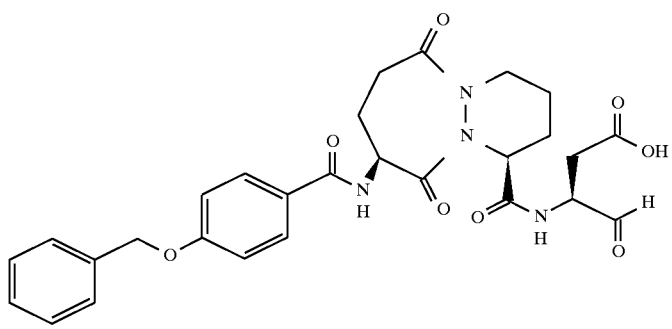
499
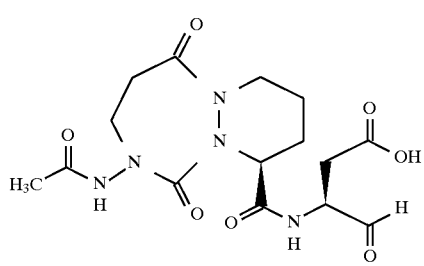
814c

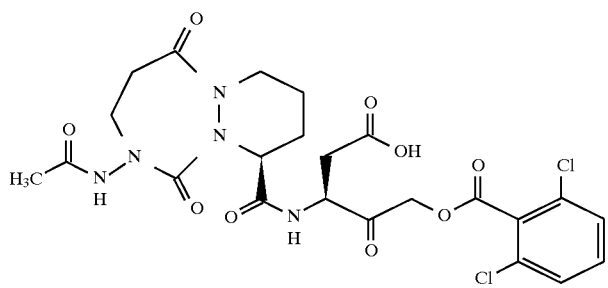
817c
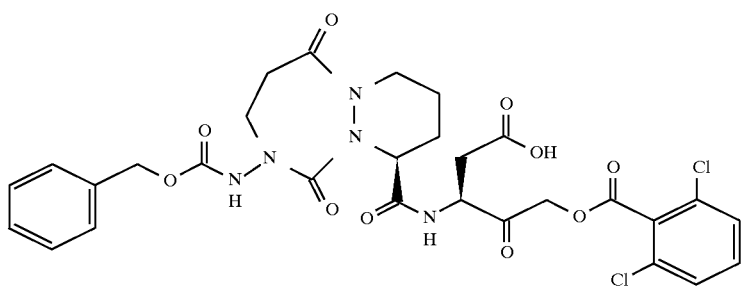
817d
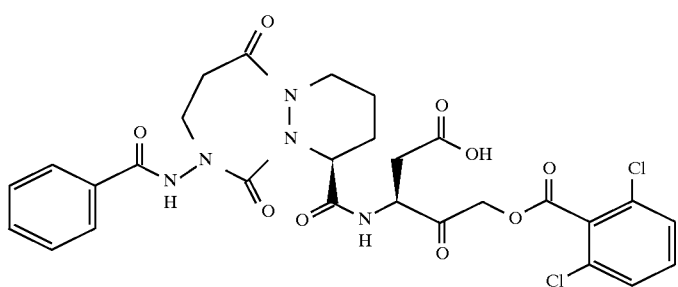
817e
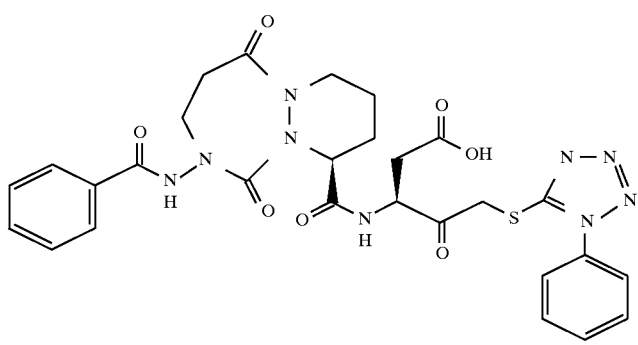
880
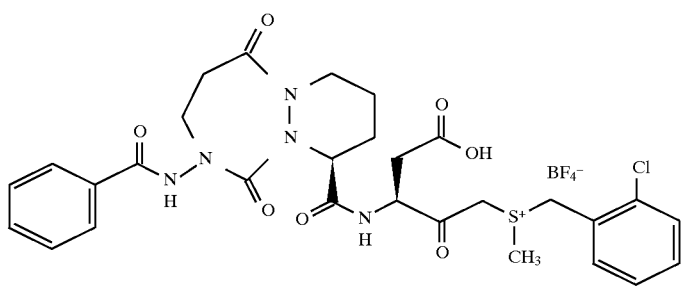
881

882
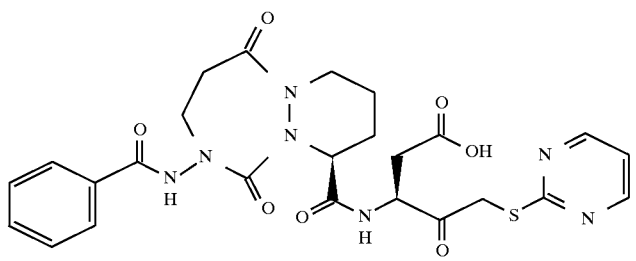
883
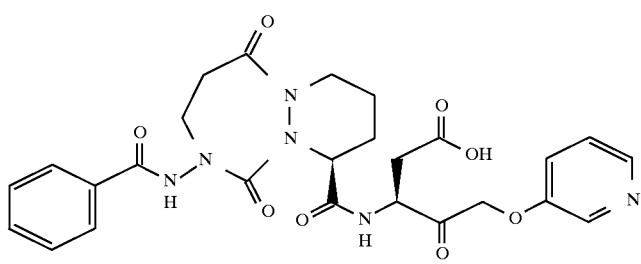
884
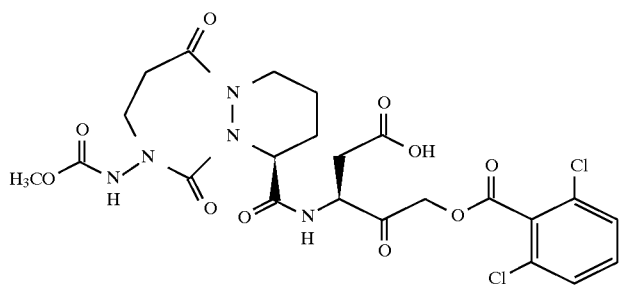
885
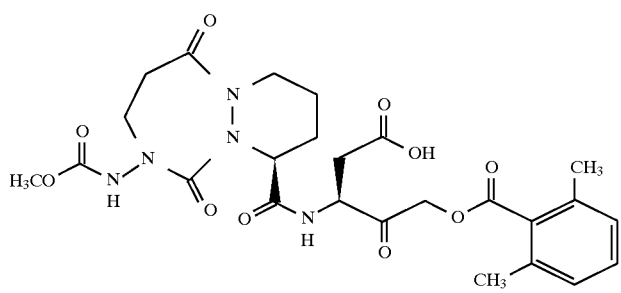
886
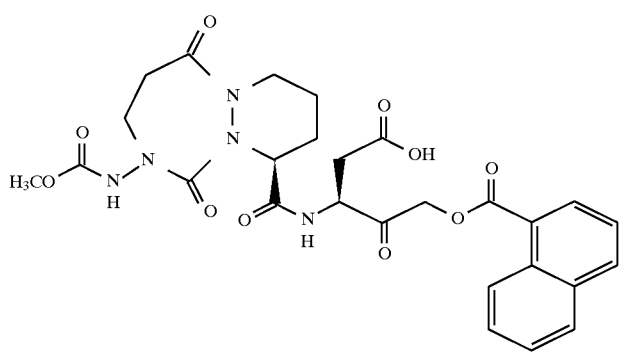

-continued
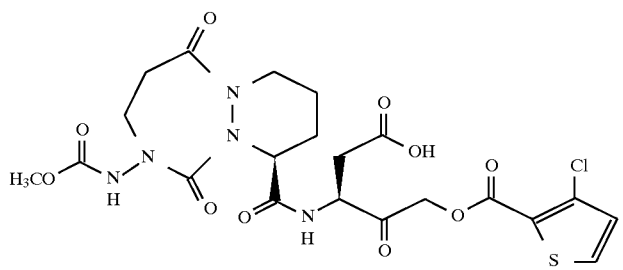
887
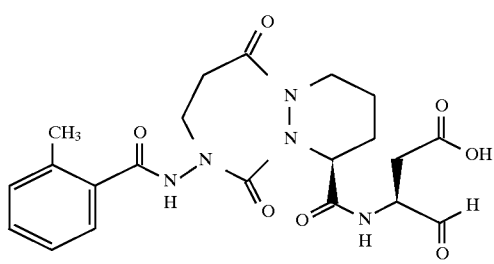
1004
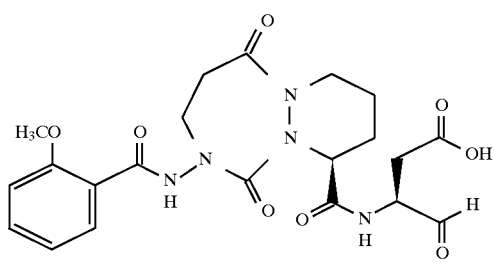
1005
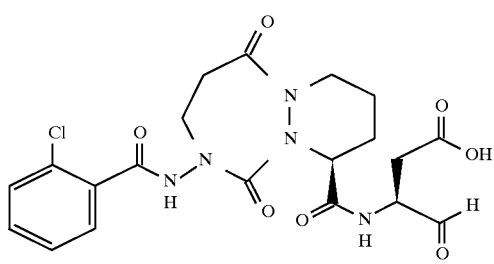
1006
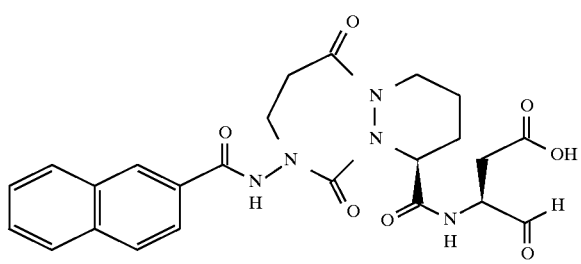
1007
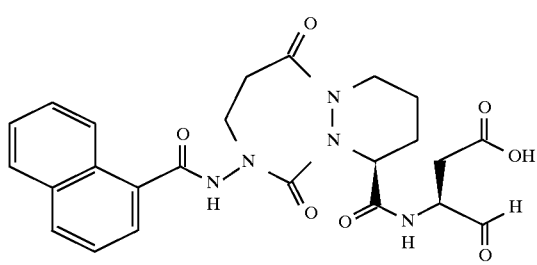
1008

103 -continued
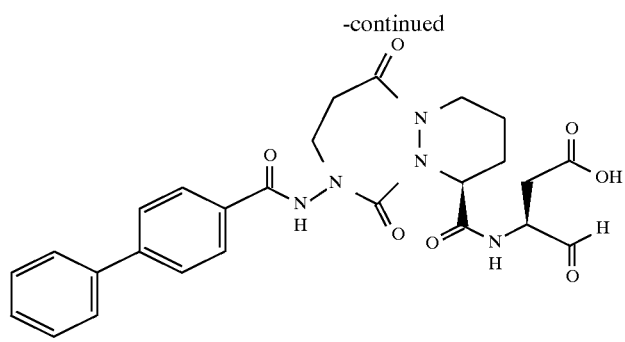
1009
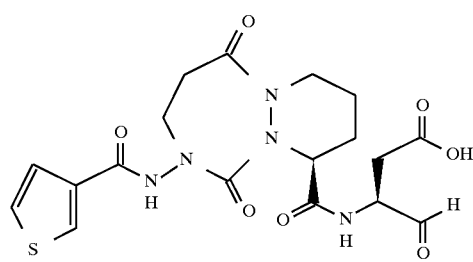
1010
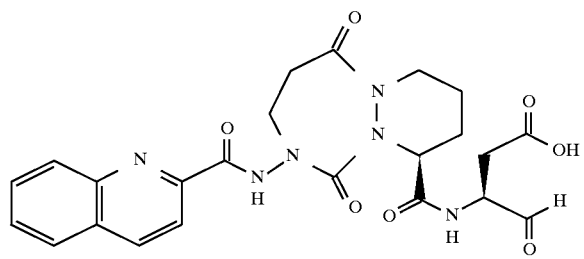
1011
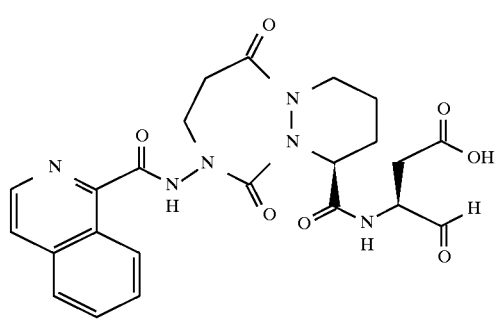
1012
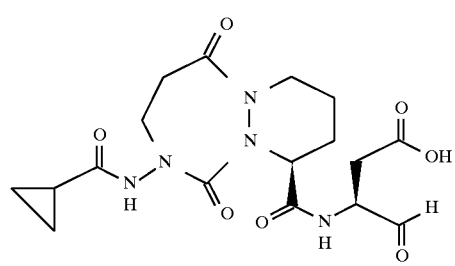
1013
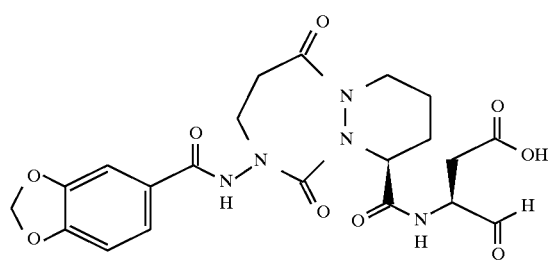
1015
104

1016
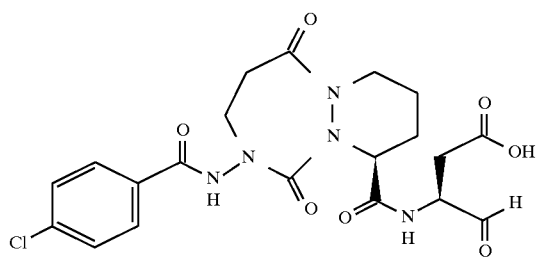
1017
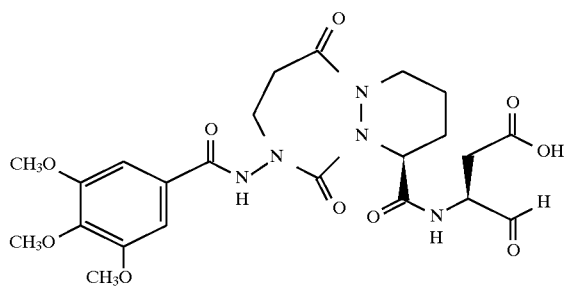
1018
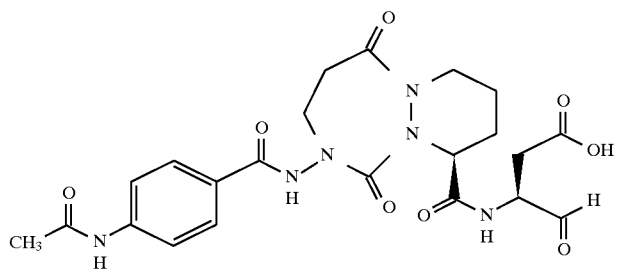
1019
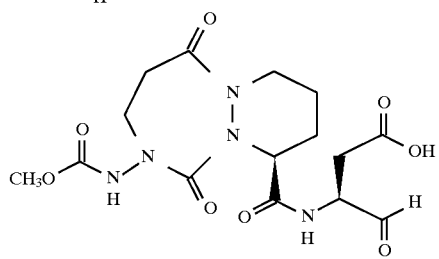
1020
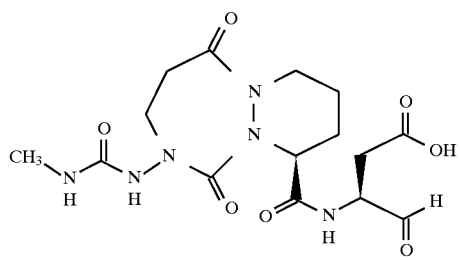
1022
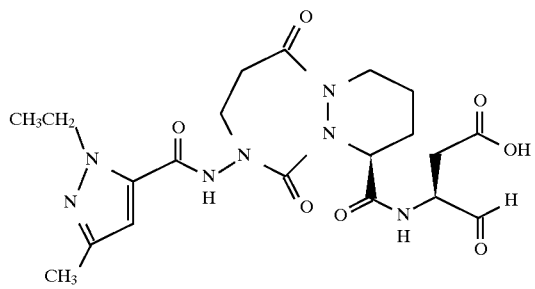

-continued
1023
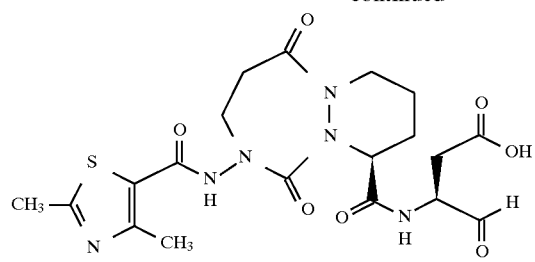
1024
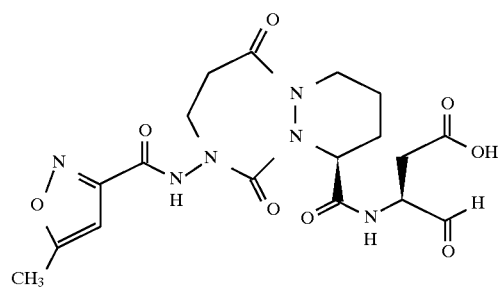
1025
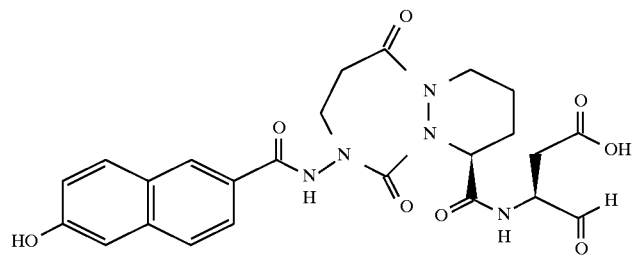
1026
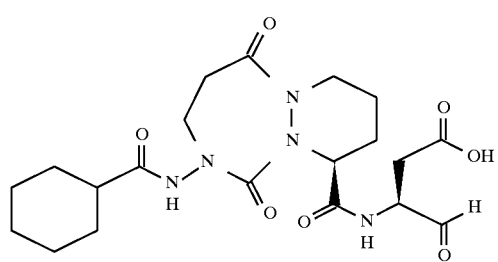
1030
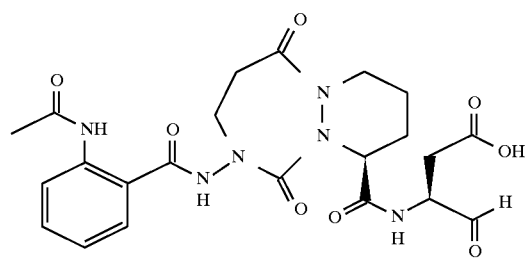
1031
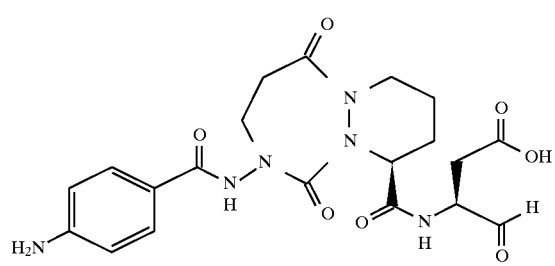

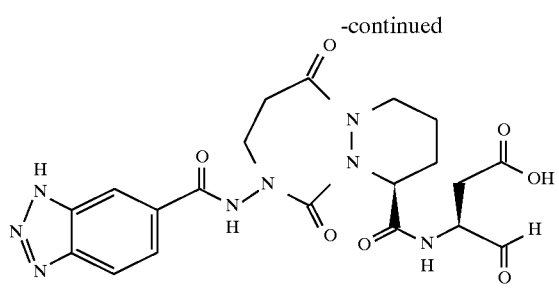
1032
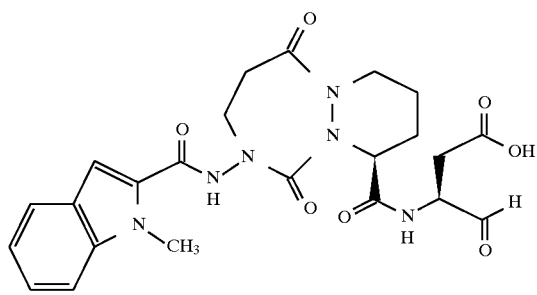
1033
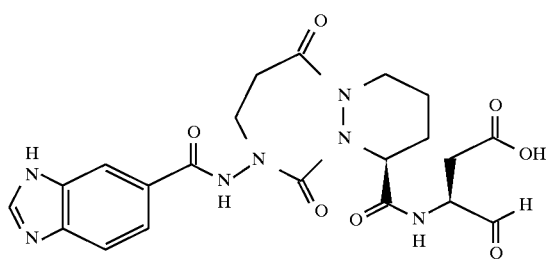
1034
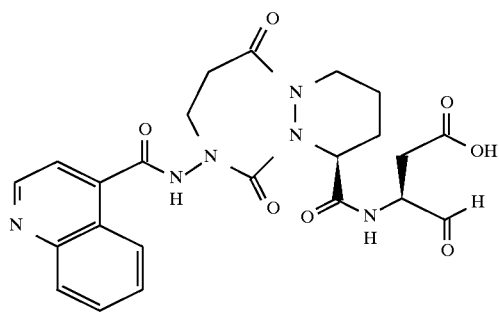
1035
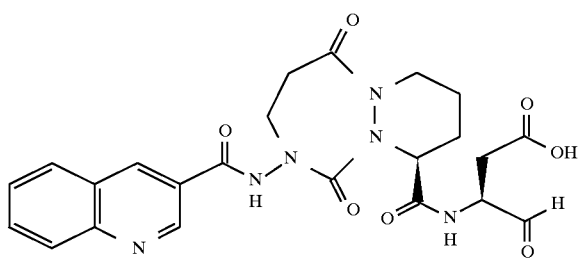
1036
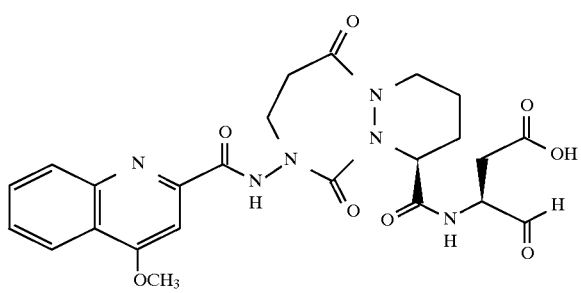
1037

1038
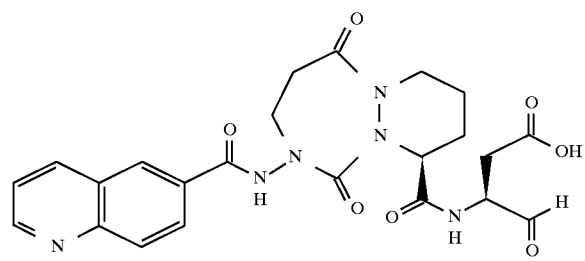
1039
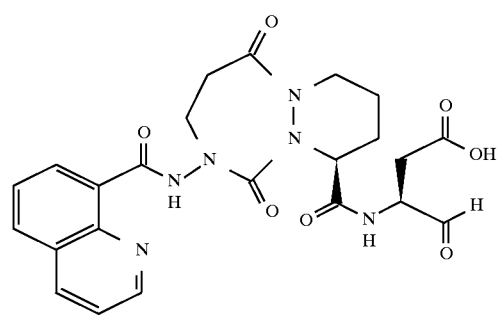
1040
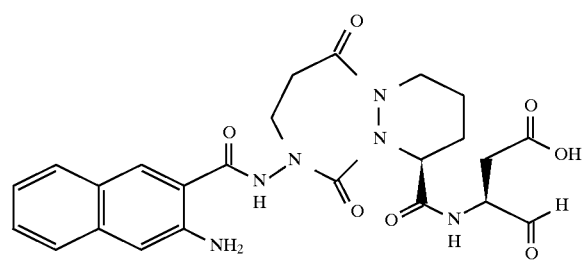
1041
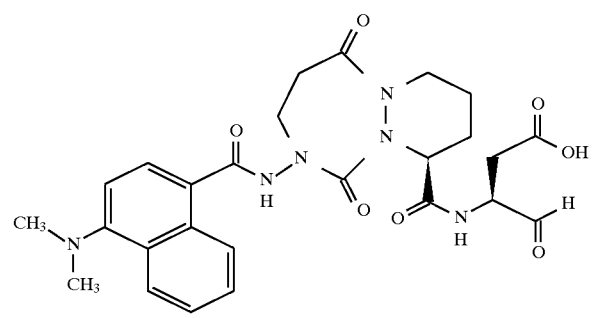
1042
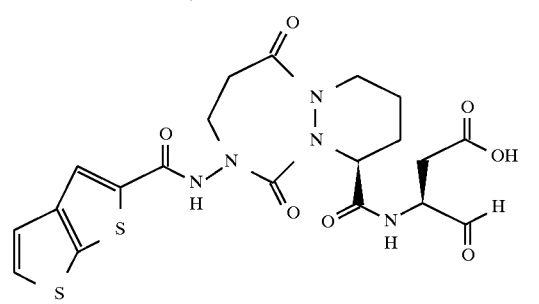

-continued
| | |
|---|---|
| 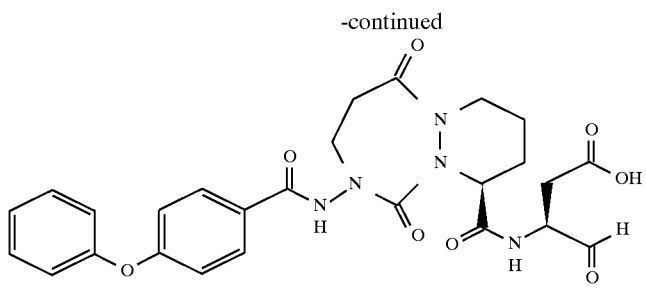 | 1043 |
| 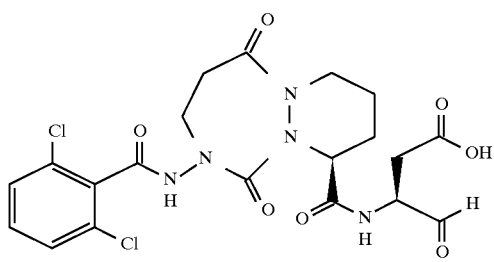 | 1044 |
| 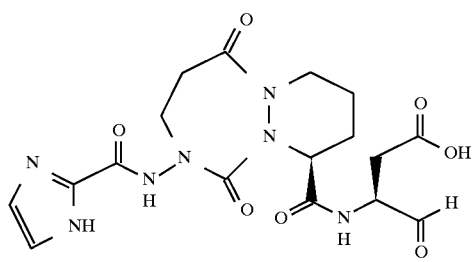 | 1045 |
| 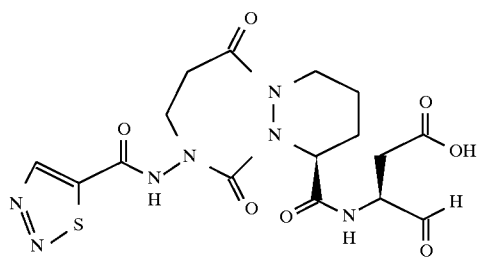 | 1046 |
| 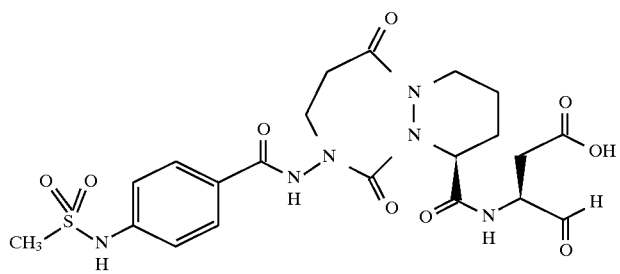 | 1047 |
| 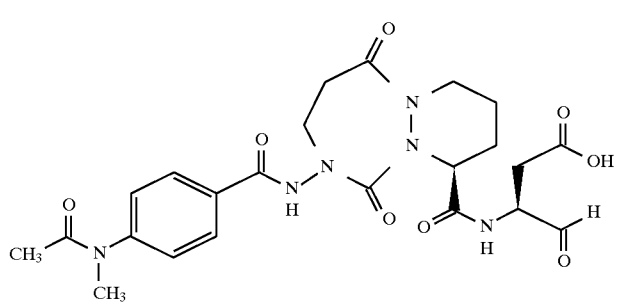 | 1048 |

-continued
| | |
|---|---|
| 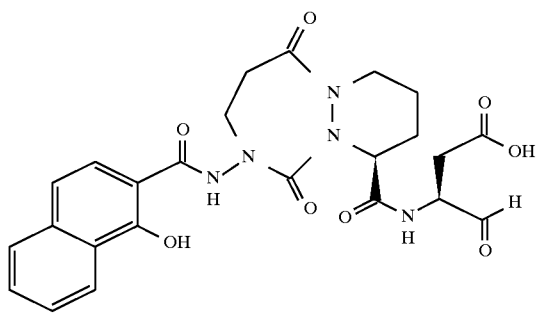 | 1049 |
| 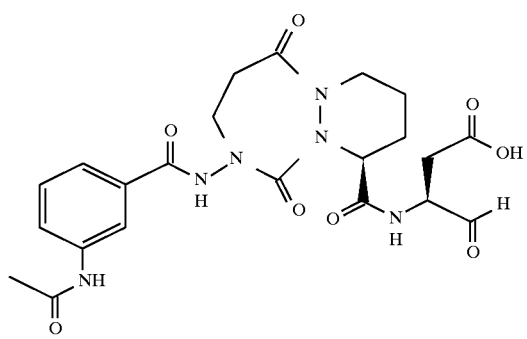 | 1050 |
| 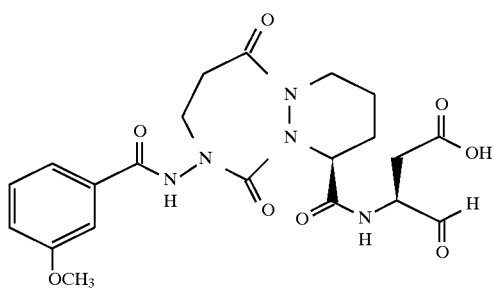 | 1051 |
| 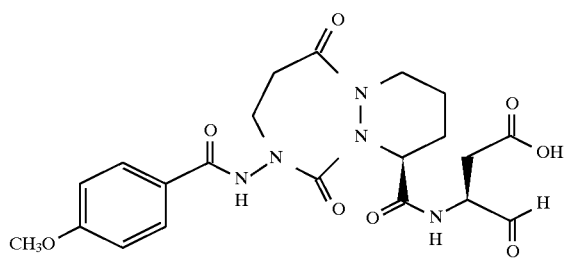 | 1052 |
| 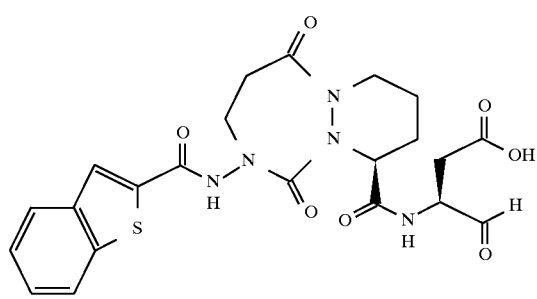 | 1053 |

1054
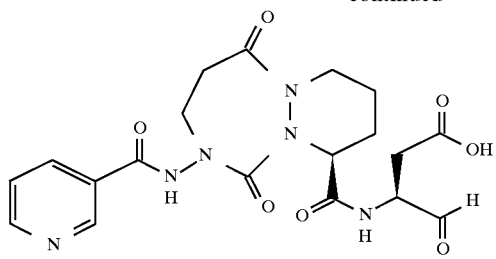
1055
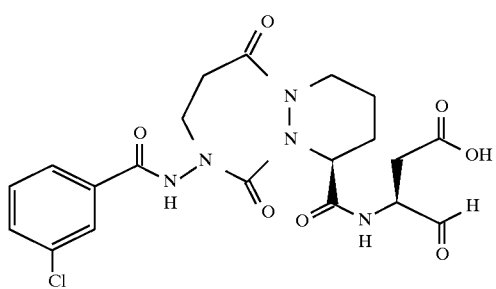
1056
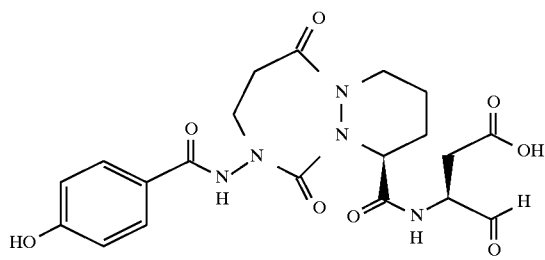
1057
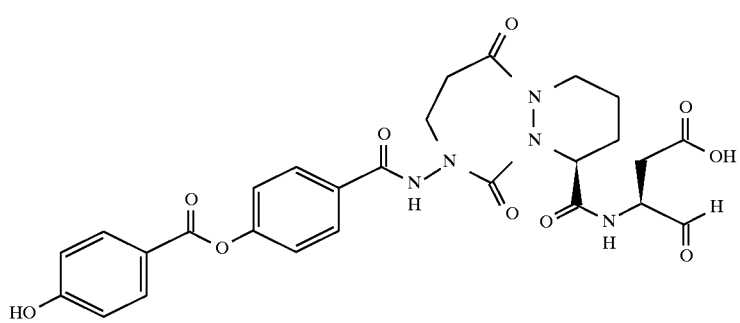
1058
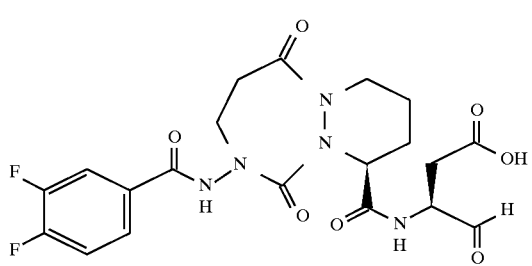
1059
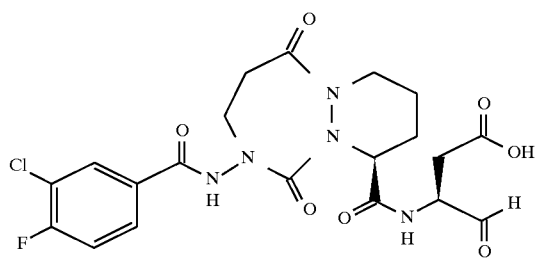

-continued
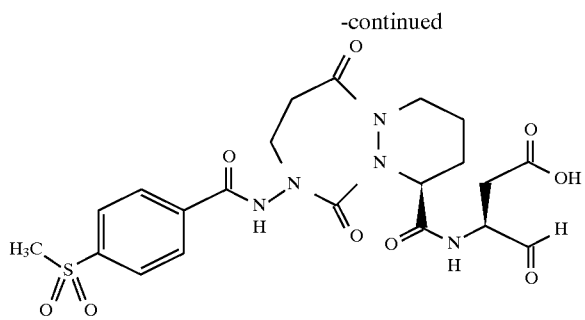
1060
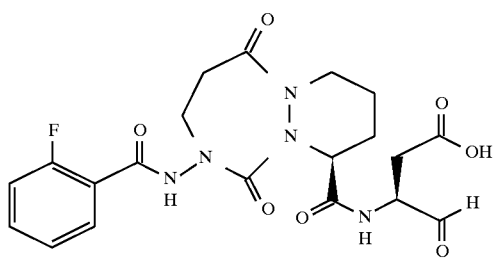
1061
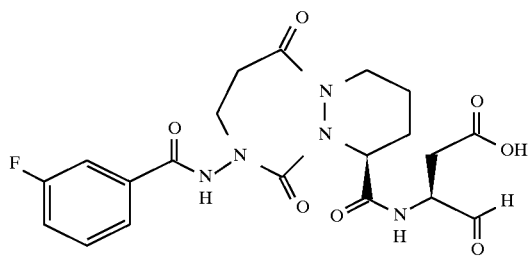
1062
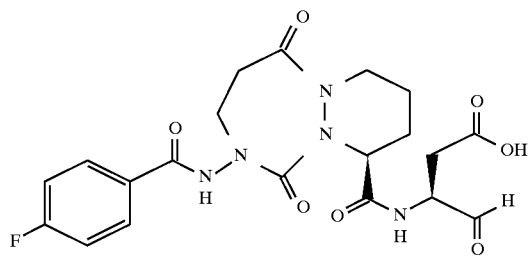
1063
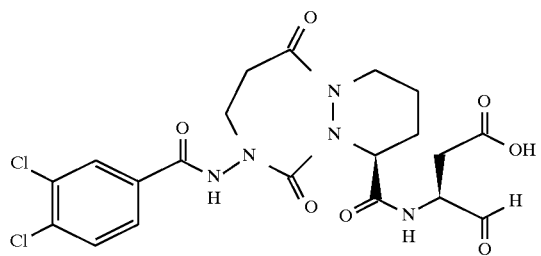
1064
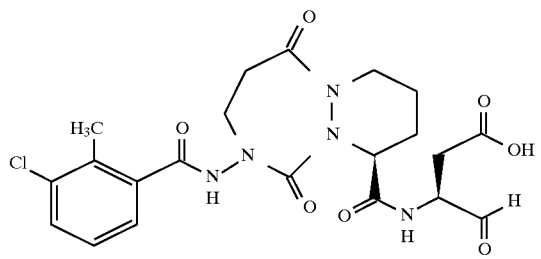
1065

1066
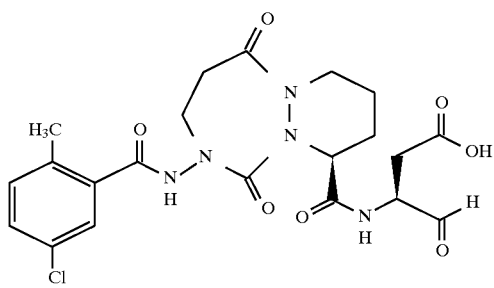
1067
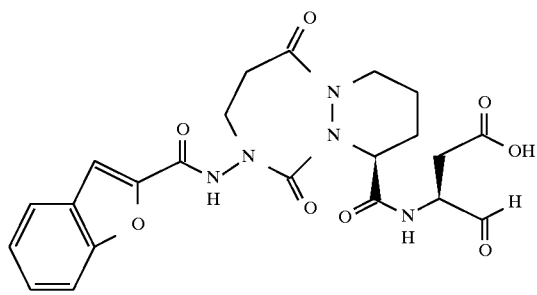
1068
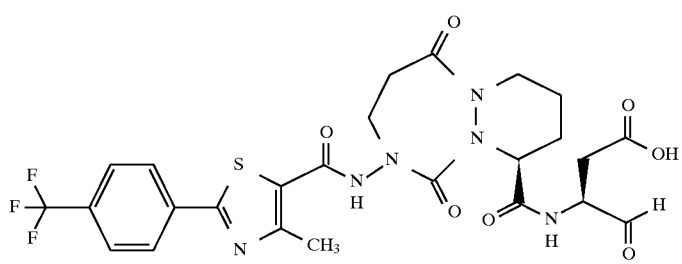
1069
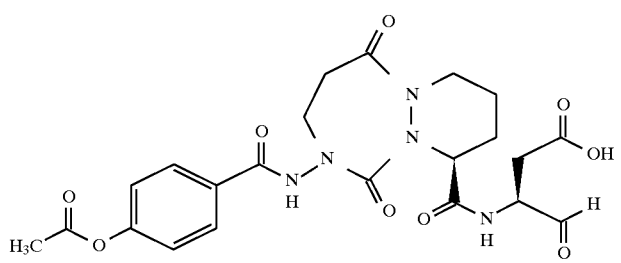
1070
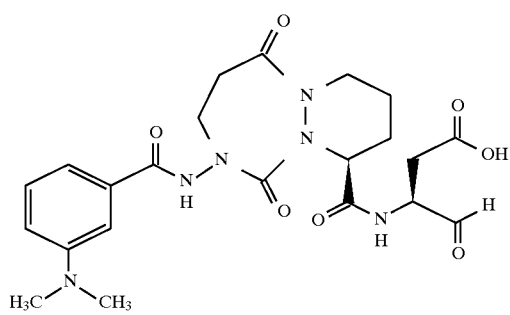

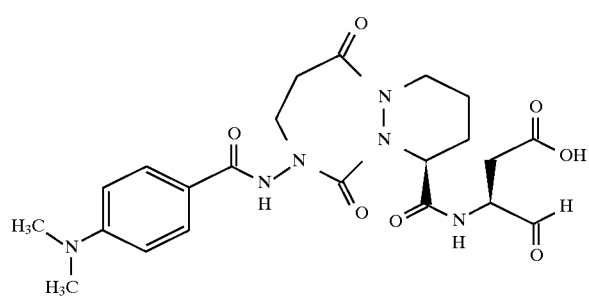
1071
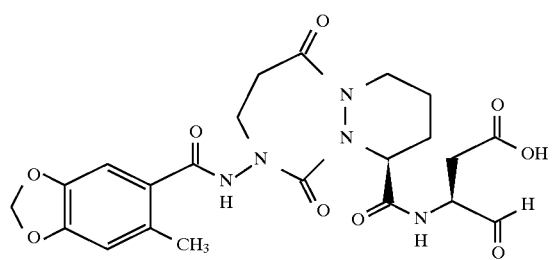
1073
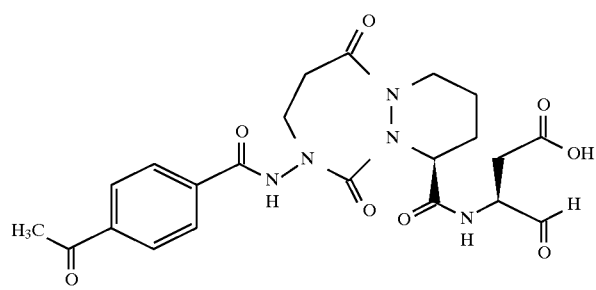
1074
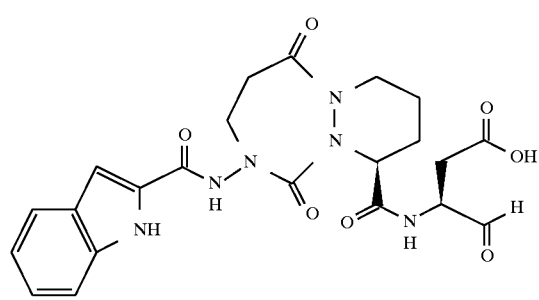
1075
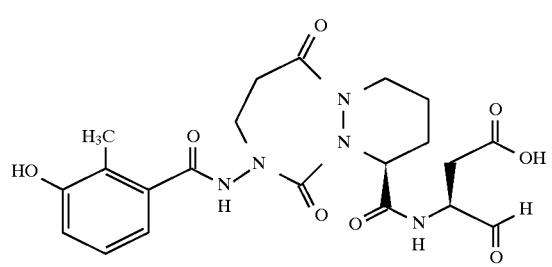
1076

-continued
| | |
|---|---|
| 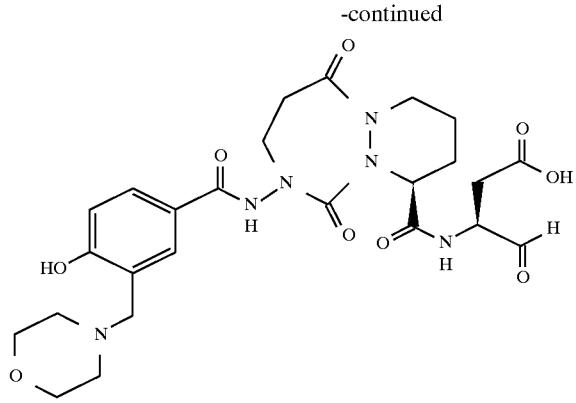 | 1077 |
| 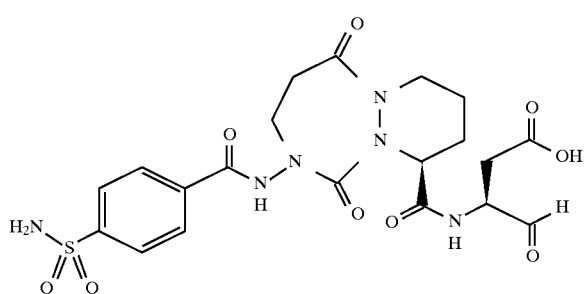 | 1078 |
| 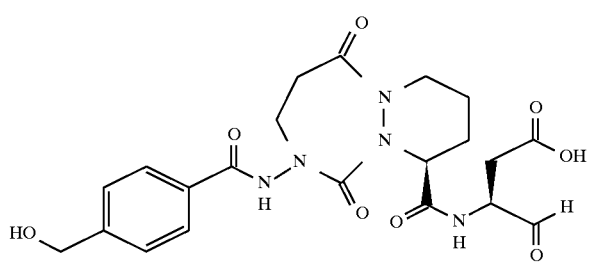 | 1079 |
| 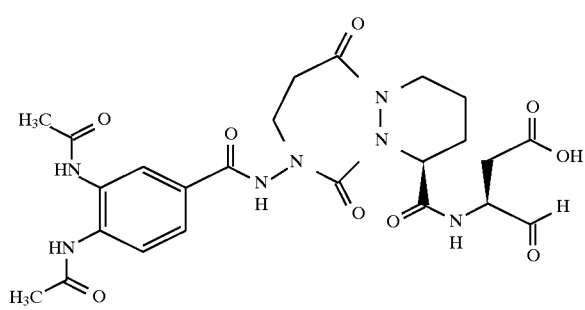 | 1080 |
| 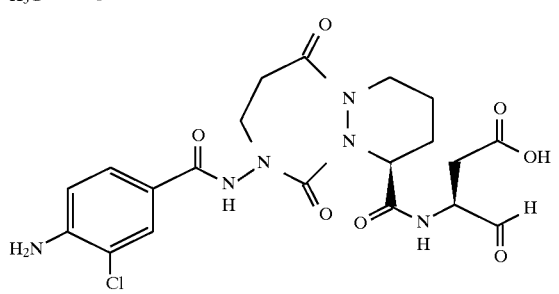 | 1081 |

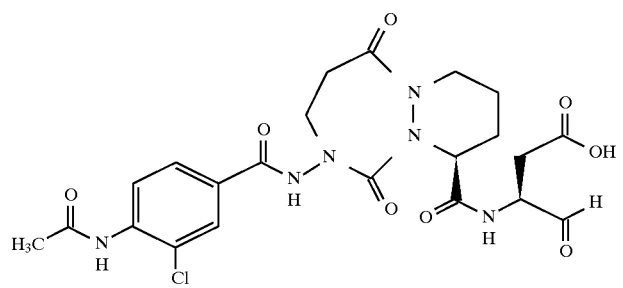
1081s
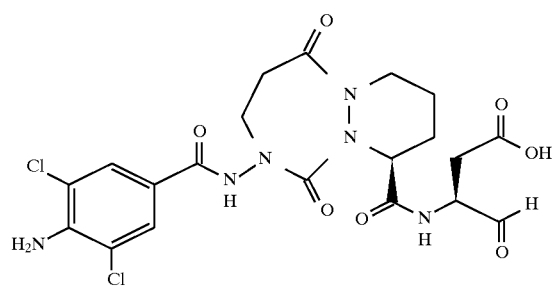
1082
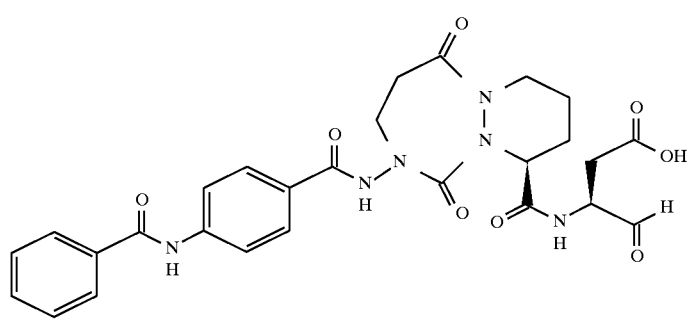
1083
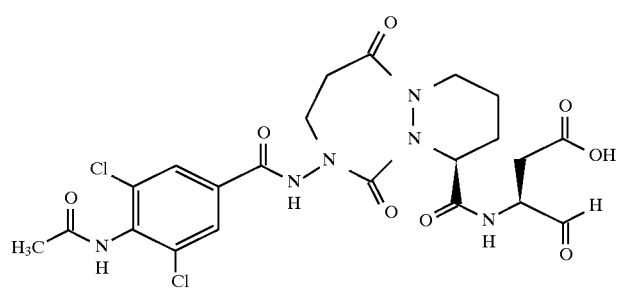
1082s
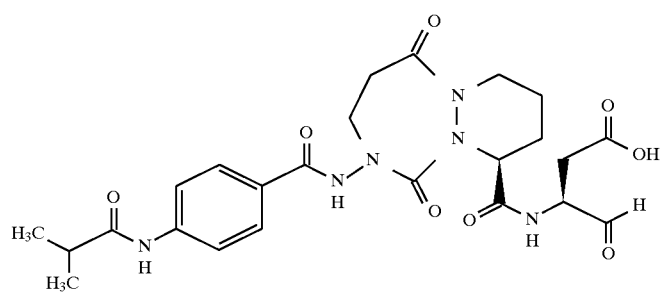
1084

1085
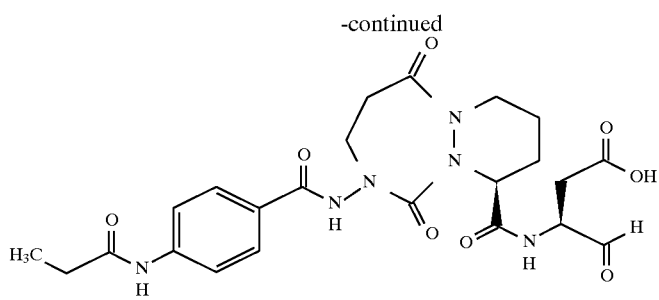
1086
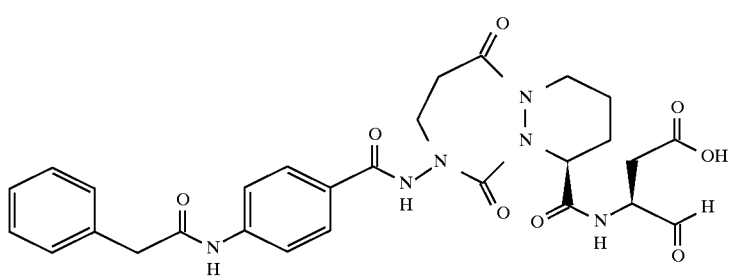
1087
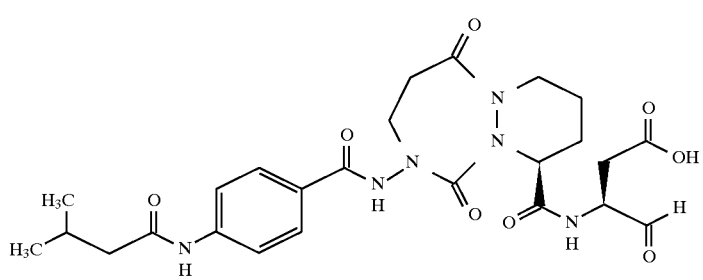
1088
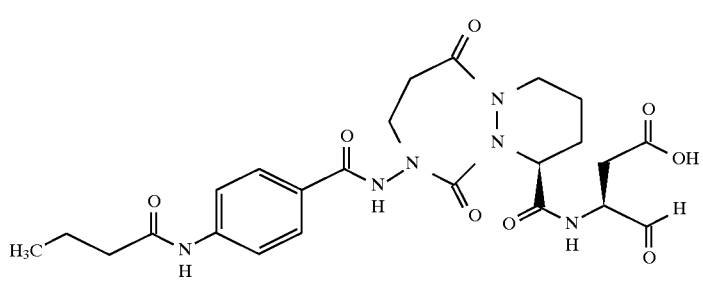
1089
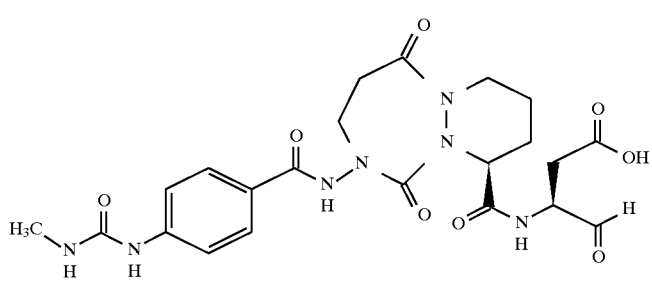
1090
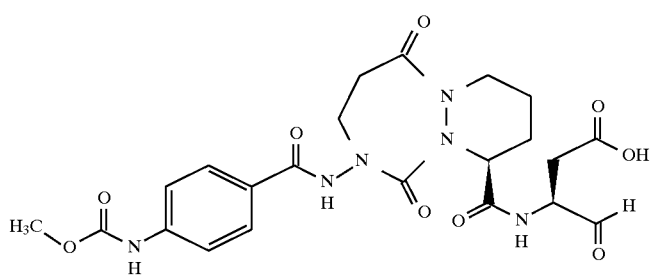

-continued
1091
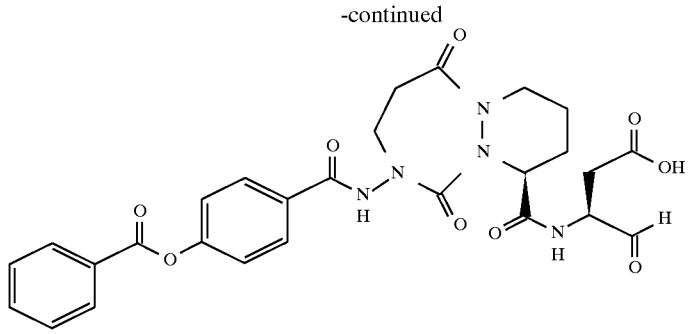
1093
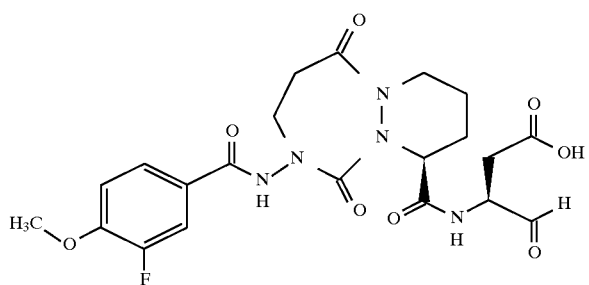
1094
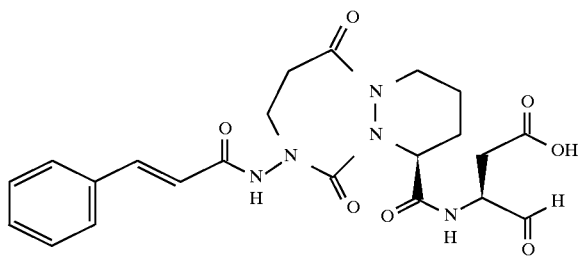
1095
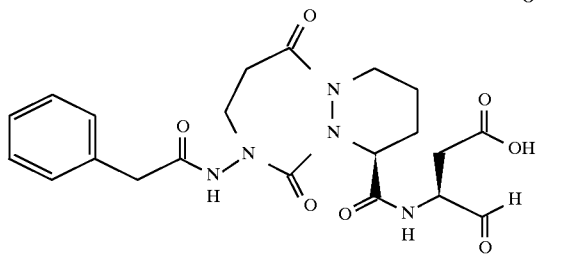
1096
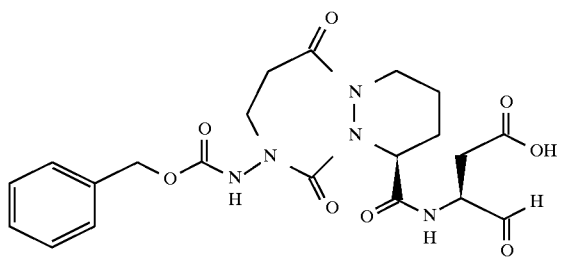
1097
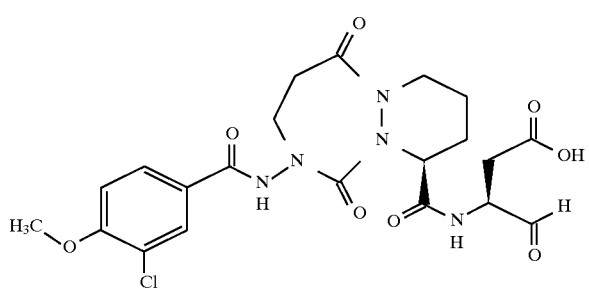

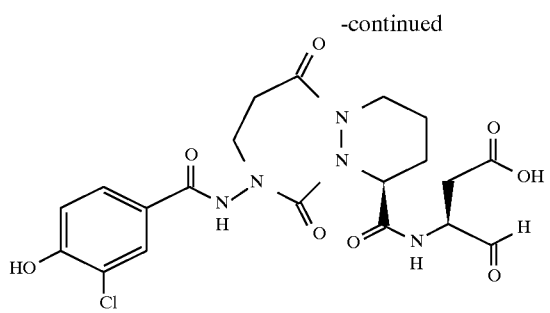
1098
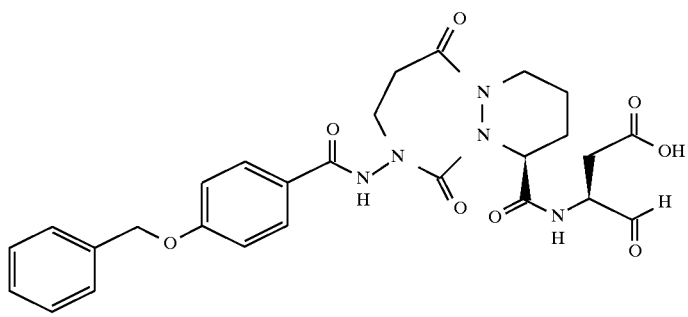
1099
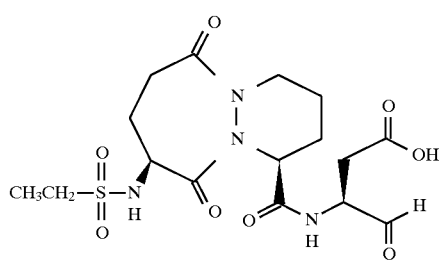
421
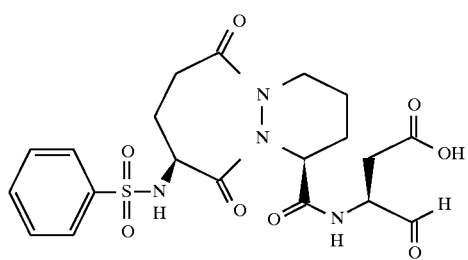
427
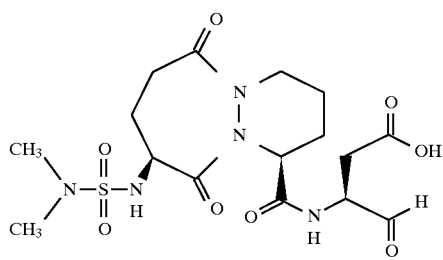
428
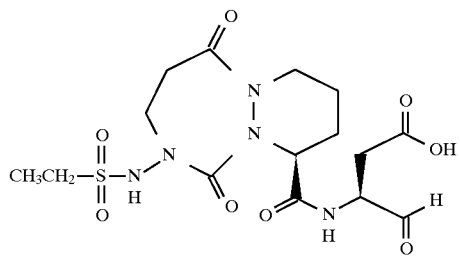
1021

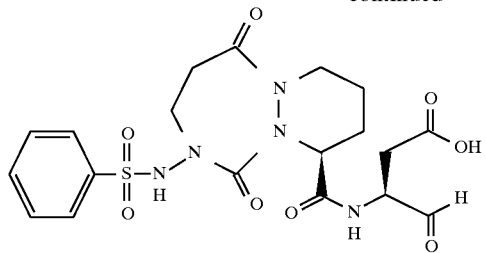
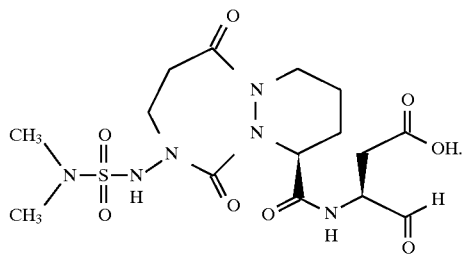
Specific compounds of this invention also include, but are not limited to, those compounds whose structures comprise scaffolds 1–22:
1
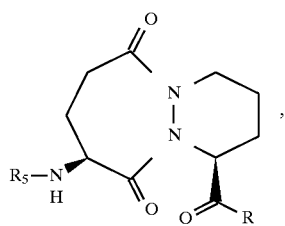
2
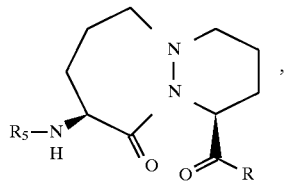
3
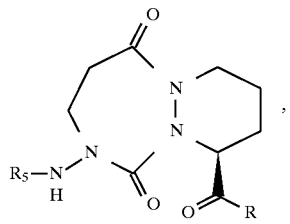
4
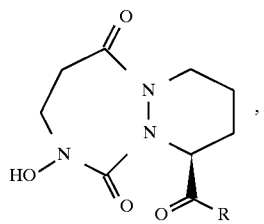
-continued
5
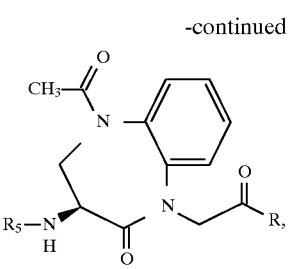
6
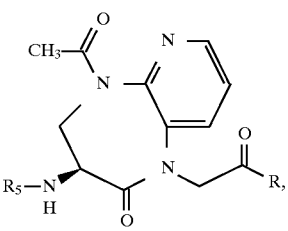
7
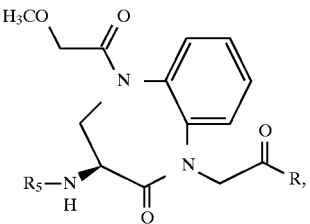
8
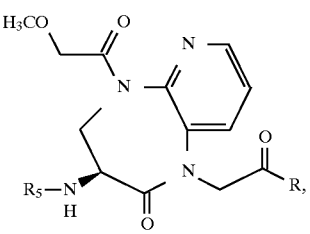

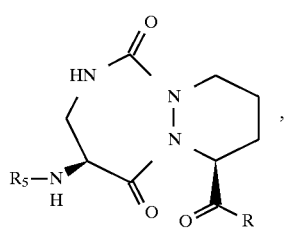
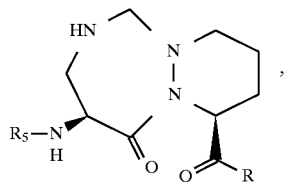
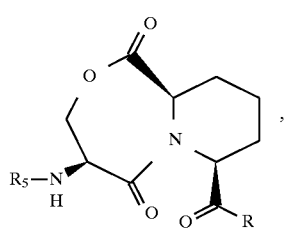
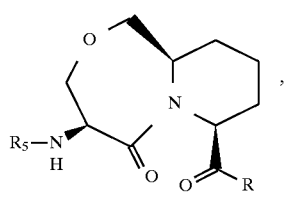
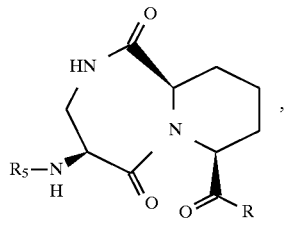
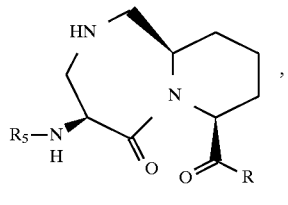
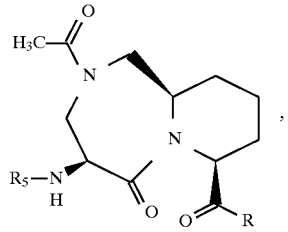
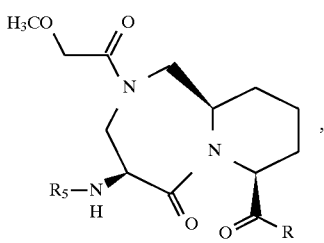
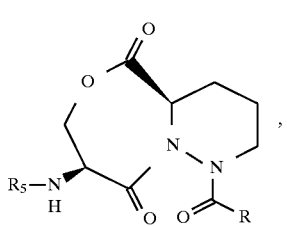
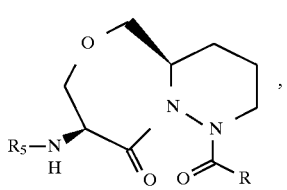
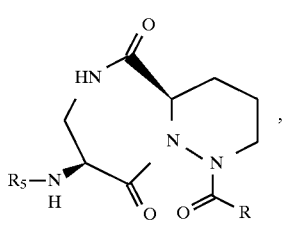
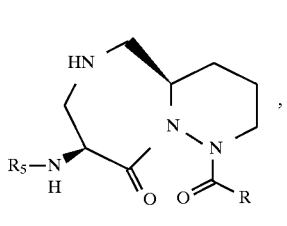
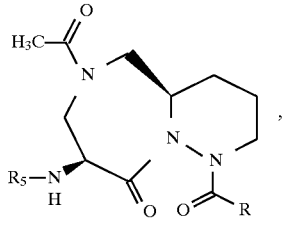
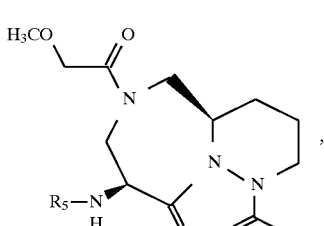

wherein:

R is

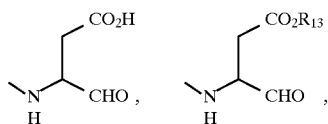

wherein $R_{13}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, or

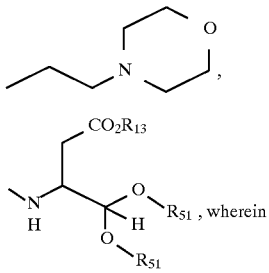

$R_{13}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, or

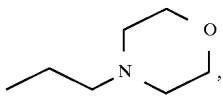

and each $R_{51}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, or taken together form a ethylenedioxy acetal or a propylenedioxy acetal; or

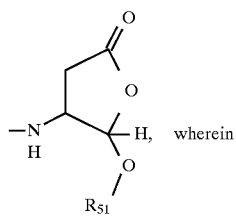

$R_{51}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, —C(O)—CH$_3$ or —C(O)—Ph;

$R_5$ in each of the above compounds is the same as any one of the $R_5$ moieties shown for any one of compounds 139, 214c, 214e, 404–413, 415–491, 493–501.

Specific compounds of this invention also include, but are not limited to, compounds comprising scaffolds 1–28, wherein R, $R_{51}$, and $R_5$ are as defined above, and in which the —C(O)— of the $R_5$ moiety of any one of compounds 214c, 214e, 404–413, 415–418, 422–426, 430–456, 458–466, 468, 470–471, 473–491, 493, 495, 497–501 is replaced with —CH$_2$—, —C(O)C(O)—, or —CH$_2$C(O)C(O)—.

The ICE inhibitors of another embodiment (D) of this invention are those of formula (I):

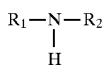  (I)

wherein:

$R_1$ is selected from the group consisting of the following formulae:

(e10) 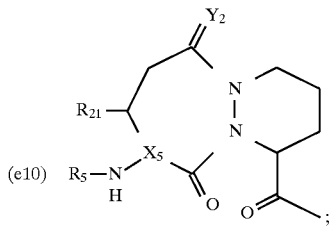

(e11) 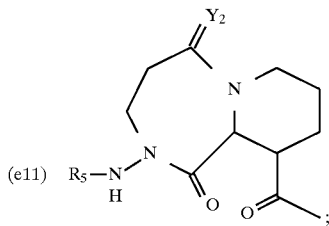

(e12) 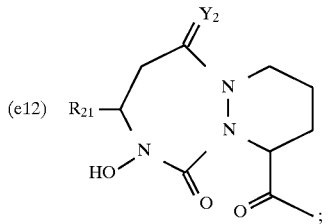

(w2) 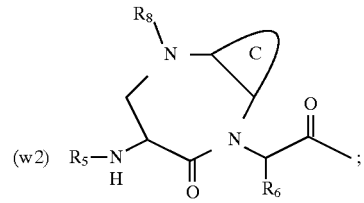

(y1) 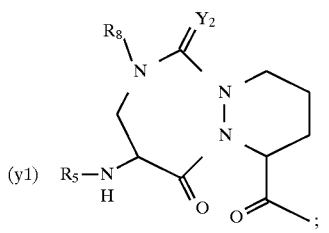

(y2) 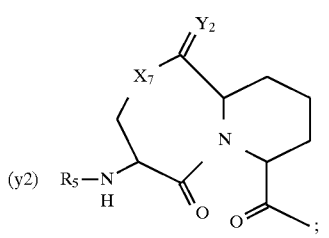

(z) 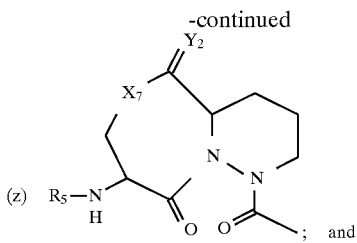; and ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_2$ is:

(a) 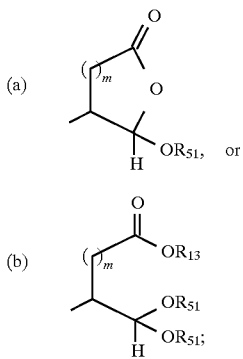

m is 1 or 2;

each $R_5$ is independently selected from the group consisting of:
—C(O)—$R_{10}$,
—C(O)O—$R_9$,
—C(O)—N($R_{10}$) ($R_{10}$)
—S(O)$_2$—$R_9$,
—S(O)$_2$—NH—$R_{10}$,
—C(O)—CH$_2$—O—$R_9$,
—C(O)C(O)—$R_{10}$,
—$R_9$,
—H,
—C(O)C(O)—O$R_{10}$, and
—C(O)C(O)—N($R_9$) ($R_{10}$);

$X_5$ is

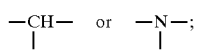

$Y_2$ is $H_2$ or O;
$X_7$ is —N($R_8$)— or —O—;
$R_6$ is selected from the group consisting of —H and —CH$_3$;
$R_8$ is selected from the group consisting of:
—C(O)—$R_{10}$,
—C(O)O—$R_9$,
—C(O)—N(H)—$R_{10}$,
—S(O)$_2$—$R_9$,
—S(O)$_2$—NH—$R_{10}$,
—C(O)—CH$_2$—O$R_{10}$,
—C(O)C(O)—$R_{10}$;
—C(O)—CH$_2$N($R_{10}$) ($R_{10}$),
—C(O)—CH$_2$C(O)—O—$R_9$,
—C(O)—CH$_2$C(O)—$R_9$,
—H, and
—C(O)—C(O)—O$R_{10}$;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

$R_{13}$ is selected from the group consisting of H, Ar$_3$, and a C$_{1-6}$ straight or branched alkyl group optionally substituted with Ar$_3$, —CONH$_2$, —OR$_5$, —OH, —OR$_9$, or —CO$_2$H;

each $R_{51}$ is independently selected from the group consisting of $R_9$, —C(O)—$R_9$, —C(O)—N(H)—$R_9$, or each $R_{51}$ taken together forms a saturated 4–8 member carbocyclic ring or heterocyclic ring containing —O—, —S—, or —NH—;

each $R_{21}$ is independently selected from the group consisting of —H or a —C$_{1-6}$ straight or branched alkyl group;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —Q$_1$;

each $Q_1$ is independently selected from the group consisting of —NH$_2$, —CO$_2$H, —Cl, —F, —Br, —I, —NO$_2$, —CN, =O, —OH, —perfluoro C$_{1-3}$ alkyl, R$_5$, —OR$_5$, —NHR$_5$, OR$_9$, —N(R$_9$) (R$_{10}$), R$_9$, —C(O)—R$_{10}$, and

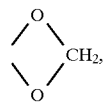

provided that when —Ar$_3$ is substituted with a Q$_1$ group which comprises one or more additional —Ar$_3$ groups, said additional —Ar$_3$ groups are not substituted with another —Ar$_3$.

Preferably, R$_5$ is selected from the group consisting of:
—C(O)—R$_{10}$,
—C(O)O—R$_9$, and
—C(O)—NH—R$_{10}$.

Alternatively, R$_5$ is selected from the group consisting of:
—S(O)$_2$—R$_9$,
—S(O)$_2$—NH—R$_{10}$,
—C(O)—C(O)—R$_{10}$,
—R$_9$, and
—C(O)—C(O)—OR$_{10}$.

More preferably:
m is 1;
R$_{13}$ is H or a —C$_{1-4}$ straight or branched alkyl group optionally substituted with —Ar$_3$, —OH, —OR$_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by —$Q_1$;

each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$N(R_9)(R_{10})$, and

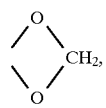

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

The ICE inhibitors of another embodiment (E) of this invention are those of formula (II):

wherein:

m is 1 or 2;

$R_1$ is selected from the group consisting of the following formulae:

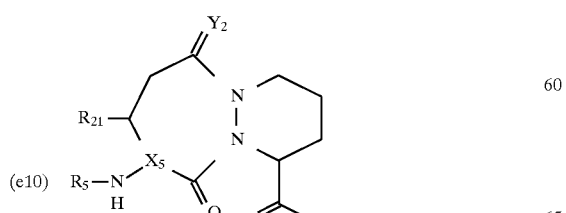

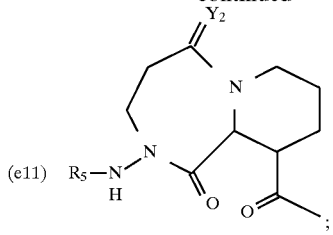

(e11)

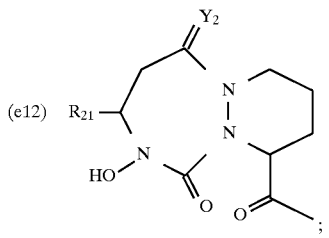

(e12)

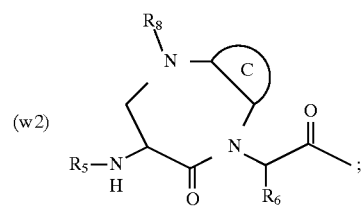

(w2)

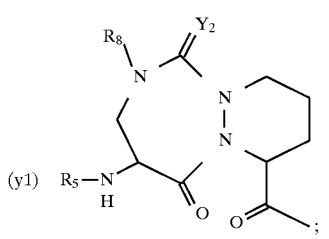

(y1)

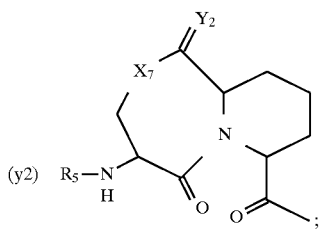

(y2)

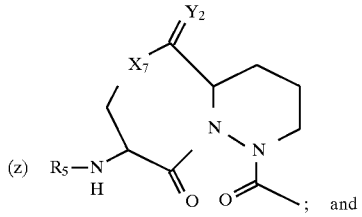

(z) ; and ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is selected from the group consisting of:
—CN,
—C(O)—H,
—C(O)—$CH_2$—$T_1$—$R_{11}$,
—C(O)—$CH_2$—F,
—C=N—O—$R_9$, and
—CO—$Ar_2$;

each $R_5$ is independently selected from the group consisting of:
—C(O)—$R_{10}$,
—C(O)O—$R_9$,
—C(O)—N($R_{10}$) ($R_{10}$)
—S(O)$_2$—$R_9$,
—S(O)$_2$—NH—$R_{10}$,
—C(O)—CH$_2$—O—$R_9$,
—C(O)C(O)—$R_{10}$,
—$R_9$,
—H,
—C(O)C(O)—O$R_{10}$, and
—C(O)C(O)—N($R_9$) ($R_{10}$);

$X_5$ is

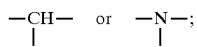

$Y_2$ is $H_2$ or O;
$X_7$ is —N($R_8$)— or —O—;
each $T_1$ is independently selected from the group consisting of —O—, —S—, —S(O)—, and —S(O)$_2$—;
$R_6$ is selected from the group consisting of —H and —CH$_3$;
$R_8$ is selected from the group consisting of:
—C(O)—$R_{10}$,
—C(O)O—$R_9$,
—C(O)—NH—$R_{10}$,
—S(O)$_2$—$R_9$,
—S(O)$_2$—NH—$R_{10}$,
—C(O)—CH$_2$—O$R_{10}$,
—C(O)C(O)—$R_{10}$,
—C(O)—CH$_2$—N($R_{10}$) ($R_{10}$),
—C(O)—CH$_2$C(O)—O—$R_9$,
—C(O)—CH$_2$C(O)—$R_9$,
—H, and
—C(O)—C(O)—O$R_{10}$;

each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;

each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;

each $R_{11}$ is independently selected from the group consisting of:
—$Ar_4$,
—(CH$_2$)$_{1-3}$—$Ar_4$,
—H, and
—C(O)—$Ar_4$;

$R_{15}$ is selected from the group consisting of —OH, —O$Ar_3$, —N(H)—OH, and a —O$C_{1-6}$ straight or branched alkyl group optionally substituted with —$Ar_3$, —CONH$_2$, —O$R_5$, —OH, —O$R_9$, or —CO$_2$H;

each $R_{21}$ is independently selected from the group consisting of —H or a —$C_{1-6}$ straight or branched alkyl group;

$Ar_2$ is independently selected from the following group, in which any ring may optionally be singly or multiply substituted by —$Q_1$:

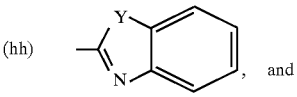

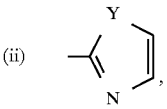

wherein each Y is independently selected from the group consisting of O and S;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N($R_5$)—, and —N($R_9$)— said heterocycle group optionally containing one or more double bonds, said heterocycle group optionally comprising one or more aromatic rings, and said cyclic group optionally being singly or multiply substituted by —$Q_1$;

each $Ar_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N($R_5$)—, and —N($R_9$)— said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —NH$_2$, —CO$_2$H, —Cl, —F, —Br, —I, —NO$_2$, —CN, =O, —OH, —perfluoro $C_{1-3}$ alkyl, $R_5$, —O$R_5$, —NH$R_5$, O$R_9$, —N($R_9$) ($R_{10}$), $R_9$, —C(O)—$R_{10}$, and

provided that when —$Ar_3$ is substituted with a $Q_1$ group which comprises one or more additional —$Ar_3$ groups, said additional —$Ar_3$ groups are not substituted with another —$Ar_3$.

Preferred compounds of embodiment E employ formula (II), wherein $R_1$ is (e11) and the other substituents are as defined above.

Other preferred compounds of embodiment E employ formula (II), wherein $R_1$ is (e12) and the other substituents are as defined above.

Other preferred compounds of embodiment E employ formula (II) wherein $R_1$ is (y1) and the other substituents are as defined above.

Other preferred compounds of embodiment E employ formula (II) wherein $R_1$ is (y2) and the other substituents are as defined above.

Other preferred compounds of embodiment E of employ formula (II) wherein $R_1$ is (z) and the other substituents are as defined above.

Other preferred compound of embodiment E employ formula (II) wherein $R_1$ is (w2) and the other substituents are as defined above.

More preferably, $R_1$ is (w2) and m is 1;

ring C is benzo, pyrido, or thieno;

$R_3$ is selected from the group consisting of —C(O)—H, —C(O)—$Ar_2$, and —C(O)$CH_2$—$T_1$—$R_{11}$;

$R_5$ is selected from the group consisting of:
—C(O)—$R_{10}$, wherein $R_{10}$ is —$Ar_3$;
—C(O)O—$R_9$, wherein $R_9$ is —$CH_2$—$Ar_3$;
—C(O)C(O)—$R_{10}$, wherein $R_{10}$ is —$Ar_3$;
—$R_9$, wherein $R_9$ is a $C_{1-2}$ alkyl group substituted with —$Ar_3$; and
—C(O)C(O)—$OR_{10}$, wherein $R_{10}$ is —$CH_2Ar_3$;

$T_1$ is O or S;

$R_6$ is H;

$R_8$ is selected from the group consisting —C(O)—$R_{10}$, —C(O)—$CH_2$—$OR_{10}$, and —C(O)$CH_2$—N($R_{10}$) ($R_{10}$), wherein $R_{10}$ is H, $CH_3$, or —$CH_2CH_3$;

$R_{11}$ is selected from the group consisting of —$Ar_4$, —$(CH_2)_{1-3}$—$Ar_4$, and —C(O)—$Ar_4$;

$R_{15}$ is —OH or —$OC_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$Ar_2$ is (hh);

Y is O;

each $Ar_3$ cyclic group is independently selected from the set consisting of phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl, and said cyclic group optionally being singly or multiply substituted by —$Q_1$;

each $Ar_4$ cyclic group is independently selected from the set consisting of phenyl, tetrazolyl, naphthyl, pyridinyl, oxazolyl, pyrimidinyl, or indolyl, said cyclic group optionally being singly or multiply substituted by —$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —N($R_9$) ($R_{10}$), and

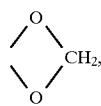

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other preferred compounds of embodiment E employ formula (II) wherein $R_1$ is (e10), $X_5$ is CH, and the other substituents are as defined above.

More preferred compounds of embodiment E employ formula (II) wherein $R_1$ is (e10), $X_5$ is CH, $R_3$ is CO—$Ar_2$, and the other substituents are as defined above.

Other more preferred compounds of embodiment E employ formula (II) wherein $R_1$ is (e10), $X_5$ is CH, $R_3$ is —C(O)—$CH_2$—$T_1$—$R_{11}$, $R_{11}$ is —$(CH_2)_{1-3}$—$Ar_4$, and the other substituents are as defined above.

Other more preferred compounds of embodiment E employ formula (II) wherein $R_1$ is (e10) and $X_5$ is CH and $R_3$ is —C(O)—$CH_2$—$T_1$—$R_{11}$, $T_1$ is O, $R_{11}$ is —C(O)—$Ar_4$, and the other substituents are as defined above.

More preferably, in these more preferred compounds, $R_5$ is selected from the group consisting of:
—C(O)—$R_{10}$,
—C(O)O—$R_9$, and
—C(O)—NH—$R_{10}$.

Alternatively, in these more preferred compounds, $R_5$ is selected from the group consisting of:
—$S(O)_2$—$R_9$,
—$S(O)_2$—NH—$R_{10}$,
—C(O)—C(O)—$R_{10}$,
—$R_9$, and
—C(O)—C(O)—$OR_{10}$.

Most preferably, in these more preferred compounds, m is 1;

$T_1$ is O or S;

$R_{15}$ is —OH or —$OC_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$Ar_2$ is (hh);

Y is O, and each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —$Q_1$;

each $Ar_4$ cyclic group is independently selected from the set consisting of phenyl, tetrazolyl, pyridinyl, oxazolyl, naphthyl, pyrimidinyl, or thienyl, said cyclic group being singly or multiply substituted by —$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —N($R_9$) ($R_{10}$), and

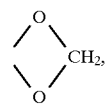

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment E employ formula (II) wherein $R_1$ is (e10), $X_5$ is CH, $R_3$ is —C(O)—H, and the other substituents are as defined above.

More preferably, in these more preferred compounds, $R_5$ is selected from the group consisting of:
- —C(O)—$R_{10}$,
- —C(O)O—$R_9$, and
- —C(O)—NH—$R_{10}$.

Alternatively, in these more preferred compounds, $R_5$ is selected from the group consisting of:
- —S(O)$_2$—$R_9$,
- —S(O)$_2$—NH—$R_{10}$,
- —C(O)—C(O)—$R_{10}$,
- —$R_9$, and
- —C(O)—C(O)—O$R_{10}$.

Most preferably, in these more preferred compounds, m is 1;

$R_{15}$ is —OH or —O$C_{1-4}$ straight or branched alkyl group optionally substituted with —$Ar_3$, —OH, —O$R_9$, or —CO$_2$H, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —CH$_3$;

each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, said cyclic group optionally being singly or multiply substituted by —$Q_1$;

each $Q_1$ is independently selected from the group consisting of —NH$_2$, —Cl, —F, —Br, —OH, —$R_9$, —NH—$R_5$ wherein $R_5$ is —C(O)—$R_{10}$ or —S(O)$_2$—$R_9$, —O$R_5$ wherein $R_5$ is —C(O)—$R_{10}$, —O$R_9$, —N($R_9$) ($R_{10}$), and

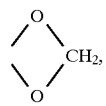

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$, Other more preferred compounds of embodiment E employ formula (II) wherein $R_1$ is (e10) and X, is CH, $R_3$ is —CO—CH$_2$—T$_1$—$R_{11}$, and $R_{11}$ is —$Ar_4$, and the other substituents are as defined above.

More preferably, in these more preferred compounds, $R_5$ is selected from the group consisting of:
- —C(O)—$R_{10}$,
- —C(O)O—$R_9$, and
- —C(O)—NH—$R_{10}$.

Alternatively, in these more preferred compounds, $R_5$ is selected from the group consisting of:
- —S(O)$_2$—$R_9$,
- —S(O)$_2$—NH—$R_{10}$,
- —C(O)—C(O)—$R_{10}$,
- —$R_9$, and
- —C(O)—C(O)—O$R_{10}$.

Most preferably, in these more preferred compounds, m is 1;

$T_1$ is O or S;

$R_{15}$ is —OH or a —O$C_{1-4}$ straight or branched alkyl group optionally substituted with —$Ar_3$, —OH, —O$R_9$, or —CO$_2$H, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —CH$_3$;

each $Ar_3$ cyclic group is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —$Q_1$;

each $Ar_4$ cyclic group is independently selected from the set consisting of phenyl, tetrazolyl, pyridinyl, oxazolyl, naphthyl, pyrimidinyl, or thienyl, said cyclic group optionally being singly or multiply substituted by —$Q_1$;

each $Q_1$ is independently selected from the group consisting of —NH$_2$, —Cl, —F, —Br, —OH, —$R_9$, —NH—$R_5$ wherein $R_5$ is —C(O)—$R_{10}$ or —S(O)$_2$—$R_9$, —O$R_5$ wherein $R_5$ is —C(O)—$R_{10}$, —O$R_9$, —N($R_9$) ($R_{10}$), and

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other preferred compounds of embodiment E employ formula (II) wherein $R_1$ is (e10), $X_5$ is N, and the other substituents are as defined above.

More preferred compounds of embodiment E, employ formula (II) wherein $R_1$ is (e10), $X_5$ is N, $R_3$ is CO—$Ar_2$, and the other substituents are as defined above.

Other more preferred compounds of embodiment E, employ formula (II) wherein $R_1$ is (e10), $X_5$ is N, $R_3$ is —C(O)—CH$_2$—T$_1$—$R_{11}$, $R_{11}$ is —(CH$_2$)$_{1-3}$—$Ar_4$, and the other substituents are as defined above.

Other more preferred compounds of embodiment E, employ formula (II) wherein $R_1$ is (e10) and $X_5$ is N and:

$R_3$ is —C(O)—CH$_2$—T$_1$—$R_{11}$;

$T_1$ is O; and $R_{11}$ is —C(O)—$Ar_4$, and the other substituents are as defined above.

More preferably, in these more preferred compounds, $R_5$ is selected from the group consisting of:
- —C(O)—$R_{10}$,
- —C(O)O—$R_9$, and
- —C(O)—NH—$R_{10}$.

Alternatively, in these more preferred compounds, $R_5$ is selected from the group consisting of:
- —S(O)$_2$—$R_9$,
- —S(O)$_2$—NH—$R_{10}$, —C(O)—C(O)—R$_{10}$,
—R$_9$, and
—C(O)—C(O)—OR$_{10}$.

Most preferably, in these more preferred compounds,
m is 1;
T$_1$ is O or S;
R$_{15}$ is —OH or a —OC$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;
R$_{21}$ is —H or —CH$_3$;
Ar$_2$ is (hh);
Y is O, and
each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —Q$_1$;
each Ar$_4$ cyclic group is independently selected from the set consisting of phenyl, tetrazolyl, pyridinyl, oxazolyl, naphthyl, pyrimidinyl, or thienyl, optionally being singly or multiply substituted by —Q$_1$;
each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$) (R$_{10}$), and

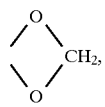

wherein each R$_9$ and R$_{10}$ are independently a —C$_{1-6}$ straight or branched alkyl group optionally substituted with Ar$_3$ wherein Ar$_3$ is phenyl;
provided that when —Ar$_3$ is substituted with a Q$_1$ group which comprises one or more additional —Ar$_3$ groups, said additional —Ar$_3$ groups are not substituted with another —Ar$_3$.

Other more preferred compounds of embodiment E, employ formula (II) wherein R$_1$ is (e10), X$_5$ is N, R$_3$ is —C(O)—H, and the other substituents are as defined above.

More preferably, in these more preferred compounds, R$_5$ is selected from the group consisting of:
—C(O)—R$_{10}$,
—C(O)O—R$_9$, and
—C(O)—NH—R$_{10}$.

Alternatively, in these more preferred compounds, R$_5$ is selected from the group consisting of:
—S(O)$_2$—R$_9$,
—S(O)$_2$—NH—R$_{10}$,
—C(O)—C(O)—R$_{10}$,
—R$_9$, and
—C(O)—C(O)—OR$_{10}$.

Most preferably, in these more preferred compounds,
m is 1;
T$_1$ is O or S;
R$_{15}$ is —OH or —OC$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;
R$_{21}$ is —H or —CH$_3$;
each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —Q$_1$;
each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$) (R$_{10}$), and

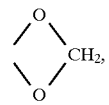

wherein each R$_9$ and R$_{10}$ are independently a —C$_{1-6}$ straight or branched alkyl group optionally substituted with Ar$_3$ wherein Ar$_3$ is phenyl;
provided that when —Ar$_3$ is substituted with a Q$_1$ group which comprises one or more additional —Ar$_3$ groups, said additional —Ar$_3$ groups are not substituted with another —Ar$_3$.

Other more preferred compounds of embodiment E, employ formula (II) wherein R$_1$ is (e10), X$_5$ is N, R$_3$ is —CO—CH$_2$—T$_1$—R$_{11}$, R$_{11}$ is —Ar$_4$, and the other substituents are as defined above.

More preferably, in these more preferred compounds, R$_5$ is selected from the group consisting of:
—C(O)—R$_{10}$,
—C(O)O—R$_9$, and
—C(O)—NH—R$_{10}$.

Alternatively, in these more preferred compounds, R$_5$ is selected from the group consisting of:
—S(O)$_2$—R$_9$,
—S(O)$_2$—NH—R$_{10}$,
—C(O)—C(O)—R$_{10}$,
—R$_9$, and
—C(O)—C(O)—OR$_{10}$.

Most preferably, in these more preferred compounds
m is 1;
T$_1$ is O or S;
R$_{15}$ is —OH or —OC$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;
R$_{21}$ is —H or —CH$_3$;
each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —Q$_1$;

each Ar₄ cyclic group is independently selected from the set consisting of phenyl, tetrazolyl, pyridinyl, oxazolyl, naphthyl, pyrimidinyl, or thienyl, said cyclic group being singly or multiply substituted by —Q₁;

each Q₁ is independently selected from the group consisting of —NH₂, —Cl, —F, —Br, —OH, —R₉, —NH—R₅ wherein R₅ is —C(O)—R₁₀ or —S(O)₂—R₉, —OR₅ wherein R₅ is —C(O)—R₁₀, —OR₉, —N(R₉)(R₁₀), and

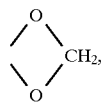

wherein each R₉ and R₁₀ are independently a —C₁₋₆ straight or branched alkyl group optionally substituted with Ar₃ wherein Ar₃ is phenyl;

provided that when —Ar₃ is substituted with a Q₁ group which comprises one or more additional —Ar₃ groups, said additional —Ar₃ groups are not substituted with another —Ar₃.

The ICE inhibitors of another embodiment (F) of this invention are those of formula (III):

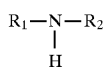   (III)

wherein:

R₁ is selected from the group consisting of the following formulae:

(e10) 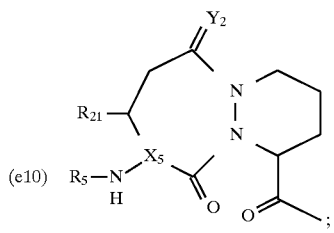

(e11) 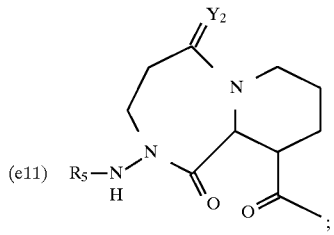

(e12) 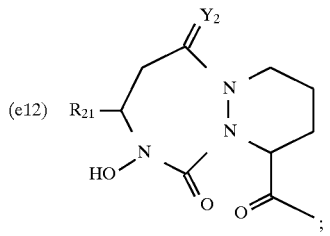

(w2) 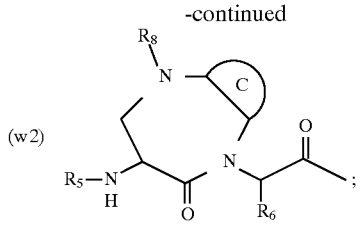

(y1) 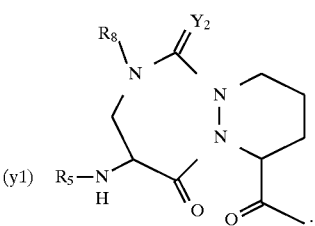

(y2) 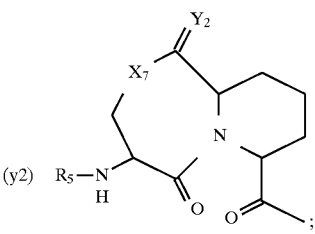

(z) 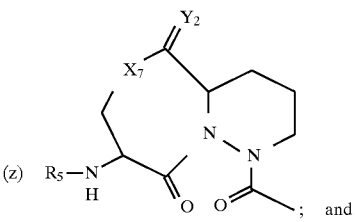 ; and ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

R₂ is (a) 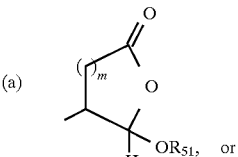   or (b) 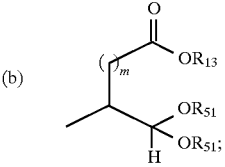;

m is 1 or 2;

each R₅ is independently selected from the group consisting of:
—C(O)—R₁₀,
—C(O)O—R₉,
—C(O)—N(R₁₀)(R₁₀)
—S(O)₂—R₉,
—S(O)₂—NH—R₁₀,
—C(O)—CH₂—O—R₉, —C(O)C(O)—R$_{10}$,
—R$_9$,
—H,
—C(O)C(O)—OR$_{10}$, and
—C(O)C(O)—N(R$_9$) (R$_{10}$);

X$_5$ is CH or N;

Y$_2$ is H$_2$ or O;

X$_7$ is —N(R$_8$)— or —O—;

R$_6$ is selected from the group consisting of —H and —CH$_3$;

R$_8$ is selected from the group consisting of:
—C(O)—R$_{10}$,
—C(O)O—R$_9$,
—C(O)—N(H)—R$_{10}$,
—S(O)$_2$—R$_9$,
—S(O)$_2$—NH—R$_{10}$,
—C(O)—CH$_2$—OR$_{10}$,
—C(O)C(O)—R$_{10}$;
—C(O)—CH$_2$N(R$_{10}$) (R$_{10}$),
—C(O)—CH$_2$C(O)—O—R$_9$,
—C(O)—CH$_2$C(O)—R$_9$,
—H, and
—C(O)—C(O)—OR$_{10}$;

each R$_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each R$_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

R$_{13}$ is selected from the group consisting of H, Ar$_3$, and a C$_{1-6}$ straight or branched alkyl group optionally substituted with Ar$_3$, —CONH$_2$, —OR$_5$, —OH, —OR$_9$, or —CO$_2$H;

each R$_{21}$ is independently selected from the group consisting of —H or a —C$_{1-6}$ straight or branched alkyl group;

each R$_{51}$ is independently selected from the group consisting of R$_9$, —C(O)—R$_9$, —C(O)—N(H)—R$_9$, or each R$_{51}$ taken together forms a saturated 4–8 member carbocyclic ring or heterocyclic ring containing —O—, —S—, or —NH—;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —Q$_1$;

each Q$_1$ is independently selected from the group consisting of —NH$_2$, —CO$_2$H, —Cl, —F, —Br, —I, —NO$_2$, —CN, =O, —OH, —perfluoro C$_{1-3}$ alkyl, R$_5$, —OR$_5$, —NHR$_5$, OR$_9$, —N(R$_9$) (R$_{10}$), R$_9$, —C(O)—R$_{10}$, and

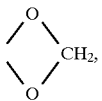

provided that when —Ar$_3$ is substituted with a Q$_1$ group which comprises one or more additional —Ar$_3$ groups, said additional —Ar$_3$ groups are not substituted with another —Ar$_3$.

Preferred compounds of embodiment F employ formula (III), wherein R$_1$ is (w2) and the other substituents are as defined above.

Preferably, when R$_1$ is (w2)
m is 1;
ring C is benzo, pyrido, or thieno;
R$_5$ is selected from the group consisting of:
—C(O)—R$_{10}$, wherein R$_{10}$ is —Ar$_3$;
—C(O)O—R$_9$, wherein R$_9$ is —CH$_2$—Ar$_3$;
—C(O)C(O)—R$_{10}$, wherein R$_{10}$ is —Ar$_3$;
—R$_9$, wherein R$_9$ is a C$_{1-2}$ alkyl group substituted with —Ar$_3$; and
—C(O)C(O)—OR$_{10}$, wherein R$_{10}$ is —CH$_2$Ar$_3$;

R$_6$ is H;

R$_8$ is selected from the group consisting —C(O)—R$_{10}$, —C(O)—CH$_2$—OR$_{10}$, and —C(O)CH$_2$—N(R$_{10}$) (R$_{10}$), wherein R$_{10}$ is H, CH$_3$, or —CH$_2$CH$_3$;

R$_{13}$ is H or a C$_{1-4}$ straight or branched alkyl group optionally substituted with Ar$_3$, —OH, —OR$_9$, —CO$_2$H, wherein the R$_9$ is a C$_{1-4}$ branched or straight chain alkyl group; wherein Ar$_3$ is morpholinyl or phenyl, wherein the phenyl is optionally substituted with Q$_1$;

Ar$_3$ is phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —NHR$_9$, and

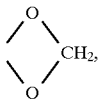

wherein each R$_9$ and R$_{10}$ are independently a —C$_{1-6}$ straight or branched alkyl group optionally substituted with Ar$_3$ wherein Ar$_3$ is phenyl;

provided that when —Ar$_3$ is substituted with a Q$_1$ group which comprises one or more additional —Ar$_3$ groups, said additional —Ar$_3$ groups are not substituted with another —Ar$_3$.

Other preferred compounds of embodiment F employ formula (III), wherein R$_1$ is (e11) and the other substituents are as defined above.

Other preferred compounds of embodiment F employ formula (III), wherein R$_1$ is (e12) and the other substituents are as defined above.

Other preferred compounds of embodiment F employ formula (III), wherein R$_1$ is (y1) and the other substituents are as defined above.

Other preferred compounds of embodiment F employ formula (III), wherein R$_1$ is (y2) and the other substituents are as defined above.

Other preferred compounds of embodiment F employ formula (III), wherein $R_1$ is (z) and the other substituents are as defined above.

Other preferred compounds of embodiment F employ formula (III), wherein $R_1$ is (e10) and $X_5$ is CH (also referred to herein as e10-B), and the other substituents are as defined above.

Other preferred compounds of embodiment F employ formula (III), wherein $R_1$ is (e10) and $X_5$ is N, (also referred to herein as e10-A) and the other substituents are as defined above.

Preferably, when $R_1$ is (e11), (e12), (y1), (y2), (z), (e10-A), and (e10-B), $R_5$ is selected from the group consisting of:
—C(O)—$R_{10}$,
—C(O)O—$R_9$, and
—C(O)—NH—$R_{10}$.

Alternatively, when $R_1$ is (e11), (e12), (y1), (y2), (z), (e10-A), and (e10-B), $R_5$ is selected from the group consisting of:
—S(O)$_2$—$R_9$,
—S(O)$_2$—NH—$R_{10}$,
—C(O)—C(O)—$R_{10}$,
—$R_9$,
—C(O)—C(O)—$OR_{10}$, and
—C(O)C(O)—N($R_9$) ($R_{10}$).

More preferably, $R_5$ is R—C(O)—C(O)—$R_{10}$.
Alternatively, $R_5$ is —C(O)—C(O)—$OR_{10}$.
More preferably when $R_1$ is (e11), (e12), (y1), (y2), (z), (e10-A), and (e10-B):

m is 1;

$R_{21}$ is —H or —CH$_3$;

$R_{51}$ is a $C_{1-6}$ straight or branched alkyl group optionally substituted with Ar$_3$, wherein the Ar$_3$ cyclic group is phenyl, said cyclic group optionally being multiply or singly substituted by —$Q_1$;

each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, or indolyl, and said cyclic group optionally being singly or multiply substituted by —$Q_1$;

each $Q_1$ is independently selected from the group consisting of —NH$_2$, —Cl, —F, —Br, —OH, —$R_9$, —NH—$R_5$
wherein $R_5$ is —C(O)—$R_{10}$ or —S(O)$_2$—$R_9$, —OR$_5$ wherein $R_5$ is —C(O)—$R_{10}$, —OR$_9$, —N($R_9$) ($R_{10}$), and

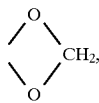

wherein each $R_9$ and $R_{10}$ are independently a —$C_{1-6}$ straight or branched alkyl group optionally substituted with Ar$_3$, wherein the Ar$_3$ cyclic group is phenyl, and said cyclic group optionally being singly or multiply substituted by —$Q_1$;

provided that when —Ar$_3$ is substituted with a —$Q_1$ group which comprises one or more additional —Ar$_3$ groups, said additional —Ar$_3$ groups are not substituted with another —Ar$_3$.

More preferably, in these more preferred compounds, the Ar$_3$ cyclic group is selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, benzofuranyl, and indolyl, and said cyclic group optionally being singly or multiply substituted by —$Q_1$.

Compounds in a preferred form of this embodiment F are those wherein:

$R_5$ is —C(O)—$R_{10}$, wherein:

$R_{10}$ is Ar$_3$, wherein the Ar$_3$ cyclic group is phenyl, said cyclic group optionally being singly or multiply substituted by:
—F,
—Cl,
—N(H)—$R_5$, wherein —$R_5$ is —H or —C(O)—$R_{10}$, wherein $R_{10}$ is a —$C_{1-6}$ straight or branched alkyl group optionally substituted with Ar$_3$, wherein the Ar$_3$ cyclic group is phenyl, said cyclic group optionally being singly or multiply substituted by —$Q_1$,
—N($R_9$) ($R_{10}$), wherein $R_9$ and $R_{10}$ are independently a —$C_{1-4}$ straight or branched alkyl group, or
—O—$R_5$, wherein $R_5$ is H or a —$C_{1-4}$ straight or branched alkyl group.

More preferably the Ar$_3$ cyclic group is phenyl optionally being singly or multiply substituted at the 3- or 5-position by —Cl or at the 4-position by —NH—$R_5$, —N($R_9$) ($R_{10}$), or —O—$R_5$.

Other preferred compounds of embodiment F include those wherein $R_5$ is —C(O)—$R_{10}$, wherein $R_{10}$ is Ar$_3$ and the Ar$_3$ cyclic group is selected from the group consisting of indolyl, benzimidazolyl, thienyl, and benzo[b]thiophenyl, and said cyclic group optionally being singly or multiply substituted by —$Q_1$;

Other preferred compounds of embodiment F include those wherein $R_5$ is —C(O)—$R_{10}$, wherein $R_{10}$ is Ar$_3$ and the Ar$_3$ cyclic group is selected from quinolyl and isoquinolyl, and said cyclic group optionally being singly or multiply substituted by —$Q_1$.

Other preferred compounds of embodiment F are those wherein $R_5$ is —C(O)—$R_{10}$, wherein $R_{10}$ is Ar$_3$, wherein the Ar$_3$ cyclic group is phenyl, substituted by

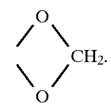

In another form of embodiment F the compounds are as described above, further provided that when:

m is 1;

$R_1$ is (e10)

$X_5$ is CH;

$R_{15}$ is —OH;

$R_{21}$ is —H; and $Y_2$ is O and $R_3$ is —C(O)—H, then $R_5$ cannot be:
—C(O)—$R_{10}$, wherein $R_{10}$ is —Ar$_3$ and the Ar$_3$ cyclic group is phenyl, unsubstituted by —$Q_1$, 4-(carboxymethoxy)phenyl, 2-fluorophenyl, 2-pyridyl, N-(4-methylpiperazino)methylphenyl, or
—C(O)—OR$_9$, wherein $R_9$ is —CH$_2$—Ar$_3$, and the Ar$_3$ cyclic group is phenyl, unsubstituted by —$Q_1$,; and when $Y_2$ is O, $R_3$ is —C(O)—CH$_2$—T$_1$—$R_{11}$, T$_1$ is O, and $R_{11}$ is Ar$_4$, wherein the Ar$_4$ cyclic group is 5-(1-(4-chlorophenyl)-3-trifluoromethyl)pyrazolyl), then $R_5$ cannot be:
—C(O)—$R_{10}$, wherein $R_{10}$ is —Ar$_3$ and the Ar$_3$ cyclic group is 4-(dimethylaminomethyl)phenyl, phenyl, 4-(carboxymethylthio)phenyl, 4-(carboxyethylthio)phenyl, 4-(carboxyethyl)phenyl, 4-(carboxypropyl)phenyl, 2-fluorophenyl, 2-pyridyl, N-(4-methylpiperazino)methylphenyl, or
—C(O)—OR$_9$, wherein R$_9$ is —CH$_2$—Ar$_3$ and the Ar$_3$ cyclic group is phenyl;

and when R$_{11}$ is Ar$_4$, wherein the Ar$_4$ cyclic group is 5-(1-phenyl-3-trifluoromethyl)pyrazolyl), then R$_5$ cannot be:
—C(O)—OR$_9$, wherein R$_9$ is —CH$_2$—Ar$_3$, and the Ar$_3$ cyclic group is phenyl;

and when R$_{11}$ is Ar$_4$, wherein the Ar$_4$ cyclic group is 5-(1-(2-pyridyl)-3-trifluoromethyl)pyrazolyl), then R$_5$ cannot be:
—C(O)—R$_{10}$, wherein R$_{10}$ is —Ar$_3$ and the Ar$_3$ cyclic group is 4-(dimethylaminomethyl)phenyl, or
—C(O)—OR$_9$, wherein R$_9$ is —CH$_2$—Ar$_3$, and the Ar$_3$ cyclic group is phenyl, unsubstituted by —Q$_1$,; and when Y$_2$ is O, R$_3$ is —C(O)—CH$_2$—T$_1$—R$_{11}$, T$_1$ is O, and R$_{11}$ is —C(O)—Ar$_4$, wherein the Ar$_4$ cyclic group is 2,5-dichlorophenyl, then R$_5$ cannot be:
—C(O)—R$_{10}$, wherein R$_{10}$ is —Ar$_3$ and the Ar$_3$ cyclic group is 4-(dimethylaminomethyl)phenyl, 4-(N-morpholinomethyl)phenyl, 4-(N-methylpiperazino)methyl)phenyl, 4-(N-(2-methyl)imidazolylmethyl)phenyl, 5-benzimidazolyl, 5-benztriazolyl, N-carboethoxy-5-benztriazolyl, N-carboethoxy-5-benzimidazolyl, or
—C(O)—OR$_9$, wherein R$_9$ is —CH$_2$—Ar$_3$, and the Ar$_3$ cyclic group is phenyl, unsubstituted by —Q$_1$,; and when Y$_2$ is H$_2$, R$_3$ is —C(O)—CH$_2$—T$_1$—R$_{11}$, T$_1$ is O, and R$_{11}$ is —C(O)—Ar$_4$, wherein the Ar$_4$ cyclic group is 2,5-dichlorophenyl, then R$_5$ cannot be:
—C(O)—OR$_9$, wherein R$_9$ is —CH$_2$—Ar$_3$ and the Ar$_3$ cyclic group is phenyl.

In another form of embodiment F, preferred compounds are those wherein R$_{21}$ is —H.

Alternatively, preferred compounds are those wherein R$_{21}$ is —CH$_3$.

Preferred compounds of this embodiment include, but are not limited to:

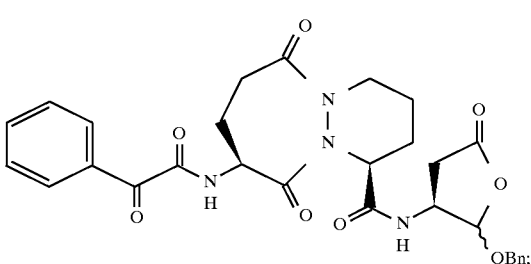

2001

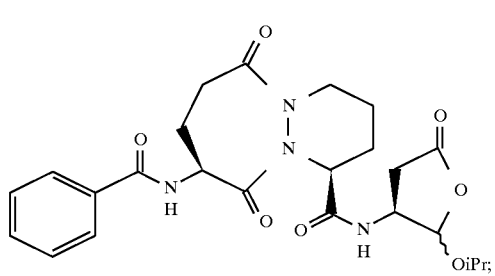

2100a

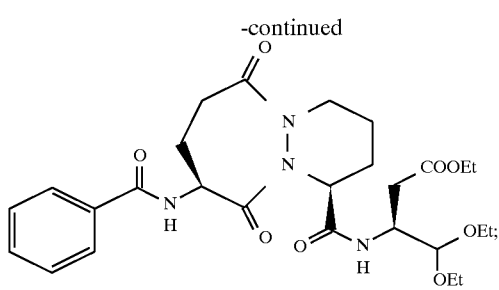

2100b

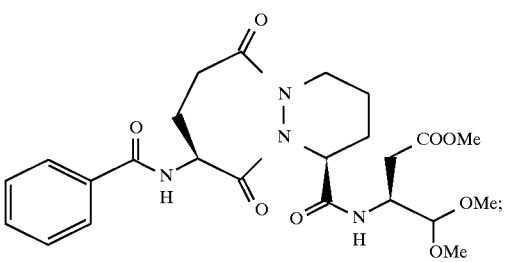

2100c

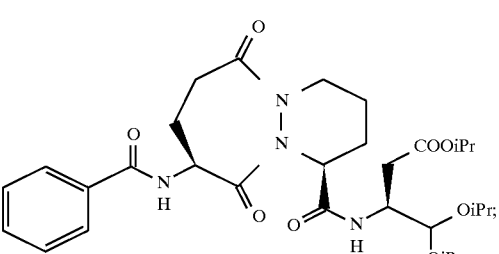

2100d

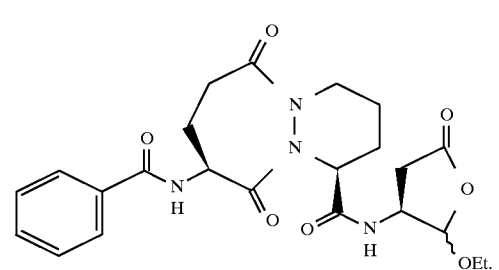

2100e

Preferred compounds of embodiment F employ formula (III), wherein R$_1$ is (w2) and the other substituents are as defined above.

More preferably, R$_1$ is (w2) and
m is 1;
ring C is benzo, pyrido, or thieno;
R$_3$ is selected from the group consisting of —C(O)—H, —C(O)—Ar$_2$, and —C(O)CH$_2$—T$_1$—R$_{11}$;
R$_5$ is selected from the group consisting of:
—C(O)—R$_{10}$, wherein R$_{10}$ is —Ar$_3$;
—C(O)O—R$_9$, wherein R$_9$ is —CH$_2$—Ar$_3$;
—C(O)C(O)—R$_{10}$, wherein R$_{10}$ is —Ar$_3$;
—R$_9$, wherein R$_9$ is a C$_{1-2}$ alkyl group substituted with —Ar$_3$; and
—C(O)C(O)—OR$_{10}$, wherein R$_{10}$ is —CH$_2$Ar$_3$;
T$_1$ is O or S;
R$_6$ is H;
R$_8$ is selected from the group consisting —C(O)—R$_{10}$, —C(O)—CH$_2$—OR$_{10}$, and —C(O)CH$_2$—N(R$_{10}$)(R$_{10}$), wherein R$_{10}$ is H, CH$_3$, or —CH$_2$CH$_3$;
R$_{11}$ is selected from the group consisting of —Ar$_4$, —(CH$_2$)$_{1-3}$—Ar$_4$, and —C(O)—Ar$_4$;
R$_{15}$ is —OH or —OC$_{1-4}$ straight or branched alkyl group optionally substituted with —Ar$_3$, —OH, —OR$_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$Ar_2$ is (hh);

Y is O;

each $Ar_3$ cyclic group is independently selected from the set consisting of phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl, and said cyclic group optionally being singly or multiply substituted by —$Q_1$;

each $Ar_4$ cyclic group is independently selected from the set consisting of phenyl, tetrazolyl, naphthyl, pyridinyl, oxazolyl, pyrimidinyl, or indolyl, said cyclic group optionally being singly or multiply substituted by —$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$N(R_9)(R_{10})$, and $$\begin{array}{c} O \\ / \ \backslash \\ \ \ \ \ CH_2, \\ \backslash \ / \\ O \end{array}$$

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other preferred compounds of embodiment F employ formula (III), wherein $R_1$ is (e11) and the other substituents are as defined above.

Other preferred compounds of embodiment F employ formula (III), wherein $R_1$ is (e12) and the other substituents are as defined above.

Other preferred compounds of embodiment F employ formula (III) wherein $R_1$ is (y1) and the other substituents are as defined above.

Other preferred compounds of embodiment F employ formula (III) wherein $R_1$ is (y2) and the other substituents are as defined above.

Other preferred compounds of embodiment F of employ formula (III) wherein $R_1$ is (z) and the other substituents are as defined above.

Other preferred compounds of embodiment F employ formula (III) wherein $R_1$ is (e10), $X_5$ is CH, and the other substituents are as defined above.

Other preferred compounds of embodiment F employ formula (III) wherein $R_1$ is (e10), $X_5$ is N, and the other substituents are as defined above.

More preferably, in these more preferred compounds, $R_5$ is selected from the group consisting of:

—C(O)—$R_{10}$,

—C(O)O—$R_9$, and

—C(O)—NH—$R_{10}$.

Alternatively, in these more preferred compounds, $R_5$ is selected from the group consisting of:

—$S(O)_2$—$R_9$,

—$S(O)_2$—NH—$R_{10}$,

—C(O)—C(O)—$R_{10}$,

—$R_9$,

—C(O)—C(O)—$OR_{10}$, and

—C(O)C(O)—$N(R_9)(R_{10})$.

Most preferably, in these more preferred compounds, m is 1;

$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by —$Q_1$;

each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$N(R_9)(R_{10})$, and $$\begin{array}{c} O \\ / \ \backslash \\ \ \ \ \ CH_2, \\ \backslash \ / \\ O \end{array}$$

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Preferred components of embodiment (F) include, but are not limited to:

2001

-continued

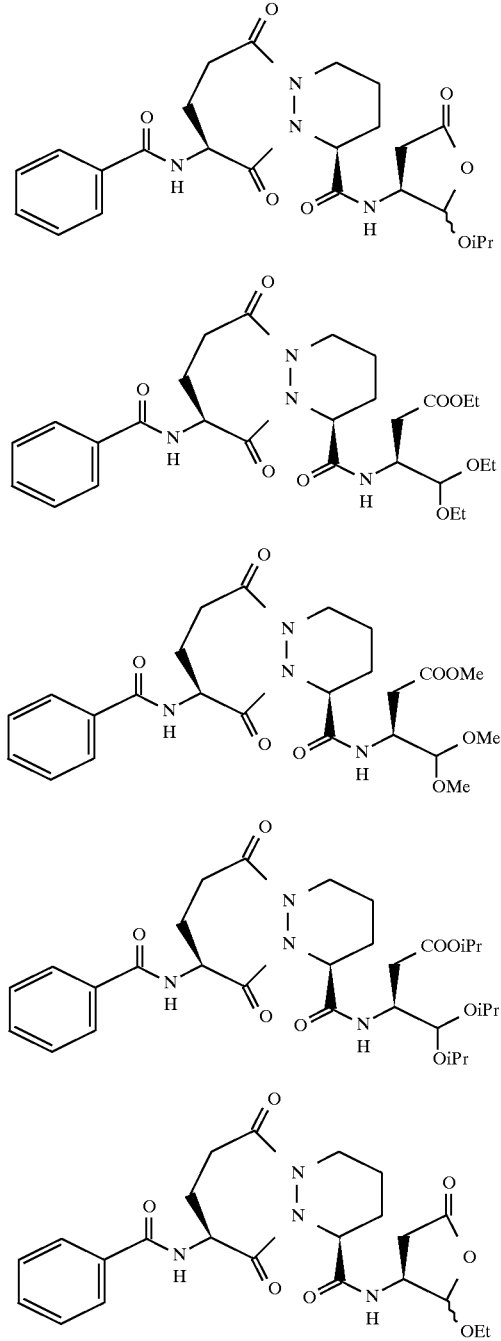

2100a

2100b

2100c

2100d

2100e

The ICE inhibitors of another embodiment (G) of this invention are those of formula (IV):

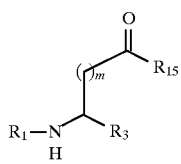

(IV)

wherein:

m is 1 or 2;

R₁ is selected from the group consisting of the following formulae:

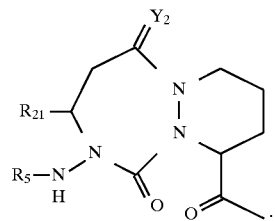

(e10-A)

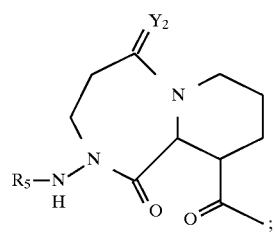

(e11)

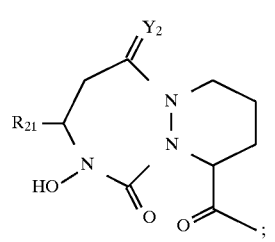

(e12)

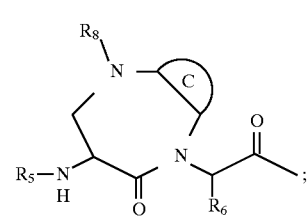

(w2)

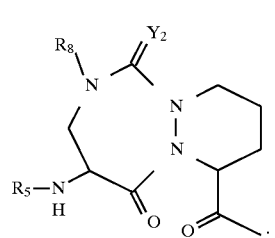

(y1)

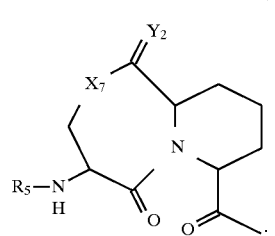

(y2)

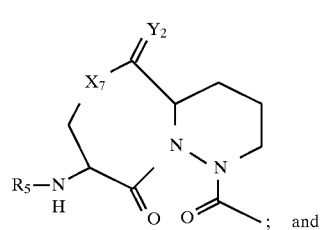

(z)

ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is selected from the group consisting of:
—CN,
—C(O)—H,
—C(O)—CH$_2$—T$_1$—R$_{11}$,
—C(O)—CH$_2$—F,
—C=N—O—R$_9$, and
—CO—Ar$_2$;

each $R_5$ is independently selected from the group consisting of:
—C(O)—R$_{10}$,
—C(O)O—R$_9$,
—C(O)—N(R$_{10}$) (R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H,
—C(O)C(O)—OR$_{10}$, and
—C(O)C(O)—N(R$_9$) (R$_{10}$);

$Y_2$ is H$_2$ or O;

$X_7$ is —N(R$_8$)— or —O—;

each $T_1$ is independently selected from the group consisting of —O—, —S—, —S(O)—, and —S(O)$_2$—;

$R_6$ is selected from the group consisting of —H and —CH$_3$;

$R_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$;
—C(O)—CH$_2$—N(R$_{10}$) (R$_{10}$),
—C(O)—CH$_2$C(O)—O—R$_9$,
—C(O)—CH$_2$C(O)—R$_9$,
—H, and
—C(O)—C(O)—OR$_{10}$;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each $R_{11}$ is independently selected from the group consisting of:
—Ar$_4$,
—(CH$_2$)$_{1-3}$—Ar$_4$,
—H, and
—C(O)—Ar$_4$;

$R_{15}$ is selected from the group consisting of —OH, —OAr$_3$, —N(H)—OH, and —OC$_{1-6}$, wherein C$_{1-6}$ is a straight or branched alkyl group optionally substituted with Ar$_3$, —CONH$_2$, —OR$_5$, —OH, —OR$_9$, or —CO$_2$H;

each $R_{21}$ is independently selected from the group consisting of —H or a —C$_{1-6}$ straight or branched alkyl group;

Ar$_2$ is independently selected from the following group, in which any ring may optionally be singly or multiply substituted by —Q$_1$ or phenyl, optionally substituted by Q$_1$:

(hh) 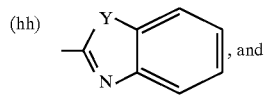, and (ii) 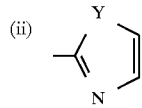

wherein each Y is independently selected from the group consisting of O and S;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by —Q$_1$;

each Ar$_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by —Q$_1$;

each $Q_1$ is independently selected from the group consisting of —NH$_2$, —CO$_2$H, —Cl, —F, —Br, —I, —NO$_2$, —CN, =O, —OH, —perfluoro C$_{1-3}$ alkyl, R$_5$, —OR$_5$, —NHR$_5$, OR$_9$, —N(R$_9$) (R$_{10}$), R$_9$, —C(O)—R$_{10}$, and

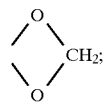

provided that when —Ar$_3$ is substituted with a Q$_1$ group which comprises one or more additional —Ar$_3$ groups, said additional —Ar$_3$ groups are not substituted with another —Ar$_3$;

Preferred compounds of embodiment G employ formula (IV), wherein R$_1$ is (w2) and the other substituents are as defined above.

Preferably, when R$_1$ is (w2)

m is 1;

ring C is benzo, pyrido, or thieno;

$R_5$ is selected from the group consisting of:
—C(O)—R$_{10}$, wherein R$_{10}$ is —Ar$_3$;
—C(O)O—R$_9$, wherein R$_9$ is —CH$_2$—Ar$_3$;
—C(O)C(O)—R$_{10}$, wherein R$_{10}$ is —Ar$_3$;
—R$_9$, wherein R$_9$ is a C$_{1-2}$ alkyl group substituted with —Ar$_3$; and —C(O)C(O)—OR$_{10}$, wherein R$_{10}$ is —CH$_2$Ar$_3$;

R$_6$ is H;

R$_8$ is selected from the group consisting —C(O)—R$_{10}$, —C(O)—CH$_2$—OR$_{10}$, and —C(O)CH$_2$—N(R$_{10}$) (R$_{10}$), wherein R$_{10}$ is H, CH$_3$, or —CH$_2$CH$_3$;

R$_{13}$ is H or a C$_{1-4}$ straight or branched alkyl group optionally substituted with Ar$_3$, —OH, —OR$_9$, —CO$_2$H, wherein the R$_9$ is a C$_{1-4}$ branched or straight chain alkyl group; wherein Ar$_3$ is morpholinyl or phenyl, wherein the phenyl is optionally substituted with Q$_1$;

Ar$_3$ is phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —NHR$_9$, and

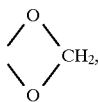

wherein each R$_9$ and R$_{10}$ are independently a —C$_{1-6}$ straight or branched alkyl group optionally substituted with Ar$_3$ wherein Ar$_3$ is phenyl;

provided that when —Ar$_3$ is substituted with a Q$_1$ group which comprises one or more additional —Ar$_3$ groups, said additional —Ar$_3$ groups are not substituted with another —Ar$_3$.

Other preferred compounds of embodiment G employ formula (IV) wherein R$_1$ is (e10-A) and the other substituents are as defined above.

Other preferred compounds of embodiment G employ formula (IV) wherein R$_1$ is (e11) and the other substituents are as defined above.

Other preferred compounds of embodiment G employ formula (IV) wherein R$_1$ is (e12) and the other substituents are as defined above.

Other preferred compounds of embodiment G employ formula (IV) wherein R$_1$ is (y1) and the other substituents are as defined above.

Other preferred compounds of embodiment G employ formula (IV) wherein R$_1$ is (y2) and the other substituents are as defined above.

Other preferred compounds of embodiment G employ formula (IV) wherein R$_1$ is (z) and the other substituents are as defined above.

More preferred compounds of embodiment G are those wherein R$_3$ is —CO—Ar$_2$.

Most preferably, when R$_3$ is —CO—Ar$_2$, Y is O.

Other more preferred compounds are those wherein R$_3$ is —C(O)—CH$_2$—T$_1$—R$_{11}$ and R$_{11}$ is —(CH$_2$)$_{1-3}$—Ar$_4$.

Most preferably, when R$_3$ is —C(O)—CH$_2$—T$_1$—R$_{11}$ and R$_{11}$ is —(CH$_2$)$_{1-3}$—Ar$_4$, T$_1$ is O.

Other more preferred compounds are those wherein:

R$_3$ is —C(O)—CH$_2$—T$_1$—R$_{11}$;

T$_1$ is O; and

R$_{11}$ is —C(O)—Ar$_4$.

Other more preferred compounds are those wherein R$_3$ is —C(O)—H.

Other more preferred compounds are those wherein R$_3$ is —CO—CH$_2$—T$_1$—R$_{11}$ and R$_{11}$ is —Ar$_4$.

More preferably, when R$_3$ is —CO—CH$_2$—T$_1$—R$_{11}$ and R$_{11}$ is —Ar$_4$, T$_1$ is O or S.

More preferably, when R$_1$, is (e11), (e12), (y1), (y2), (z), (e10-A), and (e10-B), R$_5$ is selected from the group consisting of:

—C(O)—R$_{10}$,

—C(O)O—R$_9$, and

—C(O)—NH—R$_{10}$.

Alternatively, when R$_1$, is (e11), (e12), (y1), (y2), (z), (e10-A), and (e10-B), R$_5$ is selected from the group consisting of:

—S(O)$_2$—R$_9$,

—S(O)$_2$—NH—R$_{10}$,

—C(O)—C(O)—R$_{10}$,

—R$_9$,

—C(O)—C(O)—OR$_{10}$, and

—C(O)—C(O)—N(R$_9$) (R$_{10}$).

More preferably, R$_5$ is —C(O)—C(O)—R$_{10}$.

Alternatively, R$_5$ is —C(O)—C(O)—OR$_{10}$.

Most preferably, when R$_1$ is (e11), (e12), (y1), (y2), (z), (e10-A), and (e10-B),:

m is 1;

R$_{21}$ is —H or —CH$_3$;

R$_{51}$ is a C$_{1-6}$ straight or branched alkyl group optionally substituted with Ar$_3$, wherein the Ar$_3$ cyclic group is phenyl, said cyclic group optionally being multiply or singly substituted by —Q$_1$;

each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, or indolyl, and said cyclic group optionally being singly or multiply substituted by —Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$) (R$_{10}$), and

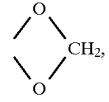

wherein each R$_9$ and R$_{10}$ are independently a —C$_{1-6}$ straight or branched alkyl group optionally substituted with Ar$_3$, wherein the Ar$_3$ cyclic group is phenyl, and said cyclic group optionally being singly or multiply substituted by —Q$_1$;

provided that when —Ar$_3$ is substituted with a —Q$_1$ group which comprises one or more additional —Ar$_3$ groups, said additional —Ar$_3$ groups are not substituted with another —Ar$_3$.

More preferably, in these more preferred compounds, the Ar$_3$ cyclic group is selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, benzofuranyl, and indolyl, and said cyclic group optionally being singly or multiply substituted by —Q$_1$.

Compounds in a preferred form of embodiment G are those wherein R$_{21}$ is H and the other substituents are as defined above.

Compounds in another preferred form of embodiment G are those wherein $R_{21}$ is $CH_3$ and the other substituents are as defined above.

The ICE inhibitors of another embodiment (H) of this invention are those of formula (V):

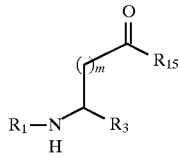

(V)

wherein:

m is 1 or 2;

$R_1$ is:

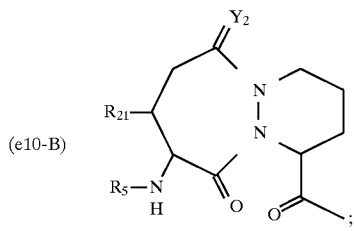

(e10-B)

$R_3$ is selected from the group consisting of:
—CN,
—C(O)—H,
—C(O)—CH$_2$—T$_1$—R$_{11}$,
—C(O)—CH$_2$—F,
—C=N—O—R$_9$, and
—CO—Ar$_2$;

each $R_5$ is independently selected from the group consisting of:
—C(O)—R$_{10}$,
—C(O)O—R$_9$,
—C(O)—N(R$_{10}$) (R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H, and
—C(O)C(O)—N(R$_9$) (R$_{10}$), and
—C(O)C(O)—OR$_{10}$;

$Y_2$ is $H_2$ or O;

each $T_1$ is independently selected from the group consisting of —O—, —S—, —S(O)—, and —S(O)$_2$—;

$R_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$) (R$_{10}$),
—C(O)—CH$_2$C(O)—O—R$_9$,
—C(O)—CH$_2$C(O)—R$_9$,
—H, and
—C(O)—C(O)—OR$_{10}$;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each $R_{11}$ is independently selected from the group consisting of:
—Ar$_4$,
—(CH$_2$)$_{1-3}$—Ar$_4$,
—H, and
—C(O)—Ar$_4$;

$R_{15}$ is selected from the group consisting of —OH, —OAr$_3$, —N(H)—OH, and —OC$_{1-6}$, wherein C$_{1-6}$ is a straight or branched alkyl group optionally substituted with Ar$_3$, —CONH$_2$, —OR$_5$, —OH, —OR$_9$, or —CO$_2$H;

$R_{21}$ is —CH$_3$;

Ar$_2$ is independently selected from the following group, in which any ring may optionally be singly or multiply substituted by —Q$_1$ or phenyl, optionally substituted by Q$_1$:

(hh) 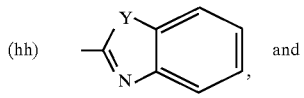 and (ii) 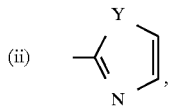, wherein each Y is independently selected from the group consisting of O and S;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by —Q$_1$;

each Ar$_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by —Q$_1$;

each Q$_1$ is independently selected from the group consisting of —NH$_2$, —CO$_2$H, —Cl, —F, —Br, —I, —NO$_2$, —CN, =O, —OH, —perfluoro C$_{1-3}$ alkyl, R$_5$, —OR$_5$, —NHR$_5$, OR$_9$, —N(R$_9$) (R$_{10}$), R$_9$, —C(O)—R$_{10}$, and

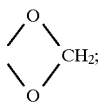

provided that when —Ar₃ is substituted with a Q₁ group which comprises one or more additional —Ar₃ groups, said additional —Ar₃ groups are not substituted with another —Ar₃;

Compounds of another form of embodiment (I) (form 1) are those of formula (V):

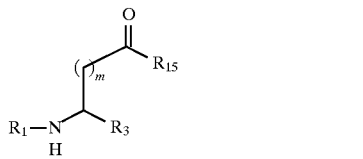

wherein:
m is 1 or 2;
R₁ is:

(e10-B) 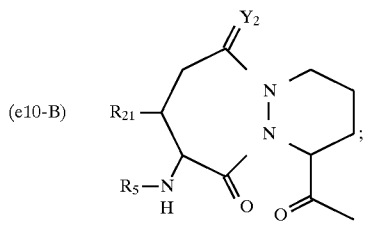

R₃ is selected from the group consisting of:
—CN,
—C(O)—H,
—C(O)—CH₂—T₁—R₁₁,
—C(O)—CH₂—F,
—C=N—O—R₉, and
—CO—Ar₂;

each R₅ is —C(O)C(O)—OR₁₀;
Y₂ is H₂ or O;
each T₁ is independently selected from the group consisting of —O—, —S—, —S(O)—, and —S(O)₂—;
R₈ is selected from the group consisting of:
—C(O)—R₁₀,
—C(O)O—R₉,
—C(O)—NH—R₁₀,
—S(O)₂—R₉,
—S(O)₂—NH—R₁₀,
—C(O)—CH₂—OR₁₀,
—C(O)C(O)—R₁₀,
—C(O)—CH₂—N(R₁₀)(R₁₀),
—C(O)—CH₂C(O)—O—R₉,
—C(O)—CH₂C(O)—R₉,
—H, and
—C(O)—C(O)—OR₁₀;

each R₉ is independently selected from the group consisting of —Ar₃ and a —C₁₋₆ straight or branched alkyl group optionally substituted with Ar₃, wherein the —C₁₋₆ alkyl group is optionally unsaturated;

each R₁₀ is independently selected from the group consisting of —H, —Ar₃, a C₃₋₆ cycloalkyl group, and a —C₁₋₆ straight or branched alkyl group optionally substituted with Ar₃, wherein the —C₁₋₆ alkyl group is optionally unsaturated;

each R₁₁ is independently selected from the group consisting of:
—Ar₄,
—(CH₂)₁₋₃—Ar₄,
—H, and
—C(O)—Ar₄;

R₁₅ is selected from the group consisting of —OH, —OAr₃, —N(H)—OH, and —OC₁₋₆, wherein C₁₋₆ is a straight or branched alkyl group optionally substituted with Ar₃, —CONH₂, —OR₅, —OH, —OR₉, or —CO₂H;

each R₂₁ is independently selected from the group consisting of —H or a —C₁₋₆ straight or branched alkyl group;

Ar₂ is independently selected from the following group, in which any ring may optionally be singly or multiply substituted by —Q₁ or phenyl, optionally substituted by Q₁:

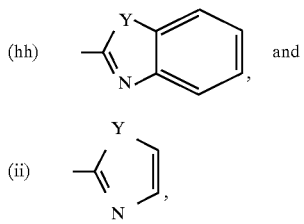

wherein each Y is independently selected from the group consisting of O and S;

each Ar₃ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO₂, =N—, and —NH—, —N(R₅)—, and —N(R₉)— said heterocycle group optionally containing one or more double bonds, said heterocycle group optionally comprising one or more aromatic rings, and said cyclic group optionally being singly or multiply substituted by —Q₁;

each Ar₄ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO₂, =N—, —NH—, —N(R₅)—, and —N(R₉)— said heterocycle group optionally containing one or more double bonds, said heterocycle group optionally comprising one or more aromatic rings, and said cyclic group optionally being singly or multiply substituted by —Q₁;

each Q₁ is independently selected from the group consisting of —NH₂, —CO₂H, —Cl, —F, —Br, —I, —NO₂, —CN, =O, —OH, —perfluoro C₁₋₃ alkyl, R₅, —OR₅, —NHR₅, OR₉, —N(R₉)(R₁₀), R₉, —C(O)—R₁₀, and

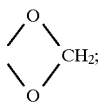

provided that when —Ar$_3$ is substituted with a Q$_1$ group which comprises one or more additional —Ar$_3$ groups, said additional —Ar$_3$ groups are not substituted with another —Ar$_3$;

Alternatively, compounds of this form of embodiment I (form 2) are those wherein R$_{21}$ is —CH$_3$.

Compounds of another form of embodiment (J) (form 1) are those of formula (V):

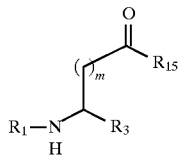

(V)

wherein:
m is 1 or 2;
R$_1$ is:

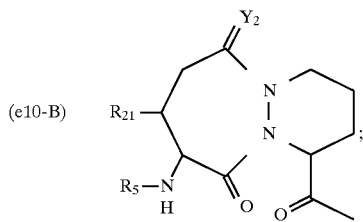

(e10-B)

R$_3$ is selected from the group consisting of:
—CN,
—C(O)—H,
—C(O)—CH$_2$—T$_1$—R$_{11}$,
—C(O)—CH$_2$—F,
—C=N—O—R$_9$, and
—CO—Ar$_2$;

each R$_5$ is independently selected from the group consisting of:
—C(O)—R$_{10}$,
—C(O)O—R$_9$,
—C(O)—N(R$_{10}$) (R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H,
—C(O)C(O)—OR$_{10}$, and
—C(O)C(O)—N(R$_9$) (R$_{10}$);
Y$_2$ is H$_2$ or O;

each T$_1$ is independently selected from the group consisting of —O—, —S—, —S(O)—, and —S(O)$_2$—;

R$_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$) (R$_{10}$),
—C(O)—CH$_2$C(O)—O—R$_9$,
—C(O)—CH$_2$C(O)—R$_9$,
—H,
—C(O)—C(O)—OR$_{10}$, and
—C(O)—C(O)—N(R$_9$) (R$_{10}$);

each R$_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each R$_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each R$_{11}$ is independently selected from the group consisting of:
—Ar$_4$,
—(CH$_2$)$_{1-3}$—Ar$_4$,
—H, and
—C(O)—Ar$_4$;

R$_{15}$ is selected from the group consisting of —OH, —OAr$_3$, —N(H)—OH, and —OC$_{1-6}$, wherein C$_{1-6}$ is a straight or branched alkyl group optionally substituted with Ar$_3$, —CONH$_2$, —OR$_5$, —OH, —OR$_9$, or —CO$_2$H;

each R$_{21}$ is independently selected from the group consisting of —H or a —C$_{1-6}$ straight or branched alkyl group;

Ar$_2$ is independently selected from the following group, in which any ring may optionally be singly or multiply substituted by —Q$_1$ or phenyl, optionally substituted by Q$_1$:

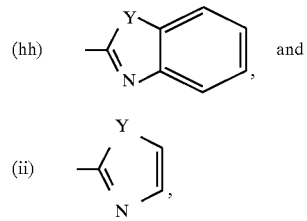

(hh)

and (ii)

wherein each Y is independently selected from the group consisting of O and S;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by —Q$_1$;

each Ar$_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N($R_5$)—, and —N($R_9$)— said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —$NH_2$, —$CO_2H$, —Cl, —F, —Br, —I, —$NO_2$, —CN, =O, —OH, —perfluoro $C_{1-3}$ alkyl, $R_5$, —$OR_5$, —$NHR_5$, $OR_9$, —N($R_9$) ($R_{10}$), $R_9$, —C(O)—$R_{10}$, and

provided that when —$Ar_3$ is substituted with a $Q_1$ group which comprises one or more additional —$Ar_3$ groups, said additional —$Ar_3$ groups are not substituted with another —$Ar_3$;

provided that when:
m is 1;
$R_1$ is (e10)
$X_5$ is CH;
$R_{15}$ is —OH;
$R_{21}$ is —H; and
$Y_2$ is O and $R_3$ is —C(O)—H, then $R_5$ cannot be:
—C(O)—$R_{10}$, wherein $R_{10}$ is —$Ar_3$ and the $Ar_3$ cyclic group is phenyl, unsubstituted by —$Q_1$, 4-(carboxymethoxy)phenyl, 2-fluorophenyl, 2-pyridyl, N-(4-methylpiperazino)methylphenyl, or
—C(O)—$OR_9$, wherein $R_9$ is —$CH_2$—$Ar_3$, and the $Ar_3$ cyclic group is phenyl, unsubstituted by —$Q_1$;; and when
$Y_2$ is O, $R_3$ is —C(O)—$CH_2$—$T_1$—$R_{11}$, $T_1$ is O, and $R_{11}$ is $Ar_4$, wherein the $Ar_4$ cyclic group is 5-(1-(4-chlorophenyl)-3-trifluoromethyl)pyrazolyl), then $R_5$ cannot be:
—C(O)—$R_{10}$, wherein $R_{10}$ is —$Ar_3$ and the $Ar_3$ cyclic group is 4-(dimethylaminomethyl)phenyl, phenyl, 4-(carboxymethylthio)phenyl, 4-(carboxyethylthio) phenyl, 4-(carboxyethyl)phenyl, 4-(carboxypropyl) phenyl, 2-fluorophenyl, 2-pyridyl, N-(4-methylpiperazino)methylphenyl, or
—C(O)—$OR_9$, wherein $R_9$ is —$CH_2$—$Ar_3$ and the $Ar_3$ cyclic group is phenyl;

and when $R_{11}$ is $Ar_4$, wherein the $Ar_4$ cyclic group is 5-(1-phenyl-3-trifluoromethyl)pyrazolyl), then $R_5$ cannot be:
—C(O)—$OR_9$, wherein $R_9$ is —$CH_2$—$Ar_3$, and the $Ar_3$ cyclic group is phenyl;

and when $R_{11}$ is $Ar_4$, wherein the $Ar_4$ cyclic group is 5-(1-(2-pyridyl)-3-trifluoromethyl)pyrazolyl), then $R_5$ cannot be:
—C(O)—$R_{10}$, wherein $R_{10}$ is —$Ar_3$ and the $Ar_3$ cyclic group is 4-(dimethylaminomethyl)phenyl, or
—C(O)—$OR_9$, wherein $R_9$ is —$CH_2$—$Ar_3$, and the $Ar_3$ cyclic group is phenyl, unsubstituted by —$Q_1$;; and when
$Y_2$ is O, $R_3$ is —C(O)—$CH_2$—$T_1$—$R_{11}$, $T_1$ is O, and $R_{11}$ is —C(O)—$Ar_4$, wherein the $Ar_4$ cyclic group is 2,5-dichiorophenyl, then $R_5$ cannot be:
—C(O)—$R_{10}$, wherein $R_{10}$ is —$Ar_3$ and the $Ar_3$ cyclic group is 4-(dimethylaminomethyl)phenyl, 4-(N-morpholinomethyl)phenyl, 4-(N-methylpiperazino) methyl)phenyl, 4-(N-(2-methyl)imidazolylmethyl) phenyl, 5-benzimidazolyl, 5-benztriazolyl, N-carboethoxy-5-benztriazolyl, N-carboethoxy-5-benzimidazolyl, or —C(O)—$OR_9$, wherein $R_9$ is —$CH_2$—$Ar_3$, and the $Ar_3$ cyclic group is phenyl, unsubstituted by —$Q_1$;; and when
$Y_2$ is $H_2$, $R_3$ is —C(O)—$CH_2$—$T_1$—$R_{11}$, $T_1$ is O, and $R_1$, is —C(O)—$Ar_4$, wherein the $Ar_4$ cyclic group is 2,5-dichiorophenyl, then $R_5$ cannot be:
—C(O)—$OR_9$, wherein $R_9$ is —$CH_2$—$Ar_3$ and the $Ar_3$ cyclic group is phenyl.

Compounds of another form of embodiment J (form 2) are those wherein $R_{21}$ is —$CH_3$.

Compounds of another form of embodiment J (form 3) are those wherein $R_5$ is —C(O) —C(O)—$OR_{10}$.

Compounds of another form of embodiment J (form 4) are those wherein $R_5$ is —C(O)—C(O)—$OR_{10}$ and $R_{21}$ is —$CH_3$.

Preferred compounds of embodiments H, I, and J employ formula (V), wherein $R_3$ is —CO—$Ar_2$.

More preferably, when $R_3$ is —CO—$Ar_2$ Y is O.

Preferred compounds of embodiments H, I, and J employ formula (V), wherein $R_3$ is —C(O)—$CH_2$—$T_1$—$R_{11}$ and $R_{11}$ is —$(CH_2)_{1-3}$—$Ar_4$.

More preferably, when $R_3$ is —C(O)—$CH_2$—$T_1$—$R_{11}$ and $R_{11}$ is —$(CH_2)_{1-3}$—$Ar_4$, $T_1$ is O.

Preferred compounds of embodiments H, I, and J employ formula (V), wherein $R_3$ is —C(O)—$CH_2$—$T_1$—$R_{11}$, $T_1$ is O, and $R_{11}$ is —C(O)—Ar.

Preferred compounds of embodiments H, I, and J employ formula (V), wherein $R_3$ is —C(O)—H.

Preferred compounds of embodiments H, I, and J employ formula (V), wherein $R_3$ is —CO—$CH_2$—$T_1$—$R_{11}$ and $R_{11}$ is —$Ar_4$.

More preferably, when $R_3$ is —CO—$CH_2$—$T_1$—$R_{11}$ and $R_{11}$ is —$Ar_4$, T, is O or S.

More preferred compounds of embodiments H and J (forms 1 and 2) are those wherein $R_5$ is selected from the group consisting of:
—C(O)—$R_{10}$,
—C(O)O—$R_9$, and
—C(O)—NH—$R_{10}$.

Alternatively, more preferred compounds of embodiments H and J (forms 1 and 2) are those wherein $R_5$ is selected from the group consisting of:
—S(O)$_2$—$R_9$,
—S(O)$_2$—NH—$R_{10}$,
—C(O)—C(O)—$R_{10}$,
—$R_9$,
—C(O)—C(O)—$OR_{10}$, and
—C(O)—C(O)—N($R_9$) ($R_{10}$).

Most preferably, $R_5$ is —C(O)—C(O)—$R_{10}$.
Alternatively, $R_5$ is —C(O)—C(O)—$OR_{10}$.

More preferred compounds of embodiments H, I (form 2), and J (forms 2 and 4) are those wherein:
m is 1;
$Y_2$ is O;
$R_{15}$ is —OH or —$OC_{1-4}$ straight or branched alkyl group optionally substituted with $Ar_3$, —OH, —$OR_9$, —$CO_2H$, wherein the $R_9$ is a $C_{14}$ branched or straight chain alkyl group; wherein $Ar_3$ is morpholinyl or phenyl, wherein the phenyl is optionally substituted with $Q_1$;
$Ar_2$ is (hh);
Y is O, and
each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —Q$_1$;

each Ar$_4$ cyclic group is independently selected from the group consisting of phenyl, tetrazolyl, pyridyl, oxazolyl, naphthyl, pyrimidinyl, and thienyl, and said cyclic group optionally being singly or multiply substituted by —Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O) —R$_{10}$, —OR$_9$, —N (R$_9$) (R$_{10}$), and

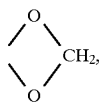

wherein each R$_9$ and R$_{10}$ are independently a —C$_{1-6}$ straight or branched alkyl group optionally substituted with Ar$_3$ wherein the Ar$_3$ cyclic group is phenyl, and said cyclic group optionally being singly or multiply substituted by —Q$_1$;

provided that when —Ar$_3$ is substituted with a Q$_1$ group which comprises one or more additional —Ar$_3$ groups, said additional —Ar$_3$ groups are not substituted with another —Ar$_3$.

More preferred compounds of embodiments I (form 1), and J (form 3) are those wherein:

m is 1;

R$_{21}$ is —H or —CH$_3$;

R$_{51}$ is a C$_{1-6}$ straight or branched alkyl group optionally substituted with Ar$_3$, wherein the Ar$_3$ cyclic group is phenyl, said cyclic group optionally being multiply or singly substituted by —Q$_1$;

each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, or indolyl, and said cyclic group optionally being singly or multiply substituted by —Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$) (R$_{10}$), and

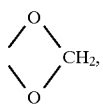

wherein each R$_9$ and R$_{10}$ are independently a —C$_{1-6}$ straight or branched alkyl group optionally substituted with Ar$_3$, wherein the Ar$_3$ cyclic group is phenyl, and said cyclic group optionally being singly or multiply substituted by —Q$_1$;

provided that when —Ar$_3$ is substituted with a —Q$_1$ group which comprises one or more additional —Ar$_3$ groups, said additional —Ar$_3$ groups are not substituted with another —Ar$_3$.

Preferably, in these more preferred compounds the Ar$_3$ cyclic group is selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, benzofuranyl, and indolyl, and said cyclic group optionally being singly or multiply substituted by —Q$_1$.

Preferred compounds of embodiments H, and J (forms 1 and 1) are those wherein:

R$_3$ is —C(O)—CH$_2$—T$_1$—R$_{11}$;

T$_1$ is O; and

R$_{11}$ is —C(O)—Ar$_4$, wherein the Ar$_4$ cyclic group is selected from the set consisting of tetrazolyl, pyridyl, oxazolyl, pyrimidinyl, and thienyl, and said cyclic group optionally being singly or multiply substituted by —Q$_1$.

Preferred compounds of embodiments H, I, and J employ formula (V), wherein R$_3$ is —CO—CH$_2$—T$_1$—R$_{11}$, R$_{11}$ is —Ar$_4$, wherein the Ar$_4$ cyclic group is pyridyl, and said cyclic group optionally being singly or multiply substituted by —Q$_1$.

Preferred compounds of embodiment J (form 1) are those wherein:

R$_3$ is —C(O)—H, and

R$_5$ is —C(O)—R$_{10}$, wherein:

R$_{10}$ is Ar$_3$1 wherein the Ar$_3$ cyclic group is phenyl optionally being singly or multiply substituted by:

—F,

—Cl,

—N(H)—R$_5$, wherein —R$_5$ is —H or —C(O) —R$_{10}$, wherein R$_{10}$ is a —C$_{1-6}$ straight or branched alkyl group optionally substituted with Ar$_3$, wherein Ar$_3$ is phenyl, —N(R$_9$) (R$_{10}$), wherein R$_9$ and R$_{10}$ are independently a —C$_{1-4}$ straight or branched alkyl group, or —O—R$_5$, wherein R$_5$ is H or a —C$_{14}$ straight or branched alkyl group.

More preferably, Ar$_3$ is phenyl being optionally singly or multiply substituted at the 3- or 5-position by —Cl or at the 4-position by —NH—R$_5$, —N(R$_9$) (R$_{10}$), or O—R$_5$.

Other more preferred compounds of embodiment J (form 1) are those wherein:

R$_3$ is —C(O)—H;

R$_5$ is —C(O)—R$_{10}$, wherein R$_{10}$ is Ar$_3$ and the Ar$_3$ cyclic group is selected from the group consisting of is indolyl, benzimidazolyl, thienyl, and benzo[b]thiophenyl, and said cyclic group optionally being singly or multiply substituted by —Q$_1$;

Other more preferred compounds of embodiment J (form 1) are those wherein:

R$_3$ is —C(O)—H;

R$_5$ is —C(O)—R$_{10}$, wherein R$_{10}$ is Ar$_3$ and the Ar$_3$ cyclic group is selected from quinolyl and isoquinolyl, and said cyclic group optionally being singly or multiply substituted by —Q$_1$.

Other more preferred compounds of embodiment J (form 1) are those wherein:

R$_3$ is —C(O)—H;

R$_5$ is —C(O)—R$_{10}$, wherein R$_{10}$ is Ar$_3$ and the Ar$_3$ cyclic group is phenyl, substituted by

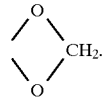

Preferred compounds of embodiment (J) include, but are not limited to:

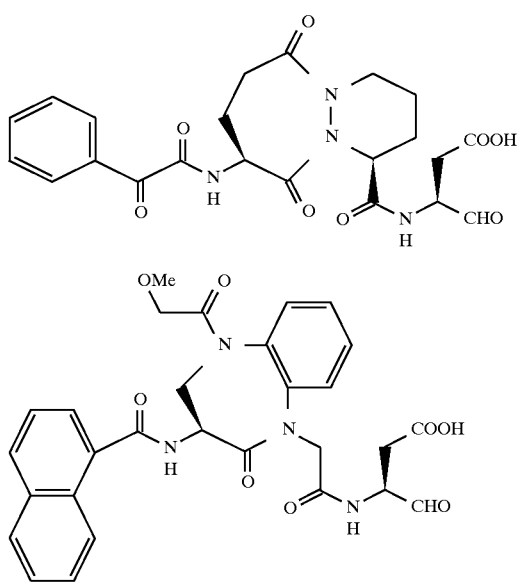

The compounds of this invention have a molecular weight of less than or equal to about 700 Daltons, and more preferably between about 400 and 600 Daltons. These preferred compounds may be readily absorbed by the bloodstream of patients upon oral administration. This oral availability makes such compounds excellent agents for orally-administered treatment and prevention regimens against IL-1 or apoptosis-mediated diseases.

The ICE inhibitors of this invention may be synthesized using conventional techniques. Advantageously, these compounds are conveniently synthesized from readily available starting materials.

The compounds of this invention are among the most readily synthesized ICE inhibitors known. Previously described ICE inhibitors often contain four or more chiral centers and numerous peptide linkages. The relative ease with which the compounds of this invention can be synthesized represents an advantage in the large scale production of these compounds.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups in $R_3$ and carboxylic acid groups in T, may take hemi-ketal (or hemi-acetal) or hydrated forms. For example, compounds of embodiment (A) may take the forms depicted below:

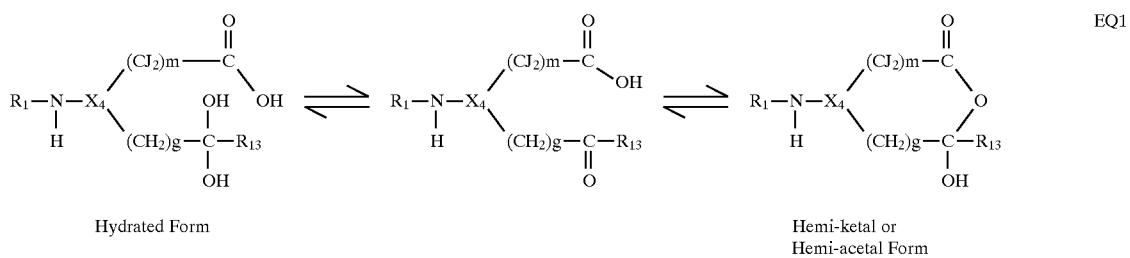

Depending on the choice of solvent and other conditions known to the practitioner skilled in the art, compounds of this invention may also take acyloxy ketal, acyloxy acetal, ketal or acetal form:

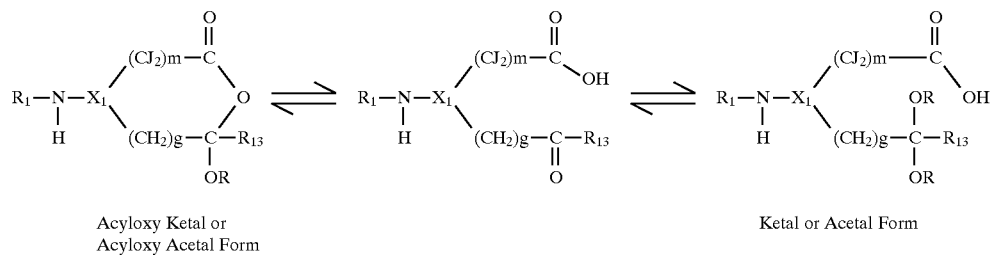

In addition, it should be understood that the equilibrium forms of the compounds of this invention may include tautomeric forms. All such forms of these compounds are expressly included in the present invention.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Such pro-drug forms typically demonstrate little or no activity in in vitro assays. Some examples of pro-drug forms include ketal, acetal, oxime, and hydrazone forms of compounds which contain ketone or aldehyde groups, especially where they occur in the $R_3$ group of the compounds of this invention. Other examples of pro-drug forms include the hemi-ketal, hemi-acetal, acyloxy ketal, acyloxy acetal, ketal, and acetal forms that are described in EQ1 and EQ2.

The compounds of this invention are excellent ligands for ICE. Accordingly, these compounds are capable of targeting and inhibiting events in IL-1 and apoptosis-mediated diseases, and, thus, the ultimate activity of that protein in inflammatory diseases, autoimmune diseases, proliferative disorders, infectious diseases, and degenerative diseases. For example, the compounds of this invention inhibit the conversion of precursor IL-1β to mature IL-1β by inhibiting ICE. Because ICE is essential for the production of mature IL-1, inhibition of that enzyme effectively blocks initiation of IL-1-mediated physiological effects and symptoms, such as inflammation, by inhibiting the production of mature IL-1. Thus, by inhibiting IL-1β precursor activity, the compounds of this invention effectively function as IL-1 inhibitors.

The compounds of this invention may be employed in a conventional manner for the treatment of diseases which are mediated by IL-1 or apoptosis. Such methods of treatment, their dosage levels and requirements may be selected by those of ordinary skill in the art from available methods and techniques. For example, a compound of this invention may be combined lo with a pharmaceutically acceptable adjuvant for administration to a patient suffering from an IL-1- or apoptosis-mediated disease in a pharmaceutically acceptable manner and in an amount effective to lessen the severity of that disease.

Alternatively, the compounds of this invention may be used in compositions and methods for treating or protecting individuals against IL-1- or apoptosis-mediated diseases over extended periods of time. The compounds may be employed in such compositions either alone or together with other compounds of this invention in a manner consistent with the conventional utilization of ICE inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1- or apoptosis-mediated diseases.

The compounds of this invention may also be co-administered with other ICE inhibitors to increase the effect of therapy or prophylaxis against various IL-1- or apoptosis-mediated diseases.

In addition, the compounds of this invention may be used in combination either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM—CSF, methionine enkephalin, interferon alpha, diethyldithiocarbamate, tumor necrosis factor, naltrexone and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of an ICE inhibitor of this invention and another therapeutic or prophylactic agent.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in *Ph. Helv* (*Pharmacoplia Halselica*) or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 1 and 50 mg/kg body weight per day of the active ingredient compound are useful in the prevention and treatment of IL-1- and apoptosis-mediated diseases, including inflammatory diseases, autoimmune diseases, proliferative disorders, infectious diseases, degenerative diseases, necrotic diseases, osteoarthritis, acute pancreatitis, chronic pancreatitis, asthma, adult respiratory distress syndrome, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, graft vs. host disease, osteoporosis, multiple myeloma-related bone disorder, acute myelogenous leukemia, chronic myelogenous leukemia, metastatic melanoma, Kaposi's sarcoma, multiple myeloma sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke. Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The IL-1 mediated diseases which may be treated or prevented by the compounds of this invention include, but are not limited to, inflammatory diseases, autoimmune diseases, proliferative disorders, infectious diseases, and degenerative diseases. The apoptosis-mediated diseases which may be treated or prevented by the compounds of this invention include degenerative diseases.

Inflammatory diseases which may be treated or prevented include, but are not limited to osteoarthritis, acute pancreatitis, chronic pancreatitis, asthma, and adult respiratory distress syndrome. Preferably the inflammatory disease is osteoarthritis or acute pancreatitis.

Autoimmune diseases which may be treated or prevented include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, and graft vs. host disease. Preferably the autoimmune disease is rheumatoid arthritis, inflammatory bowel disease, Crohn's disease, or psoriasis, Destructive bone disorders which may be treated or prevented include, but are not limited to, osteoporosis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Infectious diseases which may be treated or prevented include, but are not limited to, sepsis, septic shock, and Shigellosis.

The IL-1-mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

The apoptosis-mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Although this invention focuses on the use of the compounds disclosed herein for preventing and treating IL-1 and apoptosis-mediated diseases, the compounds of this invention can also be used as inhibitory agents for other cysteine proteases.

The compounds of this invention are also useful as commercial reagents which effectively bind to ICE or other cysteine proteases. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cystine protease inhibitors will be evident to those of ordinary skill in the art.

In order that this invention be more fully understood, the following examples are set forth. These examples are for the purpose of illustration only and are not to be construed as limiting the scope of the invention in any way.

EXAMPLE 1

Inhibition of ICE

We obtained inhibition constants ($K_i$) and $IC_{50}$ values for compounds of this invention using the three methods described below:

1. Enzyme assay with UV-visible substrate This assay is run using an Succinyl-Tyr-Val-Ala-Asp-pNitroanilide substrate. Synthesis of analogous substrates is described by L. A. Reiter (Int. J. Peptide Protein Res. 43, 87–96 (1994)). The assay mixture contains:

65 μl buffer (10 mM Tris, 1 mM DTT, 0.1% CHAPS @pH 8.1)

10 μl ICE (50 nN final concentration to give a rate of ~1 mOD/min)

5 μl DMSO/Inhibitor mixture

20 μl 400 μM Substrate (80 μM final concentration)

100μl total reaction volume

The visible ICE assay is run in a 96-well microtiter plate. Buffer, ICE and DMSO (if inhibitor is present) are added to the wells in the order listed. The components are left to incubate at room temperature for 15 minutes starting at the time that all components are present in all wells. The microtiter plate reader is set to incubate at 37° C. After the 15 minute incubation, substrate is added directly to the wells and the reaction is monitored by following the release of the chromophore (pNA) at 405–603 nm at 37° C. for 20 minutes. A linear fit of the data is performed and the rate is calculated in mOD/min. DMSO is only present during experiments involving inhibitors, buffer is used to make up the volume to 100 μl in the other experiments.

2. Enzyme Assay with Fluorescent Substrate

This assay is run essentially according to Thornberry et al. (Nature 356: 768–774 (1992)), using substrate 17 referenced in that article. The substrate is: Acetyl-Tyr-Val-Ala-Asp-amino-4-methylcoumarin (AMC). The following components are mixed:

65 μl buffer(10 mM Tris,1 mM DTT, 0.1% CHAPS @pH8.1)

10 μl ICE (2–10 nM final concentration)

5 μl DMSO/inhibitor solution

20 μl 150 μM Substrate (30 μM final)

100 μl total reaction volume

The assay is run in a 96 well microtiter plate. Buffer and ICE are added to the wells. The components are left to incubate at 37° C. for 15 minutes in a temperature-controlled wellplate. After the 15 minute incubation, the reaction is started by adding substrate directly to the wells and the reaction is monitored @37° C. for 30 minutes by following the release of the AMC fluorophore using an excitation wavelength for 380 nm and an emission wavelength of 460 nm. A linear fit of the data for each well is performed and a rate is determined in fluorescence units per second.

For determination of enzyme inhibition constants ($K_i$) or the mode of inhibition (competitive, uncompetitive or noncompetitive), the rate data determined in the enzyme assays at varying inhibitor concentrations are computer-fit to standard enzyme kinetic equations (see I. H. Segel, *Enzyme Kinetics,* Wiley-Interscience, 1975).

The determination of second order rate constants for irreversible inhibitors was performed by fitting the fluorescence vs time data to the progress equations of Morrison. Morrison, J. F., *Mol. Cell. Biophys.,* 2, pp. 347–368 (1985). Thornberry et al. have published a description of these methods for measurement of rate constants of irreversible inhibitors of ICE. Thornberry, N. A., et al. *Biochemistry,* 33, pp. 3923–3940 (1994). For compounds where no prior complex formation can be observed kinetically, the second order rate constants ($k_{inact}$) are derived directly from the slope of the linear plots of $k_{obs}$ vs. [I]. For compounds where prior complex formation to the enzyme can be detected, the hyperbolic plots of $k_{obs}$ vs. [I] are fit to the equation for saturation kinetics to first generate $K_i$ and k'. The second order rate constant $k_{inact}$ is then given by k'/$K_i$.

3. PBMC Cell assay

IL-1β Assay with a Mixed Population of Human Peripheral Blood Mononuclear Cells (PBMC) or Enriched Adherent Mononuclear Cells Processing of pre-IL-1β by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4x the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

Generally 5–6 compound dilutions are tested and the cellular component of the assay is performed in duplicate, with duplicate ELISA determinations on each cell culture supernatant.

PBMC Isolation and IL-1 Assay

Buffy coat cells isolated from one pint human blood (yielding 40–45 ml final volume plasma plus cells) are diluted with media to 80 ml and LeukoPREP separation tubes (Becton Dickinson) are each overlaid with 10 ml of cell suspension. After 15 min centrifugation at 1500–1800 xg, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300 xg for 15 min. Resuspend the PBMC pellet in a small volume of media, count cells and adjust to $6 \times 10^6$ cells/ml.

For the cellular assay, 1.0 ml of the cell suspension is added to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16–18 hr at 37° C. in the presence of 5% $CO_2$.

At the end of the incubation period, cells are harvested and transferred to 15 ml conical centrifuge tubes. After centrifugation for 10 min at 200 xg, supernatants are harvested and transferred to 1.5 ml Eppendorf tubes. It may be noted that the cell pellet may be utilized for a biochemical evaluation of pre-IL-1β and/or mature IL-1β content in cytosol extracts by western blotting or ELISA with pre-IL-1β specific antisera.

Isolation of Adherent Mononuclear cells

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5–3.0 \times 10^5$ cells per well. The addition of test compounds, LPS, cell incubation conditions and processing of supernatants proceeds as described above.

ELISA

We have used Quantikine kits (R&D Systems) for measurement of mature IL-1β. Assays are performed according to the manufacturer's directions. Mature IL-1β levels of about 1–3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

EXAMPLE 2

Pharmacokinetic Studies in the Mouse

Peptidyl ICE inhibitors are cleared rapidly with clearance rates greater than 100 ml/min/kg. Compounds with lower clearance rates have improved pharmacokinetic properties relative to peptidyl ICE inhibitors.

We obtained the rate of clearance in the mouse (ml/min/kg) for several compounds of this invention using the method described below:

Sample Preparation and Dosing

Compounds were dissolved in sterile TRIS solution (0.02M or 0.05M) at a concentration of 2.5 mg/ml. Where necessary to ensure a complete solution, the sample was first dissolved in a minimum of dimethylacetamide (maximum of 5% of total solution volume) then diluted with the TRIS solution.

The drug solution was administered to CD-1 mice (Charles River Laboratories—26–31 g) via the tail vein at a dose volume of 10 ml/kg giving a drug dose of 25 mg/kg.

Mice were dosed in groups of 5 for each timepoint (generally from 2 minutes to 2 hours) then at the appropriate time the animals were anaesthetised with halothane and the blood collected into individual heparinized tubes by jugular severance. The blood samples were cooled to 0° C. then the plasma separated and stored at −20° C. until assayed.

Bioassay

Drug concentration in the plasma samples were determined by HPLC analysis with UV or MS (ESP) detection. Reverse phase chromatography was employed using a variety of bonded phases from C1 to C18 with eluents composed of aqueous buffer/acetonitrile mixtures run under isocratic conditions.

Quantitation was by external standard methods with calibration curves constructed by spiking plasma with drug solutions to give concentrations in the range of 0.5 to 50 µg/ml.

Prior to analysis the plasma samples were deproteinated by the addition of acetonitrile, methanol, trichloroacetic acid or perchloric acid followed by centrifugation at 10,000 g for 10 minutes. Sample volumes of 20 µl to 50 µl were injected for analysis.

Compound 214e

Dosing and sampling

The drug was dissolved in sterile 0.02M Tris to give a 2.5 mg/ml solution which was administered to 11 groups of 5 male CD-1 mice via the tail vein at a dose of 25 mg/kg. At each of the following timepoints: 2, 5, 10, 15, 20, 30, 45, 60, 90 and 120 minutes a group of animals was anaesthetised and the blood collected into heparinized tubes. After separation the plasma was stored at −20° C. until assayed.

Assay

Aliquots of plasma (150 µl) were treated with 5% perchloric acid (5 µl) then mixed by vortexing and allowed to stand for 90 minutes prior to centrifugation. The resulting supernatant was separated and 20 µl was injected for HPLC analysis.

HPLC Conditions

| Column | 100 × 4.6 mm | Kromasil KR 100 5C4 |
|---|---|---|
| Mobile Phase | 0.1 m Tris pH 7.5 | 86% |
| | Acetonitrile | 14% |
| Flowrate | 1 ml/min | |
| Detection | UV at 210 nm | |
| Retention Time | 3.4 mins | |

The results of the analysis indicated a decrease in the mean plasma level of the drug from ~70 µg/ml at 2 minutes to <2 µg/ml at 90 and 120 minutes.

Compound 217e

Dosing and sampling

The drug was dissolved in sterile 0.02M Tris to give a 2.5 mg/ml solution which was administered to 11 groups of 5 male CD-1 mice via the tail vein at a dose of 25 mg/kg. At each of the following timepoints: 2, 5, 10, 15, 20, 30, 45, 60, 90 and 120 minutes a group of animals was anaesthetised and the blood collected into heparinized tubes. After separation the plasma was stored at −20° until assayed.

Assay

Aliquots of plasma (100 μl) were diluted with acetonitrile (100 μl) then mixed by vortexing for 20 seconds before centrifugation for 10 minutes. The resulting supernatant was separated and 20 μl was injected for HPLC analysis.

HPLC Conditions

| Column | 150 × 4.6 mm | Zorbax SBC8 |
|---|---|---|
| Mobile Phase | 0.05M Phosphate buffer pH 7.1 | 72% |
| | Acetonitrile | 28% |
| Flowrate | 1.4 ml/min | |
| Detection | UV at 210 nm | |
| Retention Time | 3.0 and 3.6 mins (diasteromers) | |

The results of the analysis indicated a decrease in mean plasma concentrations from ~55 μg/ml at 2 minutes to <0.2 μg/ml at 60–120 minutes.

EXAMPLE 3

Peptidyl ICE inhibitors are cleared rapidly with clearance rates greater than 80 ml/min/kg. Compounds with lower clearance rates have improved pharmacokinetic properties relative to peptidyl ICE inhibitors.

We obtained the rate of clearance in the rat (ml/min/kg) for several compounds of this invention using the method described below:

In vivo Rat Clearance Assay

Cannulations of the jugular and carotid vessels of rats under anesthesia were performed one day prior to the pharmacokinetic study. M. J. Free, R. A. Jaffee; 'Cannulation techniques for the collection blood and other bodily fluids'; in: *Animal Models;* p. 480–495; N. J. Alexander, Ed.; Academic Press; (1978). Drug (10 mg/mL) was administered via the jugular vein in a vehicle usually consisting of: propylene glycol/saline, containing 100 mM sodium bicarbonate in a 1:1 ratio. Animals were dosed with 10–20 mg drug/kg and blood samples were drawn at 0, 2, 5, 7, 10, 15, 20, 30, 60, and 90 minutes from an indwelling carotid catheter. The blood was centrifuged to plasma and stored at −20° C. until analysis. Pharmacokinetic analysis of data was performed by nonlinear regression using standard software such as RStrip (MicroMath Software, Utah) and/or Pcnonlin (SCI Software, N.C.) to obtain clearance values.

Analytical

Rat plasma was extracted with an equal volume of acetonitrile (containing 0.1% TFA). Samples were then centrifuged at approximately 1,000 x g and the supernatant analyzed by gradient HPLC. A typical assay procedure is described below.

200 μL of plasma was precipitated with 200 μL of 0.1% trifluoroacetic acid (TFA) in acetonitrile and 10 μL of a 50% aqueous zinc chloride solution, vortexed then centrifuged at ~1000 x g and the supernatant collected and analyzed by HPLC.

HPLC procedure
Column: Zorbax SB—CN (4.6×150 mm) (51μ particle size)
Column temperature: 50° C.
Flow rate: 1.0 mL/min
Injection volume: 75 μL.
Mobile phase: A=0.1% TFA in water and B=100% acetonitrile
Gradient employed: 100% A to 30% A in 15.5 min 0% A at 16 min 100% A at 19.2 min
Wavelength: 214 nm A standard curve was run at 20, 10, 5, 2 and 1 μg/mL concentrations.

EXAMPLE 4

Whole Blood Assay for IL-1β Production

We obtained $IC_{50}$ values for several compounds of this invention using the method described below:

Purpose

The whole blood assay is a simple method for measuring the production of IL-1β (or other cytokines) and the activity of potential inhibitors. The complexity of this assay system, with its full complement of lymphoid and inflammatory cell types, spectrum of plasma proteins and red blood cells is an ideal in vitro representation of human in vivo physiologic conditions.

Materials
Pyrogen-free syringes (~30 cc)
Pyrogen-free sterile vacuum tubes containing lyophilized $Na_2EDTA$ (4.5 mg/10 ml tube)
Human whole blood sample (~30–50 cc)
1.5 ml Eppendorf tubes
Test compound stock solutions (~25mM in DMSO or other solvent)
Endotoxin-free sodium chloride solution (0.9%) and HBSS
Lipopolysaccharide (Sigma; Cat.# L-3012) stock solution at 1 mg/ml in HBSS
IL-1β ELISA Kit (R & D Systems; Cat # DLB50)
TNFα ELISA Kit (R & D Systems; Cat # DTA50)
Water bath or incubator Whole Blood Assay Experimental Procedure Set incubator or water bath at 30° C. Aliquot 0.25 ml of blood into 1.5 ml Eppendorf tubes. Note: be sure to invert the whole blood sample tubes after every two aliquots. Differences in replicates may result if the cells sediment and are not uniformly suspended. Use of a positive displacement pipette will also minimize differences between replicate aliquots.

Prepare drug dilutions in sterile pyrogen-free saline by serial dilution. A dilution series which brackets the apparent $K_i$ for a test compound determined in an ICE inhibition assay is generally used for the primary compound screen. For extremely hydrophobic compounds, we have prepared compound dilutions in fresh plasma obtained from the same blood donor or in PBS-containing 5% DMSO to enhance solubility.

Add 25 μl test compound dilution or vehicle control and gently mix the sample. Then add 5.0 μl LPS solution (250 ng/ml stocked prepared fresh: 5.0 ng/ml final concentration LPS), and mix again. Incubate the tubes at 30° C. in a water bath for 16–18 hr with occasional mixing. Alternatively, the tubes can be placed in a rotator set at 4 rpm for the same incubation period. This assay should be set up in duplicate or triplicate with the following controls: negative control- no LPS; positive control- no test inhibitor; vehicle control- the highest concentration of DMSO or compound solvent used in the experiment. Additional saline is added to all control tubes to normalize volumes for both control and experimental whole blood test samples After the incubation period, whole blood samples are centrifuged for 10 minutes at ~2000 rpm in the microfuge, plasma is transferred to a fresh microfuge tube and centrifuged at 1000 x g to pellet residual platelets if necessary. Plasma samples may be stored frozen at ~70° C. prior to assay for cytokine levels by ELISA.

ELISA

We have used R & D Systems (614 McKinley Place N.E. Minneapolis, Minn. 55413) Quantikine kits for measurement of IL-1β β and TNF-α. The assays are performed according to the manufacturer's directions. We have observed IL-1β levels of ~1–5 ng/ml in positive controls among a range of individuals. A 1:200 dilution of plasma for all samples has been sufficient in our experiments for ELISA results to fall on the linear range of the ELISA standard curves. It may be necessary to optimize standard dilutions if you observe differences in the whole blood assay. Nerad, J. L. et al., *J. Leukocyte Biol.*, 52, pp. 687–692 (1992).

EXAMPLE 5

Inhibition of ICE homolops

1. Isolation of ICE homologs

Expression of TX in insect cells using a baculovirus expression system. We have subcloned Tx cDNA (Faucheu et al., 1995) into a modified pVL1393 transfer vector, co-transfected the resultant plasmid (pVL1393/TX) into insect cells with viral DNA and identified the recombinant baculovirus. After the generation of high titer recombinant virus stock, the medium was examined for TX activity using the visible ICE assay. Typically, infection of *Spodoptera frugiperda* (Sf9) insect cells at an MOI of 5 with recombinant virus stock resulted in a maximum expression after 48 hours of 4.7 μg/ml. ICE was used as a standard in the assay.

Amino terminal T7 tagged versions of ICE or TX were also expressed. Designed originally to assist the identification and purification of the recombinant proteins, the various constructs have also allowed examination of different levels of expression and of the relative levels of apoptosis experienced by the different homologs. Apoptosis in the infected Sf9 cells (examined using a Trypan Blue exclusion assay) was increased in the lines expressing ICE or TX relative to cells infected with the viral DNA alone.

Expression and purification of N-terminally (His)$_6$tagged CPP32 in *E. coli*. A cDNA encoding a CPP32 (Alnemri et al, 1994) polypeptide starting at Ser (29) was PCR amplified with primers that add in frame XhoI sites to both the 5' and 3' ends of the cDNA and the resulting XhoI fragment ligated into a Xho I-cut pET-15b expression vector to create an in frame fusion with (his)$_6$ tag at the n-terminus of the fusion protein. The predicted recombinant protein starts with the amino acid sequence of MGSSHHHHHHSSGLVPRGSHMLE, where LVPRGS represents a thrombin cleavage site, followed by CPP32 starting at Ser (29). *E. coli* BL21(DE3) carrying the plasmid were grown to log phase at 30° C. and were then induced with 0.8 mM IPTG. Cells were harvested two hours after IPTG addition. Lysates were prepared and soluble proteins were purified by Ni-agarose chromatography. All of the expressed CPP32 protein was in the processed form. N-terminal sequencing analysis indicated that the processing occurred at the authentic site between Asp (175) and Ser (176). Approximately 50 μg of CPP32 protein from 200 ml culture. As determined by active site titration, the purified proteins were fully active. The protease preparation were also very active in vitro in cleaving PARP as well as the synthetic DEVD-AMC substrate (Nicholson et al, 1995).

2. Inhibition of ICE homologs

The selectivity of a panel of reversible inhibitors for ICE homologs is depicted in Table 1. ICE enzyme assays were performed according to Wilson et al (1994) using a YVAD-AMC substrate (Thornberry et al, 1992). Assay of TX activity was performed using the ICE substrate under identical conditions to ICE. Assay of CPP32 was performed using a DEVD-AMC substrate (Nicholson et al., 1995). In general, there is low selectivity between ICE and TX for a wide range of scaffolds. None of the synthetic ICE compounds tested are effective inhibitors of CPP32. Assay of the reversible compounds at the highest concentration (1 μM) revealed no inhibition.

TABLE 1

| Compound | $K_i$ ICE (nM) | $K_i$ TX (nM) | $K_i$ CPP32 (nM) |
|---|---|---|---|
| 214e | 7.5 | 7.0 ± 1.1 | >1000 |
| 135a | 90 | 55 ± 9 | >1000 |
| 125b | 60 | 57 ± 13 | >1000 |
| 137 | 40 | 40 ± 7 | >1000 |

Second-order rate constants for inactivation of ICE and ICE homologs with selected irreversible inhibitors are presented below (Table 2). The irreversible compounds studied are broad spectrum inhibitors of ICE and its homologs. Some selectivity, however, is observed with the irreversible compounds comparing inhibition of ICE and CPP32.

TABLE 2

| Compound | $k_{inact}$ (ICE) $M^{-1} s^{-1}$ | $k_{inact}$ (TX) $M^{-1} s^{-1}$ | $k_{inact}$ (CPP32) $M^{-1} s^{-1}$ |
|---|---|---|---|
| 138 | 120,000 | 150,000 | 550,000 |
| 217d | 475,000 | 250,000 | 150,000 |
| 108a | 100,000 | 25,000 | nd |

EXAMPLE 6

Inhibition of apoptosis

Fas-Induced Apoptosis in U937 cells. Compounds were evaluated for their ability to block anti—Fas-induced apopotosis. In a preliminary experiment using RT-PCR, we detected mRNA encoding ICE, TX, ICH-1, CPP32 and CMH-1 in unstimulated U937 cells. We used this cell line for apoptosis studies. U937 cells were seeded in culture at $1 \times 10^5$ cells/ml and grown to ~$5 \times 10^6$ cells/ml. For apoptosis experiments, $2 \times 10^6$ cells were plated in 24-well tissue culture plates in 1 ml RPMI1640-10% FBS and stimulated with 100 ng/ml anti—Fas antigen antibody (Medical and Biological Laboratories, Ltd.). After a 24 hr incubation at 37° C., the percentage of apoptotic cells was determined by FACS analysis using ApoTag reagents.

All compounds were tested initially at 20 μM and titrations were performed with active compounds to determine IC$_{50}$ values. Inhibition of apoptosis (>75% at 20 μM) was observed for 108a, 136, and 138. An IC$_{50}$ of 0.8 μM was determined for 217e compared to no inhibition of anti—Fas-induced apoptosis by 214e at 20 μM.

EXAMPLE 7

In vivo acute assay for efficacy as anti-inflammatory agent

LPS-Induced IL-1β Production.

Figure 3:
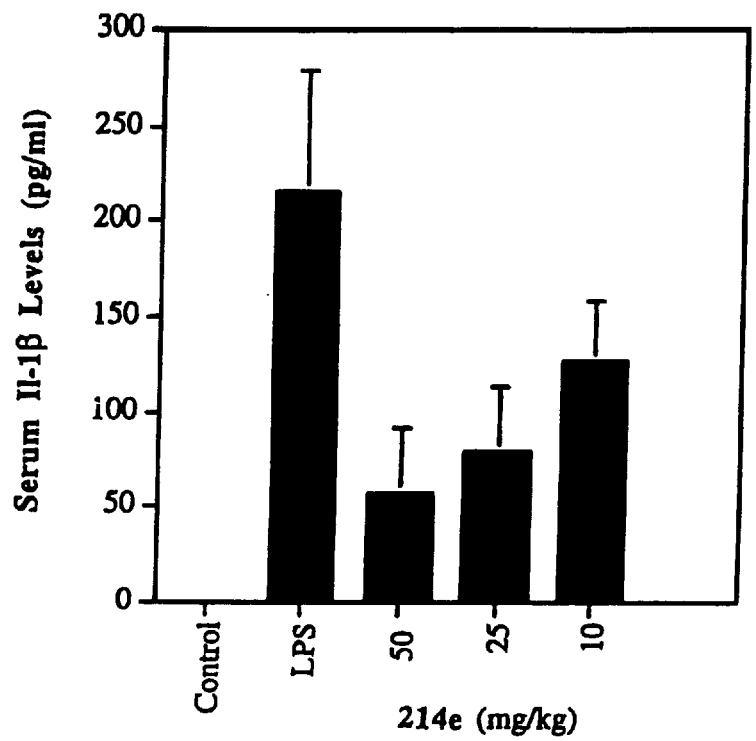
FIG. 3 depicts inhibition of IL-1β production by 214e in LPS-challenged mice.
Figure 4:
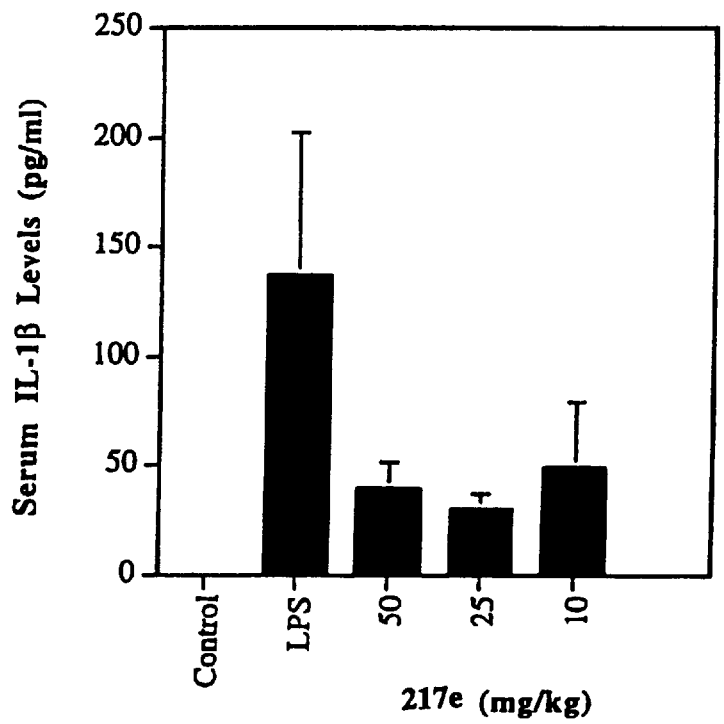
FIG. 4 depicts inhibition of IL-1β production by 217e in LPS-challenged mice.

Efficacy of 214e and 217e was evaluated in CD1 mice (n=6 per condition) challenged with LPS (20 mg/kg IP). The test compounds were prepared in olive oil:DMSO:ethanol (90:5:5) and administered by IP injection one hour after LPS. Blood was collected seven hours after LPS challenge. Serum IL-1β levels were measure by ELISA. Results in FIG. 3 show a dose dependent inhibition of IL-1β secretion by 214e, with an $ED_{50}$ of approximately 15 mg/kg. Similar results were obtained in a second experiment. A significant inhibition of IL-1β secretion was also observed in 217e treated mice (FIG. 4). However, a clear dose response was not apparent.

Figure 5:
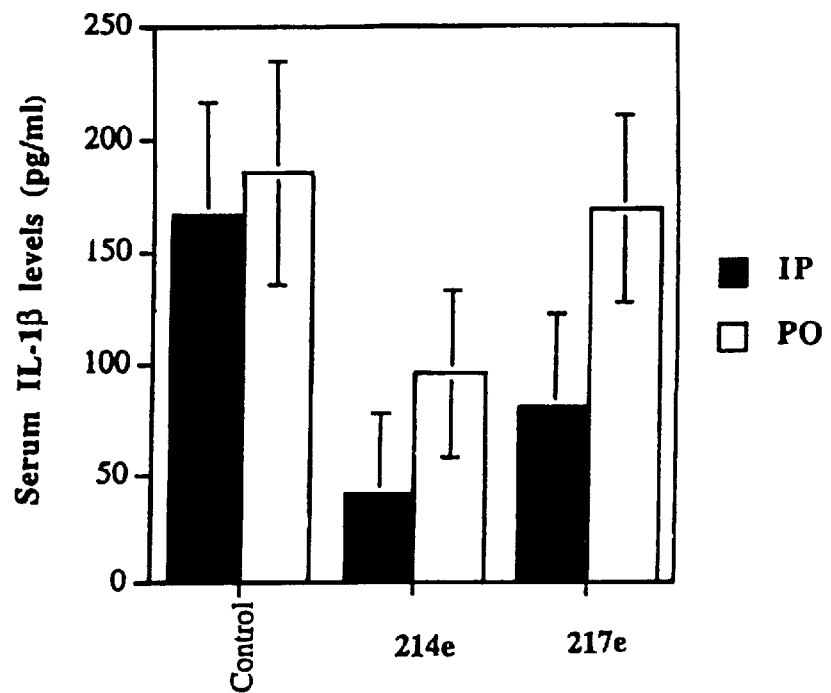
FIG. 5 depicts inhibition of IL-1β production by 214e and 217e in LPS-challenged mice after intraperitoneal (IP) or oral (PO) administration (50 mg/kg).
Figure 6:
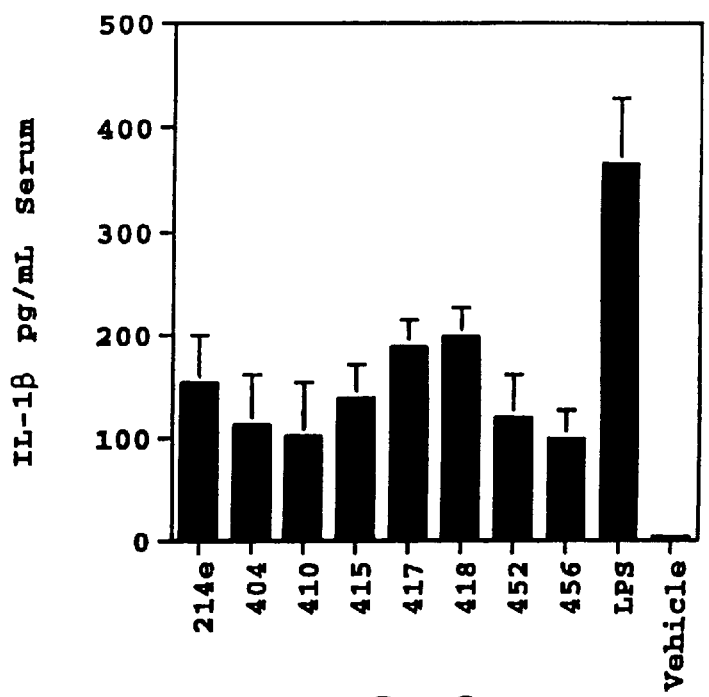
FIG. 6 depicts inhibition of IL-1β production by 214e and analogs of 214e in LPS-challenged mice after IP administration (50 mg/kg).
Figure 7:
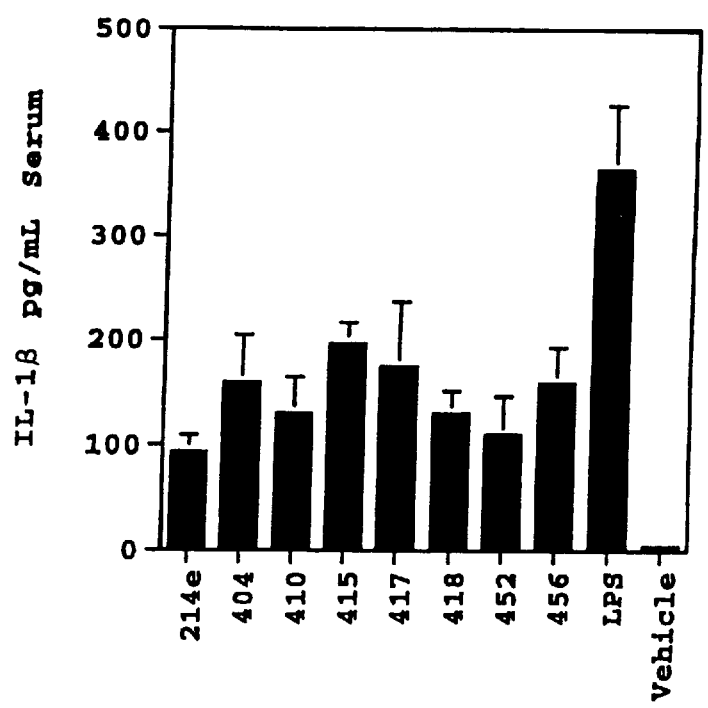
FIG. 7 depicts inhibition of IL-1β production by 214e and analogs of 214e in LPS-challenged mice after (PO) administration.
Figure 8A:
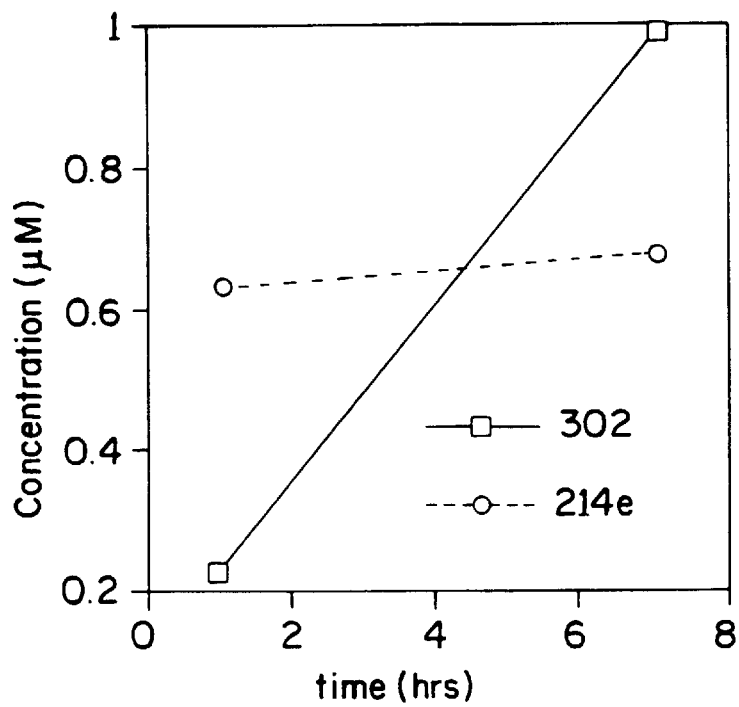
FIGS. 8A and 8B depict blood levels in mice after oral administration of 302 and 304a in 0.5% CMC/water at 50 mg/kg.
Figure 8B:
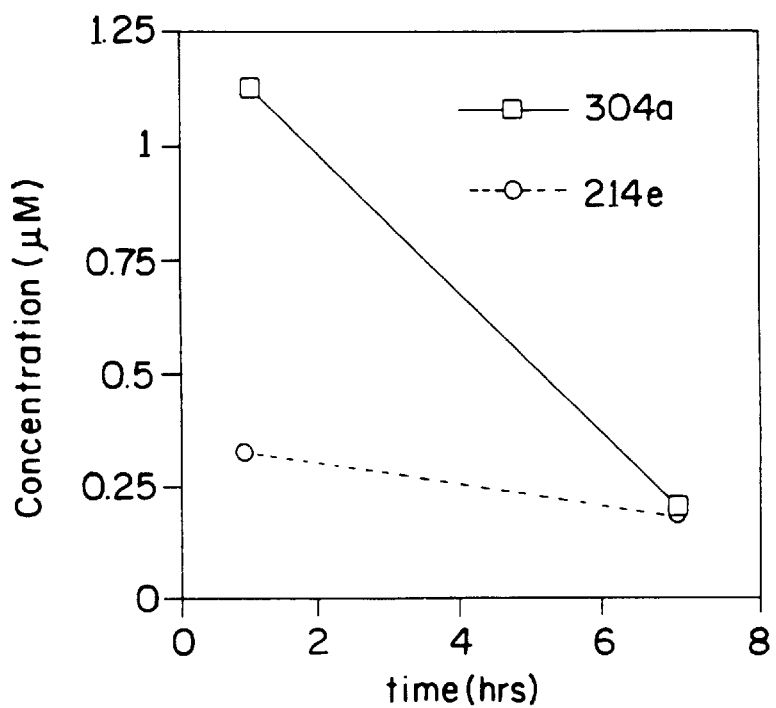

Compounds 214e and 217e (50 mg/kg) were also administered by oral gavage to assess absorption. Results in FIG. 5 show that 214e, but not 217e when administered orally inhibited IL-1β secretion, suggesting potential for oral efficacy of ICE inhibitors as anti-inflammatory agents.

Table 8. % Inhibition of IL-P production by analogs of 214e in LPS-challenged mice after PO and IP administration (50 mg/kg).

TABLE 3

| Compound | PO % Inhibition | IP % Inhibition |
|---|---|---|
| 214e | 75 | 78 |
| 265 | 27 | 30 |
| 416 | 52 | 39 |
| 434 | 80 | 74 |
| 438 | 13 | 40 |
| 442 | 10 | 0 |
| 2002 | — | 78 |

TABLE 4

Comparison of 214e Prodrugs Efficacy in LPS Challenged Mice: Time Course Inhibition of IL-1β Production

| Compound | Time of Compound Administration (relative to time of LPS challenge, PO, 50 mg/kg) | | | |
|---|---|---|---|---|
| | −2 hr | −1 hr | 0 hr | +1 hr |
| 214e | | | | 55% |
| 304a | 30 | 33 | 68 | 37 |
| 2100e | 49 | 54 | 94 | 66 |
| 2100a | 8 | 71 | 67 | 58 |
| 213e | 0 | 48 | 41 | 89 |
| 302 | 0 | 27 | 21 | 26 |
| 2100c | 0 | 0 | 85 | 40 |
| 2100d | 42 | 35 | 52 | 26 |
| 2100b | 0 | 0 | 47 | 26 |
| 2001 | ~63 | ~62 | ~57 | ~54 |

EXAMPLE 8

Measurement of blood levels of prodrugs of 214e

Mice were administered a p.o. dose of compounds 302 and 304a (50 mg/kg) prepared in 0.5% carboxymethylcellulose. Blood samples were collected at 1 and 7 hours after dosing. Serum was extracted by precipitation with an equal volume of acetonitrile containing 2% formic acid followed by centrifugation. The supernatant was analyzed by liquid chromatograhy/mass spectrometry (ESI-MS) with a detection level of 0.03 to 3 μg/ml. Compounds 302 and 304a showed detectable blood levels when administered orally, 214e itself shows no blood levels above 0.10 μg/mL when administered orally. Compounds 302 and 304a are prodrugs of 214e and are metabolized to 214e in vivo.

EXAMPLE 9

We obtained the following data for compounds of this invention using the methods described in Examples 1–8. The structures of the compounds of Example 9 are shown in Example 10 and FIG. 1.

| Compound | UV-Visible Ki (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 47b | 27 | 1800 | <600 | 338 | |
| 47a | 19 | 2600 | 5100 | 79 | 32 |
| 135a | 90 | 2800 | 5000 | >100 | |
| 135b | 320 | 1600 | 1700 | | |
| 125b | 60 | 800 | 4500 | | |
| 108b | 400 | 25000 | | | >100 |
| 137 | 40 | 1700 | 14000 | | |
| 139 | 350 | 2000 | | | |
| 213e | 130 | 900 | 600 | | |
| 214c | 1200 | 5000 | | | |
| 214e | 7.5 | 1600 | 1300 | 23 | 12 |
| 217c | | 1700 | 7000 | | |
| 217e | | 175 | 2000 | >50 | |
| 220b | 600 | 2125 | | | |
| 223b | 99 | 5000 | | | |
| 223e | 1.6 | 3000 | >20000 | 89 | |
| 226e | 15 | 1100 | 1800 | 109 | |
| 227e | 7 | 234 | 550 | | |
| 230e | | 325 | 300 | 67 | |
| 232e | 1100 | 4500 | | 22 | |
| 235e | 510 | 4750 | | 36 | |
| 238e | 500 | 4250 | | | 22 |
| 246 | 12 | 950 | 10000 | 31 | |
| 257 | 13 | 11000 | | | |
| 265 | 47 | 4300 | | 23 | 20 |
| 281 | 50 | 600 | | | |
| 302 | 4500 | >20000 | >20000 | | |
| 304a | 200 | 1,400 | 2400 | | |
| 307a | 55 | 14500 | | | |
| 307b | 165 | | | | |
| 404 | 2.9 | 1650 | 1100 | 64 | 24 |
| 405 | 6.5 | 1700 | 2100 | | |
| 406 | 4 | 1650 | 2300 | | |
| 407 | 0.4 | 540 | 1700 | | |
| 408 | 0.5 | 1100 | 1000 | 41 | |
| 409 | 3.7 | 2500 | | | |
| 410 | 17 | 2000 | 2800 | 32 | 20 |
| 411 | 0.9 | 540 | 1900 | | |
| 412 | 1.3 | 580 | 700 | | 25 |
| 413 | 750 | 6200 | | | |
| 415 | 2.5 | 990 | 450 | 26 | 18 |
| 416 | 12 | 1200 | 3400 | | 47 |
| 417 | 8 | 2000 | 6000 | 33 | |
| 418 | 2.2 | 1050 | 7800 | | 5.9 |
| 419 | 280 | >8000 | | 64 | |
| 420 | 1200 | 8000 | | | |
| 421 | 200 | 4300 | | | |
| 422 | 50 | 2200 | 1200 | | |
| 423 | 10 | 2100 | 1500 | | 45 |
| 424 | 45 | 2500 | 4000 | | |
| 425 | 0.8 | 650 | 650 | | |
| 426 | 90 | 4500 | | | |
| 427 | 180 | 4500 | | | 36 |
| 428 | 280 | | | | |
| 429 | 7000 | | | | |
| 430 | 60 | >8000 | | | |
| 431 | 8 | >8000 | 8000 | | |
| 432 | 1.6 | | 2000 | | |
| 433 | 2.9 | 1000 | 1100 | | |
| 434 | 4.9 | 1600 | 1800 | | 20 |
| 435 | 8 | 4400 | | | |
| 436 | 7.5 | 2700 | | | |
| 437 | 12 | 1800 | | | |
| 438 | 28 | 1000 | 700 | | 22 |
| 439 | 3.7 | 2800 | 3200 | | |
| 440 | 2.3 | 5000 | 2000 | | |
| 441 | 1 | 2500 | 4500 | | |
| 442 | 3.2 | 900 | 2000 | | 54 |
| 443 | 3.6 | 2800 | 1500 | | |
| 444 | 15 | 3500 | 3500 | | |
| 445 | 135 | | 4000 | | |

-continued

| Compound | UV-Visible Ki (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 446 | 62 | | 3000 | | |
| 447 | 5.8 | 2500 | 1500 | | |
| 448 | 130 | | 4000 | | |
| 449 | 12 | 1500 | 3200 | | |
| 450 | 5 | 800 | 2200 | | |
| 451 | 4 | 1800 | 1500 | | |
| 452 | 4.5 | 600 | 650 | | 27.3 |
| 453 | 0.65 | 1300 | 1900 | | |
| 454 | 45 | 2500 | | | |
| 455 | 1.2 | 400 | 2800 | | 54 |
| 456 | 4.5 | 600 | 600 | | 12.7 |
| 457 | 6.2 | 2000 | | | |
| 458 | 20 | 2900 | | | |
| 459 | 5 | 1800 | | | |
| 460 | 115 | | | | |
| 461 | 47 | | | | |
| 462 | 40 | | | | |
| 463 | 14 | 2400 | | | |
| 464 | 2.5 | 1000 | >1000 | | |
| 465 | 3 | 1000 | 800 | | |
| 466 | 0.8 | 1400 | 600 | | |
| 467 | 11 | 1900 | | | |
| 469 | 4.5 | 850 | 2500 | | |
| 470 | 5 | 500 | 360 | | |
| 471 | 6 | 750 | 400 | | |
| 472 | 140 | | | | |
| 473 | 1 | 1000 | 400 | | |
| 474 | 85 | | | | |
| 475 | 5.5 | 690 | | | |
| 476 | 7 | 1600 | | | |
| 477 | 60 | | | | |
| 478 | 380 | | | | |
| 479 | 15 | 900 | 700 | | |
| 480 | 25 | 2300 | | | |
| 481 | 1.2 | 390 | 600 | | |
| 482 | <0.2 | 340 | 380 | | |
| 483 | 1.7 | 900 | 700 | | |
| 484 | 2 | 1550 | | | |
| 485 | 2 | 900 | 900 | | |
| 486 | 2.3 | 480 | 500 | | |
| 487 | 2.4 | 650 | 500 | | |
| 488 | 1.5 | 940 | 750 | | |
| 489 | 6 | 2250 | | | |
| 490 | 4.3 | 980 | 700 | | |
| 491 | 5 | 2500 | | | |
| 493 | 25 | 1200 | 800 | | |
| 494 | 15 | 1350 | | | |
| 495 | 43 | | | | |
| 496 | 16 | 1550 | | | |
| 497 | 3.5 | 740 | 350 | | |
| 498 | 1.5 | 560 | 500 | | |
| 499 | 3.5 | 1200 | | | |
| 605a | 90 | 2600 | >20000 | | |
| 605b | 45 | 10000 | | | |
| 605c | 615 | 4500 | | | |
| 605d | 95 | 5100 | 16000 | 33 | |
| 605e | 29 | 2250 | | | |
| 605f | 475 | 12500 | | | |
| 605g | 165 | 22500 | | | |
| 605h | 460 | >25000 | | | |
| 605i | 680 | >20000 | | | |
| 605j | 110 | 8750 | | | |
| 605m | 650 | 20000 | | | |
| 605n | 12 | 2100 | >20000 | 28 | |
| 605o | 72 | | 18000 | | |
| 605p | 125 | 3200 | >20000 | | |
| 605q | 1000 | | | | |
| 605s | 150 | 6000 | | | |
| 605t | 33 | | | | |
| 609a | 114 | >30000 | | | |
| 609b | 27 | >20000 | | | |
| 619 | 300 | | | | |
| 620 | 35 | 1000 | 19000 | | |
| 621 | 7.2 | 1300 | >20000 | | |
| 622 | 35 | | | | |
| 623 | 9 | | | | |
| 624 | 300 | | | | |
| 625 | 105 | | | | |
| 626 | 260 | | | | |
| 627 | 43 | 3250 | | | |
| 628 | 36 | 2750 | | | |
| 629 | 230 | | | | |
| 630 | 270 | | | | |
| 631 | 805 | | | | |
| 632 | 148 | | | | |
| 633 | 92 | 5750 | | | |
| 634 | 1400 | | | | |
| 635 | 55 | 1900 | | | |
| 605v | 1100 | >30000 | | | |
| 2201 | 9 | 2000 | | | |
| 2100e | 250 | 800 | 600 | | |
| 2100a | 100 | 1100 | 850 | | |
| 2002 | 4 | 810 | | 70 | |
| 2100d | >100000 | >20000 | | | |
| 2100c | 7400 | | | | |
| 2100b | 8000 | >20000 | | | |
| 2001 | 135 | | | | |
| 1027 | 4000 | | | | |
| 1015 | 40 | | | | |

| Compound | Fluorescent Assay $k_{inact}$ $M^{-1} s^{-1}$ | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 108a | | 17500 | | | |
| 136 | | 870 | 2800 | 93 | |
| 138 | $1.2 \times 10^5$ | 900 | 2900 | 130 | |
| 217d | $4.7 \times 10^5$ | 340 | 4000 | 116 | |
| 280 | $4 \times 10^5$ | 650 | >1000 | | 187 |
| 283 | $1 \times 10^5$ | <200 | 450 | | 104 |
| 284 | $3.5 \times 10^5$ | 470 | 550 | | 100 |
| 285 | $4.3 \times 10^5$ | 810 | 1000 | | |

EXAMPLE 10

Compound 139 was synthesized by a method similar to the method used to synthesize 47a.

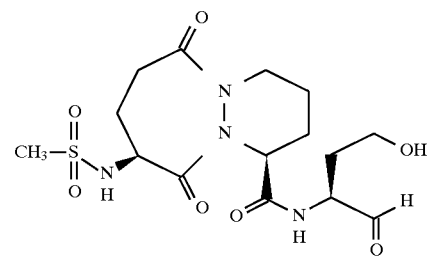

139

Compounds 136 and 138 were synthesized by a method similar to the method used to synthesize 57b.

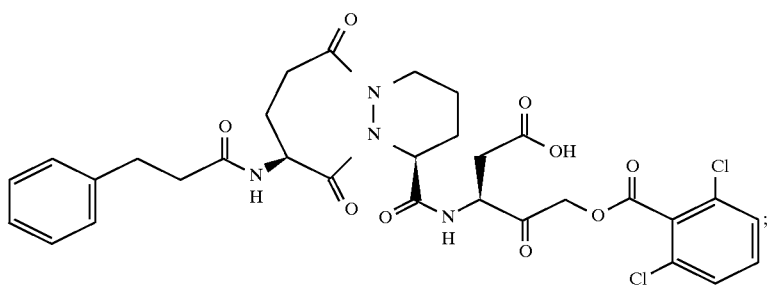
136
and
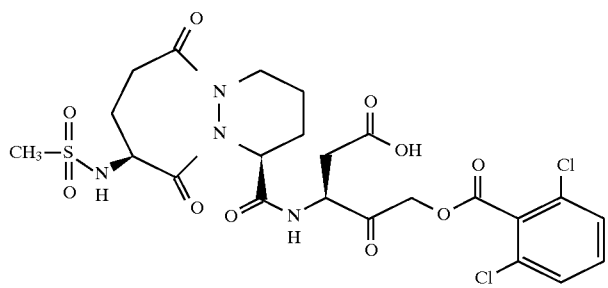
138
Compounds 135a, 135b, and 137 were synthesized by a method similar to the method used to synthesize 69a.
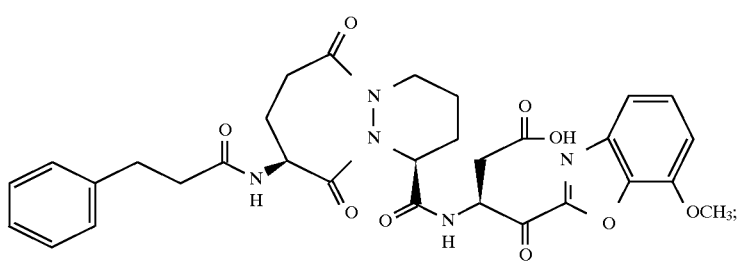
135a
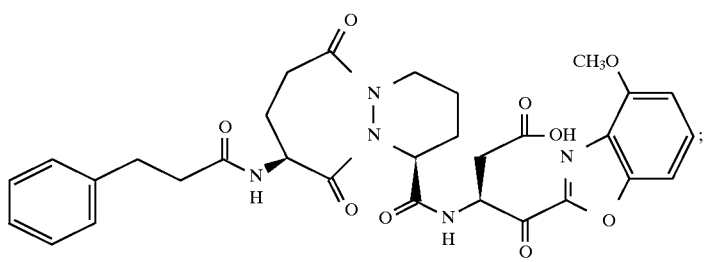
135b
and
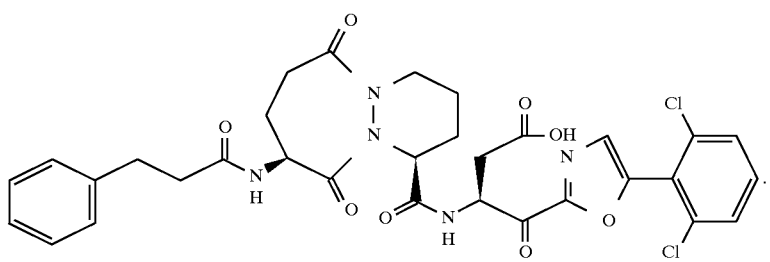
137
Compounds 813e, 814c, 814e, 817c, 817d, 817e, 820b, 823b, 823e, 826e, 827e, 830e, 832e, 835e, 838e, 846, 857, 865, 902, 904a, 907a, 907b, 1004–1013, 1015–1045, 1046–1068, 1070–1091, and 1093–1099 were synthesized by methods similar to those used to synthesize compound 264 and the corresponding compounds in examples 10 and 11.

Compounds 47a, 47b, 108a, 108b, 125b, 213e, 214c, 217c, 217d, 217e, 220b, 223b, 223e, 226e, 227e, 230e, 232e, 235e, 238e, 246, 257, 264, 265, 280–287, 302, 304a, 307a, and 307b were synthesized as described below.

H. N-(N-Acetyl-tyrosinyl-valinyl-pipecolyl)-3-amino4-oxobutanoic acid.

Step A. N-(N-tert-Butoxycarbonylpipecolyl)-4amino-5-benzyloxy-2-oxotetrahydrofuran Reaction of N-tert-butoxycarbonylpipecolic acid (460 mg, 2.0 mmol) and N-allyloxycarbonyl-4-amino5-benzyloxy-2-oxotetrahydrofuran (530 mg, 1.82 mmol) was carried out by a method analogous to that reported by Chapman (Bioorg. & Med. Chem. Lett. 1992, 2, 613–618.) to give 654 mg of the title compound.

$^1$H NMR (500 MHz, CDCl$_3$ (existing as rotamers) δ7.35 (m, 5H), 6.88 (br. s, 1H), 4.9–4.45(m, 4H), 3.95+(br. m, 2H), 3.06 (m, 1H), 2.9 (m, 1H), 2.7 (br. m, 1H), 2.45 (m, 1H), 2.2 (m, 1H), 1.7–1.5 (m, 3H), 1.45 (two s, 9H).

Step B. N-Pipecolyl-4-amino-5-benzyloxy-2oxotetrahydrofuran

N-(N-tert—Butoxycarbonylpipecolyl)-4-amino-5benzyloxy-2-oxo-tetrahydrofuran (654 mg) was dissolved in 15 ml of 25% trifluoroacetic acid in dichloromethane and stirred at room temperature. The mixture was concentrated to give a gummy residue. The residue was dissolved in dichloromethane and washed with 10% sodium bicarbonate. The organic layer was dried over anhydrous sodium sulfate, filtered, and concentrated to give 422 mg of the title compound as a beige solid.

$^1$H NMR (500 MHz, CDCl$_3$) δ7.38 (m, 5H), 7.15 (d, 1H), 5.55 (d, 1H), 4.95–4.8 (m, 1H), 4.78 (m, 1H), 4.65 (d, 1H), 4.45 (m, 1H), 3.2 (m, 0.5H), 3.05 (m, 0.5H), 2.95 (m, 0.5H), 2.85 (m, 0.5H), 2.65 (m, 1H), 2.55–2.38(m, 1H), 1.95 (m, 1H), 1.8 (m, 1H), 1.6 (m, 2H), 1.38 (m, 2H).

Step C. N-(N-Acetyl-tyrosinyl-valinylpipecolyl)-4-amino-5-benzyloxy-2-oxo tetrahydrofuran N-Acetyl-tyrosinyl-valine (464 mg, 1.44 mmol) and N-Pipecolyl-4-amino-5-benzyloxy-2-oxotetrahydrofuran (412 mg, 1.3 mmol) were dissolved in 5 ml each of dimethylformamide and dichloromethane and cooled to 0° C. To the cooled solution was added 1-hydroxybenzotriazole (HOBT; 210 mg, 1.56 mmol) followed by the addition of 1-(3-dimethylaminopropyl)-3-ethyl carbodiimide hydrochloride (EDC; 326 mg, 1.7 mmol). After stirring for 18 hours, the mixture was diluted with ethyl acetate and washed with water, 10% sodium hydrogen sulfate, 10% sodium bicarbonate, and water. The organic layer was concentrated to give a crude solid that was purified by flash chromatography (SiO$_2$) eluting with 94:6:1 (dichloromethane:isopropanol: pyridine) to give 370 mg of the title compound.

$^1$H NMR (500 MHz, CD$_3$OD (existing as diastereomers as well as rotamers)) δ7.35 (m, 5H), 7.05 (m, 2H), 6.68 (m, 2H), 5.65 & 5.25 (m, 1H), 4.9–3.95 (m, 8H), 3.4–2.6 (m, 4H), 2.5–2.1 (m, 1H), 1.98 (s, 1H), 1.9 (s, 1H) , 1.85 (s, 1H), 1.8–1.6 (m, 2H) 1.55–1.3 (m, 4H), 0.95–0.85 (m, 6H).

Step D. N-(N-Acetyl-tyrosinyl-valinylpipecolyl)-3-amino-4-oxobutanoic acid

To a solution of 100 mg of N-(N-Acetyl-tyrosinyl-valinyl-pipecolyl)-4-amino-5-benzyloxy-2-oxotetrahydrofuran in 10 ml of methanol was added 60 mg of Pd(OH)$_2$ on carbon and the mixture placed under an atmosphere of hydrogen via a balloon. The mixture was filtered through Celite and concentrated providing a white solid. This crude solid was dissolved in 2 ml of methanol and triturated with diethyl ether affording 26 mg of the title compound.

$^1$H NMR (500 MHz, CD$_3$OD (existing as diastereomers as well as rotamers)) δ7.1 (m, 2H), 6.7 (m, 2H), 5.2 (br. m, 1H), 4.8–3.6 (m, 6H), 3.2–2.5 (m, 4H), 2.5–2.1 (m, 1H), 1.95 (three s, 3H), 1.9–1.3 (m, 6H), 1.1–0.7 (m, 6H).

K. N-[N-Acetyl-tyrosinyl-valinyl-(4-benzyloxy)prolinyl]-3-amino-4-oxobutanoic acid Step A. N-(N-Allyloxycarbonyl-4-benzyloxyprolinyl)-3-amino-4-oxobutanoic acid tert-butyl ester semicarbazone The title compound was prepared by the reaction of N-allyloxycarbonyl-4-benzyloxyproline and 3-amino-4-oxobutanoic acid tert-butyl ester semicarbazone (T. L. Graybill et. al., Abstracts of papers, 206th National Meeting of the American Chemical Society, Abstract MEDI-235. Chicago, Ill. (1993)) under similar peptide coupling conditions as reported above (compound H; Step C).

$^1$H NMR (500 MHz, CDCl$_3$) δ9.05 (br. s, 1H), 7.85 (br. m, 1H), 7.4–7.2 (m, 5H), 7.15 (br. s, 1H), 6.55 (br. s, 1H), 5.9 (m, 1H), 5.1–4.9 (br. m, 2H), 4.65–4.4 (m, 4H), 4.2 (br. m, 1H), 3.75–3.5 (m, 2H), 2.75–2.55 (m, 2H), 2.5 (br. m, 1H), 2.25 (br. m, 1H) 1.4 (s, 9H).

Step B. N-(N-Acetyl-tyrosinyl-valinyl-(4benzyloxyprolinyl))-3-amino-4-oxobutanoic acid tert-butyl ester semicarbazone The title compound was prepared by reaction of N-acetyl-tyrosinyl-valine and N-(N-allyloxycarbonyl-4-benzyloxyprolinyl)-3-amino-4-oxobutanoic acid tert-butyl ester semicarbazone by reaction conditions reported for compound H, step A.

$^1$H NMR (500MHz, CD$_3$OD) δ7.35–7.2 (m, 6H), 7.0 (d, 2H), 6.65(d, 2H), 4.85 (m, 1H), 4.6–4.45 (m, 4H), 4.3 (br. m, 1H), 4.15 (m, 1H), 3.7 (m, 1H), 2.95 (m, 1H), 2.75–2.6 (m, 3H), 2.35 (m, 1H), 2.1 (m, 1H), 1.9 (s, 3H), 1.4 (s, 9H), 0.95 (d, 3H), 0.90 (s, 3H).

Step C. N-(N-Acetyl-tyrosinyl-valinyl-(4-benzyloxyprolinyl))-3-amino-4-oxobutanoic acid N-(N-Acetyl-tyrosinyl-valinyl-(4-benzyloxyprolinyl))-3-amino-4-oxobutanoic acid tert-butyl ester semicarbazone (270 mg) was dissolved into 10 ml of 25% trifluoroacetic acid in dichloromethane and stirred at room temperature for 3 hours. The mixture was concentrated to give a solid residue. The residue was dissolved into a 10 ml mixture of methanol:acetic acid:37% formaldehyde (3:1:1) and stirred at room temperature for 1 hour. The mixture was concentrated and the resulting residue purified by flash chromatography (SiO$_2$) eluting with dichloromethane/methanol/formic acid (100:5:0.5) to give 37 mg of the title compound.

$^1$H NMR (500 MHz, CD$_3$OD (existing as a 1:1 mixture of diastereomers of the hemiacetal)) δ7.4–7.25 (m, 5H), 7.0 (d, 2H), 6.65 (d, 2H), 4.65–4.05 (m, 7H), 3.75–3.4 (m, 2H), 3.05–2.3 (m, 5H), 2.2–1.95 (m, 2H), 1.90 (s, 3H), 1.0 (d, 3H), 0.95 (d, 3H).

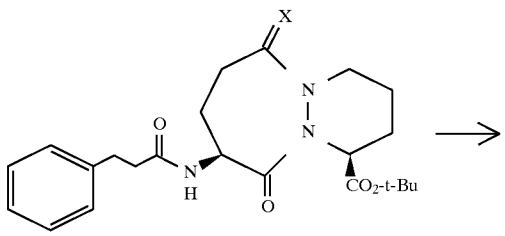

44

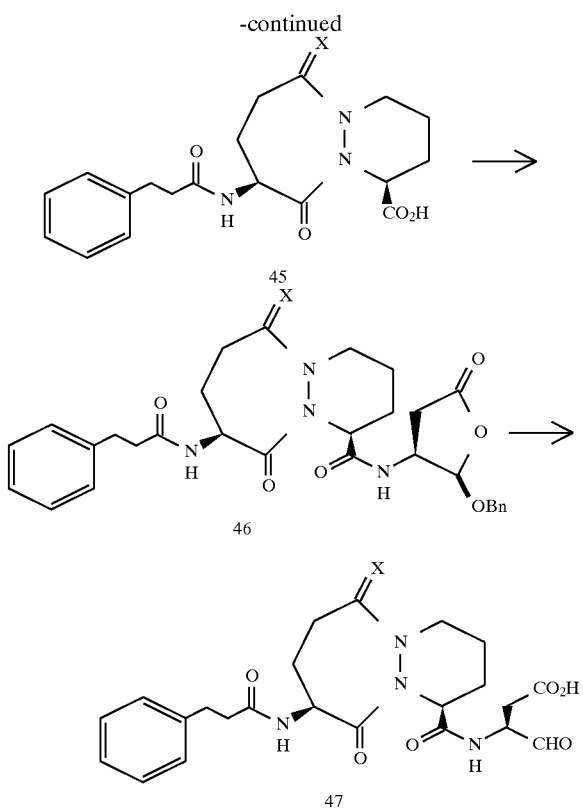

(a) X = O
(b) X = H$_2$ (1S,9S) t-Butyl 6,10-dioxo-octahydro-9-(3-phenylpropionylamino)-6H-pyridazino[1,2-a]

[1,2]diazepine-1-carboxylate (44a). To a solution of (1S, 9S)t-butyl 9-amino-6,10-dioxo-octahydro-6H-pyridazino [1,2-a][1,2]diazepine-1-carboxylate (690 mg; 2.32 mmol; GB 2128984) in dioxane (16 ml) and water (4 ml) at 0° C. was added solid sodium bicarbonate (292 mg; 3.48 mmol) followed by dropwise addition of 3-phenylpropionyl chloride (470 mg; 2.78 mmol). The mixture was stirred at room temperature for 2 h then more sodium bicarbonate (200 mg; 2.38 mmol) and 3-phenylpropionyl chloride (100 mg; 0.6 mmol) were added. The mixture was stirred for a further 2 h at room temperature, diluted with ethyl acetate (50 ml), washed with saturated sodium bicarbonate (2×25 ml) then dried (MgSO$_4$) and concentrated. The residue was purified by flash chromatography (0–50% ethyl acetate/chloroform) and finally crystallized by trituration with ether to afford 860 mg (86%) of a white solid: mp. 137°–138° C.; $[\alpha]_D^{23}$ –95.1° (c 0.549, CH$_2$Cl$_2$); IR (KBr) 3327, 1736, 1677, 1664, 1536, 1422, 1156; $^1$H NMR (CDCl$_3$) δ7.24 (5H, m), 6.50 (1H, d, J=7.5), 5.24 (1H, m), 4.90 (1H, m), 4.60 (1H, m), 3.44 (1H, m), 2.93 (2H, m), 2.84 (1H, m), 2.64 (1H, m), 2.54 (2H, m), 2.26 (2H, m), 1.70 (4H, m), 1.70 (9H, s). MS (FAB, m/z) : 430 (M$^+$+1), 374, 242, 105, 91.

(1S,9S) t—Butyl octahydro-10-oxo-9-(3-phenylpropionylamino)-6H-pyridazino-[1,2-a][1,2] diazepine-1-carboxylate (44b), was prepared from (1S, 9S) t-butyl 9-amino-octahydro-10-oxo-6H-pyridazino[1,2-a][1,2]diazepine-1-carboxylate (Attwood et al., J. Chem. Soc. Perkin 1, pp. 1011–19 (1986)) as for 44a, to afford 810 mg (81%) of a colorless oil: $[\alpha]_D^{23}$ –33.5° (c 0.545, CH$_2$Cl$_2$); IR (film) 3334, 2935, 1737, 1728, 1659, 1642; $^1$H NMR (CDCl$_3$) δ7.24 (5H, m), 6.75 (1H, d, J=6.7), 5.27 (1H, m), 4.92 (1H, m), 3.39 (1H, m), 3.03 (4H, m), 2.55 (3H, m), 2.33 (1H, m), 2.17 (1H, m), 1.80 (5H, m), 1.47 (9H, s), 1.39 (1H, m). MS(FAB, m/z) : 416 (M$^+$+1), 360, 211, 143, 97.

(1S,9S) 6,10-Dioxo-octahydro-9-(3-phenylpropionylamino)-6H-pyridazino[1,2-a] [1,2] diazepine-1-carboxylic acid (45a). To a solution of (1S,9S) t-butyl 6,10-dioxo-octahydro-9-(3-phenylpropionylamino)-6H-pyridazino[1,2-a] [1,2]diazepine-1-carboxylate (44a) (800 mg; 1.863 mmol) in dry dichloromethane (5 ml) at 0° C. was added trifluoroacetic acid (5 ml). The solution was stirred at room temperature for 3h then concentrated. Dry ether (10 ml) was added to the residue then removed under vacuum. This process was repeated three times to afford a crystalline solid. The solid was triturated with ether and filtered to afford 590 mg (85%) of a white crystalline solid: mp. 196°–197.5° C.; $[\alpha]_D^{23}$ –129.5° (c 0.2, CH$_3$OH) ; IR (KBr) 3237, 1729, 1688, 1660, 1633, 1574, 1432, 1285, 1205; $^1$H NMR (CD$_3$OD) δ8.28 (1H, d, J=7.4), 7.22 (5H, m), 5.32 (1H, dd, J=5.9, 2.9), 4.75 (1H, m), 4.51 (1H, m), 3.50 (1H, m), 3.01 (1H, m), 2.91 (2H, m), 2.55 (2H, m), 2.29 (3H, m), 1.95 (2H, m), 1.71 (2H, m). Anal. Calcd for C$_{19}$H$_{23}$N$_3$O$_5$: C, 61.12; H, 6.21; N, 11.25. Found: C, 60.80; H, 6.28; N, 10.97. MS(FAB, m/z) 374 (M++1), 242, 105, 91.

(1S, 9S) Octahydro-10-oxo-9-(3-phenylpropionylamino) $^6$H-pyridazino[1,2-a]-[1,2]diazepine-1-carboxylic acid (45b), was prepared from (IS, 9S) t-butyl octahydro-10-oxo-9-(3-phenylpropionylamino)-6H-pyridazino[1,2 a][1,2] diazepine-1-carboxylate (44b) by the method described for compound 45a to afford 657 mg (96%) of 45b as a crystalline solid: mp. 198°–202° C.; $[\alpha]_D^{23}$ –86.2° (c 0.5, CH$_3$OH); IR (KBr) 3294, 2939, 1729, 1645, 1620, 1574, 1453, 1214; $^1$H NMR (CD$_3$OD) δ7.92 (1H, d, J=7.9), 7.20 (5H, m), 5.29 (1H, m), 4.90 (1H, m), 3.47 (1H, m), 3.08 (2H, m), 2.90 (2H, m), 2.55 (3H, m), 2.36 (1H, m), 1.81 (5H, m), 1.43 (2H, m). MS(FAB, m/z) 360 (M$^+$+1), 211,143,91.

[3S, 2R,S, (1S, 9S)] N-(2-Benzyloxy-5-oxotetrahydrofuran-3-yl)-6,10-dioxo-octahydro-9-(3-phenylpropionylamino) 6H-pyridazino[1,2-a][1,2] diazepine-1-carboxamide (46a). To a solution of (1S, 9S) 6,10-dioxo-octahydro-9-(3-phenyl-propionylamino)-6H-pyridazino[1,2-a] [1,2]diazepine-1-carboxylic acid (45a) (662 mg; 1.773 mmol) in dry dichloromethane (9 ml) and dry dimethyl formamide (3 ml) at room temperature was added bis(triphenylphosphine)palladium chloride (30 mg) and (3S, 2R,S)-$^3$-allyloxycarbonylamino-2-benzyloxy-5-oxotetrahydrofuran (Chapman, Biorg. Med. Chem. Lett., 2, pp. 613–18 (1992)) (568 mg; 1.95 mmol) followed by dropwise addition of tri-n-butyltin hydride (1.19 g; 4.09 mmol). 1-Hydroxy-benzotriazole (479 mg; 3.546 mmol) was added to the mixture and the mixture was cooled to 0° C. before addition of 1-(3-dimethylaminopropyl)-3-ethylcarbodiimide hydrochloride (408 mg; 2.128 mmol). The mixture was stirred at room temperature for 3.25 h then diluted with ethyl acetate (50 ml), washed twice with dilute hydrochloric acid (20 ml), twice with saturated sodium bicarbonate (20 ml), once with brine then dried (MgSO$_4$) and concentrated. The resulting oil was purified by flash chromatography (0–100% ethyl acetate/chloroform) to afford 810 mg (81%) of 46a as a mixture of anomers: mp. 92°–94° C.; IR (KBr) 3311, 1791, 1659, 1651, 1536; $^1$H NMR(CDCl$_3$) δ7.49, 6.56 (1H, 2d, J=6.7, 7.8), 7.29 (10H, m), 6.37, 6.18 (1H, 2d, J=7.7,7.6), 5.56, 5.34 (1H, d, s, J=5.2), 5.08–4.47 (6H), 3.18–2.80 (5H), 2.62–2.28 (5H), 2.04–1.53 (5H). MS(FAB, m/z), 563 (M$^+$+1), 328, 149, 91.

[3S, 2R,S, (1S, 9S)] N-(2—Benzyloxy-5oxotetrahydrofuran-3-yl)-octahydro-10-oxo-9-(3-phenylpropionylamino)-6H-pyridazino[1,2-a][1,2] diazepine-1-carboxamide (46b), was prepared from 45b by the method described for 46a to yield 790 mg (96%) of a glass: m.p. 58°–60° C.; IR (KBr) 3316, 2940, 1793, 1678, 1641, 1523, 1453, 1120; $^1$H NMR (CDCl$_3$) δ7.28 (10 H, m), 6.52, 6.42 (1H, 2d, J=7.2, 7.1), 5.53, 5.44 (1H, d, s, J=5.2), 5.35 (1H, m), 4.6–4.9, 4.34 (4H, m), 3.1–2.8 (6H, m), 2.6–2.1 (7H), 1.95–1.05 (5H). MS(FAB, m/z), 549 (M$^+$+1), 400, 310, 279, 91. [3S, (1S, 9S)] 3-(6,10-Dioxo-octahydro-9-(3-phenylpropionylamino)-6H-pyridazino[1,2-a] [1,2] diazepine-1-carboxamido)-4-oxobutanoic acid (47a). A mixture of [3S, 2R,S, (1S, 9S)] N-(2-benzyloxy-5-oxotetrahydrofuran-3-yl)-6,10-dioxo-octahydro-9-(3-phenylpropionylamino)-6H-pyridazino[1,2-a][1,2] diazepine-1-carboxamide (46a) (205 mg; 0.364 mmol), 10% palladium on carbon (200 mg) and methanol (20 ml) was stirred under hydrogen at atmospheric pressure for 5 h. The mixture was filtered then concentrated to yield 154 mg (90%) of a glass: mp. 116°–118° C.; [α]$_D$$^{23}$–140° (c 0.1, CH$_3$OH); IR (KBr) 3323 (br), 1783, 1731, 1658, 1539, 1455, 1425; $^1$H NMR (CD$_3$OD) δ7.21 (5H, m), 5.17 (1H, m), 4.73 (1H, m), 4.50 (2H, m), 4.23 (1H, m), 3.38 (1H, m), 3.06 (1H, m), 2.91 (2H, m), 2.73–2.18 (6H, m) and 2.01–1.59 (5H, m). Anal. Calcd for C$_{23}$H$_{27}$N$_4$O$_7$+H$_2$O: C, 56.32; H, 6.16; N, 11.42. Found: C, 56.29; H, 6.11; N, 11.25. MS(FAB, m/z) 473 (M$^+$+1), 176, 149, 105, 91.

[3S,(1S,9S)]3-(Octahydro-10-oxo-9-(3-phenylpropionylamino)-6H-pyridazino-[1,2-a][1,2] diazepine-1-carboxamido)-4-oxobutanoic acid (47b), was prepared from 46b by the method described for 47a. The residue was purified by flash chromatography (0–10% methanol/chloroform) to afford 65 mg (52%) of a glass; m.p. 87°–90° C.; [α]$_D$$^{23}$–167.0° (c 0.1, methanol); IR (KBr) 3329, 2936, 1786, 1727, 1637; $^1$H NMR (CD$_3$OD) δ7.23 (5H, m), 5.29 (1H, m), 4.83 (1H, m), 4.59 (1H, d, J=3.6), 4.29 (1H, m), 3.3–3.0 (3H, m), 2.91 (2H, m), 2.70–2.34 (5H, m), 2.19 (2H, m), 1.75 (4H, m), 1.36 (2H, m). Anal. Calcd for C$_{23}$H$_{30}$N$_4$O$_6$+0.5H$_2$O: C, 59.09; H, 6.68; N, 11.98. Found: C, 58.97; 6.68; N, 11.73. MS(FAB, m/z) 459 (M++ 1), 310, 149, 105, 91.

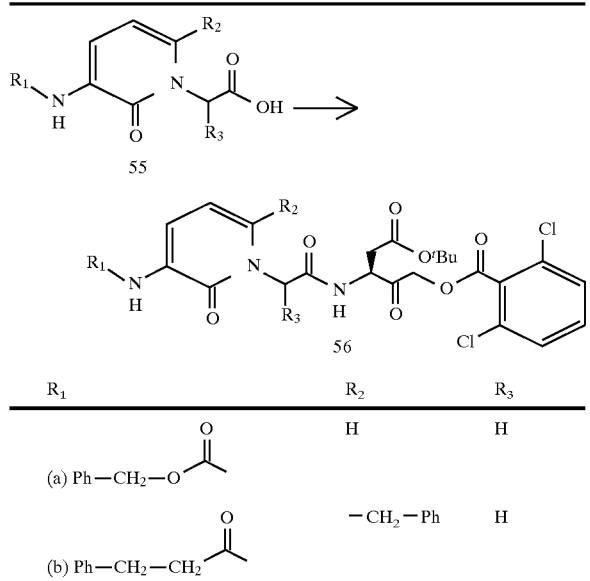

t—Butyl N-2-(3-benzyloxycarbonylamino-1,2-dihydro-2oxo-1-pyridyl)acetyl-3-amino-5-(2,6-dichlorobenzoyloxy) -4-oxo-pentanoate (56a). The acetic acid (55a) (WO 93 21213) in THF (2 ml) was stirred at room temperature and treated with 1-hydroxybenzotriazole (60 mg, 0.448 mmol) and dimethylaminopropyl-3-ethylcarbodiimide hydrochloride (47 mg, 0.246 mmol). After 5 mins water (2 drops) was added and stirring continued for 20 minutes. Bis (triphenylphosphine) palladium II chloride (6 mg) was added followed by a solution of t-butyl 3-(allyloxycarbonylamino)-4-oxo-5-(2,6-dichlorobenzoyloxy)pentanoate (WO 93 16710) (103 mg, 0.224 mmol) in THF (1 ml). Tributyltin hydride (0.09 ml, 0.336 mmol) was added dropwise over 1 hour at room temperature. The mixture was stirred for a further 3 hours and poured onto ethyl acetate, washed with 1M HCl, aqueous NaHCO$_3$, brine, dried over MgSO$_4$ and concentrated in vacuo. The residue was triturated with pentane and the supernatant discarded. The remaining solid was purified by flash chromatography (50% ethyl acetate/hexane) to afford the title compound 92 mg (63%) as a colorless oil: [α]$_D$$^{26}$–29.6° (c 1.1, CH$_2$Cl$_2$); IR (film) 3377, 3365, 3332, 3312, 1733, 1691, 1650, 1599, 1515, 1366, 1261, 1153, 1068, 747; $^1$H NMR (CDCl$_3$) δ8.09 (1H, d, J=6.8), 7.84 (1H, s), 7.58 (1H, d, J=8.3), 7.33 (8H, m), 7.02 (1H, dd, J=6.9, 1.7), 6.33 (1H, t, J=7.2), 5.20 (2H, s), 5.12 (2H, m), 4.89 (1H, dt), 4.65 (2H, m), 2.80 (2H, m), 1.38 (9H, s).

t-Butyl N-2-(6-benzyl-1,2-dihydro-2-oxo-3-(3-phenylpropionyl)amino-1-pyridyl)acetyl-3-amino-5-(2,6-dichlorobenzyloxy)-4-oxo-pentanoate (56b), was prepared by the method described for (56a) which afforded the title compound (66%) as a colorless oil: IR (film) 3364, 3313, 1738, 1688, 1648, 1600, 1566, 1514, 1433, 1369, 1254, 1152; $^1$H NMR (CDCl$_3$) δ8.40 (1H, d, J 7.6), 8.30 (1H, s), 7.28 (13H, m), 6.20 (1H, d, J =7.6), 5.12 (2H, q), 4.86 (1H, m), 4.65 (2H, q), 4.06 (2H, s), 3.07–2.61 (6H, m), 1.39 (9H, s).

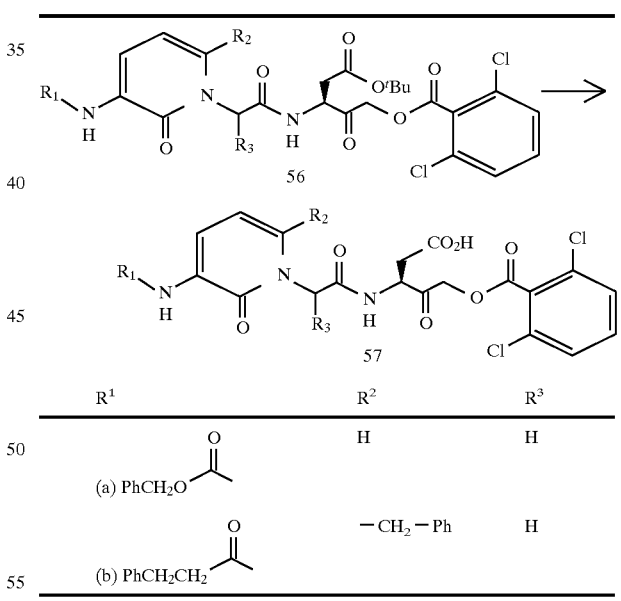

N-2(3—Benzyloxycarbonylamino-1,2-dihydro-2-oxo-1-pyridyl)acetyl-3-amino-5-(2,6-dichlorobenzoyloxy)-4-oxo-pentanoic acid (57a; O). The ester (56a) (210 mg, 0.356 mmol) in dichloromethane (0.5 ml) was cooled to 0° C. and treated with trifluoroacetic acid (0.5 ml), stirred and warmed to 20° C. over 30 minutes. The solution was evaporated to dryness under reduced pressure, redissolved in dichloromethane and concentrated (x3). The residue was triturated with ethyl acetate and diluted with ether to afford the title compound 162 mg (85%) as a colorless solid: m.p. 165°–8° C. (decomposition); [α]$_D$$^{23}$–38.8° (c 0.1, CH$_3$OH); IR (KBr)

3332, 3275, 1723, 1658, 1649, 1597, 1581, 1562, 1526, 1432, 1385, 1258, 1218, 1206; $^1$H NMR (d$_6$-DMSO) δ8.96 (1H, d, J=7.3), 8.34 (1H, s), 7.85 (1H, dd, J=7.3), 7.58 (3H, m), 7.35 (5H, m), 6.29 (1H, t, J=7.3), 5.26 (2H, m), 5.15 (2H, s), 4.69 (3H, m), 2.75 (2H, m). Anal. Calcd. C$_{27}$H$_{23}$N$_3$O$_9$Cl$_2$: C, 53.66; H, 3.84; N, 6.95. Found: C, 53.36; H, 3.90; N, 6.81. M.S. (+FAB); 604 (M$^+$+1), 285, 241, 195, 173, 149, 91.

N-2-(6-Benzyl-1,2-dihydro-2-oxo-3-(3-phenylpropionyl) amino-1-pyridyl)acetyl-3-amino-5-(2,6-dichlorobenzoyloxy)-4-oxo-pentanoic acid (57b; P), was prepared by the method described for 57a which afforded the title compound (78%) as colorless crystals: m.p. 116°–120° C. (decomposition); [α]$_D^{26}$–41.10 (c 0.1, CH$_3$OH); IR (KBr) 3299, 1739, 1715, 1689, 1666, 1645, 1598, 1563, 1518, 1432, 1209, 1151; $^1$H NMR (d$_6$-DMSO) δ9.24 (1H, s), 8.88 (1H, d, J=7.6), 8.18 (1H, d, J=7.7), 7.60 (3H, m), 7.26 (10H, m), 6.06 (1H, d, J=7.7), 5.23 (2H, ABq), 4.69 (3H, m), 3.93 (2H, s), 2.78 (6H, m). Anal. Calcd. for C$_{35}$H$_{31}$N$_3$O$_8$Cl$_2$. H$_2$O: C, 59.16; H, 4.68; N, 5.91. Found: C, 59.38; H, 4.53; N, 5.84. M.S. (+FAB); 694, (Cl=35, 37) , (M$^+$+1); 692 (Cl=35, 35) , (M$^+$+1).

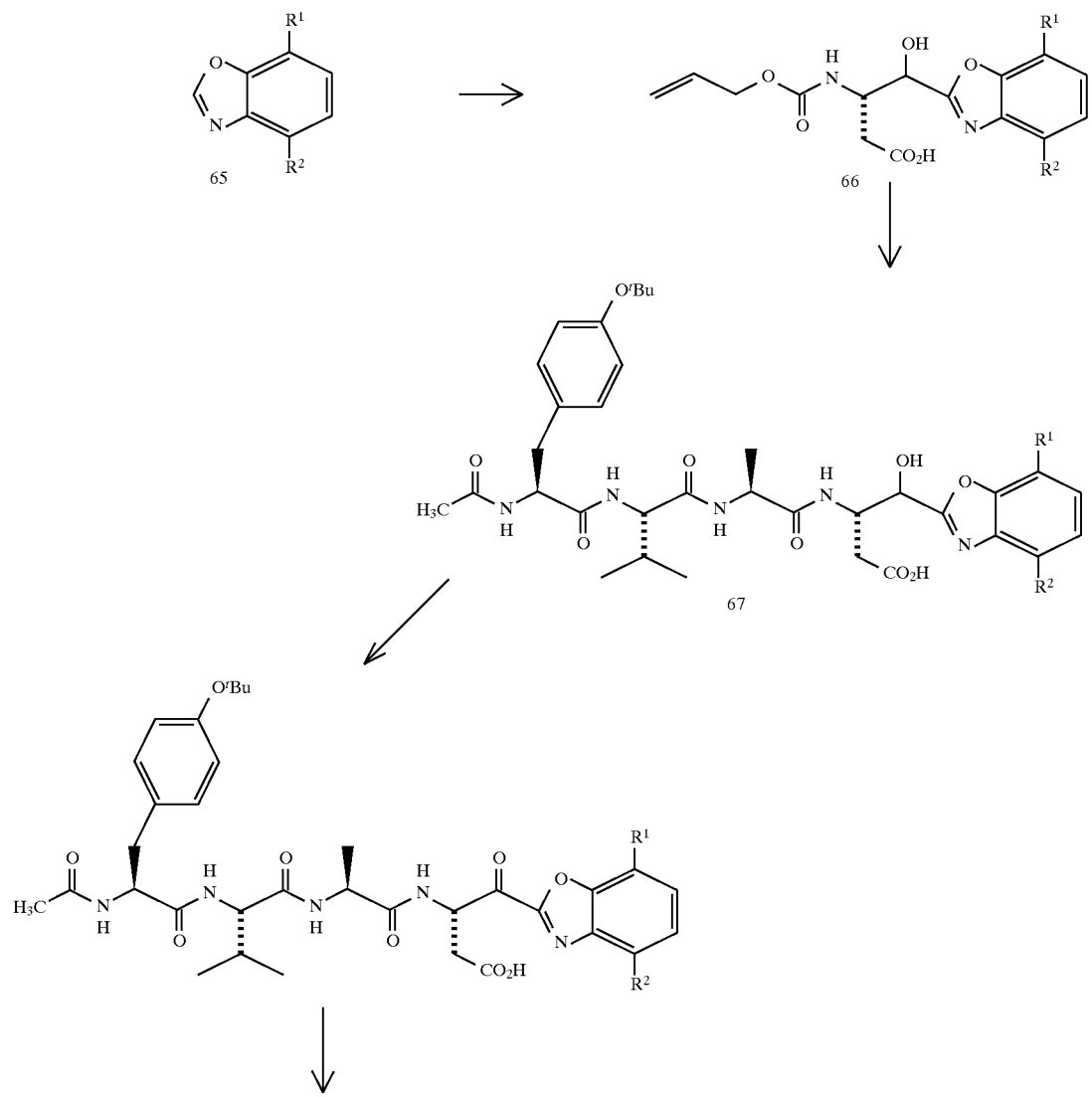

-continued

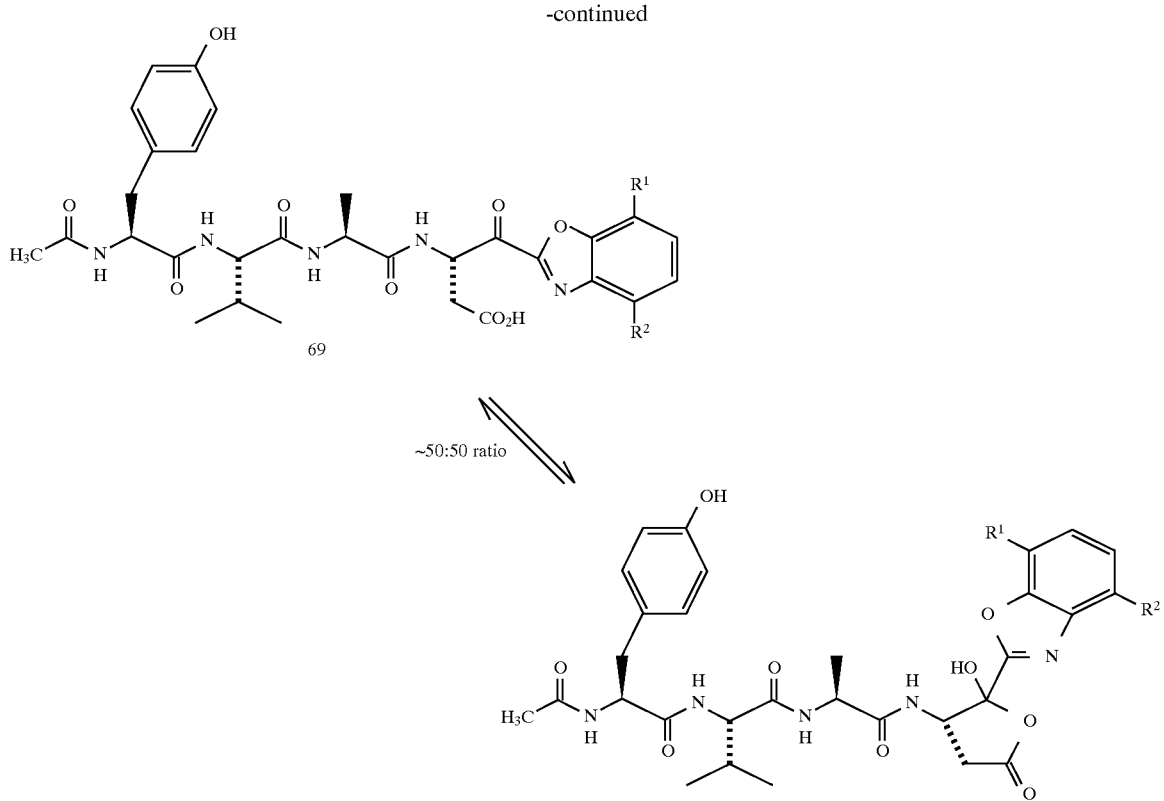

(a) R¹ = OCH₃, R² = H
(b) R¹ = H, R² = OCH₃

7-Methoxybenzoxazole (65a). A mixture of 2-nitro-6-methoxyphenol (2.62 g, 15.0 mmol) (EP 333176) and 10% Palladium on carbon (130 mg) in ethanol (50.0 ml) was stirred under an atmosphere of H₂ for 75 min. The mixture was filtered through Celite200 then immediately treated with p-toluenesulphonic acid (32.0 mg) and triethylorthoformate (6.45 ml, 38.8 mmol) then heated under reflux under an atmosphere of N₂. After 20 h p-toluenesulphonic acid (30.0 mg) and triethylorthoformate (6.45 ml, 38.8 mmol) were added. After a total of 44 h heating, the reaction was allowed to cool and reduced in vacuo. The resulting residue was purified by flash chromatography (25:75 ethyl acetate/hexane) to give 1.97 g (85%) of the title compound as a yellow solid: m.p. 28°–31° C.; IR (film) 1629, 1497, 1434, 1285, 1097; ¹H NMR (CDCl₃) δ8.09 (1H, s), 7.40 (1H, d, J=8.0), 7.28 (1H, t, J=8.0), 6.89 (1H, d, J=8.0), 4.02 (3H, S); ¹³C NMR (CDCl₃) δ152.84, 145.82, 142.50, 139.99, 125.75, 113.42, 108.80, 56.97. Anal. Calcd. for C₈H₇N₁O₂. 0.1H₂O: C, 63.65; H, 4.81; N, 9.29. Found: C, 63.43, H, 4.88, N, 9.05. M.S. (+FAB); 150 (M³⁰ +1).

4-Methoxybenzoxazole (65b). To a suspension of 4-hydroxybenzoxazole (2.00 g, 14.8 mmol) (Musser et al.,*J. Med. Chem.*, 30, pp. 62–67 (1987)) in acetone (80.0 ml) was added dried K₂CO₃ (2.25 g, 16.3 mmol) followed by iodomethane (1.38 ml, 22.2 mmol). The reaction was heated under reflux under N₂ for 4.5 h, then filtered and reduced in vacuo to afford the crude product. The resulting residue was purified by flash chromatography (25:75 ethyl acetate/hexane) to give 2.0 g (91%) of the title compound as a white crystalline solid: m.p. 72°–74° C.; IR (KBr) 3089, 1619, 1610, 1503, 1496, 1322, 1275, 1090, 1071, 780, 741; ¹H NMR (CDCl₃) δ8.02 (1H, s), 7.32 (1H, t, J=8.0), 7.18 (1H, d, J=8.0), 6.81 (1H, d, J=8.0), 4.04 (3H, s). Anal. Calcd. for C₈H₇NO₂: C, 64.42; H, 4.73; N, 9.39. Found: C, 64.40; H, 4.84; N, 9.31; m/z (EI) 149 (M⁺+1, 100%).

(3S, 4R,S) t-Butyl N-(allyloxycarbonyl)-3-amino-4-hydroxy-4-(2-(7-methoxybenzoxazolyl))butanoate (66a). To a stirred solution of 7-methoxybenzoxazole 65a (548.6mg, 3.68 mmol) in anhydrous THF (18.5 ml) at −78° C. under N₂ was added 1.56M n-butyl lithium in hexanes (2.47 ml, 3.86 mmol) dropwise, to produce a yellow colored solution. After stirring at −78° C. for 20 min, dry MgBr₂OEt₂ (1.045 g, 4.05 mmol) was added as a solid. The resulting heterogeneous mixture was warmed to −45° C. and stirred for 15 min. The reaction mixture was then recooled to −78° C. and a solution of (S)-Alloc-Asp(t-Bu)H (946.4mg, 3.68 mmol) in THF (18.5 ml) was added dropwise. The reaction was stirred at −78° C. for 30min, warmed to 0° C. and stirred for 1 h. The resulting homogeneous reaction was warmed to room temperature and stirred for 16 h. The reaction was quenched with 5% sodium bicarbonate (3.5 ml) then THF was removed in vacuo. The resulting aqueous residue was extracted with methylene chloride (x6). The combined extracts were washed with brine, dried (MgSO₄), filtered and reduced in vacuo to give 1.8 g of crude product. Flash chromatography (40:60 ethyl acetate/hexane) gave 1.21 g (81%) of the title compound, an oil, as a mixture of diastereoisomers at C-4: IR (CH₂Cl₂) 3425, 2983, 1725, 1504, 1290, 1157, 1101; ¹H NMR (CDCl₃) δ7.35–7.19 (2H, m), 6.89–6.81 (1H, m), 6.00–5.57 (2H, m), 5.32–5.05 (3H, m), 4.68–4.35 (3H, m), 4.01 (3H, s), 2.86–2.59 (2H, m), 1.45 (9H, s), 1.41 (9H, s); ¹³C NMR (CDCl₃) δ171.18, 171.09, 165.80, 165.30, 156.71, 156.60, 145.65, 142.76, 142.71, 140.82, 140.72, 133.23, 125.81, 125.72, 118.41, 118.21, 113.07, 112.87, 108.95, 82.16, 70.28, 69.98, 66.52, 66.39, 57.03, 52.57, 52.29, 37.83, 36.86, 28.65. Anal. Calcd. for $C_{20}H_{26}N_2O_7 \cdot 0.6H_2O$: C, 57.57; H, 6.57; N, 6.72. Found: C, 57.49, H, 6.34, N, 6.60. M.S. (+FAB); 407 ($M^+$+1); 351, 307, 154.

(3S, 4R,S) t-Butyl N-(allyloxycarbonyl)-3-amino-4-hydroxy-4-(2-(4-methoxybenzoxazolyl))butanoate (66b), was prepared according to the method described for 66a which afforded 1.29 g (26%, 68% based on recovered starting material) of the title compound as an oil and as a mixture of diastereoisomers at C-4: IR ($CH_2Cl_2$) 3400, 1725, 1625, 1505, 1369, 1354, 1281, 1263, 1226, 1158, 1092, 1048; $^1$H NMR ($CDCl_3$) δ7.34–7.24 (1H, ml), 7.16 (1H, d, J=8.2), 6.79 (1H, d, J=7.9), 6.00–5.50 (2H, m), 5.30–5.05 (3H, m), 4.70–4.35 (4H, m), 4.02 (3H, s), 2.90–2.45 (2H, m), 1.45–1.41 (9H, 2 x s). Anal. Calcd. for $C_{20}H_{26}N_2O_7 \cdot 0.4H_2O$: C, 58.07; H, 6.53; N, 6.77. Found: C, 58.09; H, 6.41; N, 6.63. M.S. (+FAB) ; 407 ($M^+$+1, 88%); 351 (100).

(3S, 4R,S) t-Butyl N-(N-acetyl-(S)-(O-tert-butyltyrosinyl)-(S)-valinyl-(S)-alaninyl)-3-amino-4-hydroxy-4-(2-(7-methoxybenzoxazolyl))butanoate (67a). To a stirred solution of the benzoxazole 66a (481.9 mg, 1.19 mmol) and Ac-Tyr($^t$Bu)-Val-Ala-OH (586.3 mg, 1.30 mmol) in methylene chloride (3.5 ml) and DMF (3.5 ml) was added bis(triphenylphosphine) palladium (II) chloride (18.0 mg), followed by tributyltinhydride (0.80 ml, 2.96 mmol) dropwise. Hydroxybenzotriazole (320.4 mg, 2.37 mmol) was added and the mixture cooled to 0° C. 1Ethyl-3-[3-(dimethylamino)propyl]carbodiimide hydrochloride (278.2 mg, 1.42 mmol) was added and the mixture was allowed to warm to room temperature and stirred for 16.5 h. The reaction was diluted with ethyl acetate and washed twice with 1 M sodium hydrogensulphate, twice with saturated sodium bicarbonate, water, and brine. The organic layer was dried ($MgSO_4$), filtered and reduced in vacuo to yield 2.0 g of crude product. Flash chromatography (95:5 methylene chloride/methanol) gave 844.0 mg (94%) of the title compound as a white solid: m.p. 205° C.; IR (KBr) 3399, 3304, 2977, 1729, 1643, 1506, 1367, 1290, 1161; $^1$H NMR ($d_6$-DMSO) δ8.24–7.78 (4H, m), 7.43–7.32 (2H, m), 7.23 (2H, d, J=8.5), 7.16–7.07 (1H, m), 6.93 (2H, d, J=8.5), 6.52, 6.40 (1H, 2 x d, J=5.5, J=5.0), 5.03, 4.78–4.49, 4.45–4.16 (5H, brt, 2 x m), 4.05, 4.04 (3H, 2 x s), 3.08–2.35 (14H, m), 2.11–1.89 (1H, m), 1.83 (3H, s), 1.49–1.32, 1.15, 1.0–0.81 (27H, s, 2 x m, J=7.0); $^{13}$C NMR ($d_6$-DMSO) δ175.55, 175.18, 173.88, 173.75, 173.05, 169.23, 157.28, 148.55, 146.16, 143.21, 136.63, 133.55, 128.87, 127.17, 115.78, 111.92, 84.02, 81.50, 71.40, 61.15, 60.05, 57.79, 53.39, 51.62, 43.76, 40.52, 34.58, 32.52, 31.60, 26.35, 23.11, 22.71, 21.76. Anal. Calcd. for $C_{39}H_{55}N_5O_{10} \cdot 0.5H_2O$: C, 61.40; H, 7.40; N, 9.18. Found: C, 61.43; H, 7.31; N, 9.07. M.S. (+FAB); 754 (Ml +1); 698, 338, 267.

(3S, 4R,S) t-Butyl N-(N-acetyl-(S)-(O-tert-butyltyrosinyl)-(S)-valinyl-(S)-alaninyl)-3-amino-4-hydroxy-4-(2-(4-methoxybenzoxazolyl))butanoate (67b), was prepared according to the method described for 67a which afforded 1.05g (94%) of the title compound as a fine white powder: m.p. 210°–213° C. (dec); IR (KBr) 3284, 2977, 1736, 1691, 1632, 1536, 1505, 1452, 1392, 1367, 1258, 1236, 1161, 1091; $^1$H NMR ($d_6$-DMSO) δ8.207.75 (4H, m), 7.40–7.10 (4H, m), 7.00–6.80 (3H, m), 6.45, 6.34 (1H, 2 x d, J=5.3, J=5.0), 5.00–4.10 (5H, m), 4.00, 3.99 (3H, 2 x s), 3.00–2.25 (4H, m), 1.95 (1H, m), 1.78 (3H, s), 1.39–0.80 (27H, m). Anal. Calcd. for $C_{39}H_{55}N_5O_{10} \cdot 0.5H_2O$: C, 61.40; H, 7.40; N, 9.18. Found: C, 61.58; H, 7.38; N, 8.91. M.S. (+FAB) ; 754 ($M^+$+1, 30%); 72 (100).

(3S) t-Butyl N-(N-acetyl-(S)-(O-tert-butyl-tyrosinyl)(S)-valinyl-(S)-alaninyl)-3-amino-4-(2-(7-methoxybenzoxazolyl))-4-oxobutanoate (68a). The Dess-Martin reagent (1.082 g, 2.55 mmol) (Ireland et al., *J. Org. Chem.*, 58, p. 2899 (1993); Dess et al., *J. Org. Chem.*, 48, pp. 4155–4156 (1983)) was added to a stirred suspension of the alcohol 67a (641.0 mg, 0.85 mmol) in methylene chloride (46.0 ml). The resulting mixture was stirred for 1 h before being partitioned between saturated sodium thiosulphate: saturated sodium bicarbonate (1:1, 86.0 ml) and ethyl acetate (86.0 ml). The resultant organic phase was washed in turn with saturated sodium thiosulphate: saturated sodium bicarbonate (1:1), saturated sodium bicarbonate, and brine. The organic phase was dried ($MgSO_4$), filtered and reduced in vacuo to give 660.0 mg of crude product. Flash chromatography (94:6 methylene chloride/methanol) gave 636.0 mg (100%) of the title compound as a white solid: m.p. 209° C.; $[\alpha]_D^{24}$–21.80 (c 0.16, methanol); IR (KBr) 3395, 3294, 2977, 1722, 1641, 1535, 1505, 1161; $^1$H NMR ($CDCl_3$) δ8.43–8.16 (1H, m), 7.97–7.62 (2H, m), 7.49–7.14 (3H, m), 7.08–6.95 (3H, m), 6.89–6.73 (2H, m), 5.81–5.68 (1H, m), 5.16–4.86 (2H, m), 4.53 (1H, brt), 4.03 (3H, s), 3.16–2.84 (4H, m), 2.11–1.84 (4H, m), 1.46–1.14 (21H, m), 0.92–0.78 (6H, m); $^{13}$C NMR ($CDCl_3$) δ186.28, 173.39, 171.90, 171.19, 171.03, 169.89, 156.43, 154.75, 146.32, 142.88, 140.98, 132.31, 130.54, 126.98, 124.73, 114.95, 111.42, 82.44, 78.71, 58.92, 57.20, 54.91, 53.47, 48.77, 39.43, 38.15, 32.79, 29.44, 28.60, 23.55, 20.27, 19.70, 19.34. M.S. (+FAB); 752 ($M^+$+1); 696, 336, 265.

(3S) t-Butyl N-(N-acetyl-(S)-(O)-tert-butyl-tyrosinyl)-(S)-valinyl-(S)-alaninyl)-3-amino-4-(2-(4-methoxybenzoxazolyl))-4-oxobutanoate (68b), was prepared according to the method described for the ketone 68a which afforded 420 mg (55%) of the title compound as a white solid: m.p. 211°–213° C. (dec); $[\alpha]_D^{24}$–23.9° (c 0.82, methanol); IR (KBr) 3277, 3075, 1723, 1690, 1632, 1530, 1506, 1392, 1366, 1269, 1234, 1160, 1094; $^1$H NMR ($CDCl_3$) δ8.15 (1H, brs), 7.7 (2H, brs), 7.46 (1H, t, J=8.3), 7.24 (2H, d, J=8.3), 7.10 (1H, brs), 7.03 (2H, d, J=8.3), 6.83 (3H, m), 5.74 (1H, q, J=6.9), 5.00 (2H, m), 4.51 (1H, t, J=7.0), 4.07 (3H, s), 3.20–2.95 (4H, m), 2.00 (4H, m), 1.42 (3H, d, J=6.8), 1.35 (9H, s), 1.23 (9H, s), 0.86 (6H, d, J=6.7). M.S. (+FAB) ; 752 ($M^{30}$ +1, 7%); 72 (100).

(3S) N-(N-Acetyl-(S)-tyrosinyl-(S)-valinyl-(S)-alaninyl)-3-amino-4-(2-(7-methoxybenzoxazolyl))-4-oxobutanoate (69a; R). A solution of the ester 68a (600.0 mg, 0.80 mmol) in a 1:1 mixture of methylene chloride and trifluoroacetic acid (65.0 ml) was stirred for 1 h under a dry atmosphere of $N_2$. The solution was then reduced in vacuo, taken up in ether and reduced again. This process was repeated six times to afford the crude product as an off white solid. Flash chromatography (gradient 95:5 to 80:20 methylene chloride/methanol) gave 420.8 mg (83%) of the title compound as a hygroscopic white solid. The product existed as a mixture of three isomers in $CD_3OD$, consisting of the keto form (c 50%), and its acyloxy keto form (two isomers at C-4, c 50%): m.p. decomposes above 150° C.; $[\alpha]_D^{24}$–33.2° (c 0.17, methanol) ; IR (KBr) 3300, 1715, 1658, 1650, 1531, 1517, 1204; $^1$H NMR ($CD_3OD$) δ7.46–7.19 (2H, mn), 7.16–6.91 (3H, m), 6.70–6.59 (2H, mn), 5.62–5.49 (1H, mn), 5.00–4.72 (1H, obscured mn), 4.69–4.51 (1H, m), 4.49–4.08 (2H, m), 4.05–3.89 (3H, m), 3.16–2.47 (4H, m), 2.05–1.78 (4H, m), 1.41–1.11, 1.05–0.70 (9H, 2 x m). Anal. Calcd. for $C_{31}H_{37}N_5O_{10} \cdot 3H_2O$: C, 53.67; H, 6.25; N, 10.10. Found: C, 53.76; H, 5.56; N, 10.28. M.S. (+FAB); 640 ($M^+$+1) ; 435, 147.

(3S) t-Butyl N-(N-acetyl-(S)-tyrosinyl-(S)-valinyl-(S)-alaninyl)-3-amino-4-(2-(4-methoxybenzoxazolyl))-4-oxobutanoate (69b; S), was prepared according to the method described for the acid 69a which afforded the hygroscopic title compound 252 mg (96%). The product existed as a mixture of three isomers in $CD_3OD$, consisting of the keto form, and its acycloxy ketal form (two isomers at C-4). The product existed as a single isomer in d-6 DMSO: m.p. 200°–203° C. (dec.); $[\alpha]_D^{24}$ –38.0° (c 0.23, methanol); IR (KBr) 3289, 2968, 1718, 1713, 1658, 1634, 1548, 1517, 1506, 1461, 1453, 1393, 1369, 1268, 1228, 1174, 1092; $^1H$ NMR ($d_6$-DMSO) δ9.20 (1H, brs), 8.71 (1H, d, J=6.2), 8.10 (2H, m), 7.83 (1H, d, J=8.7), 7.61 (1H, t, J=8.2), 7.46 (1H, d, J=8.2), 7.08 (3H, m), 6.65 (2H, d, J=8.3), 5.50 (1H, q, J=6.5), 4.50 (1H, mn), 4.37 (1H, m), 4.20 (1H, m), 4.05 (3H, s), 3.09–2.77 (4H, m), 1.94 (1H, m), 1.79 (3H, s), 1.23 (3H, d, J=7.0), 0.82 (6H, m). Anal. Calcd. for $C_{31}H_{37}N_5O_{10}$. $1.5H_2O$: C, 55.85; H, 6.05; N, 10.51. Found: C, 55.21; H, 5.69; N, 10.13. M.S. (+FAB) ; 640 ($M^+$+1, 22%); 107 (100).

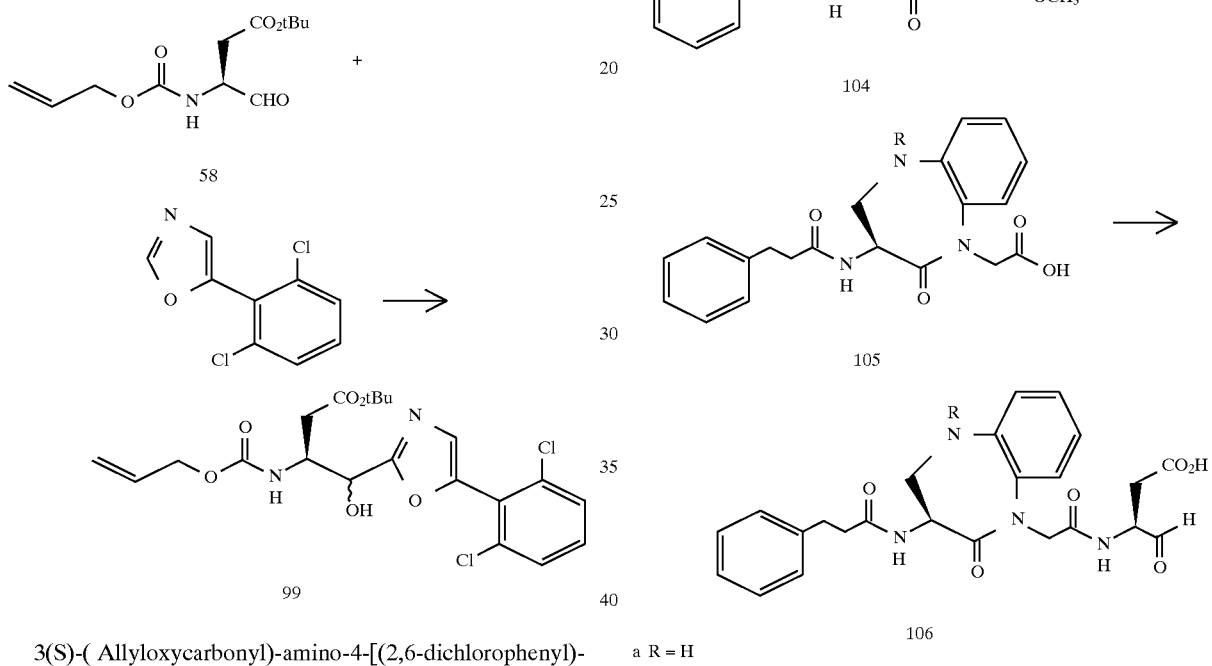

3(S)-( Allyloxycarbonyl)-amino-4-[(2,6-dichlorophenyl)-oxazol-2-yl]-4(R,S)-hydroxy-butyric acid tert-butyl ester (99). A solution of 5-(2,6-Dichlorophenyl)oxazole (2.71 g, 12.7 mmol; prepared by a similar method described in Tet. Lett. 23, p2369 (1972)) in tetrahydrofuran (65 mL) was cooled to –78° C. under a nitrogen atmosphere. To this solution was added n-butyl lithium (1.5M solution in hexanes, 8.5 mL, 13.3 mmol) and stirred at –78 ° C. for 30 min. Magnesium bromide etherate (3.6 g, 13.9 mmol) was added and the solution was allowed to warm to –45° C. for 15 min. The reaction was cooled to –78° C. and aldehyde 58 (3.26 g, 12.7 mmol; Graybill et al., *Int. J. Protein Res.*, 44, pp. 173–182 (1993)) in tetrahydrofuran (65 mL) was added dropwise. The reaction was stirred for 25 min., then allowed to warm to –40 ° C. and stirred for 3 h, and then at room temperature for 1 h. The reaction was quenched with 5% $NaHCO_3$(12 mL) and stirred for 3 h. The tetrahydrofuran was removed in vacuo and the resulting residue was extracted with dichloromethane. The organic layer was washed with saturated sodium chloride solution and dried over magnesium sulfate, filtered, and concentrated to yield 6.14 g of the title compound. Purification gave 4.79 g (80%) of 99: $^1H$ NMR ($CDCl_3$) δ1.45(s, 9H), 2.7–2.5(m, 2H), 2.8(dd, 1H), 4.2, 4.4(2 x d, 1H), 4.7–4.5(m, 3H), 5.35–5.1 (m, 2H), 5.6, 5.7(2 x d, 1H), 6.0–5.8(m, 1H), 7.2(d, 1H), 7.3(m, 1H), 7.4(m, 2H).

a R = H
b R = $COCH_2CH_2Ph$
c R = $CH_2Ph$

[2-Oxo-3(S)-($^3$-phenylpropionylamino)-2,3,4,5-tetrahydro-benzo[b][1,4]diazepin-1-yl]acetic acid methyl ester (104a). Anhydrous hydrogen chloride was bubbled into a solution of (3(S)-tert-butoxycarbonylamino-2-oxo-2,3,4, 5-tetrahydro-benzo[b][1,4]diazepin-1-yl)acetic acid methyl ester (103, 1 g, 2.86 mmol) in 25 ml of ethyl acetate for 2 minutes then stirred for 1 hour at room temperature. The reaction was evaporated to give 2-oxo-3(S)-amino-2,3,4,5-tetrahydrobenzo[b][1,4]diazepin-1-yl acetic acid methyl ester hydrochloride as a white solid. The hydrochloride salt and hydrocinnamic acid (0.47 g, 3.15 mmol) were dissolved into 20 ml of dimethylformamide and cooled to 0° C. Diisopropylethylamine (1 ml, 5.72 mmol) was added to the solution followed by the addition of N-hydroxybenzotriazole and 1-(3-dimethylaminopropyl)-3-ethylcarbodiimide hydrochloride. After stirring for 18 hours at room temperature, the mixture was diluted with 150 ml of ethyl acetate and washed with 10% sodium hydrogen sulfate, 10% sodium bicarbonate, and brine. The organic layer was dried over anhydrous sodium sulfate, filtered, and evaporated to a crude solid that was purified by flash chromatography eluting with 7:3 ethyl acetate/dichloromethane to afford 600 mg (55%)of the title compound as a white solid. ¹H NMR (CDCl₃) δ7.3–6.85 (9H,m), 6.55–6.0 (1H, d), 4.88–4.82 (1H, m), 4.72–4.65 (1H, d), 4.28–4.22 (1H, m), 3.95–3.9 (1H, m), 3.78 (3H, s), 3.65 (1H, br. s), 3.28–3.2 (1H, m), 2.95–2.84 (2H, m), 2.55–2.4 (2H, m).

(3(S)-(3-Phenylpropionylamino)-2-oxo-2,3,4,5-tetrahydrobenzo[b][1,4]diazepin-1-yl)acetic acid (105a). (3(S)-(3-Phenylpropionylamino)-2-oxo-2,3,4,5-tetrahydrobenzo[b][1,4]diazepin-1-yl)acetic acid methyl ester (104a) was dissolved in 90% methanol. Lithium hydroxide hydrate was added to the reaction and the reaction was stirred at room temperature for 4 h. The reaction was evaporated in vacuo to give a white solid. This was dissolved in 20 ml of water and acidified to pH 5 and extracted with ethyl acetate to afford 304 mg (88%) of the title compound as a white solid. ¹H NMR (CDCl₃) δ7.5–6.9 (11H, m), 4.92–4.8 (1H, m), 4.7–4.58 (1H, d), 4.38–4.25 (1H, d), 3.88–3.78 (1H, m), 3.45–3.25 (1H, m), 3.05–2.85 (2H, m), 2.55–2.45 (2H, m). 4-Oxo-3(S)-{2-[2-oxo-3(S)-(3-phenylpropionylamino)-2,3,4,5-tetrahydro-benzo[b][1,4]diazepin-1-ylacetylamino}butyric acid (106a). N-[1-(2-Benzyloxy5-oxotetrahydrofuran-3-ylcarbamoyl-methyl)-2-oxo-2,3,4,5-tetrahydro-1H-benzo[b][1,4]diazepin-3-yl]-3-phenylpropionamide was prepared from 105a by the procedure used to prepare compound H (stepA) to afford 390 mg (93%) of the product as diastereomers. ¹H NMR (CD₃OD) δ7.58–7.22 (14H, m), 5.78–5.73 (0.5 H, d), 5.64 (0.5 H, s), 5.0–4.72 (4H, m), 4.54–4.42 (2H, m), 3.82–3.76 (0.5 H, m), 3.68–3.62 (o.5 H, m), 3.28–3.21 (0.5H, m), 3.19–3.12 (0.5H, m), 3.07–2.98 (2H, m), 2.78–2.48 (4H, m).

The resulting product was converted to 106a by the method described to prepare compound H (StepD) to afford the title compound as a white solid (17%): ¹H NMR (CD₃OD) δ7.54–6.98 (9H, m), 5.58–5.44 (1H, m), 4.8–4.2 (4H, m), 3.96–3.3 (2H, m), 3.30–3.05 (1H, m), 2.98–2.25 (5H, m).

[2-Oxo-5-(3-phenylpropionyl)-3-(S)-(3phenylpropionylamino)-2,3,4,5-tetrahydrobenzo[b][1,4]diazepin-1-yl]acetic acid methyl ester (104b). Anhydrous hydrogen chloride was bubbled into a solution of (³(S)-tert-butoxycarbonylamino-2oxo-2,3,4,5-tetrahydro-benzo[b][1,4]diazepin-1-yl)acetic acid methyl ester (103, 1 g, 2.86 mmol) in 25 ml of ethyl acetate for 2 minutes then stirred for 1 hour at room temperature. The reaction was evaporated to give 2-oxo-3(S)-amino-2,3,4,5-tetrahydrobenzo[b][1,4]diazepin-1-yl acetic acid methyl ester hydrochloride as a white solid. The hydrochloride salt was suspended into 20 ml of dichloromethane and cooled to 0° C. Triethylamine (1.6 ml, 11.5 mmol) was added to the suspension followed by the dropwise addition of dihydrocinnamoyl chloride (0.9 ml, 6 mmol). The mixture was warmed to room temperature and stirred for 18 hours. The mixture was diluted with 25 ml of dichloromethane and washed twice with 50 ml of water and once with 50 ml of brine. The organic layer was dried over anhydrous sodium sulfate, filtered, and evaporated to give a viscous, yellow oil that was purified by flash chromatography eluting with 1:1 ethyl acetate/dichloromethane to afford 1.35 g (92%) of the title product as a white solid. ¹H NMR (CDCl₃) δ7.45–7.02 (14 H, m), 6.37–6.32 (1H, d), 4.78–4.72 (1H, m), 4.52–4.3 (3H, m), 3.82–3.77 (1H,m), 3.74 (3H, s), 3.03–2.87 (4H, m), 2.58–2.45 (2H, m), 2.45–2.35 (1H, m), 2.25–2.16 (1H, m).

[2-Oxo-5-(3-phenylpropionyl)-3-(3(S)-phenylpropionylamino)-2,3,4,5-tetrahydrobenzo[b][1,4]diazepin-1-yl]acetic acid (105b). [2-Oxo-5-(3-phenylpropionyl)-3-(3-phenylpropionylamino)-2,3,4,5-tetrahydrobenzo[b][1,4]diazepin-1-yl]acetic acid methyl ester (104b; 680 mg, 1.32 mmol) was hydrolyzed by the procedure used to hydrolyze 105a to afford 645 mg (98%) of the title compound as a white solid. ¹H NMR (CDCl₃) δ7.58 (1H, br. s), 7.5–7.42 (1H, m), 7.35–6.95 (14H, m), 4.95–4.88 (1H, m), 4.64–4.55 (1H, d), 4.54–4.45 (1H, t), 4.15–4.05 (1H, d), 3.75 (1H, m), 3.05–2.75 (4H, m), 2.58–2.45 (2H, m), 2.45–2.28 (1H, m), 2.25–2.14 (1H, m).

2-Oxo-3(S)-{2-[2-oxo-5-(3-phenylpropionyl)-3(S)-(3-phenyl-propionyl-amino)-2,3,4,5-tetrahydrobenzo[b][1,4]diazepin-1-yl] acetylamino}butyric acid (106b). [2-Oxo-5-(3-phenylpropionyl)-3-(3-phenylpropionylamino)-2,3,4,5-tetrahydrobenzo[b][1,4]diazepin-1-yl]acetic acid and 3amino-4-oxobutyric acid tert-butylester semicarbazone were coupled by the procedure used in the preparation of compound K (step A) to give 350 mg (85%) of a white solid. ¹H NMR (CDCl₃) δ9.05 (1H, br. s), 7.58–7.55 (1H,d), 7.5–7.35 (1H, m), 7.35–6.95 (14 H, m), 6.75–6.72 (1H, d), 6.25 (1H, br. s), 5.25 (1H, br. s), 4.95–4.88 (1H, m), 4.8–4.72 (1H, m), 4.55–4.4 (2H, m), 3.92–3.88 (1H, d), 3.73–3.68 (1H, m), 2.95–2.8 (4H, m), 2.8–2.72 (1H, m), 2.62–2.55 (1H, m), 2.55–2.45 (2H, m), 2.4–2.32 (1H, m), 2.2–2.12 (1H, m), 1.45 (9H, s). 4-Oxo-3-{2-[2-oxo-5-(3-phenylpropionyl)-3-(3-phenylpropionyl-amino)-2,3,4,5-tetrahydrobenzo[b][1,4]diazepin-1-yl]-acetyl amino}butyric acid tert-butyl ester semicarbazone was deprotected as described in the preparation of compound K (step C) to give 118 mg (47%) of the title compound as a white solid. ¹H NMR (CD₃OD) δ7.48–6.95 (14 H, m), 4.65–4.15 (6H, m), 3.5–3.4 (1H, m), 2.85–2.72 (4H, m), 2.65–2.5 (1H, m), 2.5–2.34 (3H, m), 2.34–2.15 (2H, m).

[5-Benzyl-2-oxo-3(S)-(3-phenylpropionylamino)-2,3,4,5-tetrahydro-benzo[b][1,4]diazepin-1-yl]acetic acid methyl ester (104c). [2-Oxo-3-(3-phenylpropionylamino)-2,3,4,5-tetrahydrobenzo-[b][1,4]diazepin-1-yl]acetic acid methyl ester (104a; 500 mg, 1.31 mmol), calcium carbonate (155 mg, 1.58 mmol), and benzyl bromide (170 μl, 1.44 mmol) were taken into 10 ml of dimethylformamide and heated to 80° C. for 8 hours. The mixture was diluted with 150 ml of ethyl acetate and washed 4 times with 50 ml of water. The organic layer was dried over anhydrous sodium sulfate, filtered, and evaporated to give a viscous, yellow oil that was purified by flash chromatography eluting with dichloromethane/ethyl acetate (8:2) to give 460 mg (75%) of the title compound as a white solid. ¹H NMR (CDCl₃) δ7.34–7.05 (14 H, m), 6.32–6.28 (1H, d), 4.84–4.76 (1H, d), 4.76–4.70 (1H, m), 4.43–4.37 (1H, d), 4.26–4.18 (1H, d), 4.06–4.00 (1H, d), 3.79 (3H, s), 3.45–3.37 (1H, m), 3.02–2.95 (1H, m), 2.90–2.82 (2H, m), 2.5–2.34 (2H, m).

[5-Benzyl-2-oxo-3(S)-(3-phenylpropionylamino)-2,3,4,5-tetrahydro-benzo[b][1,4]diazepin-1-yl]acetic acid (105c) was prepared by the hydrolysis of the ester (102c) by the procedure reported in example 105a to give 450 mg (98%) of the title compound as a white solid: ¹H NMR (CD₃OD) δ7.5–7.05 (14 H, m), 6.4 (1H, br. s), 4.85–4.55 (2H,m), 4.5–4.21 (2H, m), 4.12–3.92 (1H, d), 3.45–3.3 (1H, m), 3.1–2.8 (3H, m), 2.55–2.28 (3H, m).

3(S)-{2-[5-Benzyl-2-oxo-3(S)-phenylpropionylamino)-2,3,4,5-tetrahydrobenzo[b][1,4]diazepin-1-yl]acetylamino}-4-oxobutyric acid (106c). [5-Benzyl-2oxo-3(S)-(3-phenylpropionylamino)-2,3,4,5-tetrahydro benzo[b1,4]diazepin-1-yl]acetic acid and 3(S)-amino-4-oxobutyric acid tert-butylester semicarbazone were coupled by the procedure used in the preparation of compound K (step A) and to afford 260 mg (85%) of a white solid: ¹H NMR (CD₃OD) δ7.35–7.0 (15 H, m)), 4.94–4.88 (1H, m), 4.68–4.58 (1H, d), 4.57–4.52 (1H, m), 4.41–4.34 (1H, d), 4.3–4.23 (1H, d), 4.1–4.04 (1H, d), 3.18–3.11 (1H, m), 3.09–2.98 (1H, m), 2.78–2.72 (2H, t), 2.65–2.57 (1H, m), 2.42–2.33 (3H, m). 3(S)-{2-[5-Benzyl-2-oxo-3(S)-(3-phenylpropionylamino)-2,3,4,5-tetrahydrobenzo[b][1,4]diazepin-1-yl]acetylamino}-4-oxobutyric acid tert-butyl ester semicarbazone was deprotected as described in the preparation of compound K (step C) to give 168 mg (81%) of the title compound as a white solid. $^1$H NMR (CD$_3$OD) δ7.37–7.0 (14H, m), 4.75–4.62 (1H, m), 4.6–4.45 (2H, m), 4.4–4.21 (2H, m), 4.15–3.95 (2H, m), 3.15–3.0 (2H, m), 2.82–2.67 (2H, m), 2.65–2.52 (1H, m), 2.5–2.32 (3H, m).

2,6-Dichlorobenzoic acid 4-tert-butoxycarbonyl-2-oxo3(S)-{2-[2-oxo-5-(3-phenylpropionyl)-3(S)-(3-phenylpropionylamino)-2,3,4,5-tetrahydrobenzo[b][1,4]diazepin-1-yl]acetyl-amino}butyl ester (107a). The resulting semicarbazone was prepared by the coupling of compound 105b and t-butyl 3-(allyloxycarbonylamino)-4-oxo-5-(2,6-dichlorobenzoyloxy)pentanoate (WO 93 16710) as described in compound 56a to give 256 mg (58%) of the title compound as a white solid. $^1$H NMR (CDCl$_3$) 6 7.45–7.04 (17H, m), 6.45–6.34 (2H, m), 5.28–5.21 (1H, m), 5.1–5.0 (1H, m), 4.95–4.90 (1H, m), 4.75–4.70 (1H, m), 4.55–4.44 (1H, m), 4.32–4.22 (1H, dd), 3.99–3.85 (1H, dd), 3.85–3.76 (1H, m), 3.06–2.83 (5H, m), 2.83–2.74 (1H, m), 2.6–2.44 (2H, m), 2.43–2.33 (1H, m), 2.24–2.15 (1H, m), 1.45 (9H, s).

2,6-Dichlorobenzoic acid 4-carboxy-2-oxo-3(S)-{2-[2oxo-5-(3-phenylpropionyl)-3(S)-(3-phenylpropionylamino)-2,3,4,5-tetrahydrobenzo[b][1,4]diazepin-1-yl]acetylamino}butyl ester (108a) was prepared from 107a by the method described for compound 57a which afforded 156 mg (68%) of the title compound as a white solid. $^1$H NMR (CD$_3$OD) δ7.5–6.9 (17H, m), 5.16–5.02 (1H, dd), 4.88–4.71 (2H, m), 4.62–4.44 (2H, m), 4.42–4.28 (2H, m), 4.27–4.18 (1H, m), 3.47–3.41 (1H, m), 2.90–2.60 (5H, m), 2.46–2.4 (2H, m), 2.39–2.18 (2H, m).

4-(7-Methoxybenzoxazol-2-yl)-4-oxo-3(S)-{2-[2-oxo-5-(3-phenylpropionyl)-3(S)-(3-phenylpropionylamino)-2,3,4,5-tetrahydrobenzo[b][1,4]diazepin-1-yl]-acetylamino}butyric acid (108b) was prepared by the method described for compound 69a to give the title compound (50%) as a white solid. $^1$H NMR (CD$_3$OD) δ7.41–6.88 (17H, m), 5.6–5.55 (0.5H, t), 5.48–5.43 (0.5H, t), 4.64–4.45 (2H, m), 4.45–4.30 (1H, m), 3.93 (1.5H, s), 3.90 (1.5 H, s), 3.47–3.34 (1H, m), 3.10–2.85 (2H, m), 2.84–2.63 (5H, m), 2.6–2.4 (2H, m), 2.3–2.1 (2H, m).

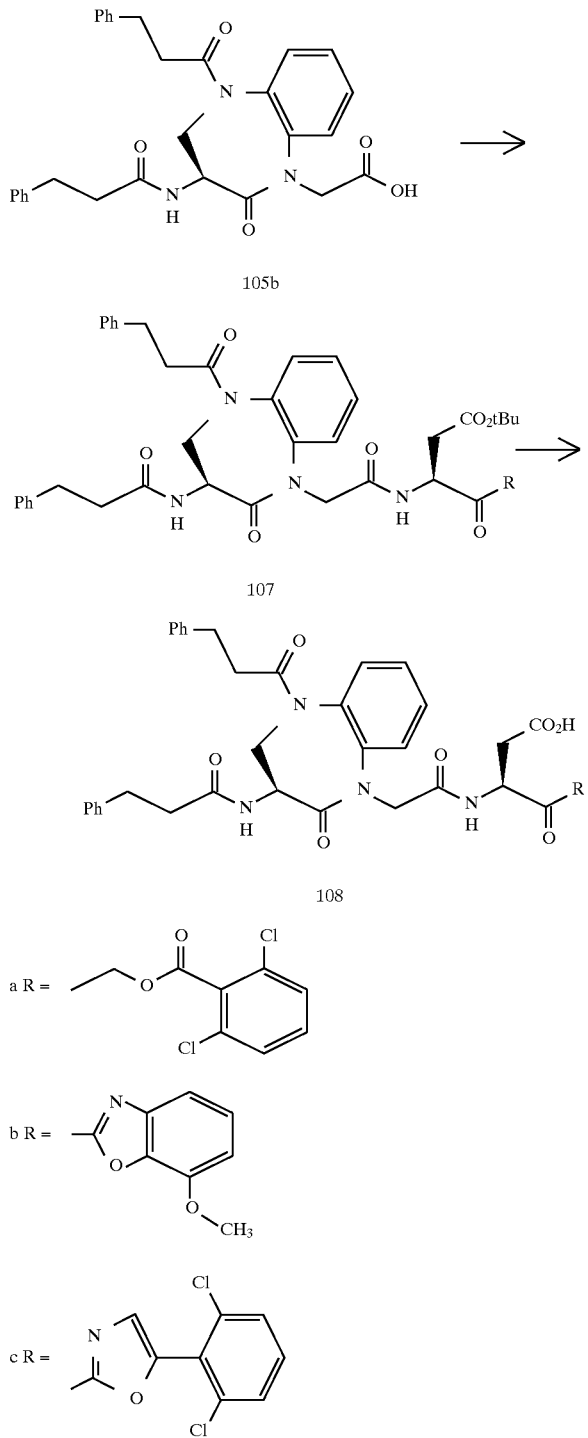

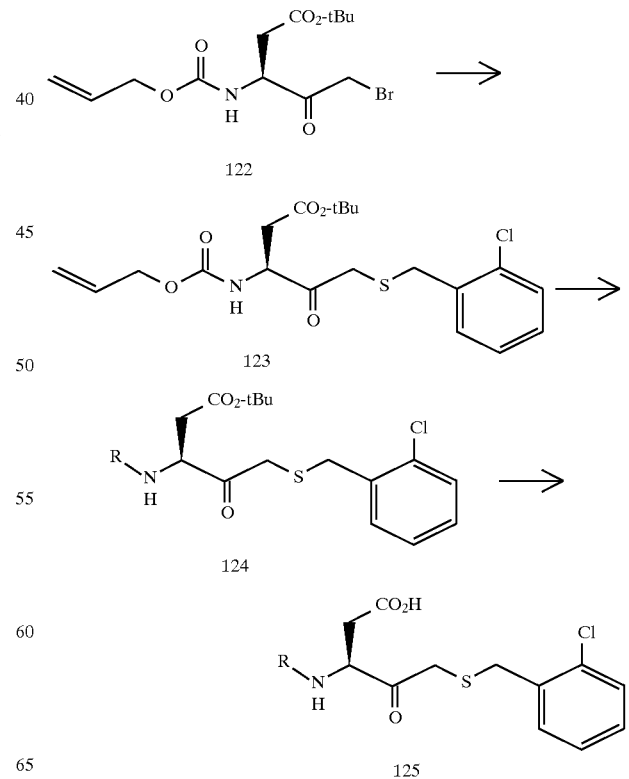

217

-continued

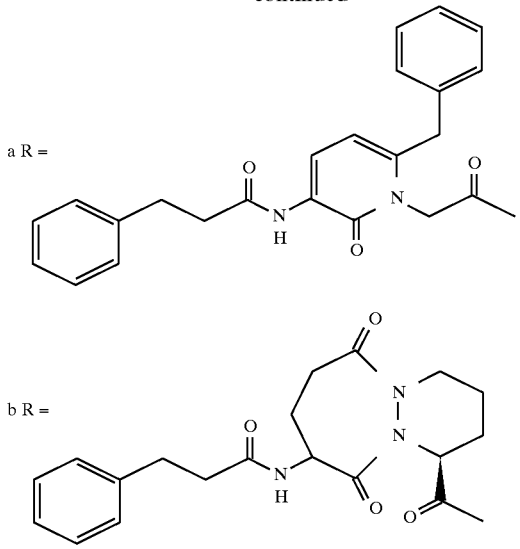

a R = b R = t-Butyl (3S) N-(allyloxycarbonyl)-3-amino-5-(2-chlorophenylmethylthio)-4-oxo-pentanoate (123). Potassium fluoride (273 mg, 4.70 mmol) and then 2-chlorophenylmethyl thiol (373 mg, 2.35 mmol) were added to a stirred solution of (3S) t-butyl N-(allyloxycarbonyl)-3-amino-5-bromo-4-oxo-pentanoate (122; 749 mg, 2.14 mmol; WO 93 16710) in dimethylformamide (20 ml). The mixture was stirred for 3.5 h, quenched with water (50 ml) and extracted with ethyl acetate (2×50 ml). The combined organic extracts were washed with water (4×50 ml) then brine (50 ml). They were dried (MgSO$_4$) and concentrated to afford an oil which was purified by flash chromatography (10–35% ethyl acetate/hexane) to afford 832 mg (91%) of a colourless solid: mp. 45°–6° C.; $[\alpha]_D^{20}$ –19.0° (c 1.0, CH$_2$Cl$_2$); IR (film) 3340, 2980, 2935, 1725, 1712, 1511, 1503, 1474, 1446, 1421, 1393, 1368, 1281, 1244, 1157, 1052, 1040, 995, 764, 739; $^1$H NMR (CDCl$_3$) δ7.36 (2H, m), 7.21 (2H, m), 5.91 (2H, m), 5.27 (2H, m), 4.76 (1H, m), 4.59 (2H, d), 3.78 (2H, s), 3.36 (2H, m), 2.91 (1H, dd), 2.74 (1H, dd), 1.43 (9H, s). Anal. Calcd for C$_{20}$H$_{26}$ClNO$_5$S: C, 56.13; H, 6.12; N, 3.27; S, 7.49. Found: C, 56.08; H, 6.11; N, 3.26; S, 7.54. MS (C.I.) 430/28 (M$^{30}$+1, 3%), 374/2 (100).

t-Butyl (3S) 3(2(6-benzyl-1,2-dihydro-2-oxo-3-(3phenylpropionylamino)-1-pyridyl)acetylamino-5-(2-chlorophenylmethylthio)-4-oxopentanoate (124a). 6-Benzyl-1,2-dihydro-2-oxo-3-(3-phenylpropionylamino)-pyridyl acetic acid (52b; 300 mg, 0.76 mmol) in THF (7 ml) was stirred with 1-hydroxybenzotriazole (205 mg, 1.52 mmol) and 1-(3-dimethylaminopropy-3-ethylcarbodiimide hydrochloride). After 3 min, water (12 drops) was added and the mixture stirred 10 min then treated with t-butyl (3S) N-(allyloxycarbonyl)-3-amino-5-(2-chlorophenylmethylthio)-4-oxopentanoate (123) (325 mg, 0.76 mmol), bis (triphenylphosphine) palladium II chloride (20 mg) and tributyltin hydride (0.6 ml, 2.28 mmol). The mixture was stirred for 5 h at room temperature, poured into ethyl acetate and washed with aqueous 1M HCl (x2), aqueous sodium bicarbonate, brine, dried (MgSO$_4$) and concentrated. The residue was triturated with pentane and the supernatant discarded. Chromatography (silica gel, 50% ethyl acetate/hexane) afforded a colourless foam (439 mg, 81%): $[\alpha]_D^{21}$ –18.3° (c 0.5, CH$_2$Cl$_2$); IR (KBr) 3356, 3311, 1722, 1689, 1646, 1599, 1567, 1513, 1367, 1154; $^1$H NMR (CDCl$_3$) δ8.39 (1H, d), 8.23 (1H, s), 7.24 (14H, m), 6.16

218

(1H, d), 4.95 (1H, m), 4.63 (2H, m), 4.02 (2H, s), 3.74 (2H, s), 3.27 (2H, s), 2.85 (6H, m), 1.40 (9H, s). Anal. Calcd for C$_{39}$H$_{42}$ClN$_3$O$_6$S: C, 65.39; H, 5.91; N, 5.87. Found: C, 65.51; H, 5.99; N,5.77.

t-Butyl[3S(1S,9S)]-3-(6,10-dioxo-1,2,3,4,7,8,9,10octahydro)-9-(3-phenylpropionylamino)-6H-pyridazine [1,2-a][1,2]diazepine-1-carboxamido-5-(2-chlorophenylmethylthio)-4-oxopentanoate (124b) was prepared by a similar method as 124a from the thioether 123 and 3S(1S,9S)-3-(6,10-dioxo-1,2,3,4,7,8,9,10-octahydro)-9-(3-phenylpropionylamino)-6H-pyridazino[1,2-a][1,2]diazepine-1-carboxylic acid (45a) to afford 452 mg (50%) of colourless foam: mp 55°–7° C.; $[\alpha]_D^{22}$ –94.0° (c 0.12, CH$_2$Cl$_2$); IR (KBr) 3288, 2934, 1741, 1722, 1686, 1666, 1644, 1523, 1433, 1260, 1225, 1146, 757; $^1$H NMR (CDCl$_3$) δ7.35 (3H, m), 7.20 (7H, m), 6.46 (1H, d), 5.21 (1H, m), 4.97 (2H, m), 4.56 (1H, m), 3.75 (2H, s), 3.25 (3H, m), 2.93 (5H, m), 2.71 (1H, dd), 2.55 (2H, m), 2.30 (1H, m), 1.92 (3H, m), 1.66 (2H, m), 1.42 (9H, s). Anal. Calcd for C$_{35}$H$_{43}$ClN$_4$O$_7$S. 0.25H$_2$O: C, 59.73; H, 6.23; Cl, 5.04; N, 7.96; S, 4.56. Found: C, 59.73; H, 6.19; Cl, 5.10; N, 7.79; S, 4.58. MS (-FAB) 697 (M-1, 100).

(3S) 3(2(6-Benzyl-1,2-dihydro-2-oxo-3-(3-phenylpropionylamino)-1-pyridyl)acetylamino-5-(2-chlorophenylmethylthio)-4-oxopentanoic acid (125a). t-Butyl-3(2(6-benzyl-1,2-dihydro-2-oxo-3-(3-phenylpropionylamino)-1-pyridyl)acetyl-amino-5-(2-chlorophenylmethylthio)-4-oxopentanoate (124a) (400 mg, 0.56 mmol) in dichloromethane (3 ml) at 0° C. was treated with trifluoroacetic acid (3 ml) and stirred at 0° C. for 1 h and room temperature for 0.5 h. The solution was concentrated then redissolved in dichloromethane and reconcentrated. This procedure was repeated three times. The residue was stirred in ether for 1 hr and filtered to yield a colourless solid (364 mg, 99%): mp. 165°–7° C.; $[\alpha]_D^{22}$ –27.7° (c 0.2, CH$_2$Cl$_2$); IR (KBr) 3289, 1712, 1682, 1657, 1645, 1593, 1562, 1527, 1497, 1416, 1203, 1182; $^1$H NMR (CDCl$_3$) δ8.47 (1H, d), 8.21 (1H, s), 7.70 (1H, d), 7.22 (14H, m), 6.24 (1H, d), 5.03 (1H, m), 4.65 (2H, m), 4.06 (2H, s), 3.69 (2H, m), 3.23 (2H, m), 2.88 (6H, m).

[3S(1S, 9S)]-3-(6,10-dioxo-1,2,3,4,7,8,9,10-octahydro)9-(3-phenylpropionyl-amino)-6H-pyridazine[1,2a][1,2]diazepine-1-carboxamido-5-(2-chlorophenylmethylthio)-4-oxopentanoic acid (125b), was prepared by a similar method as 125a from the t-butyl ester 124b to afford 362 mg (93%) of colourless powder: mp 76°–80 °C.; $[\alpha]_D^{21}$ –134° (c 0.10, MeOH); IR (KBr) 3309, 2935, 1725, 1658, 1528, 1445, 1417, 1277, 1219, 1175; $^1$H NMR (D$_6$DMSO) δ8.80 (1H, d), 8.19 (1H, d), 7.31 (9H, m), 5.09 (1H, m), 4.74 (1H, m), 4.63 (1H, m), 4.35 (1H, m), 3.76 (2H, m), 3.28 (3H, m), 2.80 (5H, m), 2.52 (4H, m), 2.16 (2H, m), 1.90 (3H, m). Anal. Calcd for C$_{31}$H$_{35}$Cl$_2$N$_4$O$_7$S. 0.25H$_2$O: C, 57.49; H, 5.53; N, 8.65; S, 4.95. Found: C, 57.35; H, 5.43; N, 8.45; S, 4.88. MS (-FAB) 641 (M-1, 100).

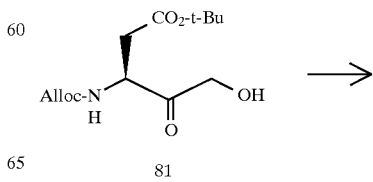

81

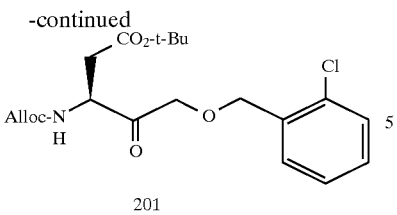

201

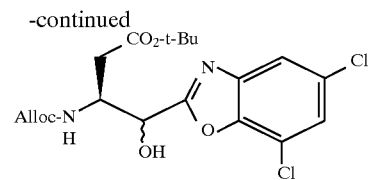

204

2-Chlorophenylmethyliodide. A mixture of 2-chlorophenylmethylbromide (4 g, 19.47 mmol) and NaI (14 g, 97.33 mmol) in acetone (40 ml) was stirred under reflux for 1 hour. The reaction mixture was cooled, filtered and concentrated in vacuo. The residue was triturated with hexane and filtered. The solution was concentrated in vacuo, and the resulting oil purified by flash chromatography (silica, hexane) to afford the title compound (4.67 g, 63%) as an oil: $^1$H NMR (CDCl$_3$) δ7.34 (4H, m), 4.54 (2H, s).

(3S) t-Butyl N-(allyloxycarbonyl)-3-amino-5-(2-chlorophenylmethyloxy)-4-oxopentanoate (201). (3S) t-Butyl N-(allyloxycarbonyl)-3-amino-5-hydroxy-4-oxopentanoate (81, Chapman, et al., Biorg. & Med. Chem. Lett., 2, pp. 613–618 (1992) 0.144 g, 0.5 mmol) and 2-chlorophenylmethyliodide (0.569 g, 1.5 mmol) in CH$_2$Cl$_2$ (4 ml) were stirred vigorously with silver oxide (0.231 g, 1 mmol) and heated at 38° C. for 40 hours. The reaction mixture was cooled, filtered and the filtrate evaporated. The residue was purified by flash chromatography (silica, 0–20% ethylacetate in hexane) to afford the product as a colourless oil (0.138 g, 67%): [α]$_D^{24}$+3.9° (c 1.3, CH$_2$Cl$_2$); $^1$H NMR (CDCl$_3$) δ7.37 (4H, m), 5.88 (2H, m), 5.26 (2H, m), 4.69 (2H, s), 4.57 (3H, m), 4.50 (1H, d), 4.35 (1H, d), 3.03 (1H, dd), 2.76 (1H, dd), 1.42 (9H, s).

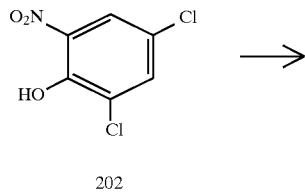

202

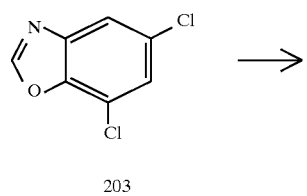

203

5,7-Dichlorobenzoxazole (203). A solution of 2,4-dichloro-6-nitrophenol (202, 40 g containing 20% moisture) in EtOAc (500 ml) was dried using MgSO$_4$, filtered and the filter cake washed with a little EtOAc. Platinum on carbon (5% sulphided—2 g) was added and the mixture hydrogenated until uptake of H$_2$ ceased. Triethyl orthoformate (160 ml) and p-toluene sulphonic acid (160 mg) were added and the mixture refluxed for 4 h. After cooling and removal of spent catalyst by filtration the solution was washed with sat. NaHCO$_3$ solution, water and brine, dried with MgSO$_4$ and evaporated to dryness. Trituration with hexane gave a solid which was collected by filtration, washed with hexane and dried to give the title compound (25.5 g, 88%) as a crystalline solid: mp 98°–99° C.; IR (KBr) 3119, 1610, 1590, 1510, 1452, 1393, 1296, 1067, 850; $^1$H NMR (CDCl$_3$) δ8.16 (1H, s), 7.69 (1H, d, J=1.9), 7.42 (1H, d, J=1.9); Anal. Calcd for C$_7$H$_3$Cl$_2$NO: C, 44.72; H, 1.61; N, 7.45; Cl, 37.70. Found: C, 44.84; H, 1.69; N, 7.31; Cl, 37.71.

(3S, 4RS) t-Butyl N-(allyloxycarbonyl)-3-amino-4-hydroxy-4-(5,7-dichlorobenzoxazol-2-yl)butanoate (204). Magnesium bromide was prepared by reaction of Mg (7.45 g, 0.30 mole) in THF (516 ml) with I$_2$ (50 mg) and 1,2-dibromoethane (26.3 ml, 57.3 g, 0.30mole) at reflux for 2 h and then cooling to –40° C. To the above was added rapidly via cannula a solution of 2-lithio-5,7-dichlorobenzoxazole at 70° C. (prepared from 5,7-dichlorobenzoxazole (203, 28.9 g, 0.154 mole) and butyl lithium (100 ml 1.52M in hexane) in THF (150 ml) at 70° C.). The mixture was stirred at –40° C. for 1 h and then cooled to –70° C. before adding a solution of (3S) t-butyl N-(allyloxycarbonyl)-3-amino-4-oxo-butanoate (Chapman, et al., Biorg. & Med. Chem. Lett., 2, pp. 613–618 (1992)) (20.3 g, 0.078 mole) in THF (160 ml) at less than –60° C. The reaction was allowed to warm to ambient temperature and was stirred for 16 h before quenching with ammonium chloride solution and extracting with 1:1 hexane:ethylacetate 600 ml. The organic solution was washed with water and brine, dried with MgSO$_4$ and evaporated to a syrup (52.9 g). Flash chromatography (SiO$_2$ 250g—11 aliquots of 1:1 hexane: CH$_2$Cl$_2$ x2, CH$_2$Cl$_2$, 5% EtOAc in CH$_2$Cl$_2$, 10% EtOAc in CH$_2$Cl$_2$, 20% EtOAc in CH$_2$Cl$_2$) gave impure product 24.6 g which on further chromatography (SiO$_2$ 1:1 hexane:ether) give the title compound as a golden-brown glass (22.7 g, 64%); IR (film) 3343, 2980, 1723, 1712, 1520, 1456, 1398, 1369, 1254, 1158, 993; $^1$H NMR (CDCl$_3$) δ7.60 (1H, m), 7.37 (1H, m), 5.72 (1H, m), 5.64 (0.5H, d), 5.10 (2.5H, m), 4.7–4.3 (4H, m), 2.9–2.6 (2H, m), 1.46 and 1.42 (9H combined, 2 x s). MS ES+Da/e 445 (M+1)$^+$ Cl 62%, 447 (M+1)$^+$Cl 37 40%, 389 100%.

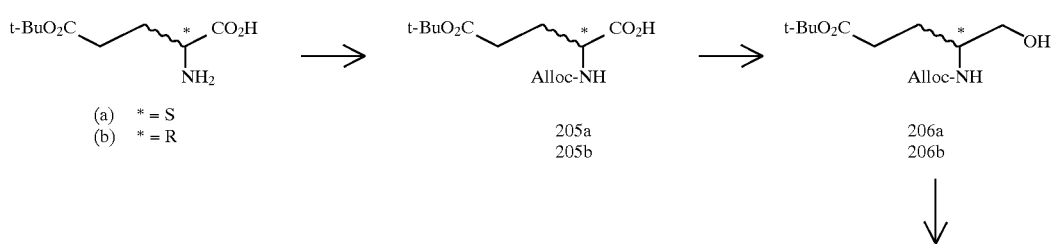

(a) * = S
(b) * = R 205a
205b 206a
206b

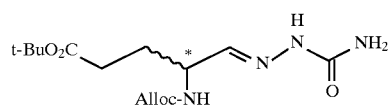 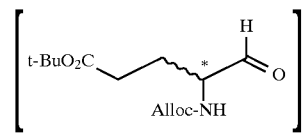

208a
208b 207a
207b (2S)-N-Allyloxycarbonyl-5-(1,1-dimethylethyl) glutamate (205a). To a mixture of THF (200 ml) and water (100 ml) containing NaHCO$_3$ (16.6 g, 0.2 mol) was added glutaric acid t-butyl ester (10 g, 49.2 mmol) and then dropwise over 20 minutes allyl chloroformate (6.8 ml, 64 mmol). The mixture was stirred for 2 hours, extracted with EtOAc, washed with a sat. hydrogenocarbonate solution, water and a sat. salt solution, dried and evaporated to an oil 205a (9.5 g, 67.2%); $[\alpha]_D^{20}$ –6° (c 1.5, MeOH) $^1$H NMR (D6-DMSO) δ6.10 (1H, d), 5.96–5.88 (1H, m), 5.31–5.12 (2H, m), 4.45 (2H, m), 3.90–3.84 (1H, t), 2.18 (2H, m), 1.85–1.76 (2H, m), 1.36 (9H, s).

(2R)-N-Allyloxycarbonyl-5-(1,1-dimethylethyl) glutamate (205b), was prepared by an analogous method to 205a to afford a colourless oil (6.27 g, 88%): $[\alpha]_D^{20}$ +16° (c 0.095, MeOH); IR (KBr) 3678, 3332, 3088, 2980, 2937, 1724, 1530, 1453, 1393, 1370, 1331, 1255, 1155, 1056, 995, 935, 845, 778, 757, 636, 583; $^1$H NMR (CDCl$_3$) δ9.24 (1H, broad s), 5.94–5.79 (1H, m), 5.58 (1H, d), 5.33–5.17 (2H, m), 4.55 (2H, d), 4.38–4.31 (1H, m), 2.41–1.95 (4H, m), 1.42 (9H, s); Anal. Calcd for C$_{13}$H$_{21}$NO$_6$: C, 54.35; H, 7.37; N, 4.88. Found: C, 54.4; H, 7.5; N, 4.8.

(4S) t-Butyl N-allyloxycarbonyl-4-amino-5-hydroxypentanoate (206a). To a solution of 205a (3.6 g, 12.5 mmol) in THF (100 ml) at 0° C. was added N-methyl morpholine (1.5 ml, 13 mmol) followed by isobutyl chloroformate, (1.1 ml, 13 mmol). After 15 minutes, this mixture was added to a suspension of NaBH$_4$ (0.95 g, 25 mmol) in THF (100 ml) and MeOH (25 ml) at –78° C. After 2 hours at –70° C., the mixture was quenched with acetic acid, diluted with EtOAc, washed with a sat. hydrogenocarbonate solution 3 times, water and a sat. solution of salt, dried and evaporated. Flash chromatography (2% MeOH in CH$_2$Cl$_2$) afforded 206a as a colourless oil (2.4 g, 70%): $[\alpha]_D^{20}$ 10° (c 3.88, CH$_2$Cl$_2$); $^1$H NMR (CDCl$_3$) δ5.84 (1H, m), 5.34–5.17 (3H, m), 4.56–4.53 (2H, m), 3.68–3.59 (2H, m), 2.98 (1H, m), 2.40–2.30 (2H, t), 1.84–1.78 (2H, m), 1.43 (9H, s); Anal. Calcd for C$_{13}$H$_{23}$NO$_5$: C, 57.13; H, 8.48; N, 5.12. Found: C, 57.1; H, 8.6; N, 6.0

(4R) t-Butyl N-allyloxycarbonyl-4-amino-5-hydroxypentanoate (206b), was prepared by an analogous method to 206a which afforded the title compound as a light yellow oil (3.42 g, 57%): $[\alpha]_D^{20}$ +14 (c 0.166, MeOH); IR (KBr) 3341, 3083, 2976, 2936, 2880, 1724, 1533, 1454, 1419, 1369, 1332, 1251, 1156, 1062, 997, 933, 846, 777, 647; $^1$H NMR (CDCl$_3$) δ5.98–5.81 (1H, m), 5.35–5.10 (3H, m), 4.55 (2H, d), 3.70–3.56 (3H, m), 2.50–2.47 (1H, broad s), 2.37–2.30 (2H, m), 1.89–1.74 (2H, m), 1.44 (9H, s); Anal. Calcd for C$_{13}$H$_{23}$NO$_5$: C, 57.13; H, 8.48; N, 5.12. Found: C, 56.9; H, 8.6; N, 5.6

(4S) t-Butyl N-Allyloxycarbonyl-4-amino-5-oxopentanoate (207a). To a solution of DMSO (1.51 g, 19.3 mmol) in CH$_2$Cl$_2$ (25 ml) at –70 ° C. was added oxalyl chloride (1.34 g, 19.3 mmol). After 10 minutes at –70° C., a solution of (206a) (2.4 g, 8.8 mmol) in CH$_2$Cl$_2$ (10 ml) was added dropwise and the mixture stirred for 15 minutes at –70° C. Diisopropylethylamine (3.4 g, 26.3 mmol) was added and the mixture stirred at –25° C. for 15 minutes then diluting with EtOAc (50 ml) washed with a solution of sodium hydrogensulfate 2M, concentrated to give an oil which was used immediately without purification: $^1$H NMR (CDCl$_3$) δ9.5 (1H, s), 6.0–5.5 (2H, m), 5.5–5.1 (2H, m), 4.5 (2H, m), 4.2 (1H, m), 2.4–2.10 (2H, m), 2.05 (2H, m), 1.36 (9H, s).

(4R) t-Butyl N-Allyloxycarbonyl-4-amino-5-oxopentanoate (207b), was prepared by an analogous method to 207a which afforded an oil (2.95 g, 96%) which was used without further purification in the next step: $[\alpha]_D^{20}$ +21° (c 0.942, MeOH); $^1$H NMR (CDCl$_3$) δ9.58 (1H, s), 6.05–5.80 (1H, m), 5.57 (1H, broad s), 5.35–5.18 (2H, m), 4.56 (2H, d), 4.34–4.24 (1H, m), 2.38–2.16 (3H, m), 1.96–1.73 (1H, m), 1.43 (9H, s).

(4S) t-Butyl N-Allyloxycarbonyl-4-amino-5-oxopentanoate semicarbazone (208a). To a solution of 207a (2.39 g, 8.8 mmol), in MeOH (20 ml) was added sodium acetate (0.72 g, 8.8 mmol) and semicarbazide (0.98 g, 8.8 mmol) stirred overnight, concentrated and diluted with CH$_2$Cl$_2$ (100 ml), washed with water, dried and concentrated. Flash chromatography (2% MeOH in CH$_2$Cl$_2$) afforded 208a (2.10 g, 73%) as an oil: $[\alpha]_D^{20}$ –21 (c 2.55°, CH$_2$Cl$_2$); $^1$H NMR (CDCl$_3$) δ9.98 (1H, s), 7.27 (1H, d), 5.8 (1H, m), 5.5 (1H, d), 5.35–5.19 (2H, m), 4.58 (2H, m), 4.14 (1H, m), 2.37 (2H, t), 2.09 (1H, m), 2.0–1.75 (2H, m); Anal. Calcd for C$_{14}$H$_{24}$N$_4$O$_5$: C, 51.21; H, 7.37; N, 17.06. Found: C, 50.2; H, 7.3; N, 16.1

(4R) t-Butyl N-Allyloxycarbonyl-4-amino-5-oxopentanoate semicarbazone (208b), was prepared by an analogous method to 208a which afforded a glassy oil (2.37 g, 66%): $[\alpha]_D^{20}$ +30 (c 0.26, CHCl$_3$); IR (KBr) 3476, 3360, 2979, 2923, 1700, 1586, 1527, 1427, 1394, 1369, 1338, 1253, 1156, 1060, 997, 929, 846, 775; $^1$H NMR (CDCl$_3$) δ9.87 (1H, s), 7.09 (1H, d), 6.05–5.75 (3H, m), 5.58 (1H, d), 5.32–5.16 (2H, m), 4.54 (2H, d), 4.35 (1H, m), 2.32–2.26 (2H, m), 2.15–1.55 (2H, m), 1.41 (9H, s); Anal. Calcd for C$_{14}$H$_{24}$N$_4$O$_5$: C, 51.21; H, 7.37; N, 17.06. Found: C, 51.0; H, 7.5; N, 16.7.

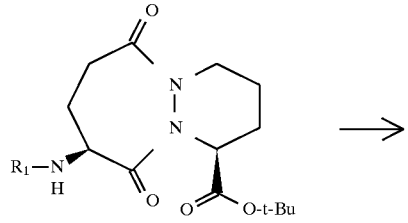

211 (b) R$_1$ = MeSO$_2$
(c) R$_1$ = MeCO
(d) R$_1$ = PhCH$_2$OCO
(e) R$_1$ = PhCO
(f) R$_1$ = Fmoc -continued

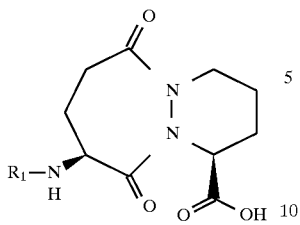

212 (b) R₁ = MeSO₂
(c) R₁ = MeCO
(d) R₁ = PhCH₂OCO
(e) R₁ = PhCO
(f) R₁ = Fmoc (1S, 9S) t-Butyl 6,10-dioxo-9-methylsulphonylamino-1,2,3,4,7,8,9,10-octahydro-6H-pyridazino-[1,2-a][1,2]diazepine-1-carboxylate (211b). A solution of t-butyl 9-amino-6,10-dioxo-1,2,3,4,7,8,9,10-octahydro-6H-pyridazino[1,2-a][1,2]diazepine-1-carboxylate (GB 2,128,984; 831mg, 2.79 mmol) and diisopropylethylamine (1.22 ml, 6.99 mmol, 2.5 equiv) in $CH_2Cl_2$ (10 ml) under dry nitrogen was treated with methanesulphonyl chloride (237 μl, 3.07 mmol 1.1 equiv). The mixture was stirred for 1 h, diluted with EtOAc (75 ml) and washed with saturated $NaHCO_3$ (50 ml) and saturated aqueous sodium chloride (30 ml), dried ($MgSO_4$) and concentrated. Flash chromatography (10–35% EtOAc in $CH_2Cl_2$) afforded 211b (806 mg, 77%) as a colourless solid: mp 68°–70 °C.; $[\alpha]_D^{23}$ –109 (c 1.09, $CH_2Cl_2$) ; IR (KBr) 3270, 2980, 2939, 1735, 1677, 1458, 1447, 1418, 1396, 1370, 1328, 1272, 1252, 1232, 1222, 1156, 1131, 991; $^1$H NMR ($CDCl_3$) δ6.15 (1H, d), 5.31 (1H, m), 4.65–4.11 (2H, m), 3.47 (1H, m) 2.99 (3H, s), 2.89 (1H, m), 2.72–2.51 (2H, m), 2.34 (1H, m), 2.26 (1H, m), 2.05–1.62 (4H, m), 1.47 (9H, s); Anal. Calcd for $C_{15}H_{23}N_3O_6S$: C, 47.97; H, 6.71; N, 11.19; S, 8.54. Found: C, 48.28; H, 6.68; N, 10.86; S, 8.28. MS (+FAB) 376 (M⁺+1, 66%), 320 (100).

(1S, 9S) t-Butyl 9-acetylamino-6,10-dioxo-1,2,3,4,7,8,9,10-octahydro-6H-pyridazino [1,2-a][1,2]diazepine-1-carboxylate (211c). Acetic anhydride (307 mg, 3.01 mmol) was added to a stirred mixture of t-butyl 9-amino-6,10-dioxo-1,2,3,4,7,8,9,10-octahydro-6H-pyridazino[1,2-a][1,2]diazepine-1-carboxylate (GB 2,128,984; 813.7 mg, 2.74 mmol), diisopropylethylamine (884 mg, 6.84 mmol) and $CH_2Cl_2$ (20 ml). The mixture was kept for 1 h then diluted with EtOAc, washed with $NaHCO_3$ solution then brine, dried ($MgSO_4$) and concentrated to yield a colourless oil. The product was purified by flash chromatography (0.5–8% MeOH/$CH_2Cl_2$) to afford 211c (804 mg, 71%) of colourless powder: mp 162°–3° C.; $[\alpha]_D^{23}$ –109 (c 1.03, $CH_2Cl_2$); IR(KBr) 3358, 2974, 1733, 1693, 1668, 1528, 1462, 1431, 1406, 1371, 1278, 1271, 1250, 1233, 1217, 1154, 1124; δ$^1$H NMR ($CDCl_3$) δ6.32 (1H, d), 5.29–5.25 (1H, m), 4.98–4.85 (1H, m), 4.68–4.58 (1H, m), 3.55–3.39 (1H, m), 2.91–2.66 (2H, m), 2.39–2.18 (2H, m), 2.03 (3H, s), 1.88–1.64 (4H, m), 1.47 (9H, s); Anal. Calcd for $C_{16}H_{25}N_3O_5$: C, 56.62; H, 7.43; N, 12.38. Found: C, 56.62; H, 7.43; N,12.36; MS (+FAB) 340 (M⁺+1, 40%), 284 (100).

(1S, 9S) t-Butyl 9-(benzyloxycarbonylamino)-6,10-dioxo-1,2,3,4,7,8,9,10-octahydro-6H-pyridazino[1,2-a][1,2]diazepine-1-carboxylate (211d). Benzyl chloroformate (1.07 g) was added dropwise to a stirred ice cold mixture of the (1S, 9S) t-butyl 9-amino-6,10-dioxo-1,2,3,4,7,8,9,10-octahydro-6H-pyridazino[1,2-a][1,2]diazepine-1-carboxylate (GB 2,128,984; 1.55 g, 5.21 mmol), $NaHCO_3$ (0.66 g, 7.82 mmol), dioxan (32 ml) and water (8 ml). The mixture was kept at 5° C. for 15 min then for 2 h at room temperature. The mixture was diluted with EtOAc (50 ml), washed twice with sat. $NaHCO_3$ solution, dried ($MgSO_4$) and concentrated. The oily residue was purified by flash chromatography to afford 211d (1.98 g, 88%) of a colourless oil: $[\alpha]_D^{24}$ –56.4 (c 1.0, $CH_2Cl_2$); IR(thin film) 3325, 2979, 2946, 1728, 1677, 1528, 1456, 1422, 1370, 1340, 1272, 1245, 1156, 1122, 1056, 916, 734, 699; $^1$H NMR ($CDCl_3$) δ7.29 (5H, m), 5.81–5.72 (1H, m), 5.26–5.20 (1H, m), 5.05 (2H, s), 4.69–4.51 (2H, m), 3.48–3.36 (1H, m), 2.81–2.51 (2H, m), 2.34–2.19 (2H, m), 1.90–1.54 (4H, m), 1.41 (9H, s); Anal. Calcd for $C_{22}H_{29}N_3O_6 \cdot H_2O$: C, 58.79; H, 6.92; N, 9.35. Found: C, 59.10; H, 6.57; N, 9.25; MS (ES +) 454 (M⁺+Na, 87%), 432 (M⁺+1, 100).

(1S, 9S) t-Butyl 9-benzoylamino-6,10-dioxo-1,2,3,4,7,8,9,10-octahydro-6H-pyridazino[1,2-a][1,2]diazepine-1-carboxylate (211e). A solution of benzoyl chloride (1.61 g, 11.47 mmol) in $CH_2Cl_2$ (15 ml) was added dropwise to a stirred ice cold mixture of (1S, 9S) t-butyl 9-amino-6,10-dioxo-1,2,3,4,7,8,9,10-octahydro-6H-pyridazino[1,2-a][1,2]diazepine-1-carboxylate (GB 2,128,984; 3.1 g, 10.43 mmol), dry $CH_2Cl_2$ (20 ml) and diisopropylethylamine (4.54 ml, 26.06 mmol). The mixture was kept cold for 1 h then left at room temperature for 0.5 h. The mixture was diluted with $CH_2Cl_2$, washed twice with brine, dried ($MgSO_4$) and concentrated. The residue was purified by flash chromatography (0–5% methanol in $CH_2Cl_2$) to afford 211e (4.0 g, 96%) of a colourless glass: mp 74°–76 °C.; $[\alpha]_D^+$ –75.0° (c 0.12, $CH_2Cl_2$). IR (KBr) 3350, 2979, 2938, 1736, 1677, 1662, 1536, 1422, 1276, 1250, 1155; $^1$H NMR ($CDCl_3$) δ8.72 (2H, m), 7.53–7.40 (3H, m), 7.07 (1H, d, J=7.2), 5.30 (1H, dd, J=3.0, 5.8), 5.12 (1H, m), 4.66 (1H, m), 3.51 (1H, m), 2.90 (2H, m), 2.38 (1H, dd, J 13.2, 6.8), 2.25 (1H, m), 1.9 (2H, m), 1.70 (1H, m). Anal. Calcd for $C_{21}H_{27}N_3O_5 \cdot 0.5H_2O$: C, 61.45; H, 6.88; N, 10.24. Found C, 61.69; H, 6.71; N, 10.18.

(1S, 9S) t-Butyl 6,10-dioxo-9-(fluoren-9-ylmethyloxycarbonylamino)-1,2,3,4,7,8,9,10-octahydro-6H-pyridazino[1,2-a][1,2]-diazepine-1-carboxylate (211f), was prepared in a similar manner to 211e, except 9-fluorenylmethylchloroformate was used instead of benzoylchloride to give a white glassy solid 211f (2.14 g, 89%): mp 190°–192 °C.; $[\alpha]_D^{25}$ –81.5° (c 0.1, $CH_2Cl_2$). IR (KBr) 3335, 2977, 1731, 1678, 1450, 1421, 1246, 1156, 742; $^1$H NMR ($CDCl_3$) δ7.60 (2H, m), 7.57 (2H, m), 7.50–7.26 (4H, m), 5.60 (1H, d, J=7.8), 5.28 (1H, m), 4.67 (2H, m), 4.38 (2H, m), 4.23 (1H, m), 3.59–3.41 (1H, m), 2.92–2.65 (2H, m), 2.41–2.21 (2H, m), 1.95–1.58 (4H, m), 1.47 (9H, s). MS(ES-, m/z) 520 (M⁺+1, 97%), 179 (100%).

(1S, 9S) 6,10-Dioxo-9-methysulphonylamino-1,2,3,4,7,8,9,10-octahydro-6H-pyridazino-[1,2-a][1,2]diazepine-1-carboxylic acid (212b), was synthesized by the same method as compound 212e (635 mg, 85%) as a colourless powder: mp 209°–12 °C.; $[\alpha]_D^{24}$ –132 (c 0.12, MeOH); IR (KBr) 3308, 2940, 1717, 1707, 1699, 1619, 1469, 1456, 1442, 1417, 1391, 1348, 1339, 1330, 1310, 1271, 1247, 1222, 1175, 1152, 1133, 993, 976; $^1$H NMR ($CD_3OD$) δ5.35 (1H, m), 4.58–4.48 (1H, m), 4.46–4.36 (1H, m), 3.60–3.42 (1H, m), 3.01–2.87 (1H, m), 2.95 (3H, s), 2.55–2.39 (1H, m), 2.32–2.20 (2H, m), 2.09–1.89 (2H, m), 1.78–1.62 (2H, m); Anal. Calcd for $C_{11}H_{17}N_3O_6S$: C, 41.37; H, 5.37; N, 13.16; S, 10.04. Found: C, 41.59; H, 5.32; N, 12.75; S, 9.76; MS(ES –) Accurate Mass calculated for $C_{11}H_{18}N_3O_6S$ (MH⁺) 320.0916. Found: 320.0943.

(1s, 9S) 9-Acetylamino-6,10-dioxo-1,2,3,4,7,8,9,10-octahydro-6H-pyridazino[1,2-a][1,2]diazepine-1-carboxylic acid (212c), was prepared from 211e the same method as compound 212e as a white glassy solid (595 mg, 77%): mp >250° C.; $[\alpha]_D^{24}$ −153 (c 0.10, MeOH) ; IR (KBr) 3280, 2942, 1742, 1697, 1675, 1650, 1616, 1548, 1470, 1443, 1281, 1249, 1202, 1187, 1171; $^1$H NMR (CD$_3$OD) δ5.35–5.31 (1H, m), 4.81–4.71 (1H, m), 4.61–4.46 (1H, m), 3.59–3.44 (2H, m), 3.11–2.94 (1H, m), 2.58–2.39 (1H, m), 2.36–2.19 (2H, m), 2.11–1.83 (3H, m), 1.99 (3H, s), 1.78–1.56 (2H, m); Anal. Calcd for C$_{12}$H$_{17}$N$_3$O$_6$: C, 50.88; H, 6.05; N, 14.83. Found: C, 50.82; H, 6.02; N, 14.58; MS (ES -) 282 (M-1, 100%): Accurate Mass calculated for C$_{12}$H$_{18}$N$_3$O$_5$ (MH$^+$): 284.1246. Found: 284.1258.

(1S, 9S) 9-Benzyloxycarbonylamino-6,10-dioxo-1,2,3,4,7,8,9,10-octahydro-6H-pyridazino [1,2-a][1,2]diazepine-1-carboxylic acid (212d), was prepared from 211d by the same method as compound 212e as colourless crystals (170 mg, 97%): mp 60°–100 ° C.; $[\alpha]_D^{22}$ −103 (c 0.10, MeOH); IR (KBr) 3341, 2947, 1728, 1675, 1531, 1456, 1422, 1339, 1272, 1248, 1221, 1174, 1122, 1056, 982, 699; $^1$H NMR (CDCl$_3$) δ7.35 (5H, s), 5.65 (1H, d), 5.48–5.40 (1H, m), 5.10 (2H, s), 4.76–4.57 (2H, m), 3.49–3.30 (2H, m), 2.92–2.59 (2H, m), 2.40–2.27 (2H, m), 1.97–1.67 (4H, m); MS (ES -) 374 (M - 1, 100%). Accurate mass calculated for C$_{18}$H$_{22}$N$_3$O$_6$ (MH$^+$): 376.1509. Found: 376.1483. Accurate mass calculated for C$_{18}$H$_{21}$N$_3$O$_6$Na (MNa$^+$): 398.1328. Found: 398.1315.

(1S, 9S) 9-Benzoylamino-6,10-dioxo-1,2,3,4,7,8,9,10-octahydro-6H-pyridazino[1,2-a][1,2]-diazepine-1-carboxylic acid (212e). TFA (20 ml) was added to an ice cold stirred solution of the t-butyl ester 211e (4.15 g, 10.34 mmol) in dry CH$_2$Cl$_2$ (20 ml). The mixture was kept cold for 1.5 h then left for 2.5 h at rt, concentrated. TFA was removed by repeated concentrations of CH$_2$Cl$_2$ether and ether solutions of the residue. Finally trituration of the residue with ether afforded 212e 3.05 g (85%) of a white glassy solid: mp 118°–126° C.; $[\alpha]_D^{24}$ −70.5° (c 0.1, CH$_2$Cl$_2$). IR (KBr) 3361, 2943, 1737, 1659, 1537, 1426, 1220, 1174; $^1$H NMR (CDCl$_3$) δ7.80 (2H, m), 7.54–7.33 (4H, m), 8.83 (brs), 5.44 (1H, m), 5.26–5.13 (1H, m), 4.66 (1H, m), 3.59–3.41 (1H, m), 2.97, 2.76 (2H, 2m), 2.36 (2H, m), 1.98 (2H, m), 1.75 (2H, m) . MS (ES-, m/z) 344 (M - 1, 100%).

(1S, 9S) 6,10-Dioxo-9-(fluoren-9-ylmethyloxycarbonylamino)-1,2,3,4,7,8,9,10-octahydro-6H-pyridazino[1,2-a][1,2]-diazepine-1-carboxylic acid (212f), was prepared from 211f in 96% yield by the same method as for 212e: mp 120°–126 ° C.; $[\alpha]_D^{25}$ −72.5° (c 0.1, CH$_2$Cl$_2$). IR (KBr) 3406, 2950, 1725, 1670, 1526, 1449, 1421, 1272, 1248, 1223, 1175, 761, 741; $^1$H NMR (CDCl$_3$) δ7.76 (2H, m), 7.62–7.26 (4H, m), 6.07, 5.76 (2H, brs, d, d, J=2.9), 5.46, 5.36 (1H, 2m), 4.79–4.54 (2H, m), 4.77 (2H, m), 4.21 (1H, m), 3.41 (1H, m), 2.89 (1H, m), 2.69 (1H, m), 2.35 (2H, m), 1.98, 1.73 (4H, 2m). MS (ES-, m/z) 462 (M+-1, 50%), 240 (100%).

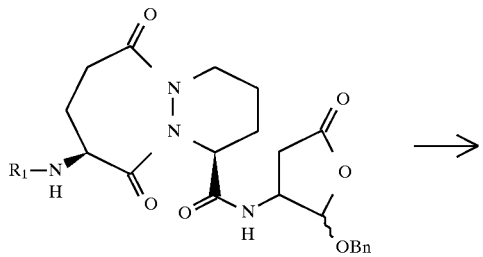

(213) (c) R$_1$ = MeCO
(e) R$_1$ = PhCO

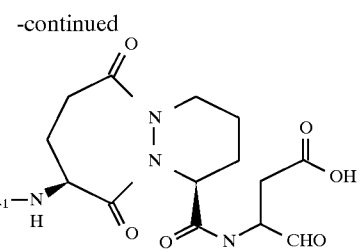

(214) (c) R$_1$ = MeCO
(e) R$_1$ = PhCO

[2RS, 3S,(1S, 9S)] N-(2-Benzyloxy-5-oxotetrahydrofuran-3-yl)-9-(acetylamino)-6,10-dioxo-1,2,3,4,7,8,9,10-octahydro-6H-pyridazino[1,2-a][1,2]diazepine-1-carboxamide (213c), was synthesized from 212c by the same method as compound 213e to afford a mixture of diastereomers (193 mg, 36%) as colourless crystals: IR (KBr) 3272, 1799, 1701, 1682, 1650, 1555, 1424, 1412, 1278, 1258, 1221, 1122, 937; $^1$H NMR (CDCl$_3$) δ7.41–7.28 (5H, m), 6.52 (0.5H, d), 6.38 (0.5H, d), 6.22 (0.5H, d), 5.57 (0.5H, d), 5.36 (0.5H, s) 5.10–5.05 (1H, m), 5.00–4.45 (5.5H, m), 3.19–2.84 (3H, m), 2.72–2.56 (1H, m), 2.51–2.25 (2H, m), 2.02 (3H, s), 1.98–1.70 (3H, m), 1.66–1.56 (3H, m); Anal. Calcd for C$_{23}$H$_{28}$N$_4$O$_7$: C, 58.47; H, 5.97; N, 11.86. Found: C, 58.37; H, 6.09; N, 11.47. MS (ES -) 471 (M-1, 100%). Accurate mass calculated for C$_{23}$H$_{29}$N$_4$O$_7$ (MH+): 473.2036. Found: 473.2012. Accurate mass calculated for C$_{23}$H$_{28}$N$_4$O$_7$Na (Mna$^+$): 495.1856. Found: 495.1853.

[1S, 9S, (2RS, 3S)]9-Benzoylamino-6,10-dioxo-1,2,3,4,7,8,9,10-octahydro-N-(2-benzyloxy-5-oxotetrahydrofuran-3-yl)-6H-pyridazino[1,2-a][1,2]diazepine-1-carboxamide (213e). Tributyltin hydride (2.2 ml, 8.18 mmol) was added dropwise to a solution of acid (212e) (1.95 g, 5.6 mmol), (3S, 2RS) 3allyloxycarbonylamino-2-benzyloxy-5-oxotetrahydrofuran (Chapman, *Biorg. & Med. Chem. Lett.*, 2, pp. 615–618 (1992); 1.80 g, 6.16 mmol) and (Ph$_3$P)$_2$PdCl$_2$ (50 mg) in dry CH$_2$Cl$_2$ (36 ml), with stirring, under dry nitrogen. After 5 min 1-hydroxybenzotriazole (1.51 g, 11.2 mmol 6.72 mmol) was added followed after cooling (ice/H$_2$O) by ethyldimethylaminopropyl carbodiimide hydrochloride (1.29 g, 6.72 mmol). After 5 mins the cooling bath was removed and the mixture was kept at room temperature for 4h, diluted with EtOAc, washed with 1M HCl, brine, sat. aq. NaHCO$_3$ and brine, dried (MgSO$_4$) and concentrated. Flash chromatography (silica gel, 0–90% EtOAc in CH$_2$Cl$_2$) gave the product as a white solid (2.34 g, 78%): IR (KBr) 3499, 1792, 1658, 1536, 1421, 1279, 1257, 1123, 977, 699; $^1$H NMR (CDCl$_3$) δ7.81 (2H, m), 7.54–7.34 (8H, m), 7.1, 6.97, 6.89, 6.48 (2H, m, d, J 7.7, d, J=7.5, d, J=7.6), 5.57, 5.28 (1H, d, J=5.2, s), 5.23–5.07 (2H, m), 4.93–4.42, 3.22–2.70, 2.51–2.26, 2.08–1.69, 1.22 (15H, 5m). Anal. Calcd for C$_{28}$H$_{30}$N$_4$O$_7$ 0.5H$_2$O: C, 61.87; H, 5.75; N, 10.32. Found C, 62.02; H, 5.65; N, 10.25.

[3S,(1S, 9S)]3-(9-Acetylamino-6,10-dioxo-1,2,3,4,7,8,9,10-octahydro-6H-pyridazino [1,2-a][1,2]diazepine-1-carboxamido)-4-oxobutanoic acid (214c), was synthesized from 213c by a method similar to the method used to synthesize 214e from 213e to provide colourless crystals (140 mg, 99%): mp 90°–180° C.; $[\alpha]_D^{22}$ −114 (c 0.10, MeOH); IR (KBr) 3334, 3070, 2946, 1787, 1658, 1543, 1422, 1277, 1258; $^1$H NMR (d$^6$DMSO) δ8.66 (1H, m), 8.18 (1H, d), 6.76 (1H, s), 5.08 (1H, m), 4.68 (1H, m), 4.30 (1H, m), 2.92–2.70 (2H, m), 2.27–2.06 (3H, m), 1.95–1.72 (4H, m), 1.85 (3H, s), 1.58 (2H, m); MS(ES -) 381 (M-1, 100%);

Accurate mass calculated for $C_{16}H_{23}N_4O_7$ (MH$^+$): 383.1567. Found: 383.1548.

[3S, (1S, 9S)]3-(9-Benzoylamino-6,10-dioxo-1,2,3,4,7,8,9,10-octahydro-6H-pyridazino[1,2-a][1,2]-diazepine-1-carboxamido)-4-oxobutanoic acid (214e). A mixture of 213e (2.29 g, 4.28 mmol), 10% palladium on carbon (1.8 g) and MeOH (160 ml) was stirred under H$_2$ at atmospheric pressure for 6.3 h. After filtering and concentrating the hydrogenation was repeated with fresh catalyst (1.8 g) for 5 h. After filtering and concentrating the residue was triturated with diethyl ether, filtered and washed well with ether to give 214e as a white solid (1.67 g, 88%): mp 143° –147° C.; [α]$_D^{23}$125° (c 0.2, CH$_3$OH). IR (KBr) 3391, 1657, 1651, 1538, 1421, 1280, 1258; $^1$H NMR (CD$_3$OD) δ7.90 (2H, m), 7.63–7.46 (3H, m), 5.25 (1H, m), 5.08–4.85 (1H, m), 4.68–4.53 (2H, m), 4.33–4.24 (1H, m), 3.62–3.44, 3.22–3.11, 2.75–2.21, 2.15–1.92, 1.73–1.66 (11H, 5m). Anal. Calcd for $C_{21}H_{24}N_4O_7 \cdot H_2O$: C, 54.54; H, 5.67; N, 12.11. Found C, 54.48; H, 5.63; N, 11.92.

$C_{28}H_{34}N_4Cl_2O_9$: C, 52.26; H, 5.64; N, 8.71. Found: C, 52.44; H, 5.87; N, 8.16. MS (ES -) 645/3/1 (M-1, 26%), 189 (81), 134 (100). Accurate mass calculated for $C_{28}H_{37}N_4Cl_2O_9$ (MH$^+$): 643.1938. Found: 643.1924. Accurate mass calculated for $C_{29}H_{36}N_4Cl_2O_9Na$ (MNa$^+$) 665.1757. Found: 665.1756.

[3S, 4RS,(1S, 9S)] t-Butyl 3-(9-benzyloxycarbonylamino-6,10-dioxo-1,2,3,4,7,8,9,10-octahydro-6H pyridazino[1,2-a][1,2]diazepine-1-carboxamido)-5-(2,6-dichlorobenzyloxy)-4-hydroxypentanoate (215d), was synthesized from 214d by the same method as compound 215e to afford a mixture of diastereomers (657 mg, 70%) as a glassy white solid: IR (KBr) 3420, 3361, 2975, 2931, 1716, 1658, 1529, 1434, 1367, 1348, 1250, 1157, 1083, 1055; $^1$H NMR (CDCl$_3$) δ7.32 (8H, m), 7.14 (1H, d), 5.81 (1H, d), 5.15 (1H, m), 5.07 (2H, s), 4.74–4.65 (1H, m), 4.58–4.22 (4H, m), 4.15–4.06 (1H, m), 3.72 (1H, m), 3.32–3.21 (1H, m), 3.04–2.94 (1H, m), 2.69–2.52 (3H, m), 2.33–2.27 (1H, m), 1.95–1.59 (4H,

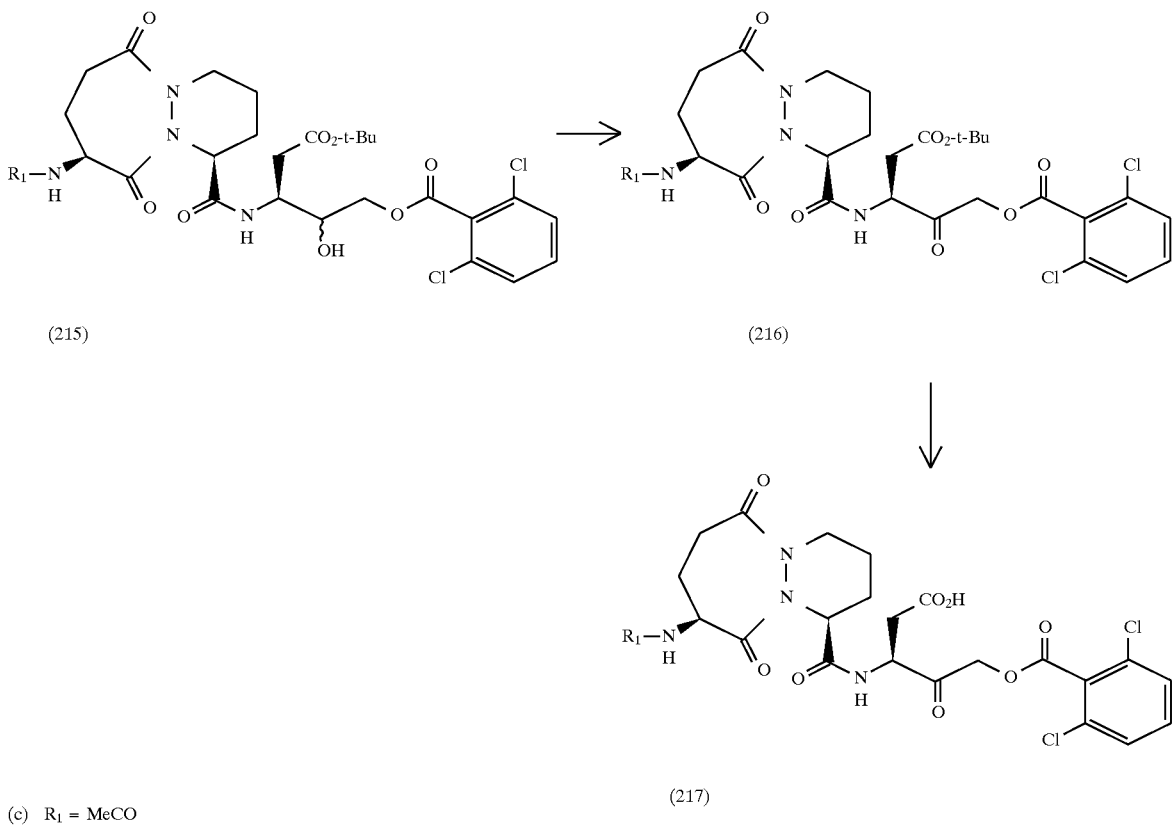

(c) R$_1$ = MeCO
(d) R$_1$ = PhCH$_2$OCO
(e) R$_1$ = PhCO

[3S, 4RS,(1S, 9S)] t-Butyl 3-[9-acetylamino-6,10-dioxo-1,2,3,4,7,8,9,10-octahydro-6H-pyridazino [1,2-a][1,2] diazepine-1-carboxamido)-5-(2,6-dichlorobenzoyloxy)-4-hydroxypentanoate (215c), was synthesized from 214c by the same method as compound 215e, to afford a mixture of diastereomers as a white glassy solid (398 mg, 84%): IR (KBr) 3338, 2977, 1738, 1658, 1562, 1541, 1433, 1368, 1277, 1150; $^1$H NMR (CDCl$_3$) δ7.36–7.32 (3H, m), 6.91 (1H, d), 6.30 (1H, d), 5.15–5.09 (1H, m) 5.01–4.88 (1H, m), 4.61–4.44 (2H, m), 4.37–4.08 (3H, m), 3.32–3.18 (1H, m), 3.04–2.89 (1H, m), 2.82–2.51 (4H, m), 2.39–2.29 (1H, m), 2.08–1.64 (4H, m) 2.02 (3H, s); Anal. Calcd for m), 1.28 (9H, s); Anal. Calcd for $C_{34}H_{40}N_4Cl_2O_{10} \cdot 0.5 H_2O$: C, 54.70; H, 5.54; N, 7.50. Found: C, 54.98; H, 5.59; N, 7.24. MS (ES -) 737/5/3 (M-1, 22%), 193/1/89 (100). Accurate mass calculated for $C_{34}H_{41}N_4Cl_2O_{10}$ (MH$^+$) 735.2120. Found: 735.2181.

[3S, 4RS,(1S, 9S)] t-Butyl 3-(9-benzoylamino-6,10=dioxo-1,2,3,4,7,8,9,10-octahydro-6H-pyridazino[1,2-a][1,2]diazepine-1-carboxamido)-5-(2,6dichlorobenzyloxy)-4-hydroxypentanoate (215e), Tributyltin hydride (4.6 ml; 11.4 mmol) was added dropwise to a stirred mixture of (3S, 4RS) t-Butyl (N-allyloxycarbonyl)-3-amino-S-(2,6-dichlorobenzoyloxy)-4-hydroxypentanoate (prepared by a method similar to the method described in Revesz et al., *Tetrahedron. Lett.*, 35, pp. 9693–9696 (1994)) (2.64 g; 5.7 mmol), (Ph$_3$P)$_2$PdCl$_2$ (50 mg), CH$_2$Cl$_2$ (100 ml) and DMF (20 ml) at room temperature. The mixture was stirred for a further 10 min was then 1-hydroxybenzotriazole (1.54 g, 11.4 mmol)was added. The mixture was cooled to 0° C. then ethyldimethylaminopropyl carbodiimide hydrochloride (1.31 g; 6.84 mmol) added. The mixture was kept at this temperature for 15 min then at room temperature for 17 h. The mixture was diluted with EtOAc (300 ml), washed with 1M HCl (2×100 ml), sat. aq. NaHCO$_3$ (3×100 ml) and brine (2×100 ml), dried (MgSO$_4$) and concentrated. The residue was purified by flash chromatography (2–5% (MeOH/CH$_2$Cl$_2$) to afford 3.24 g (81%) of 215e as a glassy solid: mp 106°–110 ° C.; IR (KBr) 3354, 1737, 1659, 1531, 1433, 1276, 1150; $^1$H NMR (CDCl$_3$) δ7.80 (2H, dd, J=7.9 and 1.5), 7.75–7.26 (6H, m), 7.14–6.76 (2H, m), 5.30–5.02 (2H, m), 4.63–4.11 (5H, m), 3.44–3.26 (2H, m), 3.10–2.30 (5H, m), 2.10–1.60 (5H, m), 1.44 (9H, s); Anal. Calcd for C$_{33}$H$_{38}$Cl$_2$N$_4$O$_9$. 0.75H$_2$O: C, 55.12; H, 5.54; N, 7.79; Cl, 9.86. Found: C, 55.04; H, 5.34; N, 7.80; Cl, 10.24. MS (ES +) 709/7/5 (M +1), 378 (59), 324 (64), 322 (100).

[3S,(1S, 9S)] t-Butyl 3-(9-acetylamino-6,10-dioxo-1,2,3,4,7,8,9,10-octahydro-6H-pyridazino[1,2-a](1,2]-diazepine-1-carboxamido)-5-(2,6-dichlorobenzoyloxy)-4-oxopentanoate (216c), was synthesized from 215c by the same method as compound 216e as a glassy white solid (300 mg, 83%): mp 80°–125 ° C.; [α]$_D^{23}$ –89.1 (c 1.08, CH$_2$Cl$_2$); IR (KBr) 3356, 2979, 2935, 1740, 1659, 1532, 1434, 1369, 1276, 1260, 1151; $^1$H NMR (CDCl$_3$) δ7.39–7.32 (3H, m), 7.13 (1H, d), 6.34 (1H, d), 5.22–5.17 (1H, m), 5.11 (1H, d), 5.04 (1H, d), 4.99–4.88 (2H, m), 4.64–4.52 (1H, m), 3.29–3.11 (1H, m), 3.05–2.67 (4H, m), 2.39–2.29 (1H, m), 2.02 (3H, s), 1.98–1.75 (4H, m), 1.46 (9H, s); Anal. Calcd for C$_{28}$H$_{34}$N$_4$Cl$_2$O$_9$: C, 52.42; H, 5.34; N, 8.73. Found: C, 52.53; H, 5.70; N, 7.85. MS (ES –) 643/41/39 (M–1, 100%). Accurate mass calculated for C$_{28}$H$_{35}$N$_4$Cl$_2$O$_9$ (MH$^+$): 641.1781. Found: 641.1735. Accurate mass calculated for C$_{28}$H$_{34}$N$_4$Cl$_2$O$_9$Na (Mna$^+$) 663.1601. Found: 663.1542.

[3S,(1S, 9S)] t-Butyl 3-(9-benzyloxycarbonylamino-6,10dioxo-1,2,3,4,7,8,9,10-octahydro-6H-pyridazino [1,2-a][1,2]diazepine-1-carboxamido)-5-(2,6dichlorobenzoyloxy)-4-oxopentanoate (216d), was synthesized from 215d by the same method as compound 216e to afford 216d as a white glassy solid (688 mg, 68%): mp 90°–170° C.; [α]$^{P25}$ –83.4 (c 1.01, CH$_2$Cl$_2$); IR (KBr) 3338, 2933, 1736, 1670, 1525, 1433, 1417, 1368, 1258, 1151, 1056, 1031; $^1$H NMR (CDCl$_3$) δ7.33 (8H, m), 7.18 (1H, d), 5.65 (1H, d), 5.19 (1H, m), 5.09 (2H, s), 4.98–4.86 (1H, m), 4.82–4.49 (2H, d), 3.30–3.07 (1H, m), 3.05–2.59 (4H, m), 2.42–2.27 (1H, m), 2.18–1.59 (5H, m), 1.42 (9H, s); MS (ES-) 737/5/3 (M, 13%), 185 (100).

[3S,(1S, 9S)] t-Butyl 3-(9-benzoylamino-6,10-dioxo-1,2,3,4,7,8,9,10-octahydro-6H-pyridazino [1,2-a][1,2]-diazepine-1-carboxamido)-5-(2,6-dichlorobenzoyloxy)-4-oxopentanoate (216e). Dess-Martin reagent (3.82g; 9.0 mmol) was added to a stirred solution of the alcohol 215e (3.17 g; 4.5 mmol) in CH$_2$Cl$_2$ (100 ml). The mixture was sirred for 1 h, diluted with EtOAc (300 ml), then washed with a 1:1 mixture of sat. Na$_2$S$_2$O$_3$ and sat. NaHCO$_3$ (100 ml) followed by brine (100 ml). The mixture was dried (MgSO$_4$) then concentrated. The residue was purified by flash chromatography to afford 2.2 g (70%) of 216e as a colourless solid: mp 102°–107° C.; [α]$_D^{32}$ –82.5 (c 0.1, CH$_2$Cl$_2$); IR (KBr) 3374, 2937, 1739, 1661, 1525, 1433, 1275, 1260, 1152; $^1$H NMR (CDCl$_3$) δ 7.85–7.78 (2H, m), 7.57–7.32 (6H, m), 7.09 (1H, d, J=7.9), 7.01 (1H, d, J 7.3), 5.25–5.16 (1H, m), 5.16–5.05 (1H, m), 5.15 (1H, d), 5.03 (1H, d), 4.99–4.90 (1H, m), 4.68–4.54 (1H, m), 3.31–3.17 (1H, m), 3.17–2.72 (4H, m), 2.45–2.35 (1H, m), 2.30–1.66 (5H, m), 1.44 (9H, s); Anal. Calcd for C$_{33}$H$_{36}$Cl$_2$N$_4$O$_9$. 0.5H$_2$O: C, 55.62; H, 5.23; N, 7.86; Cl, 9.95. Found: C, 55.79; H, 5.15; N, 7.80; Cl 9.81. MS (ES+) 729/7/5 (M+Na), 707/5/3 (M+1), 163 (100%).

[3S,(1S,9S)] 3-(9-Acetylamino-6,10-dioxo-1,2,3,4,7,8,9,10-octahydro-6H-pyridazino[1,2-a][1,2]diazepine-1-carboxamido)-5-(2,6-dichlorobenzoyloxy)-4-oxopentanoic acid (217c), was synthesized from 216c by the same method as compound 217e as a glassy white solid (166 mg, 66%): mp 85°–175° C.; [α]$_D^{25}$ –156 (c 0.13, MeOH); IR (KBr) 3373, 2929, 1742, 1659, 1562, 1533, 1433, 1412, 1274, 1266, 1223, 1197, 1145, 1138; $^1$H NMR (CD$_3$OD) δ 7.38 (3H, s), 5.14–5.03 (1H, m), 4.49–4.32 (2H, m), 3.50–3.27 (1H, m), 3.11–2.92 (1H, m), 2.84–2.62 (2H, m), 2.46–2.11 (2H, m), 2.05–1.46 (5H, m), 1.92 (3H, s); Anal. Calcd for C$_{24}$H$_{26}$N$_4$Cl$_2$O$_9$.H$_2$O: C, 47.77; H, 4.68; N, 9.29. Found: C, 47.75; N, 4.59; N, 9.07. MS (ES+) 627/5/3 (M+K, 21%), 611/9/7 (M+Na, 87), 589/7/5 (M$^+$ +1, 71), 266 (100); Accurate mass calculated for C$_{24}$H$_{27}$N$_4$Cl$_2$O$_9$ (MH$^+$): 585.1155. Found: 585.1134.

[3S,(1S,9S)] 3-(9-Benzyloxycarbonylamino-6,10-dioxo-1,2,3,4,7,8,9,10-octahydro-6H-pyridazino[1,2-a][1,2]diazepine-1-carboxamido)-5-(2,6-dichlorobenzoyloxy)-4-oxopentanoic acid (217d), was synthesized from 216d by the same method as compound 217e to afford 217d as a white glassy solid (310 mg, 96%): mp 85°–110° C.; [α]$_D^{24}$ –85.9 (c 0.13, MeOH); IR (KBr) 3351, 2945, 1738, 1669, 1524, 1433, 1258, 1147, 1057; $^1$H NMR (CD$_3$OD) δ 7.56 (4H, m), 7.45 (5H, m), 5.32 (2H, m), 5.20 (2H, s), 4.76–4.48 (3H, m), 3.65–3.38 (3H, m), 3.27–3.09 (2H, m), 3.03–2.89 (2H, m), 2.65–2.24 (3H, m), 2.19–1.62 (5H, m); MS (ES–) 679/7/5 (M–1, 100%); Accurate mass calculated for C$_{30}$H$_{31}$N$_4$Cl$_2$O$_{10}$(MH$^+$): 677.1417. Found: 677.1430.

[3S,(1S,9S)]3-(9-Benzoylamino-6,10-dioxo-1,2,3,4,7,8,9,10-octahydro-6H-pyridazino[1,2-a][1,2]diazepine-1-carboxamido)-5-(2,6-dichlorobenzoyloxy)-4oxopentanoic acid (217e), TFA (25 ml) was added dropwise to an ice cold stirred solution of the ester 216e (2.11 g, 3.0 mmol). The mixture was stirred at 0° C. for 20 min then at room temperature for 1 h. The mixture was evaporated to dryness then coevaporated with ether three times. Addition of dry ether (50 ml) and filtration afforded 1.9 g (98%) of 217e as a colourless solid: mp 126°–130° C.; [α]$_D^{30}$ –122.0 (c 0.1, MeOH); IR (KBr) 3322, 1740, 1658, 1651, 1532, 1433, 1277, 1150; $^1$H NMR (D$_6$-DMSO) δ 8.87 (1H, d, J=7.4), 8.61 (1H, d, J=7.8), 7.92–7.86 (2H, m), 7.65–7.43 (6H, m), 5.25–5.12 (3H, m), 4.94–4.60 (2H, m), 4.44–4.22 (1H, m), 3.43–3.10 (1H, m), 3.00–2.52 (3H, m), 2.45–2.10 (3H, m), 2.10–1.75 (2H, m), 1.75–1.50 (2H, m); Anal. Calcd for C$_{29}$H$_{28}$Cl$_2$N$_4$O$_9$. 1H$_2$O: C, 52.34; H, 4.54; N, 8.42; Cl, 10.66. Found: C, 52.02; H, 4.36; N, 8.12; Cl, 10.36. MS (ES–) 649/7/5 (M–1), 411 (100%).

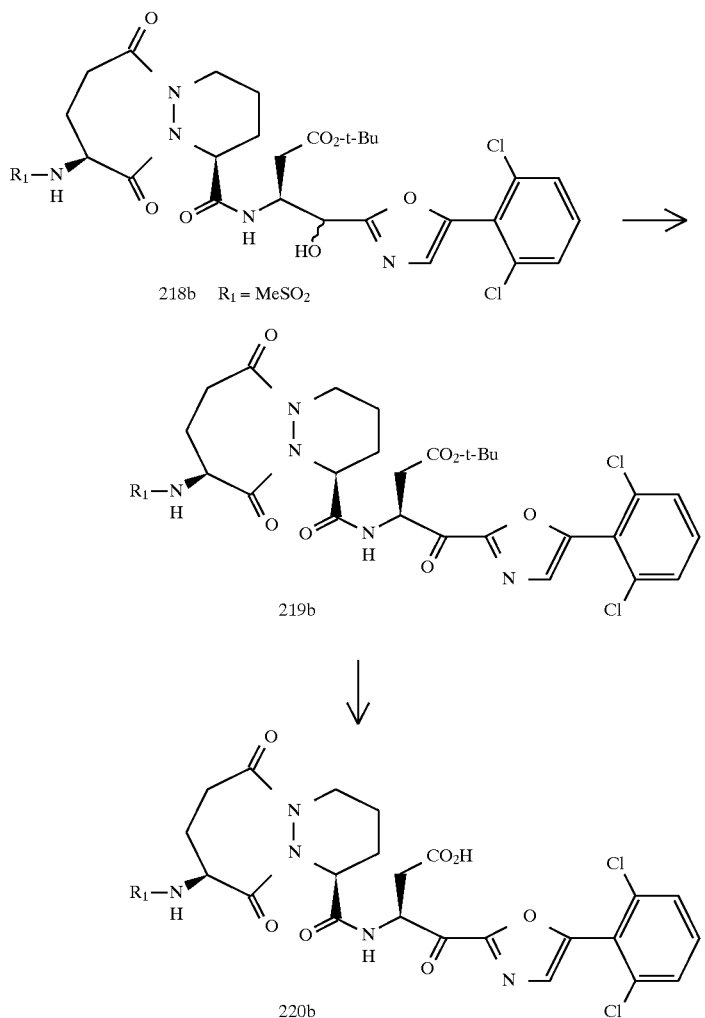

[3S, 4RS,(1S, 9S)] t-Butyl 4-[5-(2,6-dichlorophenyl)oxazol-2-yl]-3-(6,10-dioxo-9-methylsulphonylamnino-1,2,3,4,7,8,9,10-octahydro-6H-pyridazino-[1,2-a][1,2]diazepine-1-carboxamido)-4-hydroxybutanoate (218b), was prepared from the acid 212b and 99 in an analogous way to compound 215e to afford a mixture of diastereomers (865 mg, 80%) as a colourless solid: IR (KBr) 3298, 2974, 1723, 1659, 1544, 1518, 1430, 1394, 1370, 1328, 1273, 1256, 1156, 1134; $^1$H NMR (CDCl$_3$) δ 7.45–7.28 (4H, m), 7.26–7.15 (2H, m), 5.26–5.10 (2H, m), 4.80–4.67 (1H, m), 4.59–4.42 (2H, m), 3.32–3.17 (1H, m), 2.96 (3H, 2×s), 2.93–2.79 (1H, m), 2.71–2.53 (4H, m), 2.38–2.28 (1H, m), 2.07–1.81 (4H, m); Anal. Calcd for C$_{28}$H$_{35}$N$_5$Cl$_2$O$_9$S. 0.5 H$_2$O: C, 48.21; H, 5.20; N, 10.03. Found: C,48.35; H, 5.26; N, 9.48. MS (ES+) 714/2/0 (M+Na, 25%), 692/90/88 (M$^+$+1, 51), 636/4/2 (38), 246 (100). Accurate mass calculated for C$_{28}$H$_{36}$N$_5$Cl$_2$O$_9$S (MH$^+$): 688.1611. Found: 688.1615.

[3S,(1S,9S)]t-Butyl 4-[5-(2,6-dichlorophenyl)-oxazol-2-yl]-3-(6,10-dioxo-9-methylsulphonylamino-1,2,3,4,7,8,9,10-octahydro-6H-pyridazino[1,2-a][1,2]diazepine-1-carboxamido)-4-oxobutanoate (219b), was prepared from 218b in an analogous way to compound 216e as an off-white powder (675 mg, 81%): mp 100°–200° C.; [α]$_D^{24}$ −84.9 (c 1.01, CH$_2$Cl$_2$); IR (KBr) 3336, 2978, 2936, 1719, 1674, 1510, 1433, 1421, 1369, 1329, 1274, 1257, 1155, 991, 789; $^1$H NMR (CDCl$_3$) δ 7.47–7.38 (4H, m), 7.24 (1H, d), 5.61–5.53 (1H, m), 5.48 (1H, d), 5.38–5.30 (1H, m), 4.67–4.45 (2H, m), 3.48–3.18 (2H, m), 3.04–2.90 (2H, m), 2.97 (3H, s), 2.69–2.54 (1H, m), 2.42–2.32 (1H, m), 2.22–2.15 (1H, m), 2.07–1.93 (3H, m), 1.71–1.65 (2H, m), 1.38 (9H, s); Anal. Calcd for C$_{28}$H$_{33}$N$_3$Cl$_2$O$_9$S: C, 48.98; H, 4.84; N, 10.20; S, 4.67. Found: C, 48.73; H, 4.95; N, 9.65; S, 4.54. MS (ES+) 692/90/88 (M$^+$+1, 100%), 636/4/2 (71). Accurate mass calculated for C$_{28}$H$_{34}$N$_5$Cl$_2$O$_9$S (MH$^+$): 686.1454. Found: 686.1474.

[3S, (1S, 9S)] 4-[5-(2,6-Dichlorophenyl)oxazol-2-yl]-3-(6,10-dioxo-9-methylsulphonylamino-1,2,3,4,7,8,9,10-octahydro-6H-pyridazino[1,2-a][1,2]diazepine-1-carboxamido)-4-oxobutanoic acid (220b), was prepared from 219b in an analogous way to compound 217e as a pale cream powder (396 mg, 87%): mp 100°–200° C.; [α]$_D^{27}$ −129 (c 0.12, MeOH); IR (KBr) 3310, 3153, 1713, 1667, 1557, 1510, 1432, 1421, 1329, 1273, 1258, 1221, 1193, 1153, 1134, 992, 789; $^1$H NMR (d$^6$ DMSO) δ 7.88 (1H, s), 7.81–7.60 (4H, m), 5.49–5.28 (1H, m), 5.24–5.14 (1H, m), 4.46–4.22 (2H, m), 3.30–3.03 (2H, m), 2.97–2.76 (3H, m), 2.96 (3H, s), 2.46–2.24 (1H, m), 2.16–2.05 (1H, m), 2.03–1.78 (3H, m), 1.68–1.46 (2H, m); MS (ES−) 632/30/28 (M−1, 68%), 149/7/5 (100). Accurate mass calculated for C$_{24}$H$_{26}$N$_5$Cl$_2$O$_9$S (MH$^+$): 630.0828. Found: 630.0852.

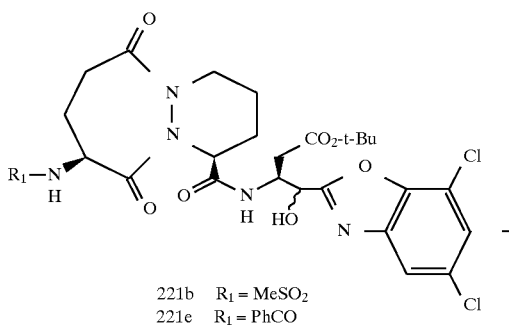

221b  R₁ = MeSO₂
221e  R₁ = PhCO

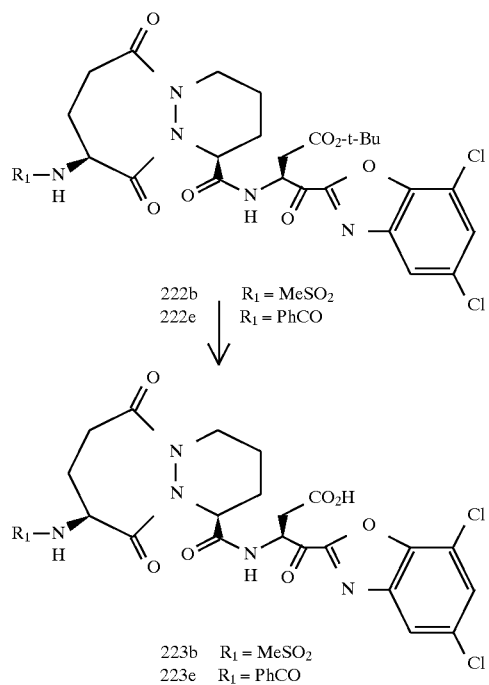

222b  R₁ = MeSO₂
222e  R₁ = PhCO

223b  R₁ = MeSO₂
223e  R₁ = PhCO

[3S, 4RS,(1S, 9S)] t-Butyl 4-(5,7-dichlorobenzoxazol-2-yl)-3-(6,10-dioxo-9-methylsulphonylamino-1,2,3,4,7,8,9,10-octahydro-6H-pyridazino[1,2-a][1,2]diazepine-1-carboxamido)-4-hydroxybutanoate (221b), was prepared from the acid 212b and (3S, 4RS) t-butyl N-(allyloxycarbonyl)-3-amino-4-hydroxy-4-(5,7-dichlorobenzoxazol-2-yl)butanoate (204) by an analogous method as that used for compound 215e to afford a mixture of diastereomers (460 mg, 70%) as a glass: IR (film) 3325, 1725, 1664, 1453, 1399, 1373, 1327, 1274, 1256, 1155; $^1$H NMR (CDCl₃) δ 7.57 (1H, m), 7.36 (2H, m), 6.06 (1H, t), 5.29 (2H, m), 4.79 (1H, m), 4.47 (1H, m), 3.23 (1H, m), 2.97 and 2.94 (3H combined, 2×s), 2.9–2.4 (4H, m), 2.30 (1H, m), 1.96 (4H, m), 1.41 and 1.37 (9H combined, 2×s). MS ES Da/e 660 (M−1)⁻ Cl³⁵ 100%, 662 (M−1)⁻ Cl³⁷.

[3S, 4RS, (1S, 9S)] t-Butyl 3-(9-benzoylamino-6,10-dioxo-1,2,3,4,7,8,9,10-octahydro-6H-pyridazino[1,2-a][1,2]diazepine-1-carboxamido)-4-(5,7-dichlorobenzoxazol-2-yl)-4-hydroxybutanoate (221e), was prepared from the acid (212e) and (3S, 4RS) t-butyl N-(allyloxycarbonyl)-3-amino-4-hydroxy-4-(5,7-dichlorobenzoxazol-2-yl)butanoate (204) by an analogous method as that used for compound 215e to afford a mixture of diastereomers (613 mg, 87%) as a glass: IR (film) 3328, 1729, 1660, 1534, 1454, 1422, 1399, 1276, 1254, 1155; $^1$H NMR (CDCl₃) δ 7.80 (2H, d), 7.60–7.35 (5H, m), 7.05 (2H, m), 5.13 (3H, m), 4.74 (1H, m), 4.51 (1H, m), 3.25 (1H, m), 3.1–2.6 (5H, m), 2.33 (1H, m), 2.1–1.5 (5H, m), 1.43 and 1.41 (9H combined, 2×s). MS ES⁺ Da/e 688 (M+1)⁺ Cl³⁵ 55%, 690 (M+1)⁺ Cl³⁷ 35%, 328 100%.

[3S,(1S, 9S)]t-Butyl 4-(5,7-dichlorobenzoxazol-2-yl)-3-(6,10-dioxo-9-methylsulphonylamino-1,2,3,4,7,8,9,10-octahydro-6H-pyridazino[1,2-a][1,2]diazepine-1-carboxamido)-4-oxobutanoate (222b), was prepared from 221b by an analogous method as that used for compound 216e to afford a colourless glass (371 mg, 86%): $[\alpha]_D^{26}$ −81.0 (c 0.1, CH₂Cl₂); IR (KBr) 3324, 2979, 2936, 1726, 1664, 1394, 1370, 1328, 1155, 991; $^1$H NMR (CDCl₃) δ 7.78 (1H, d), 7.57 (2H, m), 5.87 (1H, d), 5.69 (1H, m), 5.47 (1H, m), 4.55 (2H, m), 3.24 (2H, m), 3.0 (5H, m+s), 2.59 (1H, m), 2.39 (1H, m), 2.2–1.7 (4H, m), 1.65 (1H, m), 1.40 (9H, s).

[3S, (1S, 9S)] t-Butyl 3-(9-benzoylamino-6,10-dioxo-1,2,3,4,7,8,9,10-octahydro-6H-pyridazino[1,2-a][1,2]diazepine-1-carboxamido)-4-(5,7-dichlorobenzoxazol-2-yl)-4-oxobutanoate (222e), was prepared from 221e by an analogous method as that used for compound 216e to afford a colourless glass (480 mg, 84%): $[\alpha]_D^{25}$ −86.4° (c 0.1 CH₂Cl₂); IR (KBr) 3337, 2978, 2938, 1728, 1657, 1534, 1456, 1422, 1395, 1370, 1277, 1250, 1154; $^1$H NMR (CDCl₃) δ 7.80 (3H, m), 7.50 (4H, m), 7.20 (1H, d), 7.02 (1H, d), 5.60 (1H, m), 5.28 (1H, m), 5.15 (1H, m), 4.11 (1H, m), 3.34 (2H, m), 2.96 (3H, m), 2.40 (1H, m), 2.20 (1H, m), 1.92 (2H, m), 1.67 (2H, m), 1.38 (9H, s). MS ES⁻ Da/e 684 (M−1)⁻ Cl³⁵ 47%, 686 (M−1)⁻ Cl³⁷ 32%.

[3S,(1S,9S)] 4-(5,7-Dichlorobenzoxazol-2-yl)-3-(6,10-dioxo-9-methylsulphonylamino-1,2,3,4,7,8,9,10-octahydro-6H-pyridazino[1,2-a][1,2]diazepine-1-carboxamido)-4-oxobutanoic acid (223b), was prepared from 222b by an analogous method as that used for compound 217e to afford an off-white solid (257 mg, 78%): $[\alpha]_D^{25}$ −105.7° (c 0.1, CH₂Cl₂); IR (KBr) 3321, 1723, 1663, 1407, 1325, 1151, 992; $^1$H NMR (D₆-DMSO) δ 8.96 (1H, d), 8.18 (1H, d), 7.96 (1H, d), 5.50 (1H, m), 5.15 (1H, m), 4.30 (2H, m), 3.06 (2H, m), 2.87 (5H, m+s), 2.29 (1H, m), 1.99 (4H, m), 1.56 (2H, m).

[3S, (1S,9S)] 3-(9-Benzoylamino-6,10-dioxo-1,2,3,4,7,8,9,10-octahydro-6H-pyridazino[1,2-a][1,2]diazepine-1-carboxamido)-4-(5,7-dichlorobenzoxazol-2-yl)-4-oxobutanoic acid (223e), was prepared from 222e by an analogous method as that used for compound 217e to afford a pale cream solid (311 mg, 78%): mp 167°–180° C.; $[\alpha]_D^{23}$ −88.6° (c 0.1 CH₂Cl₂); IR (KBr) 3331, 1724, 1658, 1534, 1458, 1421, 1279, 1256, 991; $^1$H NMR (CDCl₃) δ 7.77 (4H, m), 7.4 (5H, m), 5.57 (1H, bs), 5.33 (1H, bs), 5.47 (1H, q), 4.56 (1H, bd), 3.60 (2H, m), 3.20 (3H, m), 2.76 (1H, m), 2.36 (1H, dd), 2.0 (3H, m), 1.66 (1H, m). MS ES Da/e 628 (M−1)⁻ Cl³⁵ 7%, 630 (M−1)⁻ Cl³⁷ 2.3%, 584 100%.

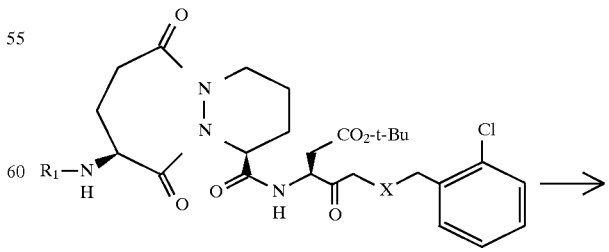

224e  R₁ = PhCO, X = S
225e  R₁ = PhCO, X = O

-continued

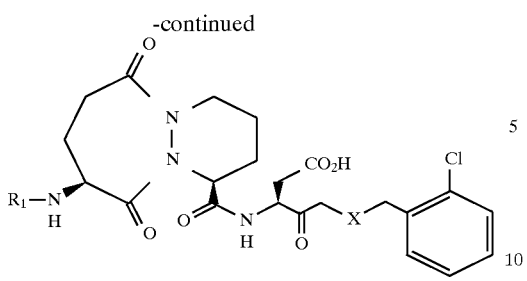

226e R₁ = PhCO, X = S
227e R₁ = PhCO, X = O

[3S, (1S, 9S)] t-Butyl 3-(9-benzoylamino-6,10-dioxo-1,2,3,4,7,8,9,10-octahydro-6H-pyridazino[1,2-a][1,2]diazepine-1-carboxamido)-5-(2-chlorophenyl)methylthio-4-oxopentanoate (224e). 1-Hydroxybenzotriazole (0.23 g, 1.71 mmol) and ethyl dimethylaminopropyl carbodiimide hydrochloride was added to a stirred solution of the acid 212e (0.295 g, 0.853 mmol) in THF (5 ml). After 5 min water (0.5 ml) was added followed, after a further 7 min, by the addition of a solution of (3S) t-butyl-3-allyloxycarbonylamino-5-(2-chloro-phenyl)methylthio-4-oxopentanoate (123, 0.478 g, 1.02 mmol) and $(PPh_3)_2PdCl_2$ (20 mg) in THF (2 ml). Tributyltin hydride (0.65 ml, 2.33 mmol) was added dropwise during 20 min. The mixture was kept for 4.5 h then diluted with EtOAc, washed with 1M HCl, brine, sat. aq. $NaHCO_3$ and then brine again. The mixture was dried ($MgSO_4$) and concentrated. The residue was triturated several times with hexane, which was decanted and discarded, then purified by flash chromatography (10–100% EtOAc in $CH_2Cl_2$) to afford 0.2 g (35%) of a white glassy solid: mp 70°–72° C.; $[\alpha]_D^{26}$ –82.5° (c 0.02, $CH_2Cl_2$). IR (KBr) 3404, 1726, 1660, 1534, 1524, 1422, 1277, 1254, 1154; $^1H$ NMR ($CDCl_3$) δ 7.83–7.78 (2H, m), 7.7, 7.75–7.32, 7.26–7.20 (7H, 3m), 7.12 (1H, d, J=8.2), 7.01 (1H, d, J=7.3), 5.23–5.08 (2H, m), 5.03–4.94 (1H, m), 4.62 (1H, dt, J=14.5), 3.78 (2H, m), 3.38–3.29 (1H, m), 3.26 (2H, s), 3.06–2.82 (4H, m), 2.71 (1H, dd, J=17.2, 4.5), 2.39 (1H, dd, J=13.2, 6.5), 2.15–1.83, 1.73–1.63 (5H, m), 1.45 (9H, s). Anal. Calcd for $C_{33}H_{39}ClN_4O_7S$: C, 59.05; H, 5.86; N, 8.35. Found: C, 59.00; H, 5.80; N, 7.92.

[3RS, (1S, 9S)] t-Butyl 3-(9-benzoylamino-6,10-dioxo-1,2,3,4,7,8,9,10-octahydro-6H-pyridazino[1,2-a][1,2]diazepine-1-carboxamido)-5-(2-chlorophenylmethyloxy)-4-oxopentanoate (225e), was prepared from acid 212e and (3S) t-butyl N-(allyloxycarbonyl)-3-amino-5-(2-chlorophenylmethyloxy)-4-oxopentanoate (201) using a method similar to that used for compound 224e, to afford 40 mg (23%) of a glassy solid: $^1H$ NMR ($CDCl_3$) δ 7.83–7.73 (2H, m), 7.67–7.10 (9H, m), 5.23–5.09 (2H, m), 4.59 (1H, m), 4.45–4.22 (2H, m), 3.7–3.19, 3.08–2.72, 2.71–2.47, 2.05–1.85, 1.72–1.61, 1.45–1.26 (20H, 6m).

[3S, (1S, 9S)] 3-(9-Benzoylamino-6,10-dioxo-1,2,3,4,7,8,9,10-octahydro-6H-pyridazino[1,2-a][1,2]diazepine-1-carboxamido)-5-(2-chlorophenyl)methylthio-4-oxopentanoic acid (226e), was prepared from 224e by an analogous method as that used for compound 217e which afforded 0.22 g (81%) of an off-white solid: mp 95°–100° C.; $[\alpha]_D^{23}$ –95.6° (c 0.2, $CH_2Cl_2$). IR (KBr) 3393, 1720, 1658, 1529, 1422, 1279; $^1H$ NMR ($D_6$-DMSO) δ 8.80 (1H, d, J=7.5), 7.89 (2H, m), 7.7 (1H, d, J=7.7), 7.56–7.28 (7H, m), 5.10 (1H, m), 4.87–4.73 (2H, m), 4.39 (1H, m), 3.77 (2H, m), 3.44, 3.35 (2H, +$H_2O$, 2m), 2.97–2.56, 2.2, 1.92, 1.61 (11H, 4m). Anal. Calcd for $C_{29}H_{31}ClN_4O_7S$ $0.5H_2O$: C, 55.02; H, 5.10; N, 8.85. Found: C, 55.00; H, 5.09; N, 8.71.

[3RS, (1S, 9S)] 3-Benzoylamino-6,10-dioxo-1,2,3,4,7,8,9,10-octahydro-6H-pyridazino[1,2-a][1,2]diazepine-1-carboxamido)-5-(2-chlorophenylmethyloxy)-4-oxopentanoic acid (227e), was prepared from 225e by an analogous method as that used for compound 217e. The product was further purified by flash chromatography (0–5% MeOH/$CH_2Cl_2$) to afford 19 mg (81%) of a glassy solid: $^1H$ NMR ($CDCl_3$) δ 7.79 (2H, m), 7.66–7.18 (9H, m), 5.30–5.10 (2H, m), 4.85 (1H, m), 4.65 (2H, m), 4.53 (1H, m), 4.28 (2H, m), 3.28, 3.01, 2.72, 2.33, 1.94, 1.60 (11H, 6m). MS (ES⁻, m/z) 597 (M⁺–1, 100%).

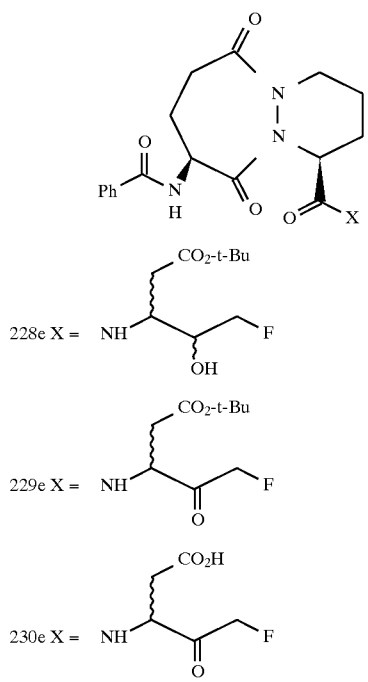

[3RS, 4RS, (1S, 9S)] t-Butyl 3-(9-benzoylamino-6,10-dioxo-1,2,3,4,7,8,9,10-octahydro-6H-pyridazino[1,2-a][1,2]-diazepine-1-carboxamido)-5-fluoro-4-(228e). 1-Hydroxybenzotriazole (0.23 g, 1.68 mmol) followed by ethyldimethylaminopropyl carbodiimide hydrochloride (0.21 g, 1.09 mmol) were added to a stirred solution of the acid 212e (0.29 g, 0.84 mmol) in $CH_2Cl_2$ (3 ml) at rt. The mixture was kept for 10 min then a solution of (3RS, 4RS) t-butyl 3-amino-5-fluoro-4-hydroxypentanoate (Revesz, L. et al. Tetrahedron Lett., 52, pp. 9693–9696 (1994); 0.29 g, 1.40 mmol) in $CH_2Cl_2$ (3 ml) was added followed by 4-dimethylaminopyridine (10 mg). The solution was stirred for 17 h, diluted with EtOAc, washed with 1M HCl, brine, sat. aq. $NaHCO_3$ and brine again, dried ($MgSO_4$) and concentrated. The residue was purified by flash chromatography (50–100% EtOAc/$CH_2Cl_2$ and 5% MeOH/EtOAc) to afford 0.25 g (56%) of a white glassy solid: IR (KBr) 3343, 1726, 1658, 1536, 1426, 1279, 1257, 1157; $^1H$ NMR ($CDCl_3$) δ 7.84–7.79 (2H, m), 7.57–7.40 (3H, m), 7.05–6.92, 6.73 (2H, 2m), 5.17–5.04 (2H, m), 4.56, 4.35–4.21, 4.04 (5H, 3m), 3.36, 3.09–2.34, 2.00 (11H, 3m), 1.46 (9H, s). Anal. Calcd for $C_{26}H_{35}FN_4O_7$ $0.5H_2O$: C, 57.45; H, 6.65; N, 10.31. Found: C, 57.64; H, 6.56; N, 10.15.

[3RS, 4RS, (1S, 9S)] t-Butyl 3-(9-benzoylamino-6,10-dioxo-1,2,3,4,7,8,9,10-octahydro-6H-pyridazino[1,2-a][1,2]-diazepine-1-carboxamido)-5-fluoro-4-oxypentanoate (229e) was prepared from 228c by an analogous method to that used for compound 216e. After purification by flash chromatography (30–50% EtOAc/$CH_2Cl_2$) the product was obtained as a white glassy solid (0.194 g, 89%): IR (KBr) 3376, 1728, 1659, 1529, 1424, 1279, 1256, 1156.

[3RS, (1S, 9S)] 3-(9-Benzoylamino-6,10-dioxo-1,2,3,4,7,8,9,10-octahydro-6H-pyridazino[1,2-a][1,2]diazepine-1-carboxamido)-5-fluoro-4-oxopentanoic acid (230e), was prepared from 229e by an analogous method to that used for compound 217e to afford 230e as a white glassy solid (100%): mp 105°–125° C.; $[\alpha]_D^{23}$ -91.4° (c 0.72, CH$_3$OH). IR (KBr) 3336, 1789, 1737, 1659, 1535, 1426, 1279, 1258, 1186; $^1$H NMR (CD$_3$OD) δ 7.71–7.68 (2H, m), 7.37–7.23 (3H, m), 5.02, 4.88–4.63, 4.37–4.0 (6H, 3m), 3.30, 2.97, 2.68–2.60, 2.37–1.54 (11H, 4m). MS(ES$^-$, m/z) 475 (M$^+$–1, 100%).

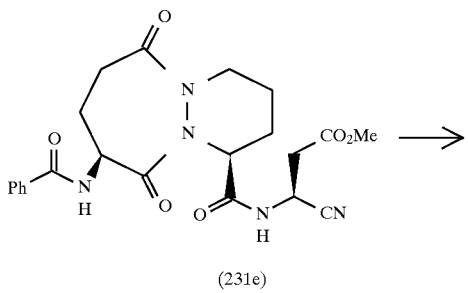

(231e)

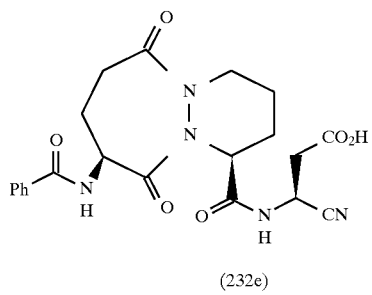

(232e)

[3S, (1S, 9S)]-Methyl 9-(benzoylamino)-3-[6,10-dioxo-1,2,3,4,7,8,9,10-octahydro-6H-pyridazino[1,2-a][1,2]diazepine-1-carboxamido]-3-cyanopropanoate (231e). N-Fluorenylmethyloxy-carbonyl-3-amino-3-cyanopropionic acid methyl ester (EP0547699A1, 385 mg, 1.1 mmol) was treated with 17 ml of diethylamine. After 1.5 h stirring at room temperature the solution was concentrated. The residue was chromatographed on silica gel (3% methanol in CH$_2$Cl$_2$) and gave the free amine as a pale yellow oil. To a solution of this oil and hydroxybenzotriazole (297 mg, 2.19 mmol) in DMF (5 ml), was added at 0° C. ethyldimethylaminopropyl carbodiimide (232 mg, 1.21 mmol, 1.1 equiv) followed by (1S, 9S) 9-(benzoylamino)-[6,10-dioxo-1,2,3,4,7,8,9,10-octahydro-6H-pyridazino[1,2-a][1,2]diazepine-1-carboxylic acid (212e). After stirring at 0° C. for 5 min and then at room temperature overnight, the mixture was diluted with CH$_2$Cl$_2$ (50 ml) and the resulting solution washed successively with 1M HCl (2×30 ml), H$_2$O (30 ml), 10% NaHCO$_3$ (2×30 ml) and sat. aq. NaCl, dried (MgSO$_4$) and concentrated. Purification by flash chromatography on silica gel (3% methanol in CH$_2$Cl$_2$) afforded the compound 231e (404 mg, 83%) as a solid: $[\alpha]_D^{20}$ -121° (c 0.14, CH$_2$Cl$_2$); $^1$H NMR (CDCl$_3$) δ 7.40–7.83 (5H, m), 7.38 (1H, d), 6.96 (1H, d), 5.27–5.07 (2H, m), 4.66–4.50 (1H, m), 3.79 (3H, s), 3.23–2.73 (6H, m), 2.47–2.33 (1H, m), 2.15–1.82 (4H, m); Anal. Calcd for C$_{22}$H$_{25}$N$_5$O$_6$: C, 58.0; H, 5.53; N, 15.38. Found: C, 57.6; H, 5.6; N, 15.0.

[3S, (1S, 9S)] 9-(Benzoylamino)-3-[6,10-dioxo-1,2,3,4,7,8,9,10-octahydro-6H-pyridazino[1,2-a][1,2]diazepine-1-carboxamido]-3-cyanopropanoic acid (232e). A solution of methyl ester 231e (400 mg, 0.88 mmol) in methanol (30 ml) and water (30 ml) was cooled at 0° C. and treated with diisopropylethylamine. The solution was stirred at 0° C. for 10 min and then at room temperature overnight. The heterogeneous mixture was concentrated and the solid obtained was chromatographed on silica gel (5% methanol/1% formic acid in CH$_2$Cl$_2$) affording the free acid 232e (170 mg, 44%) as a white solid: mp 155° C. (dec); $[\alpha]_D^{20}$ -117° (c 0.1, MeOH); IR (KBr) 3343, 3061, 2955, 1733, 1656, 1577, 1533, 1490, 1421, 1342, 1279, 1256, 1222, 1185, 708; $^1$H NMR (D$^4$-MeOH) δ 7.88–7.28 (5H, m), 5.20–5.03 (1H, m), 4.98–4.84 (2H, m), 4.75–4.53 (1H, m), 4.51–4.34 (1H, m), 3.45–3.22 (1H, m), 3.14–2.94 (1H, m), 3.14–2.94 (1H, m), 2.88–2.61 (2H, m), 2.53–1.50 (8H, m); Anal. Calcd for C$_{21}$H$_{23}$N$_5$O$_6$. 1.5H$_2$O: C,53.84; H, 5.59; N, 14.95; 0, 25.61. Found: C, 54.3; H, 5.4; N, 14.3.

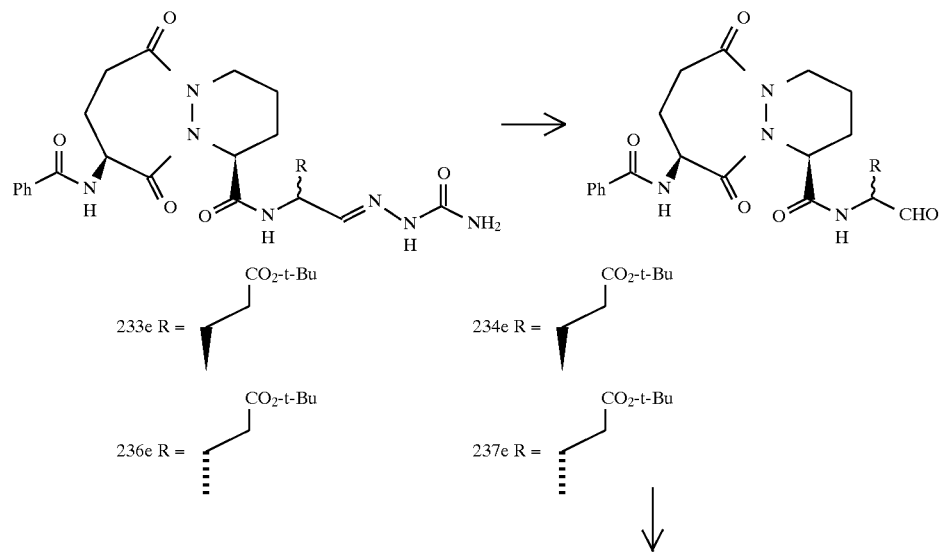

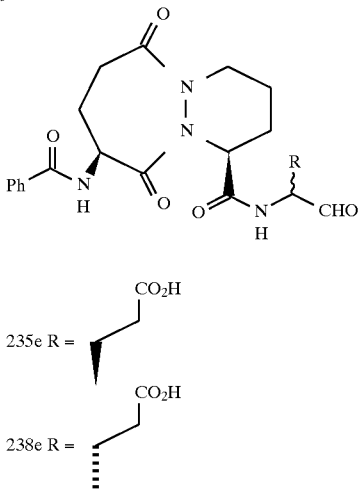

235e R = (CH2CH2CO2H with wedge/dash)

238e R = (CH2CH2CO2H with dashed bond)

[4S, (1S, 9S)] t-Butyl 4-[9-(benzoylamino)-6,10-dioxo-1,2,3,4,7,8,9,10-octahydro-6H-pyridazino[1,2-a][1,2]diazepine-1-carboxamido]-5-oxopentanoate semicarbazone (233e). A solution of (1S, 9S) 6,10-dioxo-1,2,3,4,7,8,9,10-octahydro-9-(benzoylamino)-6H-pyridazino[1,2-a][1,2]diazepine-1-carboxylic acid (212e) (345 mg, 1.0 mmol), (4S) t-butyl N-(allyloxycarbonyl)-4-amino-5-oxopentanoate semicarbazone (208a) (361 mg, 1.1 mmol, 1.1 equiv) and $(Ph_3P)_2PdCl_2$ (20 mg) in $CH_2Cl_2$ (5 ml), was treated dropwise with n-$Bu_3SnH$ (0.621 ml, 2.3 mmol, 2.1 equiv). The resulting orange brown solution was stirred at 25° C. for 10 min and then 1-hydroxybenzotriazole (297 mg, 2.2 mmol, 2 equiv) was added. The mixture was cooled to 0° C. and ethyldimethylaminopropyl carbodiimide (253 mg, 1.3 mmol, 1.2 equiv) added. After stirring at 0° C. for 10 min and then at room temperature overnight, the mixture was diluted with EtOAc (50 ml) and the resulting solution washed successively with 1M HCl (3×25 ml), 10% $NaHCO_3$ (3×25 ml) and sat. aq. NaCl, dried ($MgSO_4$) and concentrated. Flash chromatography on silica gel (2–10% methanol in $CH_2Cl_2$) afforded compound 233e (280 mg, 49%) as a tan solid: $[\alpha]_D$ -95° (c 0.09, MeOH); IR (KBr) 3477, 3333, 2968, 2932, 1633, 1580, 1535, 1423, 1378, 1335, 1259, 1156, 1085, 709; $^1H$ NMR ($CDCl_3$) δ 9.32 (1H, s), 7.83–7.39 (6H, m), 7.11–7.09 (1H, m), 6.30–5.30 (2H, brs), 5.17–5.05 (2H, m), 4.62–4.38 (2H, m), 3.30–3.15 (1H, m), 3.13–2.65 (2H, m), 2.46–2.19 (3H, m), 2.15–1.54 (8H, m), 1.42 (9H, s).

[4R, (1S, 9S)] t-Butyl 4-[9-(benzoylamino)-6,10-dioxo-1,2,3,4,7,8,9,10-octahydro-6H-pyridazino[1,2-a][1,2]diazepine-1-carboxamido]-5-oxopentanoate semicarbazone (236e), was prepared by an analogous method to that used for 233e using (4R) t-butyl N-allyloxycarbonyl-4-amino-5-oxo-pentanoate semicarbazone (208b, 435 mg, 1.33 mmol). The product was obtained as a foam (542 mg, 71%): $[\alpha]_D^{20}$ -99° (c 0.19, $CHCl_3$); IR (KBr) 3473, 3331, 3065, 2932, 2872, 1660, 1580, 1533, 1488, 1423, 1370, 1337, 1278, 1254, 1223, 1155, 1080, 1024, 983, 925, 877, 846, 801, 770, 705; $^1H$ NMR ($CDCl_3$) δ 9.42 (1H, s), 7.81 (2H, d), 7.51–7.40 (4H, m), 7.06 (1H, d), 6.50–5.50 (2H, broad s), 5.25–5.00 (2H, m), 4.60–4.45 (2H, m), 3.15–2.85 (2H, m), 2.75–2.35 (1H, m), 2.30–1.23 (11H, m), 1.42 (9H, s).

[4S, (1S, 9S)] t-Butyl 4-[9-(benzoylamino)-6,10-dioxo-1,2,3,4,7,8,9,10-octahydro-6H-pyridazino-[1,2-a][1,2]diazepine-1-carboxamido]-5-oxopentanoate (234e). A solution of semicarbazone 233e (390 mg, 0.68 mmol) in methanol (10 ml) was cooled at 0° C. and then treated with a 38% aq. solution of formaldehyde (2 ml) and 1M HCl (2 ml). The reaction mixture was then stirred overnight at room temperature. The solution was concentrated to remove the methanol. The aq. solution was extracted with EtOAc (30 ml). The organic solution was successively washed with 10% $NaHCO_3$ (30 ml) and sat. aq. NaCl (30 ml), dried ($MgSO_4$) and concentrated. Purification by flash chromatography on silica gel (2–5% methanol in $CH_2Cl_2$) afforded 234e (179 mg, 51%) as a white foam: $[\alpha]_D^{20}$ -101° (c 0.064, MeOH); IR (KBr)3346, 2976, 2934, 1730, 1657, 1535, 1456, 1425, 1278, 1255, 1156, 708; $^1H$ NMR ($CDCl_3$) δ 9.56 (1H, s), 7.88–7.38 (5H, m), 7.01 and 6.92 (2H, 2d), 5.27–5.08 (2H, m), 4.69–4.46 (1H, m), 3.50–3.27 (2H, m), 3.15–2.73 (2H, m), 2.46–1.83 (10H, m), 1.45 (9H, s).

[4R, (1S, 9S)] t-Butyl 4-[9-(benzoylamino)-6,10-dioxo-1,2,3,4,7,8,9,10-octahydro-6H-pyridazino[1,2-a][1,2]diazepine-1-carboxamido]-5-oxopentanoate (237e), was prepared from 236e by an analogous method to 234e to afford a white foam (390 mg, 85%): $[\alpha]_D^{20}$ -113° (c 0.242, $CHCl_3$); IR (KBr) 3352, 3065, 2974, 1729, 1657, 1536, 1489, 1454, 1423, 1369, 1338, 1278, 1255, 1223, 1156, 1078, 1026, 981, 846, 709.

[4S, (1S, 9S)] 4-[9-(Benzoylamino)-6,10-dioxo-1,2,3,4,7,8,9,10-octahydro-6H-pyridazino[1,2-a][1,2]diazepine-1-carboxamido]-5-oxopentanoic acid (235e). A solution of t-butyl ester 234e (179 mg, 0.35 mmol) in dry $CH_2Cl_2$ (3 ml) was cooled to 0° C. and treated with trifluoroacetic acid (2 ml). The resulting solution was stirred at 0° C. for 30 min and then at room temperature for 2 h. The solution was concentrated, the residue taken up in dry $CH_2Cl_2$ (5 ml) and the mixture again concentrated. This process was repeated once again with more $CH_2Cl_2$ (5 ml). The residue obtained was crystallized in diethyl ether. The precipitate was collected and purified on silica gel column (5% methanol in $CH_2Cl_2$) which afforded compound 235e as a white solid (111 mg, 70%): mp 142° C. (dec); $[\alpha]_D^{20}$ -85.5° (c 0.062, MeOH); IR (KBr) 3409, 3075, 2952, 1651, 1541, 1424, 1280, 1198, 1136, 717; $^1H$ NMR ($D_6$-DMSO) δ 9.40 (1H, s), 8.62 (2H, m), 7.96–7.38 (5H, m), 5.19–5.02 (1H, m), 4.98–4.79 (1H, m), 4.48–4.19 (1H, m), 3.51–3.11 (2H, m), 3.04–2.90 (2H, m), 2.38–1.46 (10H, m).

[4R, (1S, 9S)] 4-[9-(Benzoylamino)-6,10-dioxo-1,2,3,4,7,8,9,10-octahydro-6H-pyridazino[1,2-a][1,2]diazepine-1-carboxamido]-5-oxopentanoic acid (238e), was prepared from 237e by an analogous route to 235e which afforded a beige foam (190 mg, 60%): $[\alpha]_D^{20}$ −78° (c 0.145, MeOH); IR (KBr) 3400, 3070, 2955, 2925, 2855, 1653, 1576, 1541, 1490, 1445, 1427, 1342, 1280, 1258, 1205, 1189, 1137, 1075, 1023, 983, 930, 878, 843, 801, 777, 722; $^1$H NMR ($D_6$-DMSO) δ 9.40 (1H, s), 8.72–8.60 (2H, m), 7.89 (2H, d), 7.56–7.44 (3H, m), 5.17 (1H, m), 4.90–4.83 (1H, m), 4.46–4.36 (1H, m), 4.20–4.15 (1H, m), 3.40–3.30 (1H, m), 2.98–2.90 (2H, m), 2.50–1.60 (10H, m).

1.40 (1H, m); Anal. Calcd for $C_{17}H_{21}N_3O_4$. 0.25$H_2O$: C, 60.79; H, 6.45; N, 12.51. Found: C, 61.07; H, 6.35; N, 12.55. MS (ES+, m/z) 332 (58%, M$^+$+1), 211 (100).

[3S, 2RS, (1S, 9S)] N-(2-Benzyloxy-5-oxotetrahydrofuran-3-yl)-9-benzoylamino-octahydro-10-oxo-6H-pyridazino[1,2-a][1,2]diazepine-1-carboxamide (245), was prepared from (1S, 9S) 9-benzoylamino-octahydro-10-oxo-6H-pyridazino[1,2-a][1,2]-diazepine-1-

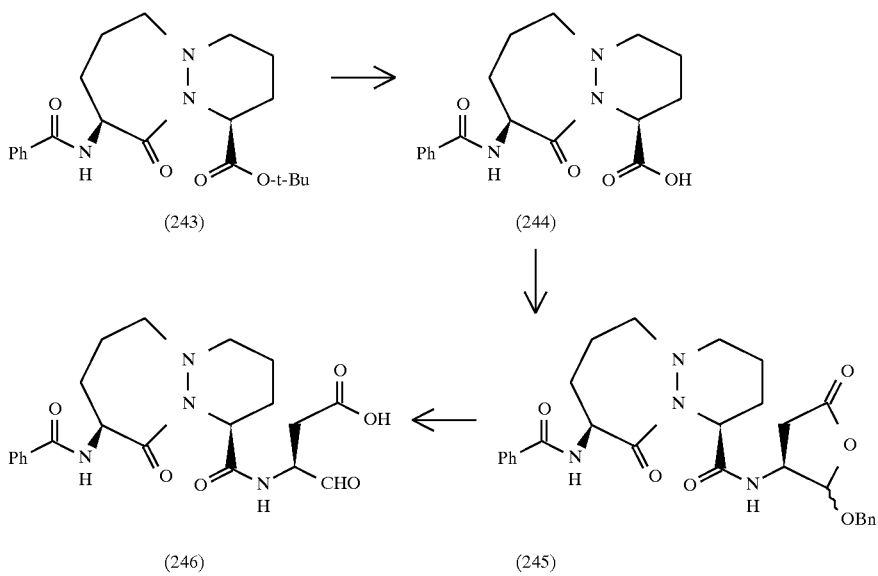

(1S, 9S) t-Butyl 9-benzoylamino-octahydro-10-oxo-6H-pyridazino[1,2-a][1,2]diazepine-1-carboxylate (243), was prepared from (1S, 9S) t-butyl 9-amino-octahydro-10-oxo-6H-pyridazino[1,2-a][1,2]diazepine-1-carboxylate (Attwood, et al. *J. Chem. Soc., Perkin* 1, pp. 1011–19 (1986)), by the method described for 211e, to afford 2.03 g (86%) of a colourless foam: $[\alpha]_D^{25}$ −15.9° (c 0.5, $CH_2Cl_2$); IR (KBr) 3400, 2976, 2937, 1740, 1644, 1537, 1448, 1425, 1367, 1154; $^1$H NMR (CDCl$_3$) δ 7.88–7.82 (2H, m), 7.60–7.38 (4H, m), 5.48 (1H, m), 4.98 (1H, m), 3.45 (1H, m), 3.22–2.96 (2H, m), 2.64 (1H, m), 2.43–2.27 (2H, m), 1.95 (2H, m), 1.82–1.36 (4H, m), 1.50 (9H, s); Anal. Calcd for $C_{21}H_{29}N_3O_4$. 0.25$H_2O$: C, 64.35; H, 7.59; N, 10.72. Found: C, 64.57; H, 7.43; N, 10.62. MS (ES+, m/z) 388 (100%, M$^+$+1).

(1S, 9S) 9-Benzoylamino-octahydro-10-oxo-6H-pyridazino[1,2-a][1,2]diazepine-1-carboxylic acid (244), was prepared from (1S, 9S) t-butyl 9-benzoylamino-octahydro-10-oxo-6H-pyridazino[1,2-a][1,2]diazepine-1-carboxylate (243), by the method described for 212e, to afford 1.52 g (89%) of a white powder: mp. 166°–169° C. (dec); $[\alpha]_D^{25}$ −56.4° (c 0.5, CH$_3$OH); IR (KBr) 3361, 2963, 2851, 1737, 1663, 1620, 1534, 1195, 1179; $^1$H NMR ($D_6$-DMSO) δ 12.93 (1H, brs), 8.44 (1H, d, J=8.4), 7.93 (2H, m), 7.54 (3H, m), 5.46 (1H, m), 4.87 (1H, m), 3.12 (2H, m), 2.64 (1H, m), 2.64 (1H, m), 2.27 (1H, m), 1.98–1.68 (7H, m), carboxylic acid (244), by the method described for 213e, to afford 601 mg (76%) of a colourless foam: IR (KBr) 3401, 2945, 1794, 1685, 1638, 1521, 1451, 1120; $^1$H NMR (CDCl$_3$) δ 7.87–7.77 (2H, m), 7.57–7.14 (10H, m), 5.59–5.47 (2H, m), 4.97–4.32 (4H, m), 3.27–1.35 (14H, m); Anal. Calcd for $C_{28}H_{32}N_4O_6$. 0.5$H_2O$: C, 63.50; H, 6.28; N, 10.58. Found: C, 63.48; H, 6.14; N, 10.52. MS (ES+, m/z) 521 (100%, M$^+$+1).

[3S, (1S, 9S)] 3-(9-Benzoylamino-octahydro-10-oxo-6H-pyridazino[1,2-a][1,2]diazepine-1-carboxamide-4-oxobutanoic acid (246), was prepared from [3S, 2RS (1S, 9S)]N-(2-benzyloxy-5-oxotetrahydrofuran-3-yl)-9-benzoylamino-octahydro-10-oxo-6H-pyridazino[1,2-a][1,2]diazepine-1-carboxamide (245), by the method described for 214e, to afford 396 mg (84%) of a white powder: mp. 110°–115° C.; $[\alpha]_D^{26}$ −126.3° (c 0.2, CH$_3$OH); IR (KBr) 3345, 2943, 1787, 1730, 1635, 1578, 1528, 1488, 1450, 1429; $^1$H NMR (CD$_3$OD) δ 7.88 (2H, m), 7.48 (3H, m), 5.55 (1H, m), 4.91 (1H, m), 4.56 (1H, m), 4.29 (1H, m), 3,41–3.05 (3H, m), 2.76–2.41 (3H, m), 2.28–2.01 (3H, m), 1.86–1.65 (4H, m), 1.36 (1H, m); Anal. Calcd for $C_{21}H_{26}N_4O_6$. 1.25$H_2O$: C, 55.68; H, 6.34; N, 12.37. Found: C, 55.68; H, 6.14; N, 12.16. MS (ES−, m/z) 429 (100%, M$^+$−1).

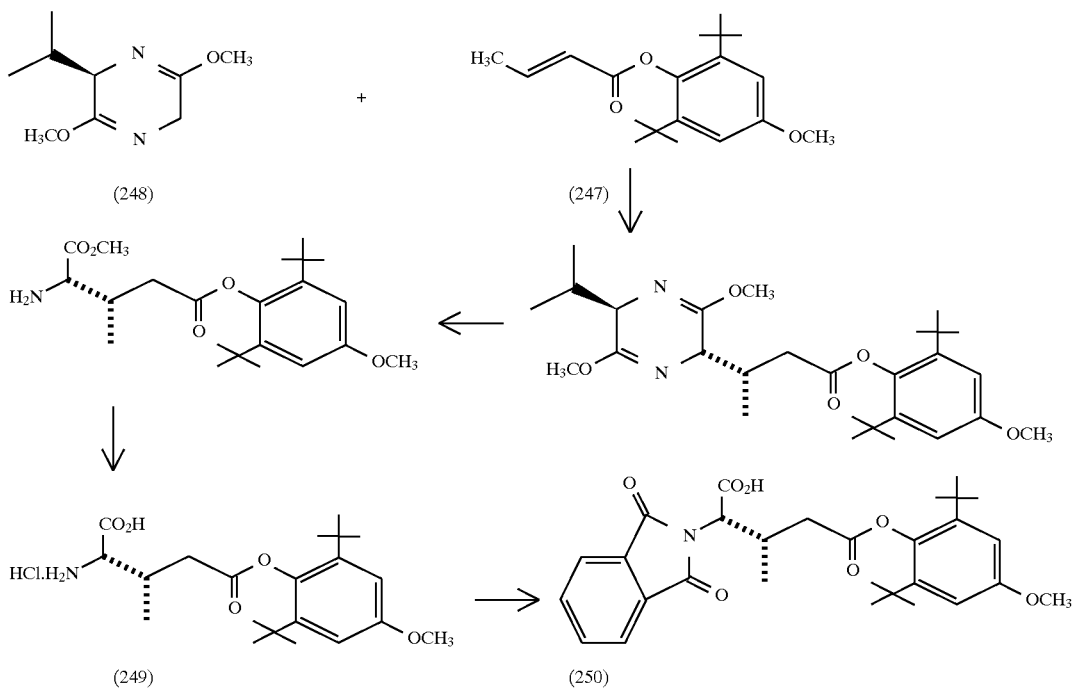

(248) + (247) → (intermediate) → (249) → (250)

[(3S, (2R, 5S)]-2,6-Di-tert-butyl-4-methoxyphenyl-3-[5-(2,5-dihydro-3,6-dimethoxy-2-(1-methylethyl)pyrazinyl)]butanoate (247). n-Butyllithium (1.6M in hexane) (22.3 ml, 35.7 mmol) was added dropwise over 20 min to a solution of (2R)-(−)-2,5-dihydro-3,6-dimethoxy-2-(1-methylethyl)pyrazine (5.8 ml, 6.0 g, 32.4 mmol) in THF (250 ml) cooled to −75° C. at a rate such that the temperature was maintained below −72° C. The reaction mixture was stirred for 1 h at −75° C. and a solution of 2,6-di-t-butyl-4-methoxyphenyl-2-butenoate (Suzuck et al. Liebigs Ann. Chem. pp. 51–61 (1992)) (9.9 g, 32.5 mmol) in THF (60 ml) was added over 30 minutes maintaining the temperature below −72° C. during the addition. The reaction mixture was kept at −75° C. for 1.5 h and a solution of glacial acetic acid (6 ml) in THF (25 ml) was added at −75° C. and the solution warmed to room temperature. The solution was poured onto 10% $NH_4Cl$ (300 ml) and extracted with diethyl ether (3×250 ml). The combined organic phases were washed with brine (2×200 ml), dried over $Na_2SO_4$ and evaporated to dryness under reduced pressure. The residual oil was purified by flash chromatography on silica gel (20% heptane in $CH_2Cl_2$) which afforded the title compound as a light yellow oil (13.5 g, 85%): $[\alpha]_D^{20}$ −64° (c 0.22, MeOH); IR (KBr) 2962, 2873, 2840, 1757, 1697, 1593, 1460, 1433, 1366, 1306, 1269, 1236, 1187, 1157, 1126, 1063, 1038, 1011, 970, 924, 892, 867, 846, 831, 797, 773, 754; $^1$H NMR (CDCl$_3$) δ 6.85 (2H, s), 4.21 (1H, t, J=3.5), 3.98 (1H, t, J=3.5), 3.79 (3H, s), 3.71 (3H, s), 3.69 (3H, s), 3.15 (1H, dd, J 17.8, 7.9), 2.86–2.81 (1H, m), 2.58 (1H, dd, J=17.8, 5.9), 2.28–2.19 (1H, m), 1.33 (18H, s), 1.02 (3H, d, J=6.8), 0.70 (6H, dd, J=13, 6.8).

(2S, 3S)-5-[2,6-Di-t-butyl-4-methoxyphenyl]1-methyl-3-methylglutamate (248). A solution of [3S, (2R, 5S)]-2,6-di-t-butyl-4-methoxyphenyl-3-[5-(2,5-dihydro-3,6-dimethoxy-2-(1-methylethyl)pyrazinyl)]butanoate (247) (22.4 g, 45.8 mmol) in acetonitrile (300 ml) and 0.25N HCl (366 ml, 2 equiv) was stirred at room temperature under nitrogen atmosphere for 4 days. The acetonitrile was evaporated under reduced pressure and diethylether (250 ml) was added to the aq. phase. The pH of the aq. phase was adjusted to pH8–9 with concentrated ammonia solution (32%) and the phases separated. The aq. phase was extracted with diethylether (2×250 ml). The combined organic phases were dried over $Na_2SO_4$ and evaporated to dryness under reduced pressure. The residual oil was purified by flash chromatography on silica gel (2% methanol in $CH_2Cl_2$) which afforded the required product as a light yellow oil (8.2 g, 45%): $[\alpha]_D^{20}$ +20° (c 0.26, MeOH); IR(KBr) 3394, 3332, 3000, 2962, 2915, 2877, 2838, 1738, 1697, 1593, 1453, 1430, 1419, 1398, 1367, 1304, 1273, 1251, 1221, 1203, 1183, 1126, 1063, 1025, 996, 932, 891, 866, 847, 800, 772, 745; $^1$H NMR (CDCl$_3$) δ 6.85 (2H, s), 3.79 (3H, s), 3.74 (3H, s), 3.72–3.69 (1H, m), 3.05–2.85 (1H, m), 2.67–2.50 (2H, m), 1.32 (18H, s), 0.93 (3H, d, J=7); Anal. Calcd for $C_{22}H_{35}NO_5$: C, 67.15; H, 8.96; N, 3.56. Found: C, 67.20; H, 9.20; N, 3.70.

(2S, 3S)-5-[2,6-Di-t-butyl-4-methoxyphenyl]3-methylglutamate (249). A solution of (2S, 3S)-5-[2,6-di-t-butyl-4-methoxyphenyl]3-methylglutamate (248) (8.0 g, 20.3 mmol) in 5N HCl (200 ml) was heated at reflux for 2 h. The reaction mixture was evaporated to dryness under reduced pressure. The residue was dissolved in cyclohexane (×4) and evaporated to dryness (×4) which afforded a white solid (7.9 g, 93%): mp 230° C.; $[\alpha]_D^{20}$ +22° (c 0.27, MeOH); IR (KBr) 3423, 2964, 1755, 1593, 1514, 1456, 1421, 1371, 1303, 1259, 1201, 1179, 1138, 1106, 1060, 966, 926, 861, 790, 710; $^1$H NMR (MeOD) δ 6.76 (2H, s), 4.02 (1H, d, J=3.7), 3.67 (3H, s), 3.05–2.85 (1H, m), 2.80–2.55 (2H, m), 1.22 (18H, s), 1.09 (3H, d, J 32 6.3); $^{13}$C NMR (MeOD) δ 174.5, 171.4, 158.6, 145.2, 143.1, 113.2, 58.3, 56.3, 39.8, 36.9, 32.5, 16.6; Anal. Calcd for $C_{21}H_{34}ClNO_5$: C, 60.64; H, 8.24; N, 3.37. Found: C, 60.80; H, 8.40; N, 3.40.

(2S, 3S)-5-[2,6-Di-t-butyl-4-methoxyphenyl]3-methyl-2-phthalimido-1,5-pentanedioate (250), Diisopropylethylamine (4.1 ml, 3.04 g, 23.5 mmol, 1.25 equiv) and phthalic anhydride (3.5 g, 23.6 mmol, 1.25 equiv) were added to a solution of (2S, 3S)-5-[2,6-di-t-butyl-4-methoxyphenyl]3-methylglutamate (249) (7.8 g, 18.6 mmol) in toluene (300 ml). and the resulting mixture was heated at reflux for 3 hours. After cooling to room temperature, the reaction mixture was evaporated to dryness and the resulting oil purified by flash chromatography on silica gel (2% methanol in $CH_2Cl_2$) which afforded the required product as a white foam (8.35 g, 87%): $[\alpha]_D^{20}$ −20° (c 1.04, MeOH); IR (KBr) 3480, 2968, 2880, 1753, 1721, 1594, 1462, 1422, 1388, 1303, 1263, 1216, 1183, 1148, 1062, 1003, 933, 899, 755, 723; $^1$H NMR (CDCl$_3$) δ 7.92–7.87 (2H, m), 7.78–7.73 (2H, m), 6.84 (2H, s), 4.95 (1H, d), 3.78 (3H, s), 3.30–3.05 (2H, m), 2.85–2.65 (1H, m), 1.30 (18H, s), 1.13 (3H, d).

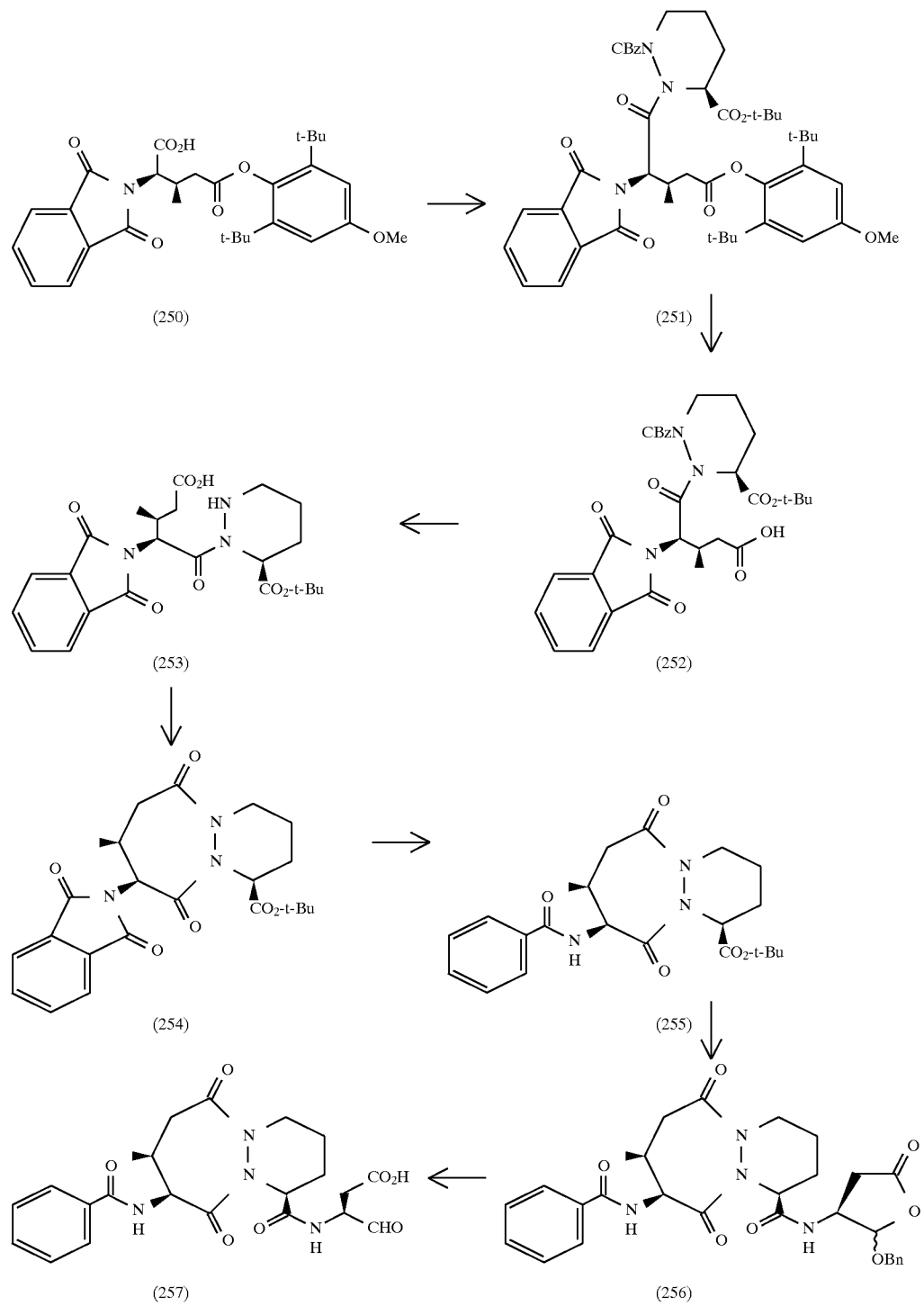

1-(2,6-di-t-Butyl-4-methoxy)-phenyl-5-(1-benzyloxycarbonyl-3-t-butoxycarbonyl-hexahydropyridazin-2-yl)-3-methyl-4-phthalimidopentan-1,5-dioate (251). A solution of the amino acid (250) (1.2 g, 2.35 mmol) in dry diethylether (10 ml) was treated with phosphorus pentachloride (0.52 g, 2.5 mmol) at room temperature for 2 h. The mixture was concentrated and treated several times with toluene and again evaporated to dryness. The resulting acid chloride was dissolved in dry THF (5 ml) and CH$_2$Cl$_2$ (5 ml) and cooled to 0° C. t-Butyl-1-(benzyloxycarbonyl)-hexahydro-3-pyridazinecarboxylate (0.753 g, 2.35 mmol, 1 equiv) and N-ethylmorpholine (3 ml) were added to the solution. The reaction mixture was stirred for 30 min at 0° C. and then overnight at room temperature. The mixture was evaporated and the resulting residue taken up with CH$_2$Cl$_2$ (30 ml). The solution was washed with 1M HCl, water, 10% NaHCO$_3$, dried (MgSO$_4$) and evaporated. The resulting white foam was purified on silica gel (0–2% methanol in CH$_2$Cl$_2$) which afforded the required compound 251 as a pale yellow glassy solid (740 mg, 39%): $[\alpha]_D^{20}$ −22 (c 0.42, MeOH); IR (KBr) 3441, 2966, 1725, 1693, 1386, 1255, 1221, 1186, 1154, 1123, 1063, 724; $^1$H NMR (CDCl$_3$) δ 7.94–7.89 (4H, m), 7.56–7.28 (5H, m), 6.84 (2H, 2s), 5.29–5.20 (2H, AB), 4.91–4.81 (1H, m), 4.05–3.88 (1H, m), 3.78 (3H, s), 3.75–3.80 (1H, m), 3.28–2.95 (2H, m), 2.23–1.51 (6H, m), 1.45 (9H, s), 1.31 (9H, s), 1.28 (9H, s), 1.27 (3H, d).

(1S, 8S, 9S) t-Butyl 6,10-dioxo-8-methyl-1,2,3,4,7,8,9, 10-octahydro-9-phthalimido-6H-pyridazino[1,2-a][1,2] diazepin-1-carboxylate (254). A solution of the protected acid (251) (715 mg, 0.893 mmol) in acetonitrile was treated with Cerium (IV) ammonium nitrate (1.8 g, 3.3 mmol, 3.7 equiv) in water (3 ml) for 4 h at room temperature. Mannitol (600 mg, 3.3 mmol, 3.7 equiv) was added and the mixture was stirred for 1 h. Diethylether (50 ml) and water (30 ml) were added to the mixture. After decantation, the aq. phase was extracted with diethylether (4×50 ml). The combined organic phase was washed with water, dried (MgSO$_4$) and concentrated. Chromatography on silica gel (10% methanol in CH$_2$Cl$_2$) afforded 5-(1-benzyloxycarbonyl-3-t-butoxycarbonyl-hexahydropyridazin-2-yl)carbonyl-3-methyl-4-phthalimidopentanoic acid (252) (360 mg, 64%): $[\alpha]_D^{20}$ −49.2 c 0.118, MeOH). This product was used without further purification (360 mg, 0.609 mmol), and was hydrogenated in methanol (30 ml) using 10% Pd/carbon (36 mg) for 3 h. The reaction mixture was filtered and the resulting solution concentrated to afford the amine (253) as a foam (270 mg, 96%) $[\alpha]_D^{20}$ −56.1 (c 0.18 MeOH). The amine (253) was dissolved in dry THF (10 ml) and phosphorous pentachloride (305 mg, 1.47 mmol, 2.5 equiv) was added. The mixture was then cooled to −5° C. and N-ethylmorpholine was added under nitrogen. The reaction mixture was stirred overnight at room temperature. The mixture was concentrated and the residue taken up with CH$_2$Cl$_2$ (20 ml), cold H$_2$O (20 ml), 1M HCl (20 ml). After decantation, the aq. phase was reextracted with CH$_2$Cl$_2$ (2×20 ml). The combined organic phase was washed with 10% NaHCO$_3$ and water, dried (MgSO$_4$) and concentrated. The resulting oil was purified on silica gel (1% methanol in CH$_2$Cl$_2$) affording the bicyclic compound (254) as a solid (65 mg, 25%): $[\alpha]_D^{20}$ −77 (c 0.208, MeOH); IR (KBr) 3471, 3434, 2975, 2928, 1767, 1723, 1443, 1389, 1284, 1243, 1151, 1112, 720; $^1$H NMR (CDCl$_3$) δ 7.94–7.69 (4H, m), 5.34–5.27 (1H, m), 4.89–4.66 (2H, m), 3.94–3.64 (2H, m), 3.02–2.84 (1H, m), 2.34–2.19 (2H, m), 1.94–1.61 (3H, m), 1.47 (9H, s), 1.14 (3H, d); Anal. Calcd for C$_{23}$H$_{27}$N$_3$O$_6$: C, 62.57; H, 6.17; N, 9.52. Found: C, 62.60; H, 6.40; N, 9.10.

(1S, 8S, 9S) t-Butyl-9-benzoylamino-6,10-dioxo-8-methyl-1,2,3,4,7,8,9,10-octahydro-6H-pyridazino[1,2-a][1, 2]diazepine-1-carboxylate (255). A solution of the bicyclic compound (254) (70 mg, 0.16 mmol) in ethanol was treated with hydrazine hydrate (0.02 ml, 4 mmol, 2.5 equiv). After 5 h stirring at room temperature, the mixture was concentrated and the resulting residue taken up in toluene and reevaporated. The residue was treated with 2M acetic acid (2 ml) for 16 h. The resulting precipitate was filtered and washed with 2M acetic acid (10 ml). The filtrate was basified with solid NaHCO$_3$ and then extracted with EtOAc. The organic solution was washed with water, dried (MgSO$_4$) and concentrated. Purification by flash chromatography on silica gel (2% methanol in CH$_2$Cl$_2$) afforded the free amine as a foam (50 mg, 100%). The amine (50 mg, 0.16 mmol) was dissolved in dioxan (1 ml) and water (0.25 ml) and treated with NaHCO$_3$ (0.034 g, 0.04 mmol) followed by benzoylchloride (0.047 ml, 0.40 mmol, 2.8 equiv). The mixture was stirred overnight at room temperature, then diluted with EtOAc (15 ml). The organic solution was washed with 10% NaHCO$_3$ and sat. aq. NaCl, dried (MgSO$_4$) and concentrated. Purification by flash chromatography on silica gel (2% methanol in CH$_2$Cl$_2$) afforded the benzamide (255) as a foam (67 mg, 100%): $^1$H NMR (CDCl$_3$) δ 7.89–7.39 (5H, m), 6.79 (1H, d), 5.32–5.20 (1H, m), 4.98–4.82 (1H, m), 4.75–4.64 (1H, m), 3.84–3.65 (1H, m), 3.09–2.89 (1H, m), 2.45–2.18 (2H, m), 2.00–1.61 (4H, m), 1.48 (9H, s), 1.28 (3H, d).

[3S, (1S, 8S, 9S)] 3-(9-benzoylamino-6,10-dioxo-8-methyl-1,2,3,4,7,8,9,10-octahydro-6H-pyridazino[1,2-a][1, 2]diazepine-1-carboxamido)-4-oxobutanoic acid (257). A solution of t-butyl ester (255) (67 mg, 0.16 mmol) in CH$_2$Cl$_2$ (1 ml) was treated at 0° C. with trifluoroacetic acid (1 ml). The resulting solution was stirred at 0° C. for 15 min and then at room temperature for 1 h. The solution was concentrated, the residue taken up in dry CH$_2$Cl$_2$ (2×2 ml) and the mixture again concentrated (×2). The residue was crystallized from diethylether. Filtration of the precipitate afforded the free acid of 255 as a grey solid (40 mg, 70%). A solution of acid (40 mg, 0.11 mmol), N-allyloxycarbonyl-4-amino-5-benzyloxy-2-oxotetrahydrofuran (Chapman, Biorg. & Med. Chem. Lett., 2, pp. 615–18 (1992); 39 mg, 0.13 mmol, 1.2 equiv) and (Ph$_3$P)$_2$PdCl$_2$ (3 mg) in a mixture of dry CH$_2$Cl$_2$ (1 ml) and dry DMF (0.2 ml) was treated dropwise with n-Bu$_3$SnH (0.089 ml, 0.33 mmol, 3 equiv). The resulting solution was stirred at 25° C. for 10 min and then 1-hydroxybenzotriazole (36 mg, 0.266 mmol, 2.4 equiv) was added. The mixture was cooled to 0° C. and ethyldimethylaminopropyl carbodiimide (31 mg, 0.16 mmol, 1.5 equiv) was added. After stirring at 0° C. for 10 min and then at room temperature overnight, the mixture was diluted with EtOAc (20 ml) and the resulting solution washed successively with 1M HCl (2×5 ml), 10% NaHCO$_3$ (2×5 ml) and sat. aq. NaCl (5 ml), dried (MgSO$_4$) and concentrated. Flash chromatography on silica gel (2% methanol in CH$_2$Cl$_2$) afforded a mixture of diastereoisomers (256) as a grey solid (50 mg, 82%). This product (256) was used without further purification (50 mg, 0.091 mmol) and was hydrogenated in methanol (5 ml) using 10% Pd/carbon (30 mg) for 24 h. The reaction mixture was filtered and the resulting solution concentrated. Flash chromatography on silica gel (2–20% methanol in CH$_2$Cl$_2$) afforded compound 257 (9 mg, 21%) as a white solid: $^1$H NMR (D$^4$-MeOH) δ 7.88–7.29 (5H, m), 5.18–4.99 (1H, m), 4.59–4.35 (3H, m), 4.26–4.11 (1H, m), 3.65–3.41 (2H, m), 3.18–2.91 (1H, m), 2.62–1.47 (8H, m), 1.29–1.00 (3H, 2d) (mixture of acetal and hemiacetal). MS (ES−) 457.

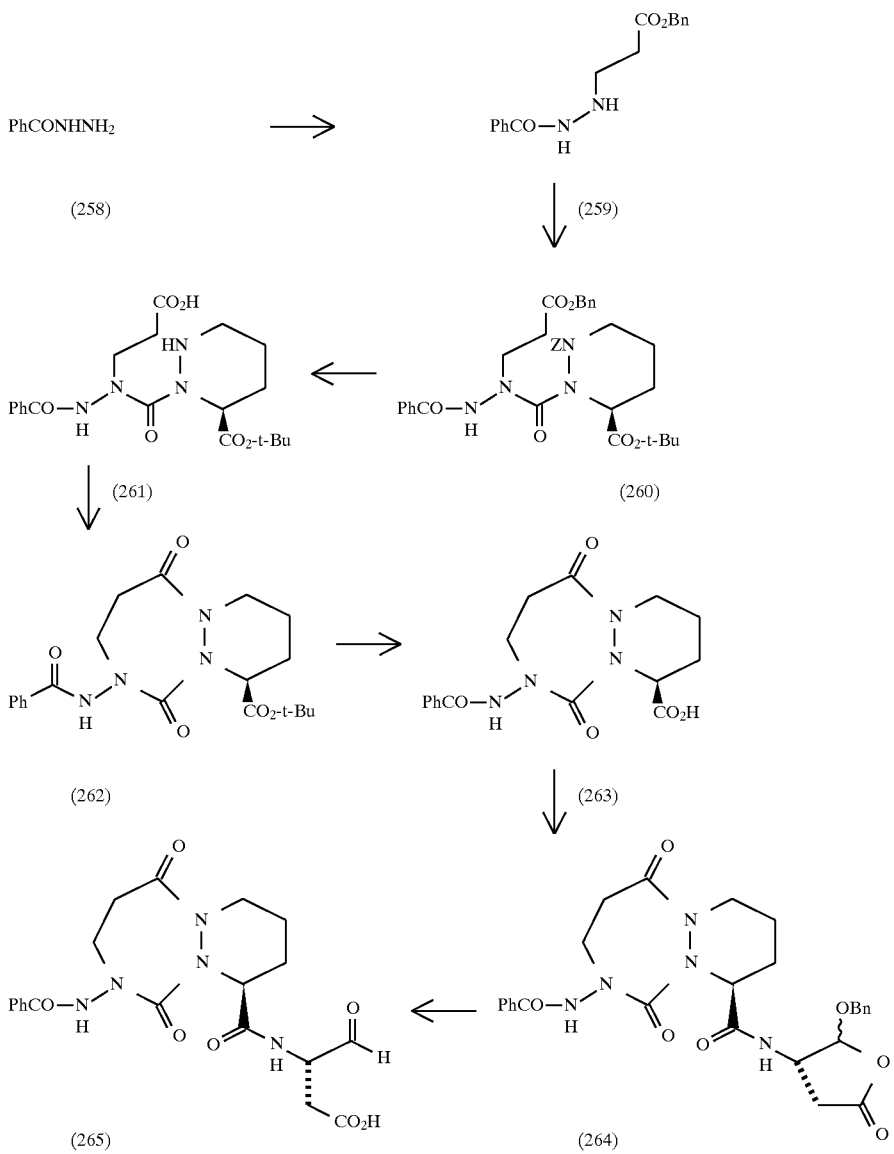

Benzyl 3-(N'-benzoylhydrazino)propanoate (259). Benzylacrylate (1.13 ml, 7.34 mmol) was added to a stirred suspension of benzoylhydrazine (285) (1.0 g, 7.34 mmol) in isopropanol (28 ml). The mixture was refluxed for 20 h, cooled to room temperature then concentrated. The residue was purified by flash chromatography (20% EtOAc in $CH_2Cl_2$) to afford 259 (1.098 g, 50%) as an oil which crystallized on standing: mp 65° C.; IR (KBr) 3283, 1723, 1644, 1316, 1201, 1156; $^1$H NMR (CDCl$_3$) δ 8.32–8.18 (1H, m), 7.81–7.70 (2H, m), 7.57–7.23 (8H, m), 5.36–4.92 (1H, brm), 5.11 (2H, s), 3.26 (2H, t, J=6.5), 2.59 (2H, t, J=6.5); $^{13}$C NMR (CDCl$_3$) δ 172.12, 167.27, 135.65, 132.54, 131.66, 128.45, 128.10, 128.06, 126.84, 66.31, 47.33, 33.31; Anal. Calcd for $C_{17}H_{18}N_2O_3$: C, 68.44; H, 6.08; N, 9.39. Found: C, 68.42; H, 6.10; N, 9.38. MS (ES+) 321 (M+Na, 38%), 299 (M$^+$+1, 100).

(3S)-1-Benzyl 3-t-butyl 2-(N'-benzoyl-N-(2-benzyloxycarbonylethyl)hydrazinocarbonyl)hexahydropyridazine-1,3-dicarboxylate (260). A solution of (3S)-1-benzyl 3-t-butyl hexahydropyridazine-1,3-dicarboxylate (Hassall et al. *J. Chem. Soc. Perkin* 1, pp. 1451–1454 (1979)) (925.3 mg, 2.89 mmol) and diisopropylethylamine (0.70 ml, 4.0 mmol) in a 1.93M toluene solution of phosgene (17.96 ml, 34.7 mmol) was stirred at room temperature for 45 min, then concentrated to leave a yellow solid. To this solid was added toluene (18 ml), hydrazide (259) (861.6 mg, 2.89 mmol) and diisopropylethylamine (0.70 ml, 4.0 mmol). The mixture was stirred at room temperature for 2.75 h, then concentrated. The resulting residue was taken up in EtOAc, washed twice with 1M HCl, brine, then dried (MgSO$_4$), filtered and concentrated to afford 2.15 g of crude material. Flash chromatography (40% EtOAc in hexane) afforded 1.65 g (89%) of the title compound as a white foam: mp 40° C.; [α]$_D$24 −55.78° (c 0.40, CH$_2$Cl$_2$); IR (KBr) 3436, 2930, 1733, 1689, 1455, 1412, 1367, 1258, 1156, 697; $^1$H NMR (CDCl$_3$) δ 8.54–8.23 (0.5H, m), 7.97–7.09 (15.5H), 5.16–4.80 (4H, m), 4.66–4.32 (1H, m), 4.24–3.55 (3.3H, m), 3.50–3.26 (0.4H, m), 3.19–2.49 (2.3H, m), 2.11–1.43 (6H, m), 1.32–1.05 (7H, m); Anal. Calcd for $C_{35}H_{40}N_4O_8 \cdot 0.5H_2O$: C, 64.31; H, 6.32; N, 8.57. Found: C, 64.18; H, 6.27; N, 8.56. MS (ES+) 662 (M+Na, 84%), 645 (M$^+$+1, 100), 384 (77).

(6S)-3-(N'benzoyl-N-(6-t-butoxycarbonylhexahydropyridazine-1-carbonyl)hydrazino)propanoic Acid (261). A solution of 260 (1.59 g, 2.47 mmol) in MeOH (142 ml) was treated with 10% Palladium on carbon (230.0 mg) and stirred under an atmosphere of $H_2$ for 1.5 h. The mixture was filtered and the solvent evaporated to afford 1.04 g (100%) of a white foam. This was used in the next step without further purification: mp <40° C.; $[\alpha]_D^{26}$ +1.6° (c 0.26, $CH_2Cl_2$); IR (KBr) 3422, 2977, 2986, 1728, 1677, 1486, 1445, 1396, 1369, 1309, 1228, 1155, 916, 716; $^1$H NMR ($CDCl_3$) δ 10.0–9.7 (1H, brm), 7.86 (2H, d, J=7.5), 7.62–7.38 (3H, m), 7.3–5.6 (2H, brm), 4.57 (1H, brd, J=4.0), 4.05–3.77 (2H, m), 3.00–2.82 (1H, m), 2.80–2.43 (3H, m), 2.20–2.03 (1H, m), 2.00–1.47 (1H, m), 1.62–1.14 (11H, m); $^{13}$C NMR ($CDCl_3$) δ 175.00, 171.17, 167.62, 160.68, 132.39, 131.77, 128.67, 127.38, 82.27, 54.38, 48.04, 46.35, 33.62, 28.02, 25.68, 21.61. MS (ES+) 443 (M+Na, 68%), 421 (M$^+$+1), 100), 365 (50), 131 (61).

(4S) t-Butyl 7-benzamido-6,10-dioxo-1,2,3,4,7,8,9,10-octahydro-6H-pyridazino[1,2-a][1,2,4]triazepine-4-carboxylate (262). To a solution of amino acid (261) (1.012 g, 2.41 mmol) in dry THF (26 ml) at 0° C. was added N-ethylmorpholine (597 μl, 4.69 mmol), followed by PCl$_5$ (651.3 mg, 3.12 mmol). The reaction was stirred at 0° C. for 2 h, then allowed to warm to rt and stirred for a further 15.5 h. The mixture was concentrated and the resulting residue taken up in EtOAc, washed twice with 1M HCl, sat. NaHCO$_3$, brine, then dried (MgSO$_4$), filtered and concentrated. Flash chromatography (20% EtOAc in $CH_2Cl_2$) gave 727.3 mg (75%) of the title compound as a white foam: $[\alpha]_D^{26}$ +51.0° (c 0.20, $CH_2Cl_2$); IR (KBr) 3436, 2979, 1733, 1670, 1483, 1437, 1420, 1299, 1243, 1156; $^1$H NMR ($CDCl_3$) δ 8.70 (1H, s), 7.78 (2H, d, J=7.0), 7.57–7.32 (3H, m), 5.08 (1H, dd, J=2.5, 5.5), 4.59–4.43 (1H, m), 4.08–3.69 (3H, m), 3.07–2.84 (1H, m), 2.57–2.35 (1H, m), 2.34–2.14 (1H, m), 2.07–1.43 (3H, m), 1.48 (9H, S); $^{13}$C NMR ($CDCl_3$) δ 172.41, 169.04, 166.35, 158.35, 132.24, 132.03, 128.61, 127.31, 82.77, 55.41, 54.07, 41.57, 32.21, 28.04, 24.97, 20.37; Anal. Calcd for $C_{20}H_{26}N_4O_5$: C, 59.69; H, 6.51; N, 13.92. Found: C, 59.53; H, 6.53; N, 13.84. MS (ES+) 425 (M+Na, 71%), 403 (M$^+$+1, 100), 145 (41).

(4S)-7-Benzamido-6,10-dioxo-1,2,3,4,7,8,9,10-octahydro-6H-pyridazino[1,2-a][1,2,4]triazepine-4-carboxylic Acid (263). A solution of ester (262) (720.0 mg, 1.80 mmol) in a 1:1 mixture of $CH_2Cl_2$ and TFA (150 ml) was stirred for 1.3 h under a dry atmosphere. The solution was then reduced in vacuo, taken up in Et$_2$O and reduced again. This process was repeated six times to afford the crude product as an off-white solid. The product was purified by flash chromatography (5% MeOH in $CH_2Cl_2$) to afford 520.0 mg (83%) of the title compound as a white foam: $[\alpha]_D^{25}$ +59.5° (c 1.82, $CH_2Cl_2$); IR (KBr) 3435, 3266, 2956, 1732, 1664, 1524, 1486, 1440, 1302; $^1$H NMR ($CDCl_3$) δ 9.13 (1H, s), 7.77 (2H, d, J=7.5), 7.57–7.32 (3H, m), 5.27–5.16 (1H, m), 4.62–4.43 (1H, m), 4.09–2.70 (3H, m), 3.14–2.89 (1H, m), 2.59–2.43 (1H, m), 2.38–2.20 (1H, m), 2.14–1.89 (1H, m), 1.82–1.59 (2H, m); $^{13}$C NMR ($CDCl_3$) δ 173.65, 172.28, 166.44, 158.42, 132.44, 131.31, 128.61, 127.39, 54.83, 54.01, 42.11, 31.79, 24.42, 20.29; MS (ES–) 345 (M–H$^+$, 100%), 161 (45).

[2RS, 3S, (4S)] N-(2-Benzyloxy-5-oxotetrahydrofuran-3-yl)-6,10-dioxo-1,2,3,4,7,8,9,10-octahydro-6H-pyridazino[1,2-a][1,2,4]triazepine-4-carboxamide (264). To a solution of acid (263) (300.0 mg, 0.87 mmol) and (2RS, 3S)-3-allyloxycarbonylamino-2-benzyloxy-5-oxotetrahydrofuran (Chapman, *Biorg. & Med. Chem. Lett.* 2, pp. 615–18 (1992)) (277.6 mg, 0.95 mmol) in dry $CH_2Cl_2$ (2.5 ml) and dry DMF (2.5 ml) at rt was added bis(triphenylphosphine) palladium chloride (13.0 mg), followed by tri-n-butyltin hydride (466.0 μl, 1.73 mmol). The reaction was stirred for 5 min, then 1-hydroxybenzotriazole (234.1 mg, 1.73 mmol) was added and the mixture was cooled to 0° C. before addition of 1-(3-dimethylaminopropyl)-3-ethylcarbodiimide hydrochloride (204.5 mg, 1.04 mmol). The mixture was allowed to warm to rt and stirred for 16.5 h. The mixture was diluted with EtOAc, washed with 1M NaHSO$_4$ twice with sat. NaHCO$_3$, then H$_2$O and brine. The organic layer was dried (MgSO$_4$), filtered and concentrated. The residue was purified by flash chromatography (5% MeOH in $CH_2Cl_2$) to afford 358.3 mg (77%) of the title compound as a white solid: IR (KBr) 3435, 1791, 1665, 1526, 1421, 1285; $^1$H NMR ($CDCl_3$) δ 8.76 and 8.49 (1H, 2×s), 7.92–7.73 (2H, m), 7.62–7.24 (8.5H, m), 6.86 (0.5H, d, J=8.0), 5.53 and 5.33 (1H, d, J=5.5, s), 4.95–4.34 (5H, m), 4.04–3.54 (3H, m), 3.03–2.64 (2H, m), 2.49–2.14 (2H, m), 2.11–1.46 (4H, m); MS (ES+) 558 (M+Na, 100%), 536 (M$^+$+1, 78), 404 (58).

[3S, (4S)]3-(7-Benzamido-6,10-dioxo-1,2,3,4,7,8,9,10-octahydro-6H-pyridazino[1,2-a][1,2,4]triazepine-4-carboxamido)-4-oxobutanoic acid (265). A mixture of 264 (350.0 mg, 0.65 mmol), 10% palladium on carbon (350 mg) and methanol (36 ml) was stirred under an atmosphere of H$_2$ for 6.5 h. The mixture was filtered and the solvent evaporated. Et$_2$O was added and the solvent removed again. This process was repeated four times to reveal 283 mg (97%) of the title compound, as a white crystalline solid: mp decarboxylates above 140° C.; $[\alpha]_D^{26}$ +33.5° (c 0.18, MeOH), IR (KBr) 3428, 1663, 1528, 1487, 1437, 1288; $^1$H NMR (D$_6$-DMSO) δ 10.56 (1H, s), 8.71–8.57 (1H, m), 7.88–7.81 (2H, m), 7.65–7.46 (3H, m), 4.97–4.85 (1H, m), 4.38–4.0 (3H, m), 3.88–3.52 (3H, m), 2.91–2.71 (2H, m), 2.50–2.38 (1H, m), 2.35–2.21 (1H, m), 2.10–1.94 (1H, m), 1.93–1.49 (3H, m); $^{13}$C NMR (D$_6$-DMSO) δ 173.66, 172.49, 169.97, 169.89, 164.96, 157.62, 132.35, 131.85, 128.39, 127.32, 53.81, 52.69, 40.90, 33.17, 31.60, 24.40, 24.13, 19.24; MS (ES–).

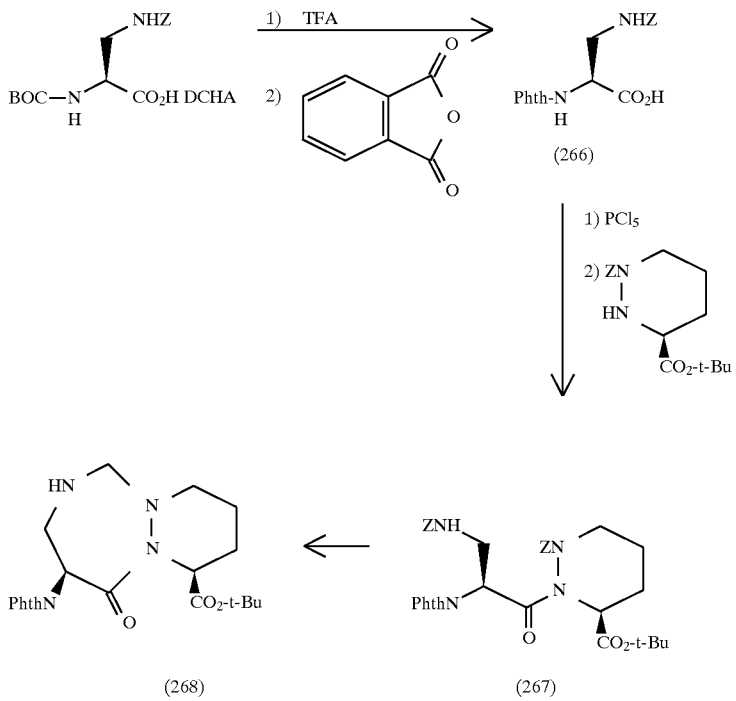

(2S) 3-Benzyloxycarbonylamino-2-phthalimidopropionic acid (266). A solution of (2S) 3-benzyloxycarbonylamino-2-tert-butoxycarbonylaminopropionic acid dicyclohexylamine salt (3 g, 5.8 mmol) in dichloromethane (200 ml) was washed four times with 1M HCl solution, dried (MgSO$_4$) and concentrated. The resulting oil was dissolved in dry dichloromethane (35 ml), cooled to 0° C. and treated with trifluoroacetic acid (35 ml). This solution was stirred at 0° C. for 1.5 h then evaporated to dryness. Dichloromethane (50 ml) was added to the residue then removed under vacuum. This process repeated six times to afford a white solid. The white solid was suspended in toluene (50 ml), treated with powdered phthalic anhydride (940 mg, 6.35 mmol) and refluxed for 18 h. The resulting solution was concentrated to afford an oil which was purified by flash chromatography (2–10% methanol/dichloromethane) to afford 266, 2.01 g (94%) as a white powder: IR (KBr) 3600–2500 br, 1776, 1714, 1530, 1469, 1455, 1392, 1263, 1131, 722; $^1$H NMR (CDCl$_3$) δ 7.83 (2H, m), 7.72 (2H, m), 7.29 (5H, m), 5.41 (1H, m), 5.03 (2H, s), 3.90 (2H, m); MS (ES−), 367 (M−1).

[3S (2S)] t-Butyl 1-benzyloxycarbonyl-2-(3-benzyloxycarbonylamino-2-phthalimidopropionyl) pyridazine-3-carboxylate (267). A suspension of the acid 266 (1.32 g, 3.58 mmol) in dry ether (37 ml) was treated with phosphorus pentachloride (1.04 g, 5 mmol) and stirred at room temperature for 2 h. The solution was filtered to remove unreacted phosphorus pentachloride then evaporated to dryness. The residue was treated with dry toluene (25 ml) then evaporated to dryness. This process was repeated several times. The resulting oil was dissolved in dry dichloromethane (25 ml), cooled to 0° C. and treated with a solution of (3S) t-butyl 1-benzyloxycarbonylpyridazine-3-carboxylate (1.15 g, 3.58 mmol) in dry dichloromethane (2 ml) followed by 5% aqueous sodium bicarbonate solution (25 ml). The mixture was stirred rapidly at room temperature for 20 h then diluted with ethyl acetate (100 ml) and acidified to pH2 with 1M HCl. The organic phase was washed twice with dilute HCl solution then brine, dried (MgSO$_4$) and concentrated. The resulting oil was purified by flash chromatography (2–20% ethyl acetate/dichloromethane then 10–20% methanol/dichloromethane) to afford (267), 1.25 g (52%) as a white powder: IR (KBr) 3367, 2955, 1722, 1517, 1455, 1387, 1369, 1251, 1153, 721; $^1$H NMR (CDCl$_3$) δ 7.81 (2H, m), 7.74 (2H, m), 7.63 (1H, brs), 7.31 (10H, m), 5.46–4.76 (5H, m), 4.07–3.54 (4H, m), 2.4 (1H, m), 2.0–1.6 (3H, m), 1.40 (9H, s); MS (ES+), 671 (M+1), 693 (M+Na).

(1S, 9S) t-Butyl 1,2,3,4,7,8,9,10-octahydro-10-oxo-9-phthalimido-6H-pyridazino[1,2-a][1,2,4]triazepine-1-carboxylate (268). A solution of ester 267 (50 mg, 0.074 mmol) in methanol (15 ml) was treated with 10% palladium on carbon (50 mg) and hydrogenated at room temperature and atmospheric pressure for 24 h. The mixture was evacuated thoroughly to remove hydrogen then treated with 37% aqueous formaldehyde (18 mg, 0.22 mmol) and stirred under nitrogen for 2 h. The mixture was filtered, evaporated to dryness and the product purified by flash chromatography (4–100% ethyl acetate/dichloromethane) to afford 268 14.5 mg (48%) as an oil: $^1$H NMR (CDCl$_3$) δ 7.85 (2H, m), 7.71 (2H, m), 5.78 (1H, dd, J=10, 5), 4.99 (1H, dd, J=6.1, 1.5), 4.07 (1H, d, J=10.6), 3.49 (1H, dd, J=14, 5), 3.39 (1H, d, J=10.3), 3.24 (1H, dd, J=14, 10.2), 3.17 (2H, m), 2.39 (1H, m), 1.84–1.46 (3H), 1.51 (9H, s); MS (ES+), 415 (M+1), 437 (M+Na).

Compounds 280–283 were prepared from 212b by a method similar to the method used to prepare 226e. Compounds 284–287 were prepared by a method similar to the method used to prepare 217e.

255 256
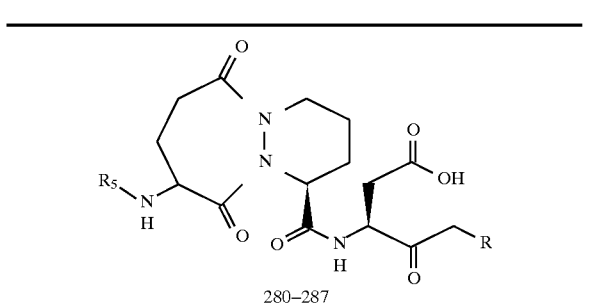
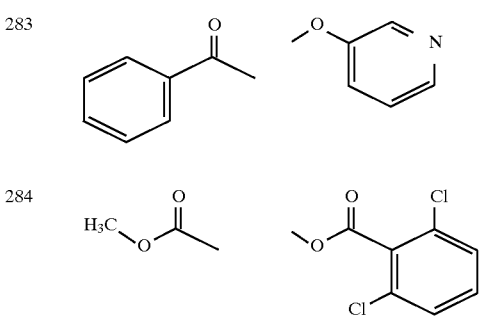
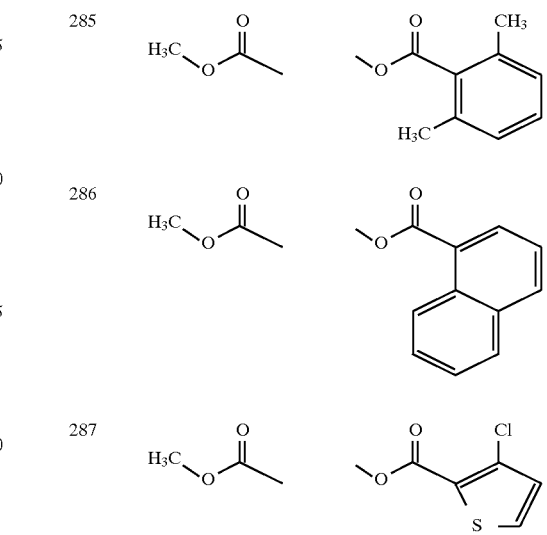
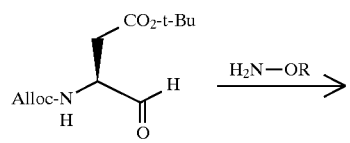
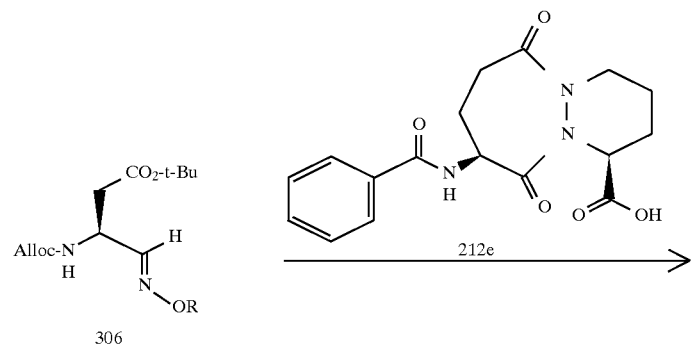

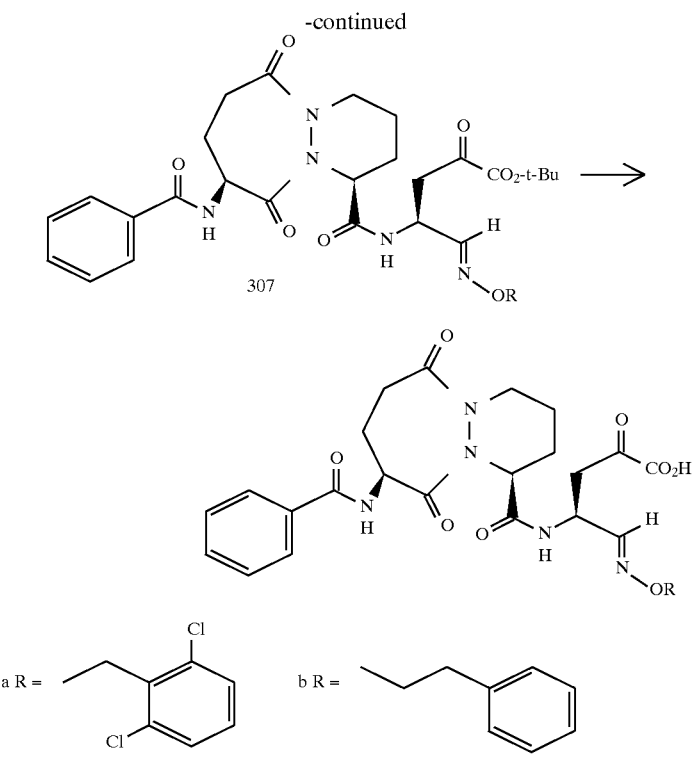

(3S) 3-Allyloxycarbonylamino-4-oxobutyric acid tert-butyl ester O-(2,6-dichlorophenylmethyl) oxime (306a) was prepared by a similar procedure as 208a except that 2,6-dichlorophenylmethoxyamine (prepared by a similar method as 306b) was used instead of semicarbazide to give 870 mg (quant.) as a clear oil.

(3S) 3-Allyloxycarbonylamino-4-oxobutyric acid tert-butyl ester O-(2-(phenyl)ethyl)oxime (306b) was prepared by a similar procedure as 208a except that 2-(phenyl)ethoxyamine (U.S. Pat. No. 5,346,911) was used instead of semicarbazide to give 395 mg (quant.) as a clear oil.

[3S, (1S, 9S) 3-(9-Benzoylamino-6,10-dioxo-1,2,3,4,7,8,9,10-octahydro-6H-pyridazino[1,2-a][1,2]diazapine-1-carboxamido)-amino]-4-oxobutanoicacid t-butyl ester, O-(2,6-dichlorophenylmethyl)oxime (307a) was prepared by a procedure similar to 233e except 306a was used instead of 207a to give 23 mg (23%) of 307a as a white solid.

[3S, (1S, 9S) 3-(9-Benzoylamino-6,10-dioxo-1,2,3,4,7,8,9,10-octahydro-6H-pyridazino[1,2-a][1,2]diazapine-1-carboxamido)-amino]-4-oxobutanoic acid t-butyl ester, O-(2-(phenyl)ethyl)oxime (307b) was prepared by a procedure similar to 233e except 306b was used instead of 207a to give 43 mg (48%) of 307b as a white solid.

[3S, (1S, 9S) 3-(9-Benzoylamino-6,10-dioxo-1,2,3,4,7,8,9,10-octahydro-6H-pyridazino[1,2-a][1,2]diazapine-1-carboxamido)-amino]-4-oxobutanoic acid, O-(2,6-dichlorophenylmethyl)oxime (308a) was prepared by from 307a a procedure similar to the preparation of 235e from 234e to give 15.2 mg (74%) as white solid: $^1$H NMR (CD$_3$OD) δ 0.9(m), 1.3(s), 1.7(m), 1.8(m), 2.0(m), 2.1–2.2 (m), 2.3(dd), 2.4–2.5(m), 2.6(m), 2.7–2.8(m), 3.1(m), 3.3 (m), 3.4–3.5(m), 4.5(m), 4.9(m), 5.1(m), 5.3(d), 5.4(s), 6.8(d), 7.2–7.5(m), 7.8(dd), 8.4(dd).

[3S, (1S, 9S) 3-(9-Benzoylamino-6,10-dioxo-1,2,3,4,7,8,9,10-octahydro-6H-pyridazino[1,2-a][1,2]diazapine-1-carboxamido)-amino]-4-oxobutanoic acid, O-(2-(phenyl)ethyl)oxime (308b) was prepared by from 307b a procedure similar to the preparation of 235e from 234e to give 25.2 mg (68%) as white solid: $^1$H NMR(CD$_3$OD) δ 1.2(m), 1.6–1.7 (m), 2.0–2.1(m), 2.2(m), 2.3(m), 2.5(m), 2.6–2.7(dd), 2.9(t), 3.0(t), 3.1(m), 3.3–3.5(m), 4.2(t), 4.25(m), 4.5(m), 5.2(t), 5.3(t), 6.7(d), 7.1–7.2(m), 7.35(dd), 7.4(m), 7.5(m), 7.8(dd), 8.3(dd).

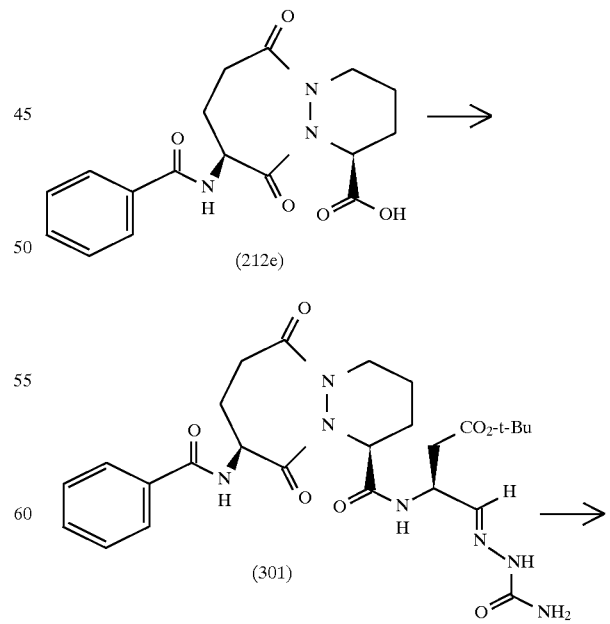

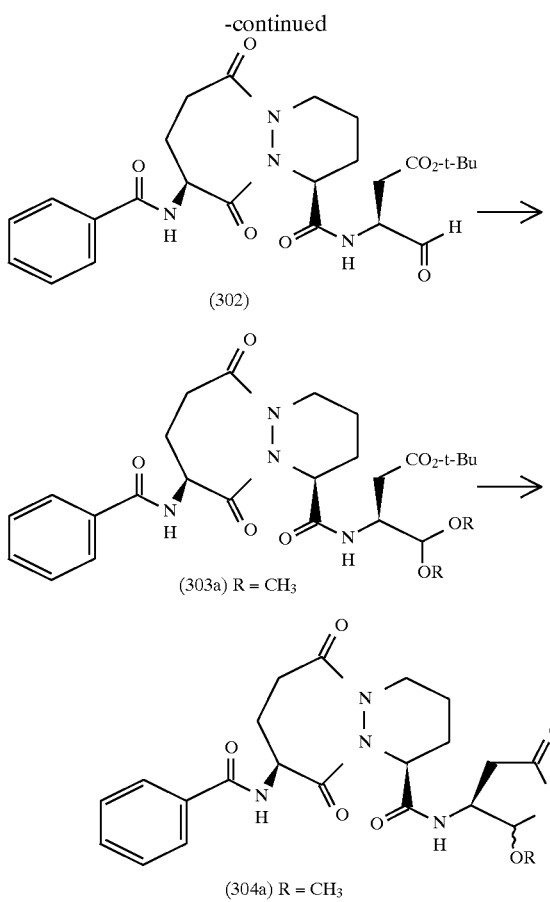

(302)

(303a) R = CH₃

(304a) R = CH₃

[3S, (1S, 9S) 3-(9-Benzoylamino-6,10-dioxo-1,2,3,4,7,8,9,10-octahydro-6H-pyriazino[1,2-a][1,2]diazapine-1-carboxamido)-amino]-4-oxobutanoic acid tert-butyl ester (302).

Step A: 301 was prepared by procedure similar to 605a (Step A), except 212e was used instead of 603a to give 540 mg (34%) to give a white solid.

Step B: 302. A solution of 301 (50.7 mg; 0.091 mmol) in 2.8 ml of MeOH/HOAc/37% aq. formaldehyde (5:1:1) was stirred at rt for 5.5 h. and the reaction was concentrated to 0.7 ml in vacuo. The residue was dissolved in 3 ml of CH₃CN and concentrated to 0.7 ml (3×), dissolved in toluene and concentrated to 0.7 ml in vacuo (2×), and concentrated to dryness. Chromatography (flash, SiO₂, 5% isopropanol/CH₂Cl₂) gave 302 (45.5 mg, 78%) as a white solid: ¹H NMR(DMSO-d₆) δ 1.0–1.15(m, 2H), 1.4(s, 9H), 1.65(m, 2H), 1.9–2.1(m, 2H), 2.15–2.4(m, 3H), 2.55(m, 1H), 2.7–3.0(m, 2H), 4.3–4.6(m, 2H), 4.9(m, 1H), 5.2(m, 1H), 7.4–7.6(m, 2H), 7.8–8.0(m, 2H), 8.6(m, 1H), 8.8(m, 1H), 9.4(s, 1H).

[1S, 9S (2RS, 3S)] 9-Benzoylamino-6,10-dioxo-1,2,3,4,7,8,9,10-octahydro-N-(2-methoxy-5-oxo-tetrahydro-furan-3-yl)-6H-pyridazino[1,2-a][1,2]diazapine-1-carboxamide. (304a).

Step A: A solution of 302 (90 mg; 0.18 mmol) in 10 ml of MeOH was treated with trimethylorthoformate (1 ml) and p-toluene sulfonic acid hydrate (5 mg; 0.026 mmol) and the reaction was stirred for 20 h. The reaction was treated with 3 ml of aq. sat. NaHCO₃ and concentrated in vacuo. The residue was taken up in EtOAc and washed with dilute aq. NaHCO₃, dried over MgSO₄ and concentrated in vacuo to give 80 mg of 303a.

Step B: 303a was dissolved in 2 ml of TFA and stirred at rt for 15 min. The reaction was dissolved in CH₂Cl₂ and concentrated in vacuo (3×). Chromatography (flash, SiO₂, 1% to 3% MeOH/CH₂Cl₂ gave 43 mg (64%) of 304a as a white solid: ¹H NMR(CDCl₃) δ 1.55–1.8(m, 2H), 1.9–2.15 (m, 4H), 2.25–2.5(m, 2H), 2.7–3.3(m, 4H), 3.45, 3.6(s, s, 3H), 4.4, 4.75(2m, 1H), 4.6(m, 1H), 4.95, 5.4(t,d, 1H), 5.1–5.2(m, 1H), 6.45, 7.05(2d, 1H), 6.95(m, 1H), 7.45(m, 2H), 7.5(m, 1H), 7.85(m, 2H).

EXAMPLE 11

Compounds 214e, 404–413, 415–445, 446–468, 470–491, and 493–499 were synthesized as described in Example 11 and FIG. 1.

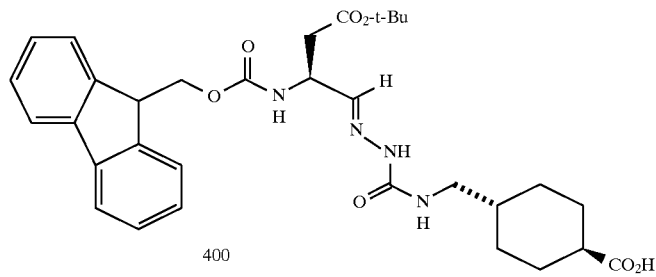

400

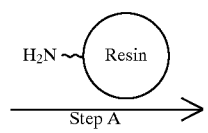

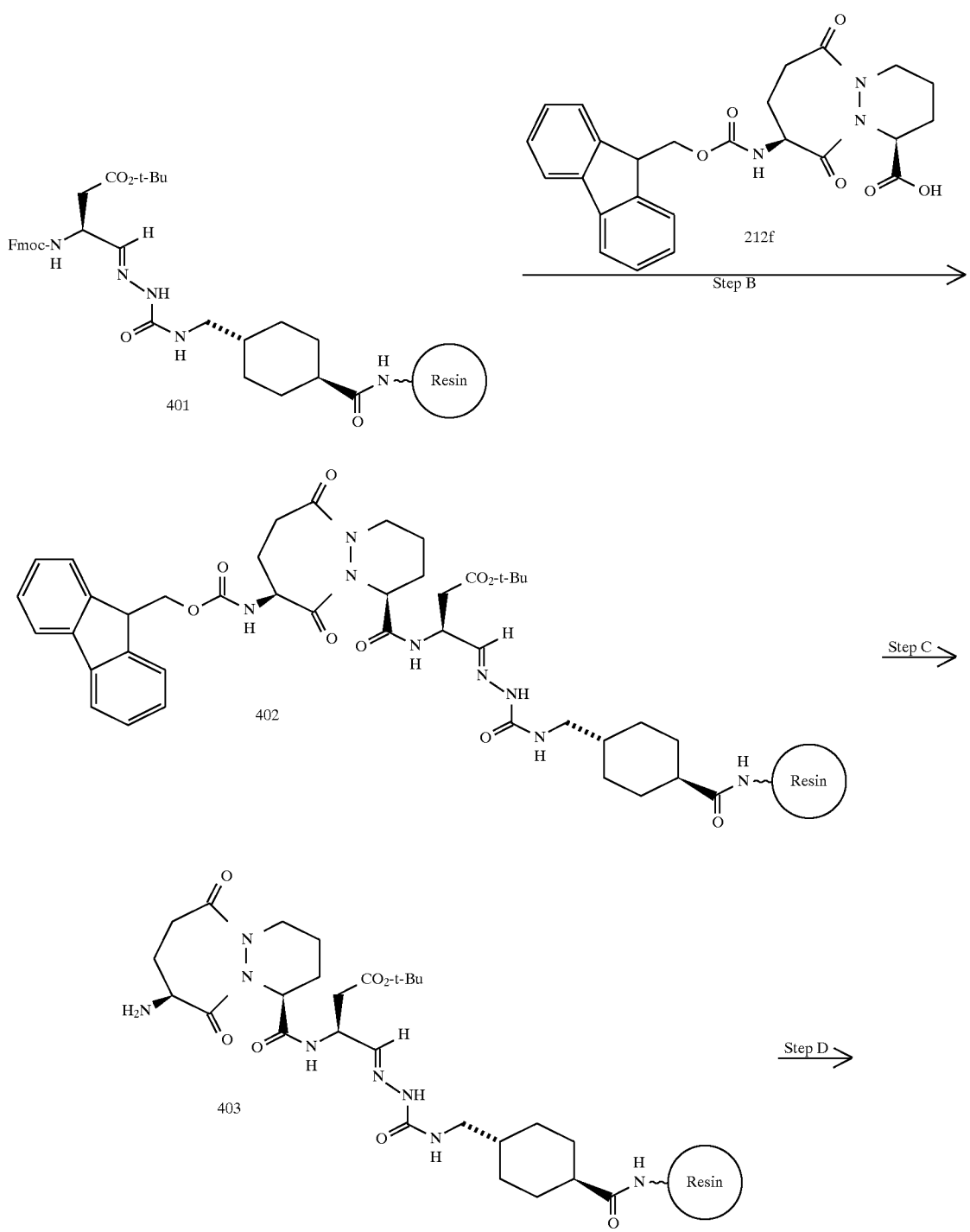

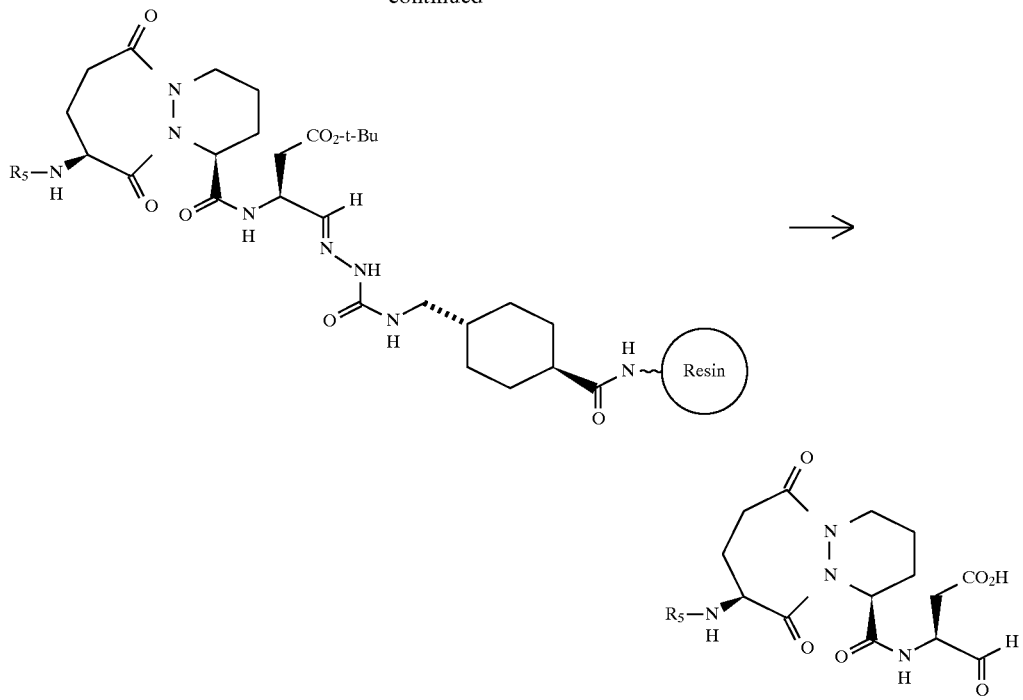

214e, 404–499

Step A. Synthesis of 401. TentaGel S® NH$_2$ resin (0.16 mmol/g, 10.0 g) was placed in a sintered glass funnel and washed with DMF (3×50 mL), 10% (v/v) DIEA in DMF (2×50 mL) and finally with DMF (4×50 mL). Sufficient DMF was added to the resin to obtain a slurry followed by 400 (1.42 g, 2.4 mmol, prepared from (3S)-3-(fluorenylmethyloxycarbonyl)-4-oxobutryic acid t-butyl ester according to A. M. Murphy et. al. J. Am. Chem. Soc., 114, 3156–3157 (1992)), 1-hydroxybenzotriazole hydrate (HOBT•H$_2$O; 0.367 g, 2.4 mmol), O-benzotriazol-1-yl-N,N,N',N'-tetramethyluronium hexafluorophosphate (HBTU; 0.91 g, 2.4 mmol), and DIEA (0.55 mL, 3.2 mmol). The reaction mixture was agitated overnight at rt using a wrist arm shaker. The resin was isolated on a sintered glass funnel by suction filtration and washed with DMF (3×50 mL). Unreacted amine groups were then capped by reacting the resin with 20% (v/v) Ac$_2$O/DMF (2×25 mL) directly in the funnel (10 min/wash). The resin was washed with DMF (3×50 mL) and CH$_2$Cl$_2$ (3×50 mL) prior to drying overnight in vacuo to yield 401 (11.0 g, quantitative yield).

Step B. Synthesis of 402. Resin 401 (6.0 g, 0.16 mmol/g, 0.96 mmol) was swelled in a sintered glass funnel by washing with DMF (3×25 mL). The Fmoc protecting group was then cleaved with 25% (v/v) piperidine/DMF (25 mL) for 10 min (intermittent stirring) and then for 20 min with fresh piperidine reagent (25 ml). The resin was then washed with DMF (3×25 ml), followed by N-methypyrrolidone (2×25 mL). After transferring the resin to a 100 mL flask, N-methypyrrolidone was added to obtain a slurry followed by 212f (0.725 g, 1.57 mmol), HOBT•H$_2$O (0.25 g, 1.6 mmol), HBTU (0.61 g, 1.6 mmol) and DIEA (0.84 mL, 4.8 mmol). The reaction mixture was agitated overnight at rt using a wrist arm shaker. The resin work-up and capping with 20% (v/v) Ac$_2$O in DMF were performed as described for 401 to yield 402 (6.21 g, quantitative yield).

Step C. Synthesis of 403. This compound was prepared from resin 402 (0.24 g, 0.038 mmol) using an Advanced ChemTech 396 Multiple Peptide synthesizer. The automated cycles consisted of a resin wash with DMF (3×1 mL), deprotection with 25% (v/v) piperidine in DMF (1 mL) for 3 min followed by fresh reagent (1 mL) for 10 min to yield resin 403. The resin was washed with DMF (3×1 mL) and N-methypyrrolidone (3×1 mL).

Step D. Method 1. [3S,(1S,9S)]-3-(6,10-Dioxo-1,2,3,4,7,8,9,10-octahydro-9-(thiophene-3-carbonylamino)-6H-pyridazine[1,2-a][1,2]diazepine-1-carboxamido)-4-oxobutanoic acid (409). Resin 403 was acylated with a solution of 0.4M thiophene-3-carboxylic acid and 0.4M HOBT in N-methypyrrolidone (1 mL), a solution of 0.4M HBTU in N-methylpyrrolidone (0.5 mL) and a solution of 1.6M DIEA in N-methypyrrolidone (0.35 mL) and the reaction was shaken for 2 hr at rt. The acylation step was repeated. Finally, the resin was washed with DMF (3×1 mL), CH$_2$Cl$_2$ (3×1 mL) and dried in vacuo. The aldehyde was cleaved from the resin and globally deprotected by treatment with 95% TFA/5% H$_2$O (v/v, 1.5 mL) for 30 min at rt. After washing the resin with cleavage reagent (1 mL), the combined filtrates were added to cold 1:1 Et$_2$O:pentane (12 mL) and the resulting precipitate was isolated by centrifugation and decantation. The resulting pellet was dissolved in 10% CH$_3$CN/90% H$_2$O/0.1% TFA (15 mL) and lyophilized to obtain crude 409 as a white powder. The compound was purified by semi-prep RP-HPLC with a Rainin Microsorb™ C18 column (5μ, 21.4×250 mm) eluting with a linear CH$_3$CN gradient (5%–45%) containing 0.1% TFA (v/v) over 45 min at 12 mL/min. Fractions containing the desired product were pooled and lyophilized to provide 409 (10.8 mg, 63%).

Step D. Method 1A. Synthesis of 418. Following a similar procedure as method 1, resin 403 was acylated with 4-(1-fluorenylmethoxycarbonylamino)benzoic acid and repeated. The Fmoc group was removed as described in Step C and the free amine was acetylated with 20% (v/v) Ac$_2$O in DMF (1 mL) and 1.6M DIEA in N-methylpyrrolidone (0.35 mL) for 2 hr at rt. The acetylation step was repeated. Cleavage of the aldehyde from the resin gave 418 (3.2 mg).

Step D. Method 1B. Synthesis of 447. Following a similar procedure as method 1A, resin 403 was acylated with 0.4M 4-(1-fluorenylmethoxycarbonylamino)benzoic acid. The acylation step was repeated once. The Fmoc group was removed as before and the free amine was reacted with 1M methanesulfonyl chloride in CH$_2$Cl$_2$ (0.5 mL) and 1M pyridine in CH$_2$Cl$_2$ (0.60 mL) for 4 hr at rt. Cleavage of the aldehyde from the resin gave 447 (10.0 mg).

Step D. Method 2. Synthesis of 214e. Following a similar procedure as method 1, resin 403 was acylated with 0.5M benzoyl chloride in N-methypyrrolidone (1 mL) and 1.6M DIEA in N-methypyrrolidone (0.35 mL) for 2 hr at rt. The acylation step was repeated. Cleavage of the aldehyde from the resin gave 214e (5.1 mg, 30%).

Step D. Method 3. Synthesis of 427. Following a similar procedure as method 1, resin 403 was reacted with 1.0M benzenesulfonyl chloride in CH$_2$Cl$_2$ (0.5 mL) and 1M pyridine in CH$_2$Cl$_2$ (0.60 mL) for 4 hr at rt. The reaction was repeated. Cleavage of the aldehyde from the resin gave 427 (7.2 mg, 40%).

Step D. Method 4. Synthesis of 420. Following a similar procedure as method 1, resin 403 was reacted with 0.5M methylisocyanate in N-methypyrrolidone (1 mL) and 1.6M DIEA in N-methypyrrolidone (0.35 mL) for 2 hr at rt. The reaction was repeated. Cleavage of the aldehyde from the resin gave 420 (8.3 mg, 55%).

Step D. Method 5. Synthesis of 445. Following a similar procedure at method 1, resin 403 was acylated with 0.27M imidazole-2-carboxylic acid (1 mL) in 2:1 DMF:H$_2$O (with 1 eq. DIEA) and 1M 1-(3-dimethylaminopropyl)-3-ethylcarbodiimide hydrochloride (EDC) in 2:1 N-methylpyrrolidone/H$_2$O (0.35 mL) for 3 hr at rt. Cleavage of the aldehyde from the resin gave 445 (9.5 mg).

Analytical HPLC methods:
(1) Waters DeltaPak C18, 300A (5$\mu$, 3.9×150 mm). Linear CH$_3$CN gradient (5%–45%) containing 0.1% TFA (v/v) over 14 min at 1 mL/min.
(2) Waters DeltaPak C18, 300A (5$\mu$, 3.9×150 mm). Linear CH$_3$CN gradient (0%–25%) containing 0.1% TFA (v/v) over 14 min at 1 mL/min.
(3) Waters DeltaPak C18, 300A (5$\mu$, 3.9×150 mm). Isocratic elution with 0.1% TFA/water (v/v) at 1 mL/min.
(4) Waters DeltaPak C18, 300A (5$\mu$, 3.9×150 mm). Linear CH$_3$CN gradient (0%–30%) containing 0.1% TFA (v/v) over 14 min at 1 mL/min.
(5) Waters DeltaPak C18, 300A (5$\mu$, 3.9×150 mm). Linear CH$_3$CN gradient (0%–35%) containing 0.1% TFA (v/v) over 14 min at 1 mL/min.

EXAMPLE 12

Compounds 605a–j, 605m–q, 605s, 605t, and 605v were synthesized as described below.

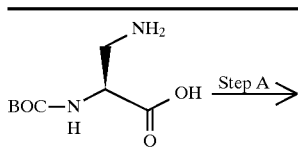

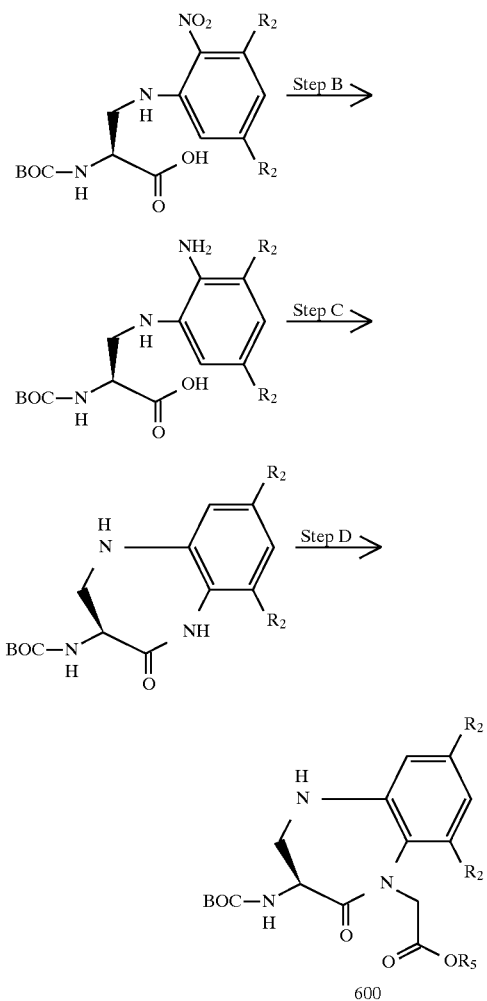

| Compound no. | R$_2$ | R$_5$ |
|---|---|---|
| 600a | H | CH$_3$ |
| 600b | H | CH$_2$Ph |
| 600c | CH$_3$ | CH$_2$Ph |

(3S)-2-Oxo-3-tert-butoxycarbonylamino-2,3,4,5-tetrahydro-1H-1,5-benzodiazepine-1-acetic acid methyl ester (600a).

Step A. (2S)-2-tert-Butoxycarbonylamino-3-(2-nitrophenyl-amino)-propionic acid. (2S)-2-tert-Butoxycarbonylamino-3-aminopropionic acid (10 g, 49 mmol), 2-fluoronitrobenzene (5.7 ml, 54 mmol), and NaHCO$_3$ (8.25 g, 98 mmol) was taken into 130 ml of DMF and heated at 80° C. for 18 h. The reaction was evaporated in vacuo to give a viscous orange residue that was dissolved in 300 ml of H$_2$O and extracted with Et$_2$O (3×150 ml). The aq. solution was acidified to pH 5 with 10% NaHSO$_4$ and extracted with EtOAc (3×250 ml). The combined extracts were dried over anhydrous Na$_2$SO$_4$, filtered, and evaporated to give 12.64 g (83%) of the title compound as an orange amorphous solid: $^1$H NMR (CD$_3$OD) δ 8.15–8.10 (1H,d), 7.54–7.48 (1H,t), 7.13–7.08 (1H, d), 6.73–6.65 (1H, t), 4.45–4.35 (1H, m), 3.9–3.8 (1H, dd), 3.65–3.55 (1H, dd), 1.45 (9H, s).

Step B. (2S)-2-tert-Butoxycarbonylamino-3-(2-aminophenyl-amino)-propionic acid. A mixture of (2S)-2-tert-Butoxycarbonylamino-3-(2-nitrophenylamino) propionic acid (12.65 g, 40.5 mmol) and 0.5 g of 10% Pd/C in 100 ml of MeOH under hydrogen at 1 atmosphere was stirred for 4 h. The solution was filtered through Celite 545 and the filtrate evaporated in vacuo to afford the 11.95 g of the title compound in quantitative yield as a dark brown solid that was used without purification: $^1$H NMR (CD$_3$OD) δ 6.75–6.70 (3H,m), 6.65–6.58 (1H, m), 4.35–4.3 1H, m), 3.6–3.38 (2H, m), 1.45 (9H, s).

Step C. (3S)-2-Oxo-3-tert-Butoxycarbonylamino-1,3,4,5-tetrahydro-1H-1,5-benzodiazepine. 1-(3-Dimethylaminopropyl)-3-ethylcarbodiimide hydrochloride (8.54 g, 44.5 mmol) was added to a cooled (0° C.) solution of (2S)-2-tert-butoxycarbonylamino-3-(2-aminophenylamino)propionic acid (11.95 g, 40.5 mmol) in 100 ml of DMF and stirred for 18 h. The reaction was poured into 700 ml of EtOAc and washed four times with 100 ml of H$_2$O. The organic layer was dried over anhydrous Na$_2$SO$_4$, filtered, and evaporated to give a brown solid that was purified by flash chromatography eluting with 3:7 EtOAc/hexane to give 8 g (71%) of the title compound: $^1$H NMR (CDCl$_3$) δ 7.78 (1H, s), 7.02–6.95 (1H, m), 6.88–6.82 (1H, m), 6.82–6.78 (1H, m), 6.75–6.70 (1H, m), 5.8–5.7 (1H, d), 4.55–4.45 (1H, m), 3.95 (1H, s), 3.9–3.82 (1H, m), 3.48–3.40 (1H,m), 1.45 (9H,s).

Step D. (3S)-2-Oxo-3-tert-butoxycarbonylamino-2,3,4,5-tetrahydro-1H-1,5-benzodiazepine-1-acetic acid methyl ester (600a). A 1.0M solution of lithium bis(trimethylsilyl) amide (3.4 ml, 3.4 mmol) in THF was added dropwise to a −78° C. solution of (3S)-2-oxo-3-tert-butoxycarbonylamino-2,3,4,5-tetrahydro-1H-1,5-benzodiazepine (0.94 g, 3.38 mmol) in 20 ml of anhydrous THF and stirred for 30 min. Methyl bromoacetate (o.44 ml, 4 mmol) was added dropwise to the reaction mixture then warmed to RT. The reaction was diluted with 100 ml of EtOAc and washed with 0.3N KHSO$_4$ (50 ml), H$_2$O (2×50 ml), and brine. The combined organics were dried over anhydrous Na$_2$SO$_4$, filtered, and evaporated to afforded a gum that was purified by flash chromatography eluting with 3:7 EtOAc/Hex. to give 0.98 g (83%) of the title compound as a white solid. $^1$H NMR (CDCl$_3$) δ 7.15–7.07 (2H, m), 6.98–6.94 (1H, m), 6.88–6.84 (1H, d), 5.62–5.55 (1H, d), 4.71–4.65 (1H, d), 4.65–4.6 (1H, m), 4.33–4.27 (1H, d), 3.96–3.90 (1H, m), 3.78 (3H, s), 3.44–3.37 (1H, m), 1.4 (9H, s).

(3S)-2-Oxo-3-tert-butoxycarbonylamino-2,3,4,5-tetrahydro-1H-1,5-benzodiazepine-1-acetic acid benzyl ester (600b). Prepared by a similar method described for the preparation of 600a (Step D), except benzyl bromoacetate was used instead of methyl bromoacetate to give 600b in quantitative yield.

(3S)-2-Oxo3-tert-butoxycarbonylamino-2,3,4,5-tetrahydro-7,9-dimethyl-1H-1,5-benzodiazepine-1-acetic acid benzyl ester (600c).

Step A. (2S)-2-tert-Butoxycarbonylamino-3-(2-nitro-3,5-dimethylphenylamino)-propionic acid. Prepared by a method similar as described for 600a (Step A), except 2-fluoro-4,6-dimethyl-nitrobenzene was used instead of 2-fluoronitrobenzene to give the desired compound in 93% yield.

Step B. (2S)-2-tert-Butoxycarbonylamino-3-(2-amino-3,5-dimethylphenyl-amino)-propionic acid. (2S)-2-tert-Butoxycarbonylamino-3-(2-nitro-3,5-dimethylphenylamino)propionic acid was converted to the title compound in quantitative yield as described in the preparation of 600a (Step B).

Step C. 2-Oxo-(3S)-3-tert-butoxycarbonylamino-2,3,4,5-tetrahydro-7,9-dimethyl-1H-1,5-benzodiazepine. A 0° C. solution of (2S)-2-tert-butoxycarbonylamino-3-(2-amino-3,5-dimethylphenyl-amino)-propionic acid (763 mg, 2.36 mmol) and N-methylmorpholine (483 mg, 4.78 mmol) in 60 ml of anhydrous THF was treated dropwise with isobutylchloroformate (352 mg, 2.5 mmol). The reaction was stirred for 2 h at 0° C., at RT for 1 h and poured over EtOAc. The mixture was washed with aq. 5% NaHSO$_4$, sat. aq. NaHCO$_3$, and sat. aq. NaCl, dried over NaSO$_4$, and concentrated in vacuo. Chromatography (flash, SiO$_2$, 10% to 25% to 50% EtOAc/CH$_2$Cl$_2$) gave 490 mg (68%) of the desired product.

Step D. (3S)-2-Oxo-3-tert-butoxycarbonylamino-2,3,4,5-tetrahydro-7,9-dimethyl-1H-1,5-benzodiazepine-1-acetic acid benzyl ester (600c). (2S)-2-tert-Butoxycarbonylamino-3-(2-amino-3,5-dimethylphenyl-amino)-propionic acid was converted to 600c, 75% by a similar method for the preparation of 600b.

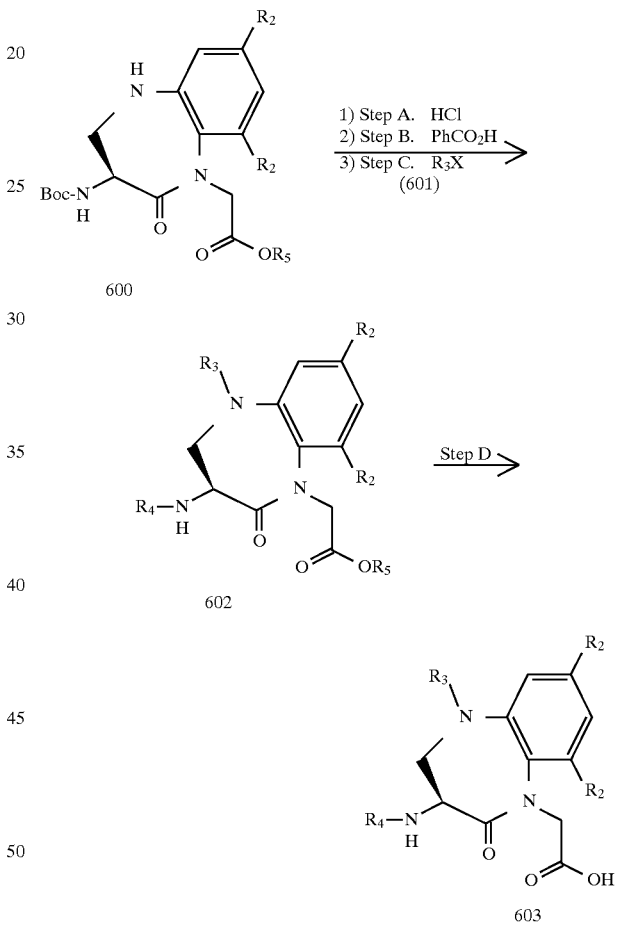

(3S)-2-Oxo-3-benzoylamino-5-(3-phenylpropionyl)-2,3,4,5-tetrahydro-1H-1,5-benzo diazepine-1-acetic acid methyl ester (602a).

Step A. Anhydrous HCl was bubbled into a solution of (3S)-2-oxo-3-tert-butoxycarbonylamino-2,3,4,5-tetrahydro-1H-1,5-benzodiazepine-1-acetic acid methyl ester (600a, 4.0 g, 11.4 mmol) in 20 ml of CH$_2$Cl$_2$ for 20 min then stirred for 1 h at RT. The reaction was evaporated to give (3S)-2-oxo-3-amino-2,3,4,5-tetrahydro-1H-1,5-benzodiazepine-1-acetic acid methyl ester hydrochloride as a white solid.

Step B. The white solid was dissolved in 70 ml of DMF and benzoic acid (1.5 g, 12.3 mmol) was added. The reaction was cooled in a ice/H$_2$O bath and treated with 1-(3- dimethylaminopropyl)-3-ethylcarbodiimide hydrochloride (2.4 g, 12.5 mmol), 1-hydroxybenzotriazole (1.7 g, 12.6 mmol) and diisopropylethylamine (3.0 g, 23.2 mmol). The reaction was stirred for 18 h at RT under nitrogen atmosphere and poured onto $H_2O$. The aq. mixture was extracted with EtOAc (2×). The combined organic layers were washed with aq. 0.5N $NaHSO_4$, $H_2O$, sat. aq. $NaHCO_3$, $H_2O$ and sat. aq. NaCl, dried over $MgSO_4$ and concentrated in vacuo. Chromatography (flash, $SiO_2$, 10% to 30% $EtOAc/CH_2Cl_2$) gave 3.4 g (85%) of (3S)-2-oxo-3-(benzoylamino)-2,3,4,5-tetrahydro-1H-1,5-benzodiazepine-1-acetic acid methyl ester as a white solid.

Step C. Method A. (3S)-2-Oxo-3-benzoylamino-5-(3-phenylpropionyl)-2,3,4,5-tetrahydro-1H-1,5-benzodiazepine-1-acetic acid methyl ester (602a). A solution of (3S)-2-oxo-3-(benzoylamino)-2,3,4,5-tetrahydro-1H-1,5-benzodiazepine-1-acetic acid methyl ester (200 mg, 0.57 mmol) in $CH_2Cl_2$ (10 ml) was treated with triethylamine (119 mg, 1.13 mmol) and 3-phenylpropionyl chloride (114 mg, 0.68 mmol). The reaction was stirred at RT for 30 min and diluted with $CH_2Cl_2$. The solution was washed with aq. 10% HCl sat. aq. $NaHCO_3$ and sat. aq. NaCl, dried over $Na_2SO_4$ and concentrated in vacuo to give 240 mg (87%) of 602a as a white foam.

Step C. Method B. (3S)-2-Oxo-3-benzoylamino-5-acetoacetyl-2,3,4,5-tetrahydro-1H-1,5-benzodiazepine-1-acetic acid benzyl ester (602g). A 0° C. solution of (3S)-2-oxo-3-(benzoylamino)-2,3,4,5-tetrahydro-1H-1,5-benzodiazepine-1-acetic acid benzyl ester (600b) (465 mg, 1.10 mmol) in $CH_2Cl_2$ (5 ml) was treated with acetoacetic acid in 1 ml of $CH_2Cl_2$ followed by slow addition of 1-(3-dimethylaminopropyl)-3-ethylcarbodiimide hydrochloride (431 mg, 2.2 mmol) in 2 ml of $CH_2Cl_2$ under $N_2$ atmosphere. After 15 min the reaction was poured onto EtOAc, washed with aq. 5% $NaHSO_4$, dried over $Na_2SO_4$ and concentrated in vacuo. Chromatography (flash, $SiO_2$, 0% to 10% to 25% $MeOH/CH_2Cl_2$) gave 580 mg of (3S)-2-oxo-3-(benzoylamino)-5-acetoacetyl-2,3,4,5-tetrahydro-1H-1,5-benzodiazepine-1-acetic acid benzyl ester as a white solid.

Step C. Method C. (3S)-2-Oxo-3-benzoylamino-5-methoxycarbonyl-2,3,4,5-tetrahydro-1H-1,5-benzodiazepine-1-acetic acid benzyl ester (602j). A vigorously-stirred, 0° C. solution of (3S)-2-oxo-3-(benzoylamino)-2,3,4,5-tetrahydro-1H-1,5-benzodiazepine-1-acetic acid benzyl ester (600b) (461 mg, 1.07 mmol) in THF (5 ml) and sat. aq. $NaHCO_3$ (2.5 ml) was treated with a THF solution (0.35 ml) of methyl chloroformate (151 mg, 1.6 mmol) and the reaction was stirred for 45 min at RT. The reaction was poured onto $CH_2Cl_2$ and washed with $H_2O$, dried over $Na_2SO_4$ and concentrated in vacuo. Chromatography (flash, $SiO_2$, 0% to 10% $MeOH/CH_2Cl_2$) gave 525 mg of 602j as a white solid.

Step C. Method D. (3S)-2-Oxo-3-benzoylamino-5-benzylaminocarbonyl-2,3,4,5-tetrahydro-1H-1,5-benzodiazepine-1-acetic acid methyl ester (602p). A solution of 600a (400 mg, 1.1 mmol) and benzylisocyanate (166 mg, 1.2 mmol) in 10 ml of $CH_2Cl_2$ and 10 ml of DMF and heated at 80° C. for 3 days. The reaction was cooled to RT poured onto $H_2O$ and extracted with EtOAc (2×). The combined organic layers were washed with $H_2O$ (4×) and sat. aq. NaCl, dried over $MgSO_4$ and concentrated in vacuo. Chromatography (flash, $SiO_2$, 50% to 80% EtOAc/hexane) gave 440 mg (80%) of 602p as a white solid.

Step C. Method E. (3S) 2-Oxo-3-benzylamino-5-(3-phenylpropionyl)-2,3,4,5-tetrahydro-1H-1,5-benzodiazepine-1-acetic acid methyl ester (602v). A solution of (3S) 2-oxo-3-amino-5-(3-phenylpropionyl)-2,3,4,5-tetrahydro-1H-1,5-benzodiazepine-1-acetic acid methyl ester hydrochloride (560 mg, 1.34 mmol), benzaldehyde (146 mg, 1.34 mmol) and sodium acetate (220 mg, 2.68 mmol) in methanol (20 ml) was treated with 4 Å sieves (2 g) and $NaCNBH_3$ (168 mg, 2.68 mmol). The reaction was stirred for 2.5 h, acidified with 10% aq. HCl to pH 2 and washed with $Et_2O$ (2×75 ml). The organic layers were concentrated in vacuo to give an oil. Chromatography (flash, $SiO_2$, 0 to 35% $EtOAc/CH_2Cl_2$) gave 250 mg (40%) of 602v as a clear oil.

Step D. Method A. (3S)-2-Oxo-3-benzoylamino-5-(3-phenylpropionyl)-2,3,4,5-tetrahydro-H-1,5-benzodiazepine-1-acetic acid (603a). (3S)-2-Oxo-3-benzoylamino-5-(3-phenylpropionyl)-2,3,4,5-tetrahydro-1H-1,5-benzo diazepine-1-acetic acid methyl ester (602a; 1.25 g, 2.57 mmol) was dissolved in 11 ml of THF, MeOH and $H_2O$ (5:5:1) and treated with LiOH•$H_2O$ (42 mg, 0.62 mmol) stirred at RT for 64 h. The reaction was concentrated in vacuo, diluted with $H_2O$ and acidified with aq. 1N HCl to give 230 mg of 603a as a white solid.

Step D. Method B. (3S) 2-Oxo-3-benzoylamino-5-acetyl-2,3,4,5-tetrahydro-1H-1,5-benzodiazepine-1-acetic acid (603d). A mixture of (3S)-2-oxo-3-(benzoylamino)-5-acetyl-2,3,4,5-tetrahydro-1H-1,5-benzodiazepine-1-acetic acid benzyl ester (602d; 510 mg, 1.08 mmol) and 5% Pd/C (250 mg) in MeOH (10 ml) stirred under $H_2$ (1 atm) for 0.5 h. The reaction was filtered and concentrated in vacuo 410 mg of 603d as a white solid.

The compounds of Table 5 were prepared as described in Table 6, using the methods of Example 12.

TABLE 5

| Compound no. | $R_2$ | $R_3$ | $R_4$ | $R_5$ |
|---|---|---|---|---|
| 602b | H | $PhCH_2C(O)$ | PhC(O) | $CH_2Ph$ |
| 602c | H | PhC(O) | PhC(O) | $CH_2Ph$ |
| 602d | H | $CH_3C(O)$ | PhC(O) | $CH_2Ph$ |
| 602e | H | $CH_3OCH_2C(O)$ | PhC(O) | $CH_2Ph$ |
| 602f | H | $(CH_3)_2CHCH_2C(O)$ | PhC(O) | $CH_2Ph$ |
| 602g | H | $CH_3C(O)CH_2C(O)$ | PhC(O) | $CH_2Ph$ |
| 602h | H | $CH_3OC(O)C(O)$ | PhC(O) | $CH_2Ph$ |
| 602i | H | $CH_3C(O)C(O)$ | PhC(O) | $CH_2Ph$ |
| 602j | H | $CH_3OC(O)$ | PhC(O) | $CH_2Ph$ |
| 602k | H | $CH_3C(O)$ | Boc | $CH_2Ph$ |
| 602l | $CH_3$ | $CH_3C(O)$ | Boc | $CH_2Ph$ |
| 602m | H | $CH_3S(O_2)$ | PhC(O) | $CH_3$ |
| 602p | H | $PhCH_2NHC(O)$ | PhC(O) | $CH_3$ |
| 602q | H | ⟨furan-2-yl-methyl⟩OCO | PhC(O) | $CH_2Ph$ |
| 602r | H | $PhCH_2CH_2C(O)$ | $PhCH_2CH_2C(O)$ | $CH_2Ph$ |
| 602s | H | 4-pyridyl$CH_2C(O)$ | PhC(O) | $CH_2Ph$ |

TABLE 6

| No. | Starting material | $R_3X$ | Step C method/ (% yield) | Step D method/ (% yield) |
|---|---|---|---|---|
| 603b | 600b | $PhCH_2C(O)Cl$ | A (98) | B (89) |
| 603c | 600b | PhC(O)Cl | A (quant.) | B (quant.) |
| 603d | 600b | $CH_3C(O)Cl$ | A (quant.) | B (quant.) |
| 603e | 600b | $CH_3OCH_2C(O)Cl$ | A (59) | B (quant.) |

TABLE 6-continued

| No. | Starting material | $R_3X$ | Step C method/ (% yield) | Step D method/ (% yield) |
|---|---|---|---|---|
| 603f | 600b | $(CH_3)_2CHCH_2C(O)Cl$ | A (88) | B (95) |
| 603g | 600b | $CH_3C(O)CH_2CO_2H$ | B (quant.) | B (quant.) |
| 603h | 600b | $CH_3OC(O)C(O)Cl$ | A (96) | B (quant.) |
| 603i | 600b | $CH_3C(O)CO_2H$ | B (87) | B (94) |
| 603j | 600b | $CH_3OC(O)Cl$ | C (quant.) | B (quant.) |
| 603k | 600b | $CH_3C(O)Cl$ | A, Step C only (quant.) | not run |
| 603l | 600c | $CH_3C(O)Cl$ | A, Step C only (quant.) | not run |
| 603m | 600a | $CH_3SO_3Cl$, $NEt_3$ instead of pyridine and THF instead of $CH_2Cl_2$ | A (76) | A (92) |
| 603p | 600a | $PhCH_2C{=}N{=}O$ | D (80) | A (86) |
| 603q | 600b | (tetrahydrofuranyl-OCOCl) | C (83) | B (71) |
| 603r | 600a | $PhCH_2CH_2C(O)Cl$ | A | |
| 603s | 600b | $4\text{-pyridyl}CH_2CO_2H$ | B (90) | B (98) |

TABLE 7

| Compound no. | $R_2$ | $R_3$ | $R_4$ | $R_5$ |
|---|---|---|---|---|
| 602n | H | $CH_3C(O)$ | Naphthylene-2-C(O) | $CH_2Ph$ |
| 602o | $CH_3$ | $CH_3C(O)$ | PhC(O) | $CH_2Ph$ |
| 602t | H | $3\text{-}CH_3PhCH_2C(O)$ | PhC(O) | $CH_2Ph$ |
| 602u | H | $CH_3C(O)$ | Fmoc | $CH_2Ph$ |
| 602v | H | $PhCH_2CH_2CO$ | $PhCH_2$ | $CH_3$ |

TABLE 8

| No. | Starting material | 1) Step C. $R_3X$ method (% yield) | 3) Step C $R_4X$ method (% yield) | Step D method (% yield) |
|---|---|---|---|---|
| 603n | 602k | $CH_3C(O)Cl$ A (quant.) | naphthylene-2-C(O)Cl A (70) | B (quant.) |
| 603o | 602l | $CH_3C(O)Cl$ A (quant.) | PhC(O)Cl A (73) | B (quant.) |
| 603t | 602k | $3\text{-}CH_3PhCH_2C(O)Cl$ A (quant.) | PhC(O)Cl A (93) | B (95) |
| 603u | 602k | $CH_3C(O)Cl$ A (quant.) | Fmoc-Cl C (82) | C (98) |
| 603v | 600a | $PhCH_2CH_2C(O)Cl$ A | PhCHO E (40) | A (95) |

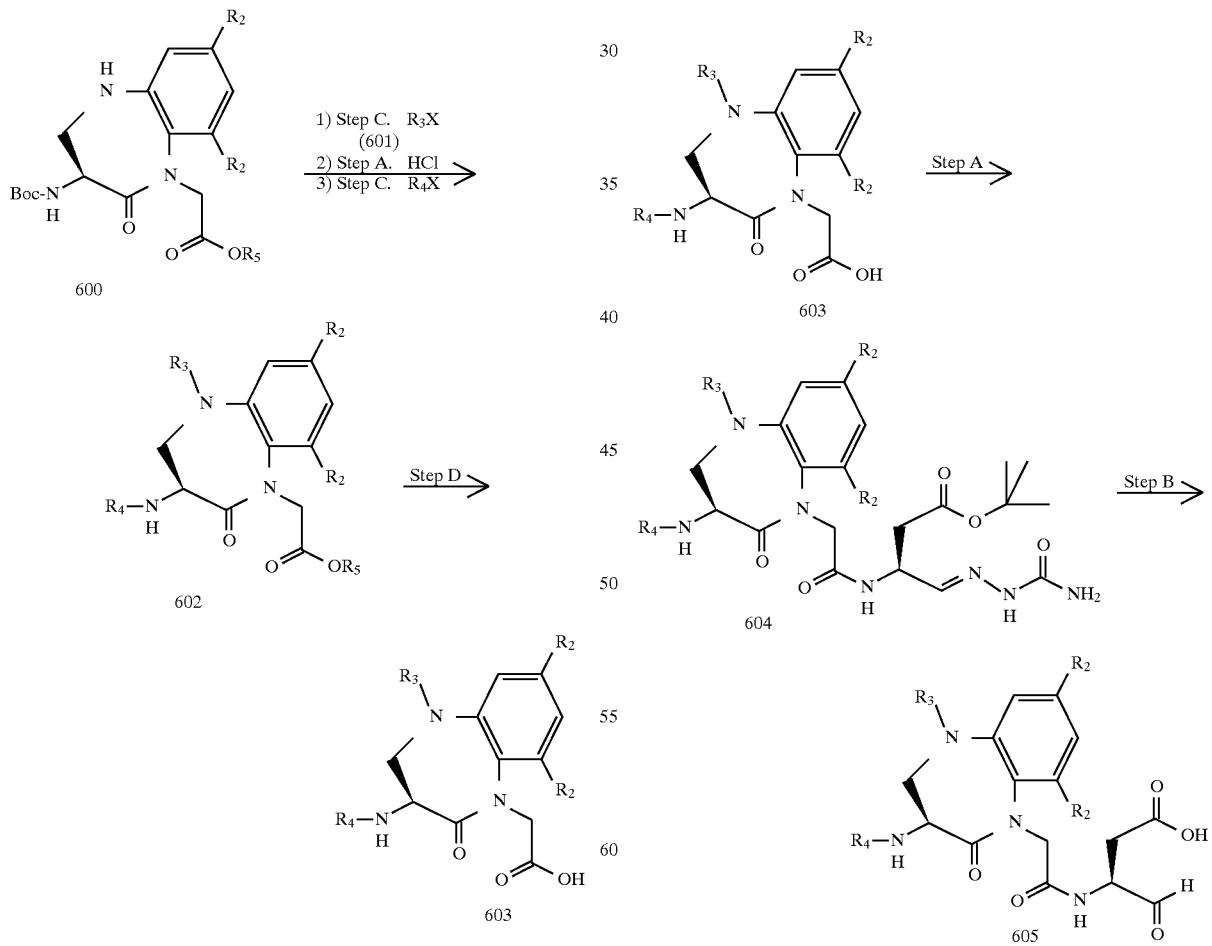

The compounds of Table 7 were prepared as described in Table 6 using the methods of Example 12.

The compounds of Table 9 were prepared by the methods described below.

TABLE 9

| compound no. | R₂ | R₃ | R₄ |
|---|---|---|---|
| 605a | H | PhCH₂CH₂C(O) | PhC(O) |
| 605b | H | PhCH₂C(O) | PhC(O) |
| 605c | H | PhC(O) | PhC(O) |
| 605d | H | CH₃C(O) | PhC(O) |
| 605e | H | CH₃OCH₂C(O) | PhC(O) |
| 605f | H | (CH₃)₂CHCH₂C(O) | PhC(O) |
| 605g | H | CH₃C(O)CH₂C(O) | PhC(O) |
| 605h | H | CH₃OC(O)C(O) | PhC(O) |
| 605i | H | CH₃C(O)C(O) | PhC(O) |
| 605j | H | CH₃OC(O) | PhC(O) |
| 605m | H | CH₃SO₃ | PhC(O) |
| 605n | H | CH₃C(O) | Naphthyl-2-C(O) |
| 605o | CH₃ | CH₃C(O) | PhC(O) |
| 605p | H | PhCH₂NHC(O) | PhC(O) |
| 605q | H | (tetrahydrofuran-OCO) | PhC(O) |
| 605s | H | 4-pyridylCH₂C(O) | PhC(O) |
| 605t | H | 3-CH₃PhCH₂C(O) | PhC(O) |
| 605v | H | PhCH₂CH₂C(O) | PhCH₂ |

(3S)-3-[(3S)-2-Oxo-3-benzoylamino-5-(3-phenylpropionyl)-2,3,4,5-tetrahydro-1H-1,5-benzodiazepin-1-acetylamino]4-oxo-butyric acid (605a).

Step A. (3S)-3-(1-Fluorenylmethyloxycarbonylamino)-4-oxobutyric acid tert-butyl ester semicarbazone (210 mg, 0.45 mol, Prepared in a similar manner to the benzyloxycarbonyl analog in Graybill et al., *Int. J. Protein Res.*, 44, pp. 173–82 (1994).) was dissolved in 10 ml of DMF and 2 ml of diethylamine and stirred for 2 h. The reaction was concentrated in vacuo to give (3S)-3-amino-4-oxobutyric acid tert-butyl ester semicarbazone. The 0° C. solution of the above residue and 603a (200 mg, 0.42 mmol) in 5 ml of DMF and 5 ml of $CH_2Cl_2$ was treated with 1-hydroxybenzotriazole (57 mg, 0.42 mmol) and 1-(3-dimethylaminopropyl)-3ethylcarbodiimide hydrochloride (98 mg, 0.51 mmol). The reaction was stirred at RT for 18 h, poured onto EtOAc (75 ml) and washed with aq. 0.3N $KHSO_4$, sat. aq. $NaHCO_3$ and sat. aq. NaCl, dried over $NaSO_4$ and concentrated in vacuo. Chromatography (flash, $SiO_2$, 0% to 4% $MeOH/0.1\%$ $NH_4OH/CH_2Cl_2$) to give 240 mg (83%) of 604a.

Step B. 604a was stirred with 10 ml of 33% TFA/$H_2O$ for 4 h and concentrated in vacuo. The residue was dissolved in 7 ml of MeOH/acetic acid/37% aq. formaldehyde (5:1:1) and stirred for 18 h. Chromatography (Reverse Phase C18, 4.4 mm ID×25 cm, 15% to 70% $CH_3CN/0.1\%$ TFA/$H_2O$) gave 32 mg (16%) of 605a as a white solid: $^1$H NMR ($CD_3OD$, existing as diastereomers of the hemiacetal) δ 7.85–7.78 (2H, d), 7.5–7.32 (6H, m), 7.32–7.28 (1H, m), 7.18–6.98 (5H, m), 4.92–4.85 (2H, m), 4.5–4.32 (2H, m), 4.31–4.20 (2H, m), 3.7–3.6 (1H, m), 2.90–2.75 (2H, m), 2.65–2.5 (1H, m), 2.48–2.25 (3H, m).

The following compounds were prepared by a similar method:

(3S)-3-[(3S)-2-Oxo-3-benzoylamino-5-phenylacetyl-2,3,4,5-tetrahydro-1H-1,5-benzodiazepin-1-acetylamino]4-oxo-butyric acid (605b). 148 mg (33%) as a white solid: $^1$H NMR($CD_3OD$) δ 7.9–6.9 (m, 16H), 4.9 (s, 2H), 4.5 (m, 1H), 4.4 (m, 2H), 3.75 (s, 1H), 3.6 (dd, 1H), 3.45 (dd, 1H), 2.7 (m, 1H), 2.5 (m, 1H).

(3S)-3-[(3S)-2-Oxo-3-benzoylamino-5-benzoyl-2,3,4,5-tetrahydro-1H-1,5-benzodiazepin-1-acetylamino]4-oxo-butyric acid (605c). 319 mg (56%) as a white solid: $^1$H NMR($CD_3OD$) δ 7.9–6.9 (m, 16H), 5.1 (m, 1H), 4.9 (dd, 1H), 4.7 (m, 1H), 4.6 (dd, 1H), 4.4 (m, 2H), 4.05 (m, 1H), 2.7 (m, 1H), 2.5 (m, 1H).

(3S)-3-[(3S)-2-Oxo-3-benzoylamino-5-acetyl-2,3,4,5-tetrahydro-1H-1,5-benzodiazepin-1-acetylamino]4-oxo-butyric acid (605d). 190 mg (38%) as a white solid: $^1$H NMR($CD_3OD$) δ 1.9(d, H), 2.4(m, 1H), 2.65(m, 1H), 3.7(m, 1H), 4.25(m, 1H), 4.45(m, 2H), 4.8–5.05(m, 3H), 7.3–7.7 (m, 7H), 7.9(d, 2H).

(3S)-3-[(3S)-2-Oxo-3-benzoylamino-5-methoxyacetyl-2,3,4,5-tetrahydro-1H-1,5-benzodiazepin-1-acetylamino]4-oxo-butyric acid (605e). 250 mg (78%) $^1$H NMR ($CD_3OD$) δ 1.87 (bs), 1.95 (s, 2H), 2.1 (bs), 2.4 (m, 2H), 2.65 (m, 2H), 3.59 (bs), 3.75 (bs), 3.87 (bs), 4.19 (m), 4.37 (m), 4.50–4.78 (bm), 4.92 (m), 5.27 (bs), 7.41–7.58 (m, 7H), and 7.87 ppm (d, 2H).

(3S)-3-[(3S)-2-Oxo-3-benzoylamino-5-(3-methylbutyryl)-2,3,4,5-tetrahydro-1H-1,5-benzodiazepin-1-acetylamino]4-oxo-butyric acid (605f). 210.5 mg (46%) as a white solid: $^1$H NMR($CD_3OD$) δ 7.9–7.4 (m, 9H), 5.1 (m, 1H), 4.9 (m, 1H), 4.6 (dd, 1H), 4.4 (m, 2H), 4.1 (d, 1H), 3.8 (m, 1H), 3.5 (q, 1H), 2.7 (m, 1H), 2.5 (m, 1H), 2.0 (m, 3H), 1.2 (t, 1H), 0.9 (d, 3H), 0.8 (d, 3H).

(3S)-3-[(3S)-2-Oxo-3-benzoylamino-5-acetoacetyl-2,3,4,5-tetrahydro-1H-1,5-benzodiazepin-1-acetylamino]4-oxo-butyric acid (605g). 81 mg (19%) as a white solid: $^1$H NMR($CD_3OD$) δ 7.9–7.3 (m, 11H), 4.9–4.8 (m, 2H), 4.6–4.4 (m, 3H), 4.3 (m, 1H), 3.75 (q, 1H), 3.55 (d, 1H), 2.7 (m, 1H), 2.5 (m, 1H), 2.05 (s, 3H).

(3S)-3-[(3S)-2-Oxo-3-benzoylamino-5-methyloxalyl-2,3,4,5-tetrahydro-1H-1,5-benzodiazepin-1-acetylamino]4-oxo-butyric acid (605h). 227 mg (54%) of a white solid: $^1$H NMR($CD_3OD$) δ 2.5(m, 1H), 2.7(m, 1H), 3.55(s, 3H), 3.8–4.0 (m, 2H), 4.4 (m, 1H), 4.6–4.8(m, 2H), 4.95(d, 1H), 5.1(m, 1H), 7.3–7.7(m, 7H), 7.9(d, 2H), 8.6 (d, 1H).

(3S)-3-[(3S)-2-Oxo-3-benzoylamino-5-acetylcarbonyl-2,3,4,5-tetrahydro-1H-1,5-benzodiazepin-1-acetylamino]4-oxo-butyric acid (605i). 150 mg (37%) as a white solid: $^1$H NMR($CD_3OD$) δ 7.9–7.3 (m, 12H), 5.1 (m, 1H), 4.65 (t, 1H), 4.55 (dd, 1H), 4.35 (m, 1H), 4.1 (d, 1H), 3.9 (q, 1H), 3.45 (q, 1H), 2.7 (m, 1H), 2.5 (m, 1H), 2.25 (s, 3H).

(3S)-3-[(3S)-2-Oxo-3-benzoylamino-5-methoxycarbonyl-2,3,4,5-tetrahydro-1H-1,5-benzodiazepin-1-acetylamino]4-oxo-butyric acid (605j). 234 mg (44%) as a white solid: $^1$H NMR($CD_3OD$) δ 7.9–7.4 (m, 12H), 5.0 (m, 1H), 4.8–4.5 (m, 3H), 4.4 (m, 1H), 4.3 (t, 1H), 3.9–3.75 (m, 2H), 3.6 (s, 3H), 2.7 (m, 1H), 2.5 (m, 1H).

(3S)-3-[(3S)-2-Oxo-3-benzoylamino-5-methanesulfonyl-2,3,4,5-tetrahydro-1H-1,5-benzodiazepin-1-acetylamino]4-oxo-butyric acid (605m). 64.5 mg (34%) as a white solid: $^1$H NMR (DMSO-$d_6$, existing as diastereomers of the hemiacetal & open form of the aldehyde) δ 9.48 (0.2H, s), 8.85–8.72 (1H, m), 8.65–8.60 (0.8 H, d), 8.30–8.26 (0.2 H, d), 7.95–7.88 (2H,d), 7.6–7.45 (6H, m), 7.44–7.38 (1H, m), 5.78–5.75 (0.2H, d), 5.48 (0.6H, s), 4.85–4.70 (2H, m), 4.62–4.54 (1H, d), 4.50–4.40 (2H, m), 4.25–4.14 (1H, m), 3.9–3.85 (1H, m), 3.16 (3H, s), 3.05–2.3 (2, m).

(3S)-3-[(3S)-2-Oxo-3-benzoylamino-5-(naphthalene-2-carbonyl)-2,3,4,5-tetrahydro-1H-1,5-benzodiazepin-1-acetylamino]4-oxo-butyric acid (605n). 103 mg (17%) as a white solid: $^1$H NMR ($CD_3OD$) δ 1.9(s, 3H), 2.5(m, 1H), 2.65(m, 1H), 3.75(m, 1H), 4.3(m,1H), 4.5–4.7(m, 3H), 4.85–5.1(m, 2H), 7.3–7.65(m, 6H), 7.85–8.05 (m, 4H), 8.45(s, 1H).

(3S)-3-[(3S)-2-Oxo-3-benzoylamino-5-acetyl-2,3,4,5-tetrahydro-7,9-dimethyl-1H-1,5-benzodiazepin-1- acetylamino]4-oxo-butyric acid (605o). 42 mg (12%) as a white solid: ¹H NMR (CD₃OD, existing as diastereomers of the hemiacetal) δ 7.85–7.74 (2H, m), 7.5–7.44 (1H, m), 7.43–7.35 (4H, m), 5.6–5.05 (2H, m), 4.82–4.42 (2H, m), 4.40–3.95 (2H, m), 3.6–3.5 (1H, m), 2.7–2.38 (2H, m), 2.32 (3H, s), 2.27 (3H, s), 1.92 (3H,s).

(3S)-3-[(3S)-2-Oxo-3-benzoylamino-5-benzylaminocarbonyl-2,3,4,5-tetrahydro-1H-1,5-benzodiazepin-1-acetylamino]4-oxo-butyric acid (605p). 165 mg (37%) as a white solid: ¹H NMR (CD3OD) δ 2.45(m, 1H), 2.7(m, 1H), 3.8(m, 1H), 4.15–4.5(m, 4H), 4.54–4.75(m, 2H), 4.8–5.0(m, 2H), 7.1–7.7(m, 12H), 7.9(d, 2H).

(3S)-3-[(3S)-2-Oxo-3-benzoylamino-5-[(3R,S) 3-tetrahydrofuranylmethyoxycarbonyl]-2,3,4,5-tetrahydro-1H-1,5-benzodiazepin-1-acetylamino]4-oxo-butyric acid (605q). 210 mg (66%) ¹H NMR (CD₃OD) δ 1.95 (s, 2H), 2.4 (m, 2H), 2.65 (m, 2H), 3.29 (s, 3H), 3.78 (m), 3.87 (bs), 4.0 (d, 1H), 4.32 (m), 4.50–4.15 (m), 4.95 (m), 5.27 (bs), 7.45–7.65 (m, 7H), and 7.89 ppm (d, 2H).

(3S)-3-[(3S)-2-Oxo-3-benzoylamino-5-(4-pyridylacetyl)-2,3,4,5-tetrahydro-1H-1,5-benzodiazepin-1-acetylamino]4-oxo-butyric acid (605s). 128 mg (19%) as a white solid: ¹H NMR (CD₃OD) δ 8.5–7.4 (m, 13H), 5.0 (m, 1H), 4.7 (m, 1H), 4.5 (m, 2H), 4.45–4.4 (m, 3H), 3.8–3.7 (m, 2H), 2.7 (m, 1H), 2.5 (m, 1H).

(3S)-3-[(3S)-2-Oxo-3-benzoylamino-5-(3-methylphenylacetyl)-2,3,4,5-tetrahydro-1H-1,5-benzodiazepin-1-acetylamino]4-oxo-butyric acid (605t). 132 mg (24%) as a white solid: ¹H NMR (CD₃OD) δ 7.8–6.7 (m, 13H), 4.9 (t, 1H), 4.75 (dd, 1H), 4.2 (dd, 1H), 4.1 (m, 2H), 3.8 (dd, 1H), 3.6 (q, 1H), 3.45 (dd, 1H), 3.3 (dd, 1H), 2.6 (m, 1H), 2.3 (m, 1H), 2.15 (s, 3H).

(3S) 3-[(3S) 2-Oxo-3-benzylamino-5-(3-phenylpropionyl)-2,3,4,5-tetrahydro-1H-1,5-benzodiazepin-1-acetylamino]4-oxo-butyric acid trifluoroacetic acid salt (605v). 88 mg (28%) as a white solid: ¹H NMR (CD₃OD) δ 7.63–7.51 (2H, m), 7.5–7.35 (7H, m), 7.25–7.10 (3H,m), 7.1–7.02 (2H, m), 5.04–4.96 (1H, m), 4.75–4.57 (2H, m), 4.38–4.26 (2H,m), 4.24–4.12 (2H, m), 4.10–4.02 (1H, d), 4.88–4.80 (1H, m), 2.90–2.80 (2H, m), 2.78–2.63 (1H,m), 2.55–2.35 (2H, m), 2.34–2.22 (1H, m).

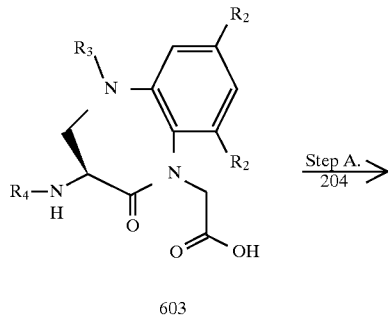

603

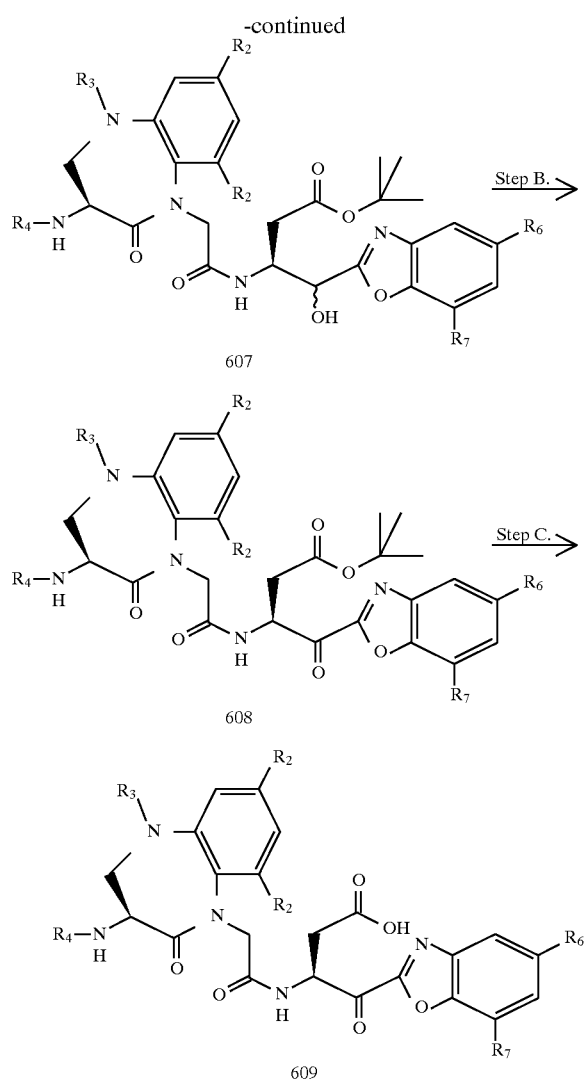

607

608

609

The compounds of Table 10 are described below.

TABLE 10

| # | R₂ | R₃ | R₄ | R₆ | R₇ |
|---|----|----|----|----|----|
| 609a | H | PhCH₂CH₂C(O) | PhCH₂CH₂C(O) | Cl | Cl |
| 609b | H | CH₃C(O) | PhC(O) | Cl | Cl |

(3S)-3-[(3S)-2-Oxo-3-(3-phenylpropionylamino)-5-(3-phenylpropionyl)-2,3,4,5-tetrahydro-1H-1,5-benzodiazepin-1-acetylamino]-4-(5,7-dichlorobenzoxazol-2-yl)-4-oxo-butyric acid (609a).

Step A. A solution of 204 (223 mg, 0.5 mmol) and 603r (300 mg; 0.36 mmol) in 4 ml of DMF and 4 ml of CH₂Cl₂ was treated with (Ph₃P)₂PdCl₂ (10 mg), 1-hydroxybenzotriazole (135 mg, 1.0 mmol) and 1-(3-dimethylaminopropyl)-3-ethylcarbodiimide hydrochloride (115 mg, 0.6 mmol). Tri-n-butyl tin hydride (219 mg, 0.75 mmol) was added dropwise to the reaction and stirred for 18 h. The reaction was poured onto EtOAc and washed with aq. 10% NaHSO₄, sat. aq. NaHCO₃ and sat. aq. NaCl, dried over Na₂SO₄ and concentrated in vacuo. Chromatography (flash, SiO₂, 0% to 50% EtOAc/hexane) gave 360 mg (86%) of 607a as a foam.

Step B. A solution of 607a (360 mg) in 5 ml of CH₂Cl₂ was added dropwise to a suspension of 1,1,1-triacetoxy-1, 1-dihydro-1,2-benziodioxol-3(1H)-one (362 mg, 0.85 mmol) in 20 ml of CH₂Cl₂. The reaction was stirred for 4.5 h, diluted with CH₂Cl₂ and washed with a 1:1 mixture of sat. aq. NaHCO₃/sat. aq. Na₂S₂O₃, sat. aq. NaHCO₃ (2×) and sat. aq. NaCl, dried over Na₂SO₄ and concentrated in vacuo. Chromatography (flash, SiO₂, 20% EtOAc/CH₂Cl₂) gave 340 mg (95%) of the ketone 608a.

Step C. 608a (300 mg, 0.36 mmol) was dissolved in 25 ml of 25% TFA/CH₂Cl₂ and stirred at RT for 5 h and concentrated in vacuo. Chromatography (flash, SiO₂, 0 to 5% MeOH/CH₂Cl₂) gave 118 mg (42%) of 609a as a white solid: $^1$H NMR (CD₃OD) δ 7.62–6.65 (16H, m), 4.85–4.7 (1H, m), 4.68–4.42 (2H, m), 4.40–4.15 (2H, m), 3.48–3.28 (1H, m), 3.0–2.9 (1H, m), 2.9–2.6 (4H, m), 2.55–2.18 (3H, m), 2.16–1.96 (2H, m).

(3S)-3-[(3S)-2-Oxo-3-benzoylamino-5-acetyl-2,3,4,5-tetrahydro-1H-1,5-benzodiazepin-1-acetylamino]-4-(5,7-dichloro-benzoxazol-2-yl)-4-oxo-butyric acid (609b) was prepared from 603d in a similar manner as 609a to give 287 mg (43% overall yield) as white solid: $^1$H NMR (DMSO-d₆) δ 1.6(s, 3H), 2.7–3.1(m, 2H), 3.45(m, 1H), 4.4(t, 1H), 4.7(m, 2H), 4.95(m, 1H), 5.2, 5.4(2s, 1H), 7.2–7.65(m, 8H), 7.9(d, 2H), 8.8(t, 1H), 8.9,9.1(2s, 1H), 12.6(br, 1H).

(3S)-3-[(3S)-2-Oxo-3-benzoylamino-5-methanesulfonyl-2,3,4,5-tetrahydro-1H-1,5-benzodiazepine-1-acetylamino]-5-(2,6-dichlorobenzoyloxy)-4-oxo-pentanoic acid (612) was prepared by a method similar as 607a (Steps A and C only) using 603m (150 mg, 0.36 mmol) instead of 603r and (3S)-3-(allyloxycarbonylamino)-4-oxo-5-(2,6-dichlorobenzoyl-oxy)pentanoic acid t-butyl ester (110; 160 mg, 0.36 mmol, WO 93/16710) instead of 606a to give 612 (56%) as a white solid: $^1$H NMR (CDCl₃) 7.85–7.10 (12H, m), 5.4–4.65 (4H, m), 4.6–4.15 (4H, m), 3.10–2.72 (5H, s & m).

EXAMPLE 13

Compounds 619–635 were synthesized as described in Example 13 and FIG. 2.

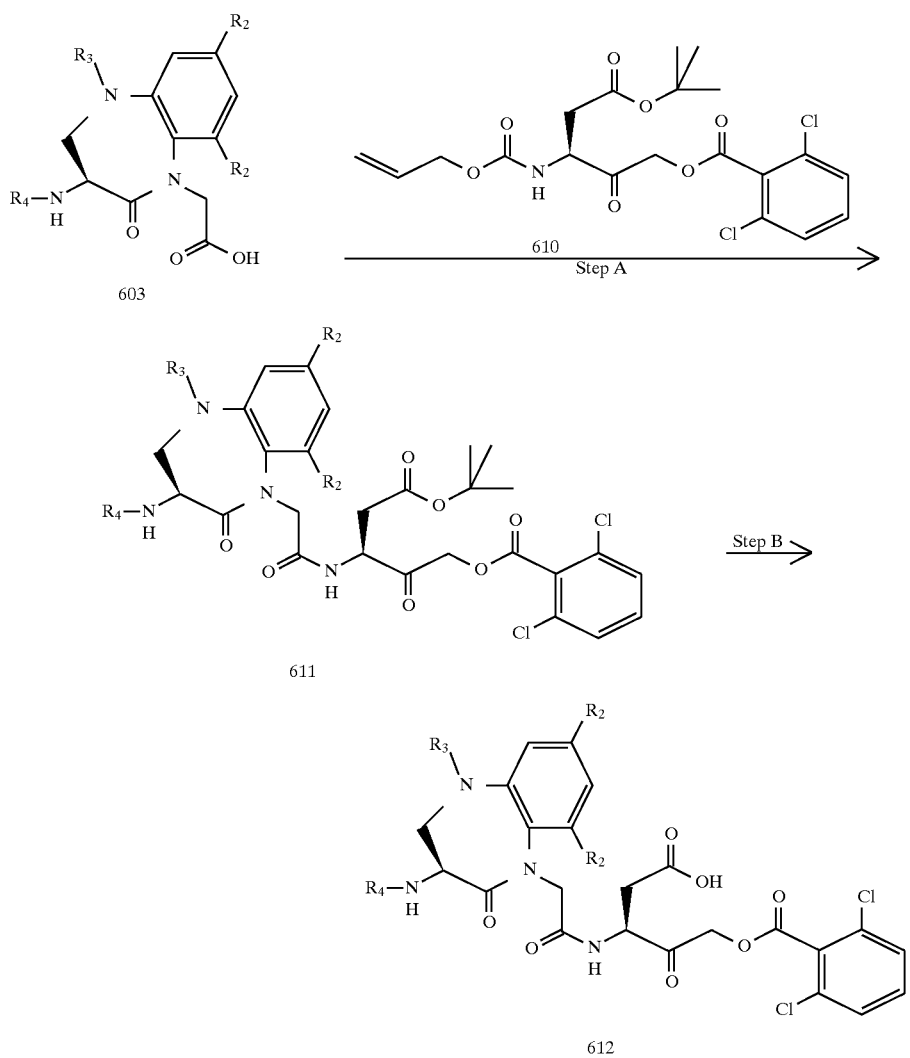

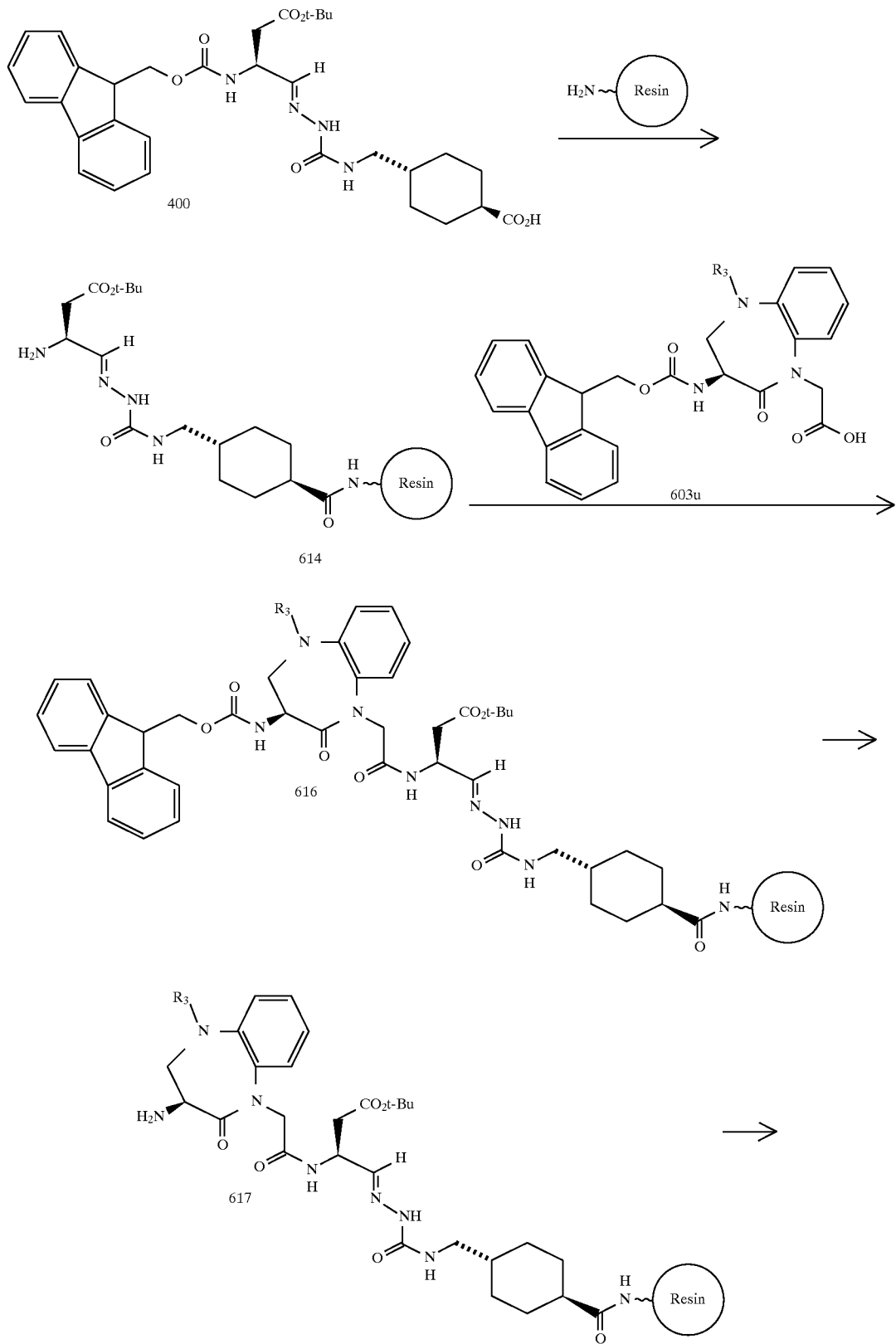

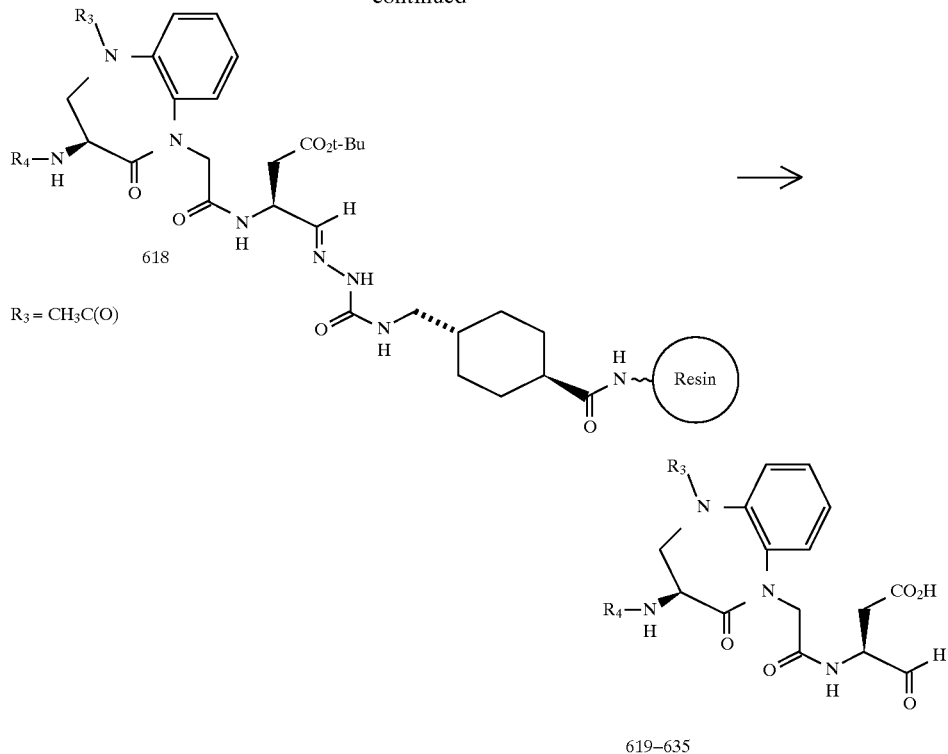

Syntheses of 619–635

Step A. Synthesis of 614. TentaGel S® NH$_2$ resin (0.16 mmol/g, 10.0 g) was placed in a sintered glass funnel and washed with dimethylformamide (3×50 mL), 10% (v/v) diisopropylethylamine (DIEA) in dimethylformamide (2×50 mL) and finally with dimethylformamide (4×50 mL). Sufficient dimethylformamide was added to the resin to obtain a slurry followed by 400 (1.42 g, 2.4 mmol, prepared from (3S) 3-(fluorenylmethyloxycarbonyl)-4-oxobutryic acid t-butyl ester according to A. M. Murphy et. al. *J. Am. Chem. Soc.*, 114, 3156–3157 (1992)), 1-hydroxybenzotriazole hydrate (HOBT.H$_2$O; 0.367 g, 2.4 mmol), O-benzotriazole-N,N,N',N'-tetramethyluronium hexafluorophosphate (HBTU; 0.91 g, 2.4 mmol), and DIEA (0.55 mL, 3.2 mmol). The reaction mixture was agitated overnight at room temperature using a wrist arm shaker. The resin was isolated on a sintered glass funnel by suction filtration and washed with dimethylformamide (3×50 mL). Unreacted amine groups were then capped by reacting the resin with 20% (v/v) acetic anhydride/dimethylformamide (2×25 mL) directly in the funnel (10 min/wash). The resin was washed with dimethylformamide (3×50 mL) and dichloromethane (3×50 mL) prior to drying overnight in vacuo to yield 614 (11.0 g, quantitative yield).

Step B. Synthesis of 616. Resin 614 (3.0 g, 0.16 mmol/g, 0.48 mmol) was swelled in a sintered glass funnel by washing with dimethylformamide (3×15 mL). The Fmoc protecting group was then cleaved with 25% (v/v) piperidine/dimethylformamide (15 mL) for 10 min (intermittent stirring) and then for 20 min with fresh piperidine reagent (15 ml). The resin was then washed with dimethylformamide (3×15 ml), followed by N-methypyrrolidone (2×15 mL). After transferring the resin to a 100 mL flask, N-methypyrrolidone was added to obtain a slurry followed by 603u (0.736 g, 0.72 mmcl), HOBT.H$_2$O (0.112 g, 0.73 mmol), HBTU (0.27 g, 0.73 mmol) and DIEA (0.26 mL, 1.5 mmol). The reaction mixture was agitated overnight at room temperature using a wrist arm shaker. The resin work-up and capping with 20% (v/v) acetic anhydride in dimethylformamide were performed as described for 614 to yield 616 (3.13 g, quantitative yield).

Step C. Synthesis of 617. This compound was prepared from resin 616 (0.24 g, 0.038 mmol) using an Advanced ChemTech 396 Multiple Peptide synthesizer. The automated cycles consisted of a resin wash with dimethylformamide (3×1 mL), deprotection with 25% (v/v) piperidine in dimethylformamide (1 mL) for 3 min followed by fresh reagent (1 mL) for 10 min to yield resin 617. The resin was washed with dimethylformamide (3×1 mL) and N-methypyrrolidone (3×1 mL).

Step D. Method 1. (624). Resin 617 was acylated with a solution of 0.4M thiophene-3-carboxylic acid and 0.4M HOBT in N-methypyrrolidone (1 mL), a solution of 0.4M HBTU in N-methylpyrrolidone (0.5 mL) and a solution of 1.6M DIEA in N-methypyrrolidone (0.35 mL) and the reaction was shaken for 2 hr at room temperature. The acylation step was repeated. Finally, the resin was washed with dimethylformamide (3×1 mL), dichloromethane (3×1 mL) and dried in vacuo. The aldehyde was cleaved from the resin and globally deprotected by treatment with 95% TFA/5% H$_2$O (v/v, 1.5 mL) for 30 min at room temperature. After washing the resin with cleavage reagent (1 mL), the combined filtrates were added to cold 1:1 ether:pentane (12 mL) and the resulting precipitate was isolated by centrifugation and decantation. The resulting pellet was dissolved in 10% acetonitrile/90% H2O/0.1% TFA (15 mL) and lyophilized to obtain crude 624 as a white powder. The compound was purified by semi-prep RP-HPLC with a Rainin Microsorb™ C18 column (5μ, 21.4×250 mm) eluting with a linear acetonitrile gradient (5%–45%) containing 0.1% TFA (v/v) over 45 min at 12 mL/min. Fractions containing the desired product were pooled and lyophilized to provide 624 (10.0 mg, 54%).

Step D. Method 1A. Synthesis of 627. Following a similar procedure as method 1, resin 617 was acylated with 4-(1-fluorenylmethoxycarbonylamino)benzoic acid and repeated. The Fmoc group was removed as described in Step C and the free amine was acetylated with 20% (v/v) acetic anhydride in dimethylformamide (1 mL) and 1.6M DIEA in N-methylpyrrolidone (0.35 mL) for 2 hr at room temperature. The acetylation step was repeated. Cleavage of the aldehyde from the resin gave 627 (4.2 mg, 20%).

Step D. Method 2. Synthesis of 632. Following a similar procedure as method 1, resin 617 was acylated with 0.5M cinnamoyl chloride in N-methypyrrolidone (1 mL) and 1.6M DIEA in N-methypyrrolidone (0.35 mL) for 2 hr at room temperature. The acylation step was repeated. Cleavage of the aldehyde from the resin gave 632 (11.1 mg, 58%).

Step D. Method 3. Synthesis of 629. Following a similar procedure as method 1, resin 617 was reacted with 1.0M benzenesulfonyl chloride in dichloromethane (0.5 mL) and 1M pyridine in dichloromethane (0.60 mL) for 4 hr at room temperature. The reaction was repeated. Cleavage of the aldehyde from the resin 629 (4.7 mg, 24%).

Analytical HPLC methods:
(1) Waters DeltaPak C18, 300A (5u, 3.9×150 mm). Linear acetonitrile gradient (5%–45%) containing 0.1% TFA (v/v) over 14 min at 1 mL/min.

EXAMPLE 14

Compounds 1605a–j, 1605m, 1605n, 1605p, 1605t, and 1605v were synthesized as described below.

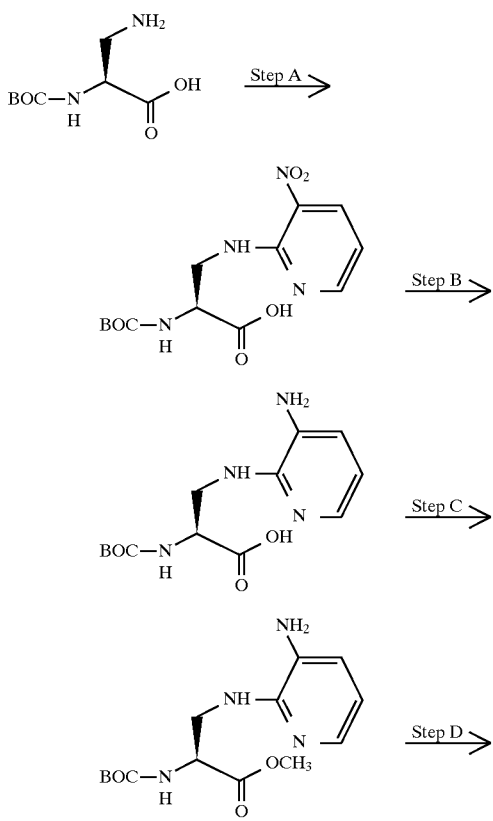

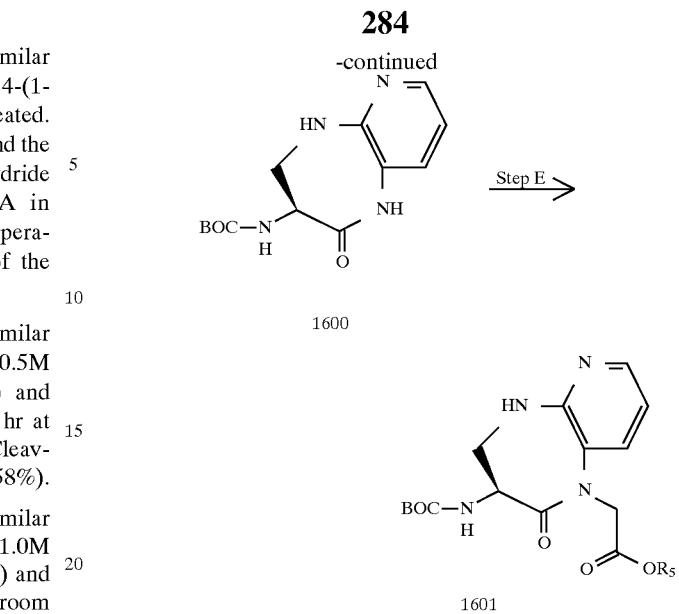

(3S) N-(2-Oxo-3-tert-butoxycarbonylamino-2,3,4,5-tetrahydro-1H-pyrido[3,4-b][1,4-diazepine (1600).

Step A. (2S) 2-tert-Butoxycarbonylamino-3-(3-nitropyridin-2-ylamino)propionic acid was prepared by a similar method as (2S) 2-tert-butoxycarbonylamino-3-(2-nitrophenyl-amino)propionic acid in Step A of the synthesis of 600a, except that 3-chloro-3-nitro pyridine was used instead of 2-fluoronitrobenzene, to give 4.05 g (64%) of a yellow solid.

Step B. (2S) 2-tert-Butoxycarbonylamino-3-(3-aminopyridin-2-ylamino)propionic acid was prepared by a similar method to (2S) 2-tert-Butoxycarbonylamino-3-(2-aminophenylamino)-propionic acid in Step B of the synthesis of 600a to give 3.68 g (quant.) as a dark solid.

Step C. (2S) 2-tert-Butoxycarbonylamino-3-(3-aminopyridin-2-ylamino)propionic acid methyl ester. A solution of (2S) 2-tert-Butoxycarbonylamino-3-(3-aminopyridin-2-ylamino)-propionic acid (360 mg, 1.21 mmol) and MeOH (59 mg, 1.82 mmol) in anhydrous $CH_2Cl_2$ (20 ml) was treated with 4-dimethylaminopyridine (DMAP, 163 mg, 1.33 mmol) and 1-(3-dimethylaminopropyl)-3-ethylcarbodiimide hydrochloride (280 mg, 1.45 mmol). The reaction was stirred for 18 h, diluted with EtOAc (150 ml), washed with water (2×), sat. aq. $NaHCO_3$, and sat. aq. NaCl, dried over $Na_2SO_4$ and concentrated in vacuo. Chromatography (flash, $SiO_2$, 0 to 5% MeOH/$CH_2Cl_2$) gave 250 mg (67%) of the title compound as a light tan solid.

Step D. (3S) N-(2-Oxo-3-tert-butoxycarbonylamino-2,3,4,5-tetrahydro-1H-pyrido[3,4-b][1,4-diazepine (1600). A solution of (2S) 2-tert-butoxycarbonylamino-3-(3-aminopyridin-2-ylamino)propionic acid methyl ester (70 mg, 0.225 mol) and 25% sodium methoxide/MeOH (130 μl, 0.56 mmol) in anhydrous MeOH (4 ml) was heated at 60° C. for 16 h. The reaction was concentrated in vacuo, the residue dissolved in 2 ml of $H_2O$ and extracted with EtOAc (3×). The combined extracts were dried over $Na_2SO_4$ and concentrated in vacuo. Chromatography (flash, $SiO_2$, 0 to 3% MeOH/$CH_2Cl_2$) gave 7.5 mg (3%) of 1600 as a light tan solid: $^1$H NMR (CD$_3$OD) δ 7.96–7.92 (1H, d), 7.75–7.65 (1H, br. s), 7.14–7.08 (1H, d), 6.73–6.65 (1H, m), 5.83–5.75 (1H, br. s), 5.4–5.25 (1H, br. s), 4.6–4.5 (1H,m), 3.95–3.84 (1H, m), 3.55–3.48 (1H, m), 1.4 (9H, s)

Step E. 1601 is prepared from 1600 following the method in Step D for the preparation 600a.

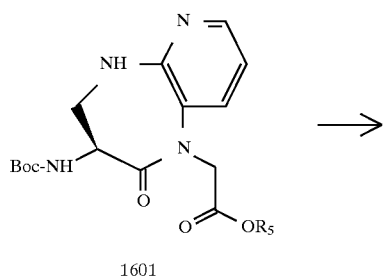

1601

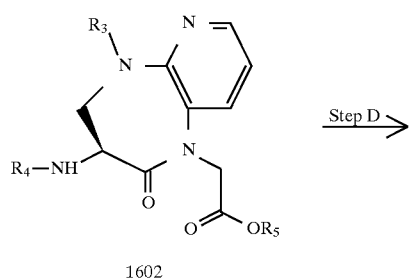

1602

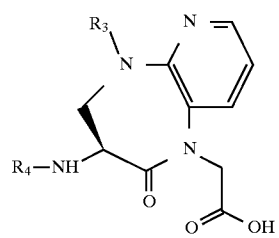

1603

Synthesis of 1603. 1603 is prepared from 1601 following the methods for the synthesis of 603 from 600.

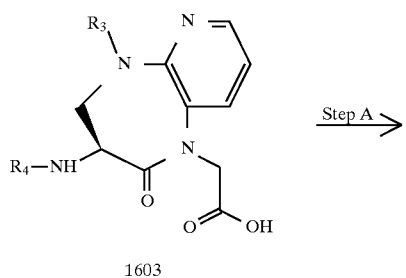

1603

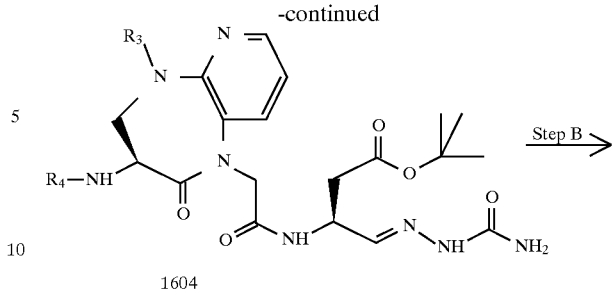

1604

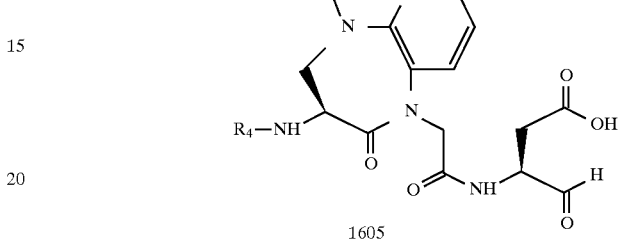

1605

Synthesis of 1605. 1605 is prepared from 1603 by methods described for the synthesis of 605 from 603.

TABLE 11

| 1605 | $R_3$ | $R_4$ |
|---|---|---|
| a | $PhCH_2CH_2CO$ | PhCO |
| b | $PhCH_2CO$ | PhCO |
| c | PhCO | PhCO |
| d | $CH_3CO$ | PhCO |
| e | $CH_3OCH_2CO$ | PhCO |
| f | $(CH_3)_2CHCH_2CO$ | PhCO |
| g | $CH_3COCH_2CO$ | PhCO |
| h | $CH_3OCOCO$ | PhCO |
| i | $CH_3COCO$ | PhCO |
| j | $CH_3OCO$ | PhCO |
| m | $CH_3SO_3$ | PhCO |
| n | $CH_3CO$ | Naphthyl-2-CO |
| p | $PhCH_2NHCO$ | PhCO |
| t | $3\text{-}CH_3PhCH_2CO$ | PhCO |
| v | $PhCH_2CH_2CO$ | $PhCH_2$ |

EXAMPLE 15

Compounds 1610–1621 are prepared from 1600 by methods similar to the methods used to prepare compounds 619–635 from 600a and 600b.

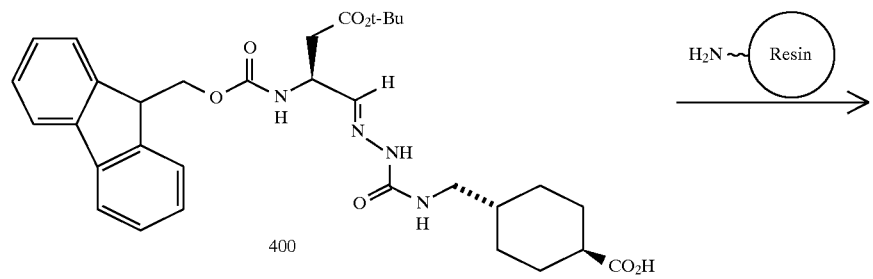

400

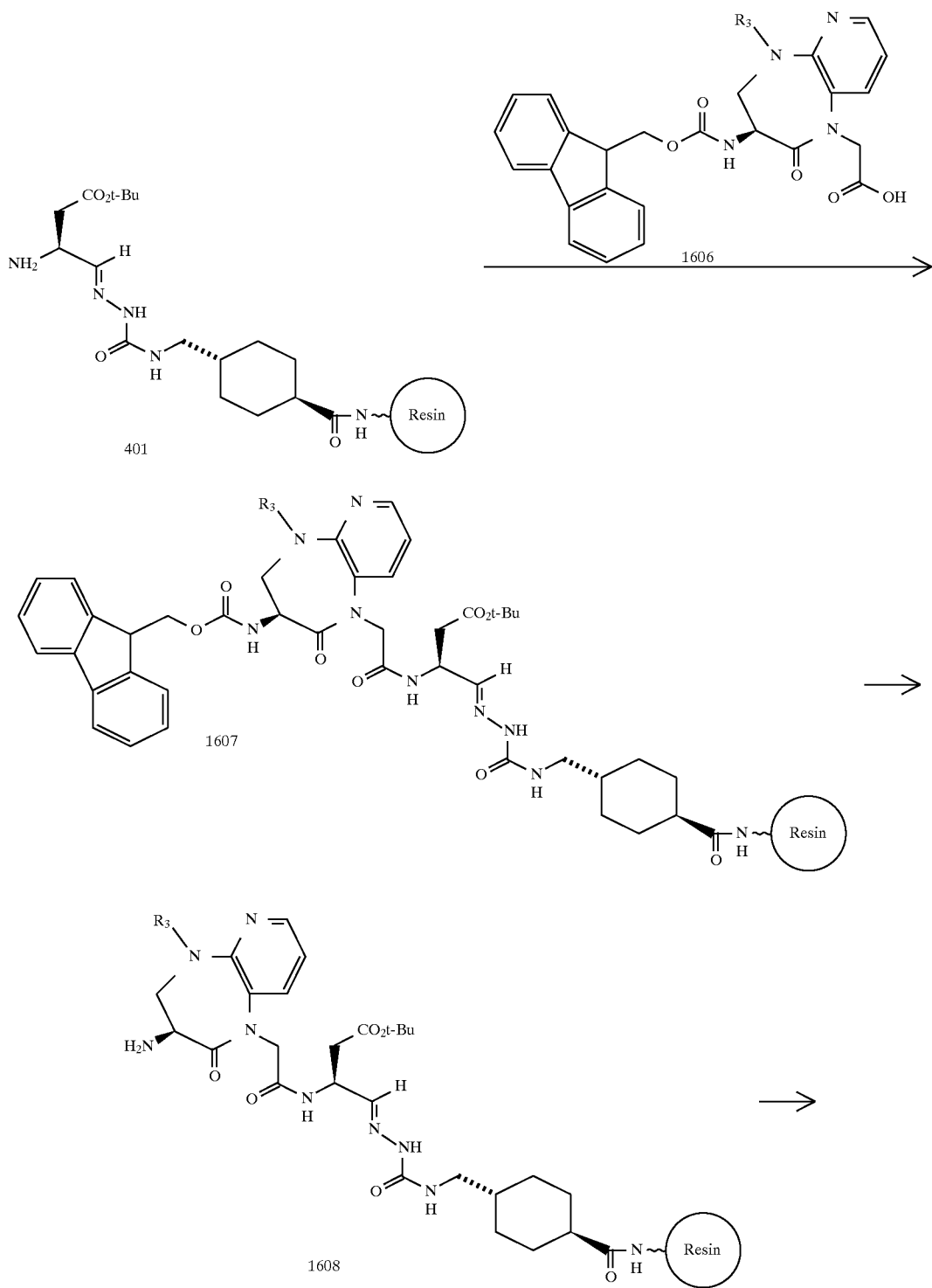

-continued
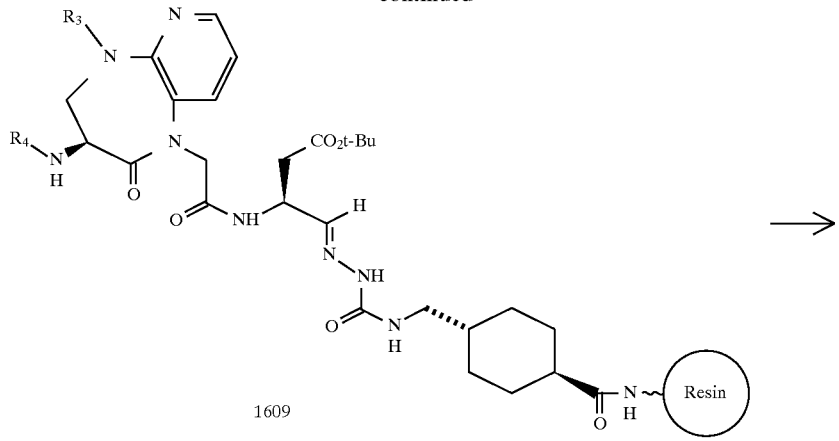
1609
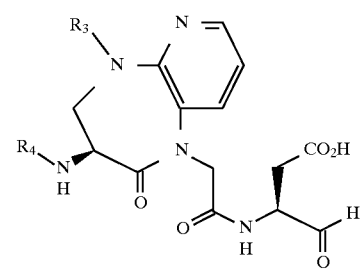
1610–1621
wherein for compounds 1610–1621,
a $R_3$=CH$_3$C(O)—
b $R_3$=CH$_3$OCH$_2$C(O)—:
$R_4$
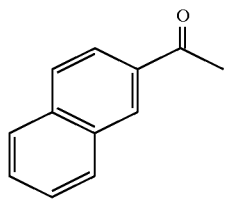
1610
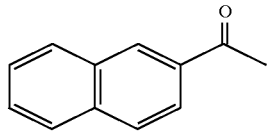
1611
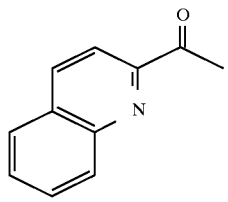
1612
-continued
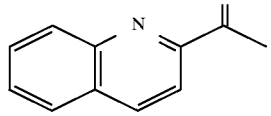
1613
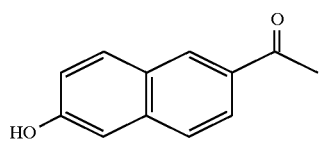
1614
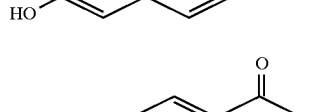
1615
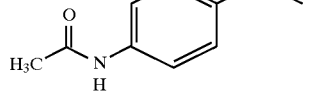
1616
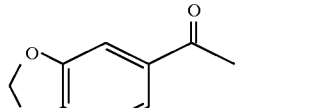
1617

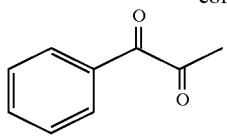
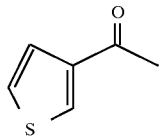
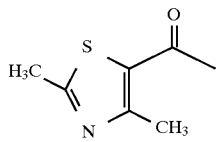
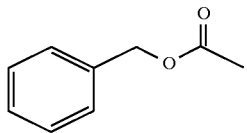
EXAMPLE 16
Compounds comprising scaffolds (e11), (y1), (y2), (z), and (e12) may be synthesized as described below.
Synthesis of Scaffold $R_1$, wherein $R_1$ is (e11) and wherein $Y_2$ is =O.
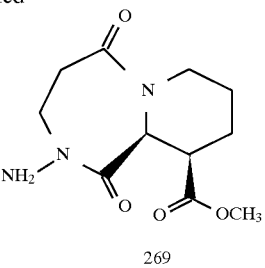
269
Synthesis of Scaffold $R_1$, wherein $R_1$ is (y1) and wherein $Y_2$ is =O.
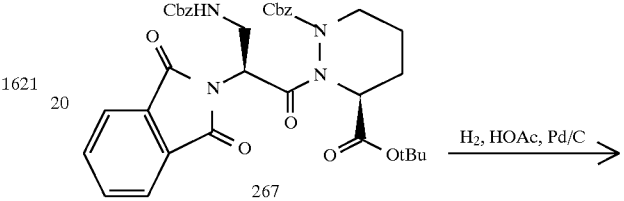
267
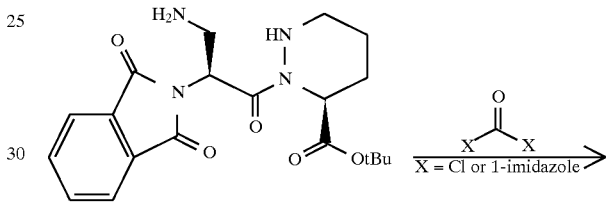
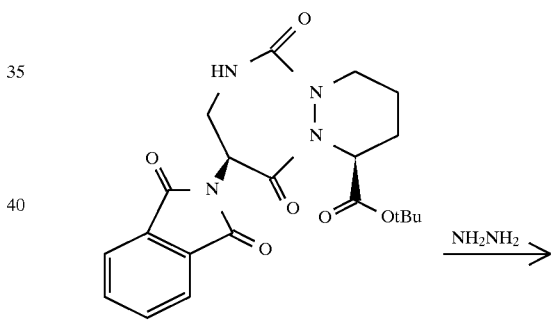
270
Synthesis of Scaffold $R_1$, wherein $R_1$ is (y2) and wherein $Y_2$ is $H_2$ and $X_7$ is O.
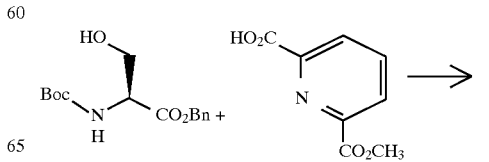

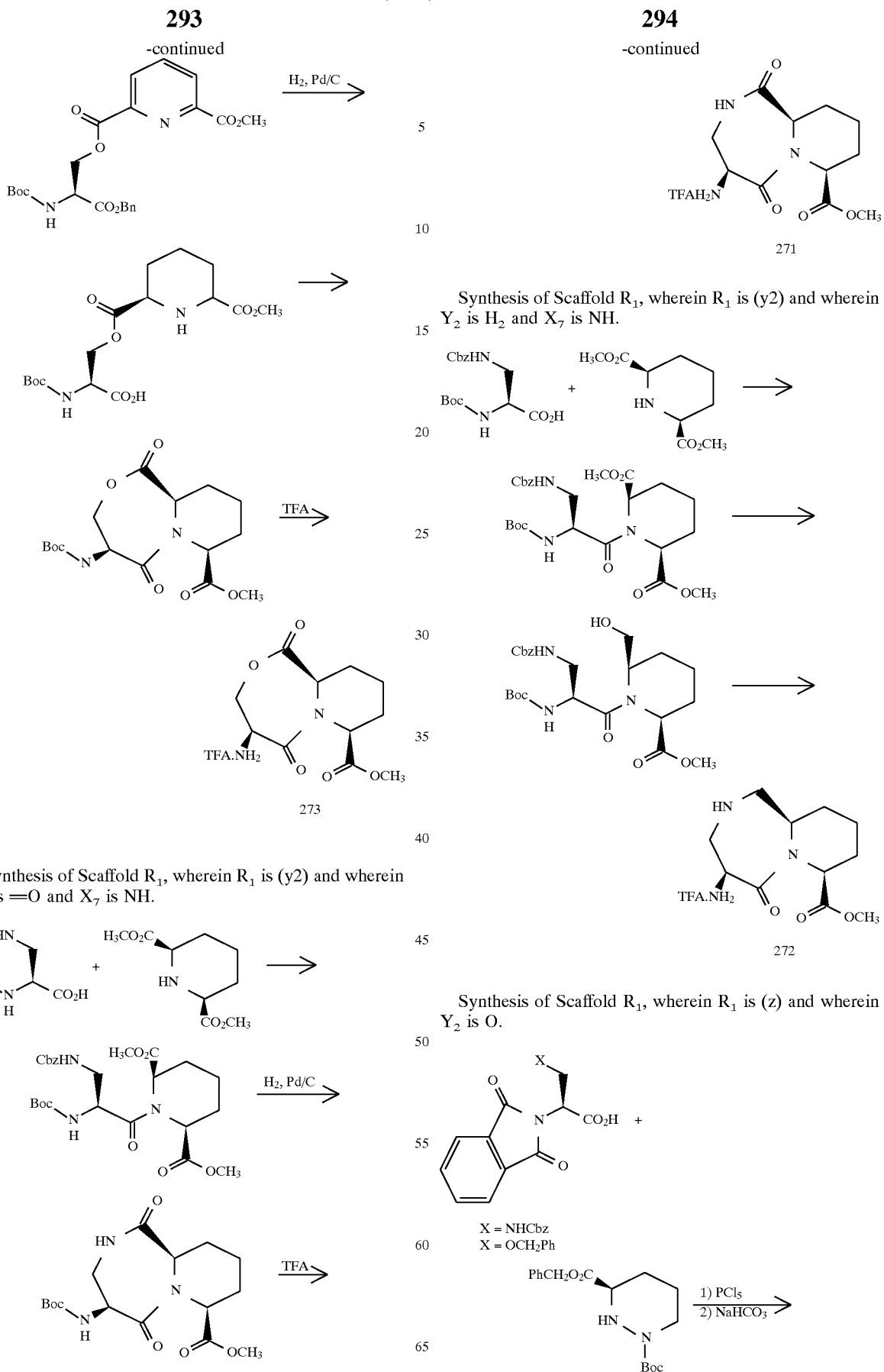

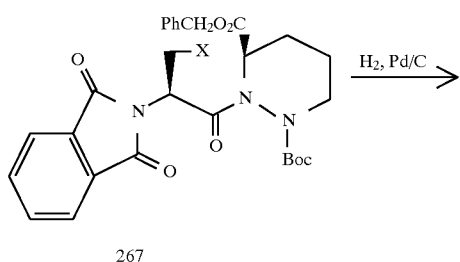
267
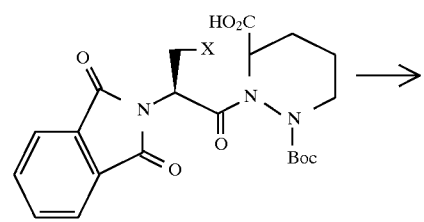
270
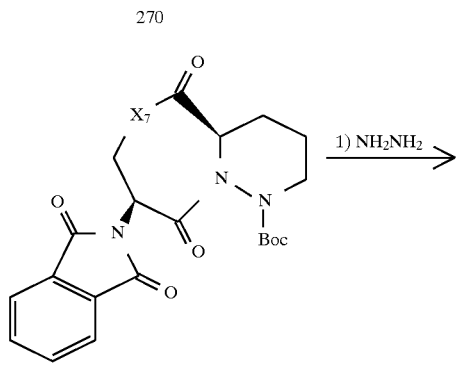
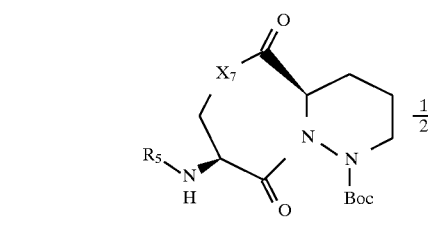
271
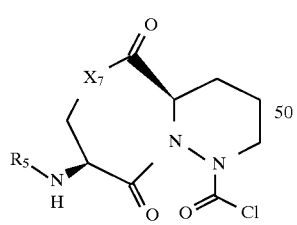
274 X₇ = NH
275 X₇ = O
Synthesis of Scaffold $R_1$, wherein $R_1$ is (e12) and wherein $Y_2$ is =O.
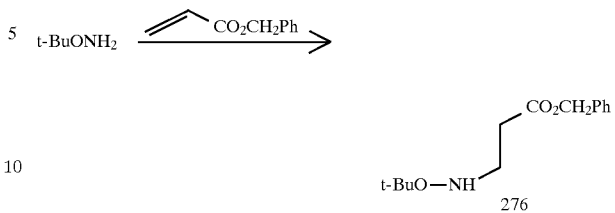
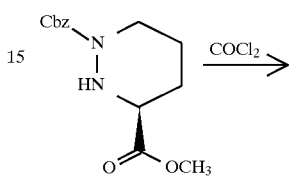
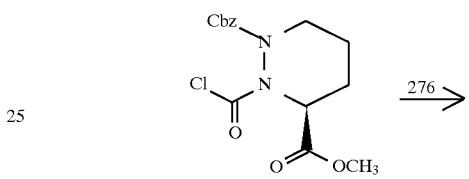
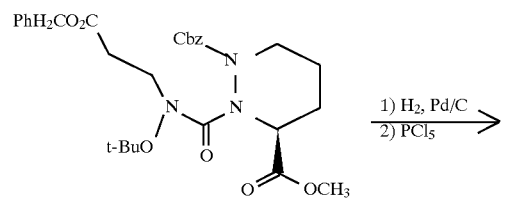
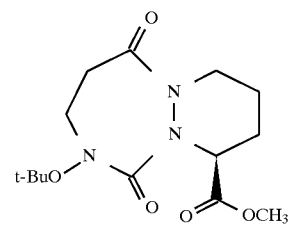
277
EXAMPLE 17
The preparation of compounds 2001, 2002, 2100a–e, and 2201 is described below.

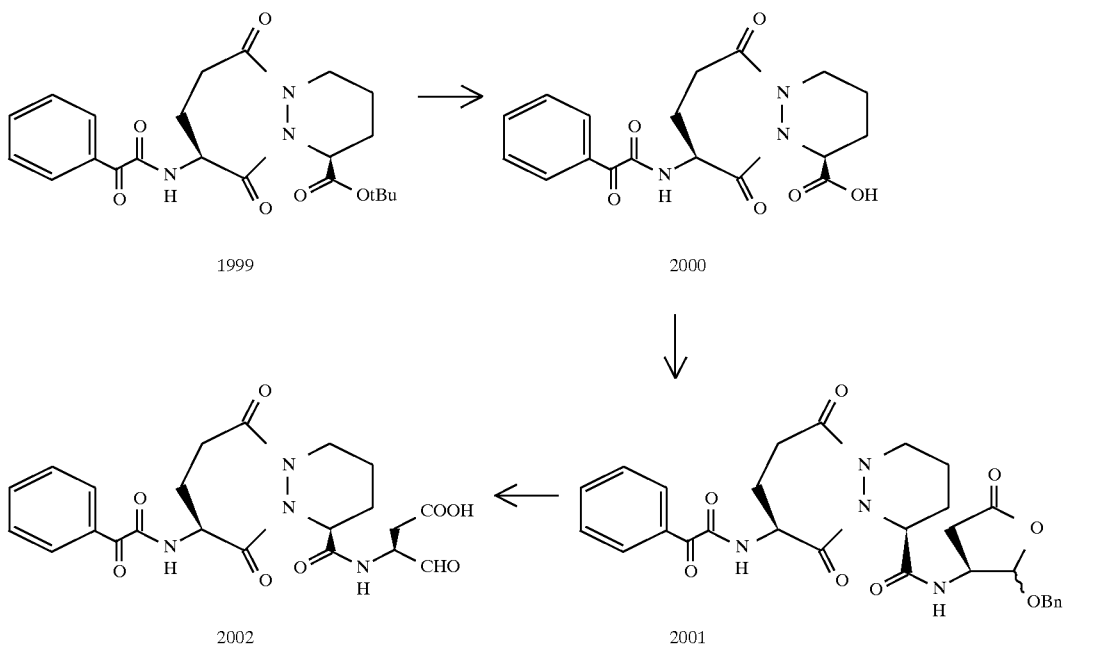

(1S, 9S) 9-Benzoylformylamino-6,10-dioxo-1,2,3,4,7,8,9,10-octahydro-6H-pyridazino[1,2-a]-[1,2]diazepine-1-carboxylic acid (2000). To a solution of t-butyl 9-amino-6,10-dioxo-1,2,3,4,7,8,9,10-octahydro-6H-pyridazino[1,2-a][1,2]diazepine-1-carboxylate (GB 2,128,984; 340 mg, 1.15 mmol) in $CH_2Cl_2$ was added benzoylformic acid (260 mg, 1.7 mmol), HOBT (230 mg, 1.7 mmol) and EDC (340 mg, 1.7 mmol). The resulting mixture was stirred at ambient temperature for 16 hours, poured into 1N HCl and extracted with $CH_2Cl_2$. The organic extracts were further washed with saturated $NaHCO_3$, dried over $MgSO_4$ and concentrated to afford 1999 as a pale yellow solid. The solid was dissolved in $CH_2Cl_2$ (25 ml) and TFA (25 ml) and stirred overnight and concentrated in vacuo to give 560 mg of 2000 as an oil.

[1S, 9S, (2RS, 3S)] 9-Benzoylformylamino-6,10-dioxo-1,2,3,4,7,8,9,10-octahydro-N-(2-benzyloxy-5-oxotetrahydrofuran-3-yl)-6H-pyridazino[1,2-a][1,2]diazepine-1-carboxamide (2001), was synthesized from 2000 by methods similar to compound 213e to afford 410 mg (63%) of 2001 as a white solid: $^1H$ NMR ($CDCl_3$; mixture of diastereomers) δ 8.25 (1H, d), 8.23 ($^1H$, d), 7.78 (1H, dd), 7.65 (1H, bm), 7.50 (2H, m), 7.40–7.25 (4H, m), 6.55 (1H, d), 5.57 (1H, d), 5.10 (1H, t), 5.05–4.95 (2H, m), 4.90, (1H, d), 4.80 (1H, d), 4.72 (1H, bm), 4.65 (1H, m), 4.55 (1H, m), 4.45 (1H, t), 3.25 (1H, m), 3.15 (1H, m), 3.00 (2H, bm), 2,90 (1H, dd), 2.70 (1H, m), 2.47 (1H, dd), 2.45 (1H, m), 2.35 (1H, m), 2.00–1.75 (4H, m), 1.60 (1H, bm).

[3S, (1S, 9S)] 3-(9-Benzoylformylamino-6,10-dioxo-1,2,3,4,7,8,9,10-octahydro-6H-pyridazino[1,2-a][1,2]diazepine-1-carboxamido)-4-oxobutanoic acid (2002). Compound 2001 (58.6 mg, 0.10 mmol) was treated with 15 ml of TFA/MeCN/water (1:2:3) and stirred at room temperature for 6.5 h. The reaction was extracted with ether. The aqueous layer was concentrated with azeotropic removal of the water using MeCN. The product was suspended in $CH_2Cl_2$, concentrated in vacuo and precipitated with ether to give 46.8 mg (99%) of 2002 as a white solid: $^1H$ NMR ($CD_3OD$) δ 9.05 (0.25H, d), 8.15 (1H, d), 7.68 (1H, t), 7.64 (0.25H, d), 7.55 (3H, t), 7.35 (0.5H, m), 5.22 (1H, t), 4.90 (1H, m), 4.58 (1H, dd), 4.50 (1H, m), 4.28 (1H, bm), 3.45 (1H, m), 3.10 (1H, bt), 2.68 (1H, ddd), 2.60–2.45 (2H, m), 2.30 (1H, dd), 2.15–2.05 (2H, m), 1.90 (2H, bm), 1.68 (1H, bm).

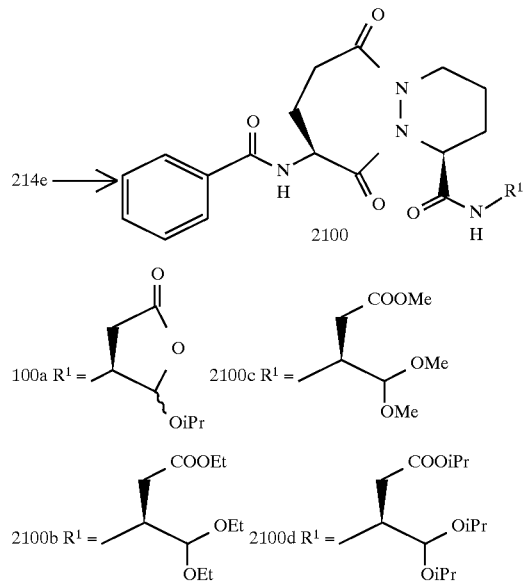

[1S, 9S, (2RS, 3S)] 9-Benzoylamino-6,10-dioxo-1,2,3,4,7,8,9,10-octahydro-N-(2-isopropoxy-5-oxo-tetrahydrofuran-3-yl)-6H-pyridazino[1,2-a][1,2]diazepine-1-carboxamide (2100a). A solution of 214e (101 mg, 0.23 mmol) in isopropanol (10 ml) was stirred at room temperature with a catalytic amount of p-toluenesulfonic acid (10 mg). After 75 minutes, the reaction mixture was poured into saturated $NaHCO_3$ and extracted with $CH_2Cl_2$. The combined extracts were dried over $Na_2SO_4$ and concentrated. Flash chromatography ($SiO_2$, $CH_2Cl_2$ to EtOAc) afforded 56 mg (51%) of 2100a as a white solid: $^1H$ NMR ($CDCl_3$; mixture of diastereomers) δ 7.9–7.8 (2H,m), 7.6–7.5 (1H, m), 7.5–7.4 (2H, m), 7.1 (0.5H, d), 6.9 (0.5H, d), 6.4

(0.5H,d), 5.6 (0.5H, d), 5.3 (0.5H, s), 5.2–5.1 (1H, m), 4.95 (0.5H, m), 4.75–4.5 (1.5H, m), 4.35 (0.5H, t), 4.1 (0.5H, m), 3.98 (0.5H, m), 3.3–2.75 (4H, m), 2.5–2.4 (2H,m), 2.25 (1H, m), 2.1–1.9 (3H,m) 1.75–1.55 (2H,m).

[3S, (1S, 9S)] 3-(9-Benzoylformylamino-6,10-dioxo-1,2,3,4,7,8,9,10-octahydro-6H-pyridazino[1,2-a][1,2]diazepine-1-carboxamido)-4,4-diethoxy-butyric acid, ethyl ester (2100b). A solution of 214e (16 mg, 0.036 mmol) in ethanol (2 ml) was stirred at room temperature with a catalytic amount of p-toluenesulfonic acid (2 mg). After 5 days, the reaction mixture was poured into saturated NaHCO$_3$ and extracted with CH$_2$Cl$_2$. The combined extracts were dried over Na$_2$SO$_4$ and concentrated. Flash chromatography (SiO$_2$, CH$_2$Cl$_2$:EtOAc 95:5 v/v) afforded 16 mg (81%) of 2100b as a white solid: $^1$H NMR (CDCl$_3$) δ 7.85–7.74 (2H,m), 7.55–7.38 (3H,m), 7.04–6.95 (1H,d), 6.61–6.48 (1H,d), 5.15–5.08 (1H,m), 4.63–4.53 (1H,m), 4.52–4.45 (1H,m), 4.42–4.35 (1H,m), 4.15–4.05 (2H,m), 3.74–3.60 (2H,m), 3.57–3.42 (2H,m), 3.39–3.28 (1H,m), 3.03–2.93 (1H,m), 2.92–2.82 (1H,m), 2.65–2.52 (2H,m), 2.42–2.25 (1H,m), 2.20–1.88 (4H,m), 1.76–1.50 (2H,m), 1.35–1.10 (9H,m).

[3S, (1S, 9S)] 3-(9-Benzoylformylamino-6,10-dioxo-1,2,3,4,7,8,9,10-octahydro-6H-pyridazino[1,2-a][1,2]diazepine-1-carboxamido)-4,4-dimethoxy-butyric acid methyl ester (2100c). A solution of 214e (165 mg, 0.37 mmol) in methanol (5 ml) was stirred at room temperature with a catalytic amount of p-toluenesulfonic acid (17.5 mg). After 4 days, the reaction mixture was diluted with EtOAc and washed with 10% NaHCO$_3$ (3×) and brine. The combined extracts were dried over Na$_2$SO$_4$ and concentrated. Flash chromatography (SiO$_2$, EtOAc) afforded 127 mg (68%) of 2100c as a white solid: $^1$H NMR (CDCl$_3$) δ 7.82 (2H, d), 7.55–7.50 (1H, m), 7.47–7.43 (2H, m), 7.02 (1H, d), 6.53 (1H, d), 5.20–5.10 (1H, m), 4.56–4.50 (1H, m), 4.45–4.50 (1H each, two m), 3.69 (3H, s), 3.41 (3H, s), 3.43 (3H, s), 3.35–3.25 (1H, m), 3.06–2.98 (1H, m), 2.94–2.83 (1H, m), 2.65–2.53 (2H, m), 2.35–2.32 (1H, m), 2.15–2.07 (1H,m), 2.00–1.89 (3H, m), 1.75–1.56 (2H, m).

[3S, (1S, 9S)] 3-(9-Benzoylformylamino-6,10-dioxo-1,2,3,4,7,8,9,10-octahydro-6H-pyridazino[1,2-a][1,2]diazepine-1-carboxamido)-4,4-diisopropoxy-butyric acid, isopropyl ester (2100d). A solution of 214e (53 mg, 0.12 mmol) in isopropanol (5 ml) was stirred at 50° C. with a catalytic amount of p-toluenesulfonic acid (5 mg). After 3 days the reaction mixture was poured into saturated NaHCO$_3$ and extracted with CH$_2$Cl$_2$. The combined extracts were dried over Na$_2$SO$_4$ and concentrated. Flash chromatography (SiO$_2$, CH$_2$Cl$_2$:EtOAc (4:1 to 1:1 v/v)) afforded 49 mg (68%) of 2100d as a white solid: $^1$H NMR (CDCl$_3$) δ 7.85 (2H, d), 7.50–7.43 (1H, m), 7.41–7.35 (2H, m), 7.02 (1H, d), 6.47 (1H, d), 5.13–5.07 (1H, m) 5.00–4.9 (1H, m), 4.61–4.55 (2H, m), 4.37–4.30(1H, m), 3.80–3.70 (1H, m), 3.90–3.80 (1H, m), 3.42–3.35 (1H, m), 3.03–2.93 (1H, m), 2.91–2.81 (1H, m), 2.62–2.50 (2H, m), 2.38–2.33 (1H, m), 2.12–2.06 (1H,m), 1.97–1.81 (3H, m), 1.70–1.60 (2H, m), 1.28–1.05 (18H,m).

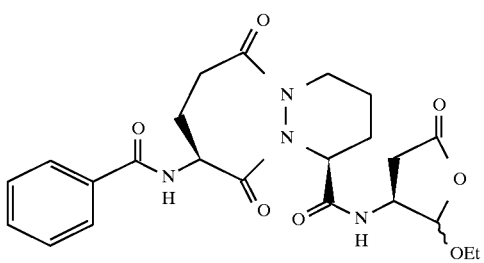

2100e

[1S, 9S, (2RS, 3S)] 9-Benzoylamino-6,10-dioxo-1,2,3,4,7,8,9,10-octahydro-N-(2-ethoxy-5-oxo-tetrahydro-furan-3-yl)-6H-pyridazino[1,2-a][1,2]diazepine-1-carboxamide (2100e), was synthesized from 302 via methods used to synthesize 304a to afford 2100e, except ethanol and triethylorthoformate were used instead of methanol and trimethylorthoformate. Chromatography (SiO$_2$, 5% ethanol/CH$_2$Cl$_2$) afforded 92 mg (68%) of a white solid: $^1$H NMR (CDCl$_3$; mixture of diastereomers) δ 7.90–7.80 (2H, m), 7.60–7.50 (1H, m), 7.50–7.40 (2H, m), 7.30 (0.5H, d), 7.00 (0.5H, d), 6.50 (0.5H, d), 5.50 (0.5H, d), 5.20–5.10 (1.5H, m), 4.95 (0.5H, m), 4.75–4.65 (0.5H, m), 4.65–4.50 (1H, m), 4.38 (0.05H, t), 4.00–3.90 (0.5H, m), 3.85–3.75 (0.5H, m), 3.75–3.65 (0.5H, m), 3.65–3.55 (0.5H, m), 3.30–2.70 (4H, m), 2.50–2.35 (2H, m), 2.30 (1H, d), 2.15–1.90 (3H, m), 1.80–1.60 (2H, m), 1.25–1.20 (3H, two t)

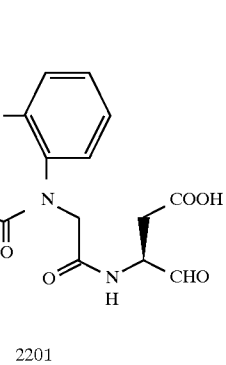

2201

(3S)-3-[(3S)-2-oxo-3-(1-naphthoyl)amino-5-methoxyacetyl-2,3,4,5-tetrahydro-1H-1,5-benzodiazepine-1-acetylamino]4-oxo-butyric acid (2201) was synthesized from 600b by the methods used to synthesize 605b to afford 2201: $^1$H NMR (CDCl$_3$) δ 8.30–8.22 (1H,m), 8.05–7.98 (1H, d), 7.96–7.83 (1H,m), 7.77–7.68 (1H,m), 7.67–7.40 (7H,m), 5.12–5.02 (1H,m), 4.98–4.41 (5H,m), 4.38–4.24 (1H,m), 4.07–4.00 (1H,d), 3.92–3.80 (2H,m), 3.32 (3H,s), 2.75–2.60 (1H,m), 2.58–2.35 (1H,m).

The data of the examples above demonstrate that compounds according to this invention display inhibitory activity towards IL-1β Converting Enzyme.

Insofar as the compounds of this invention are able to inhibit ICE in vitro and furthermore, may be delivered orally to mammals, they are of evident clinical utility for the treatment of IL-1- and apoptosis-mediated diseases. These tests are predictive of the compounds ability to inhibit ICE in vivo.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound represented by the formula:

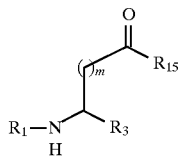 (V)

wherein:

m is 1 or 2;

$R_1$ is:

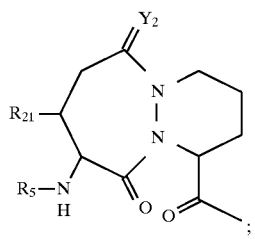 (e10-B)

$R_3$ is selected from the group consisting of:
—CN,
—C(O)—H,
—C(O)—CH$_2$—T$_1$—R$_{11}$,
—C(O)—CH$_2$—F,
—C=N—O—R$_9$, and
—CO—Ar$_2$;

each $R_5$ is independently selected from the group consisting of:
—C(O)—R$_{10}$,
—C(O)O—R$_9$,
—C(O)—N(R$_{10}$)(R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H,
—C(O)C(O)—OR$_{10}$, and
—C(O)C(O)—N(R$_9$)(R$_{10}$);

$Y_2$ is $H_2$ or O;

each $T_1$ is independently selected from the group consisting of —O—, —S—, —S(O)—, and —S(O)$_2$—;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally an unsaturated —C$_{2-6}$ alkenyl group;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally an unsaturated —C$_{2-6}$ alkenyl group;

each $R_{11}$ is independently selected from the group consisting of:
—Ar$_4$,
—(CH$_2$)$_{1-3}$—Ar$_4$,
—H, and
—C(O)—Ar$_4$;

$R_{15}$ is selected from the group consisting of —OH, —OAr$_3$, —N(H)—OH, and —OC$_{16}$, wherein C$_{1-6}$ is a straight or branched alkyl group optionally substituted with Ar$_3$, —CONH$_2$, —OR$_5$, —OH, —OR$_9$, or —CO$_2$H;

$R_{21}$ is —CH$_3$;

Ar$_2$ is independently selected from the following group, in which any ring may optionally be singly or multiply substituted by —Q$_1$ or phenyl, optionally substituted by Q$_1$:

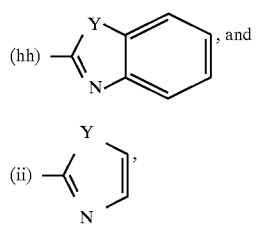

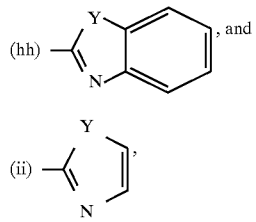

wherein each Y is independently selected from the group consisting of O and S;

each Ar$_3$ is a cyclic group independently selected from the set consisting of an aryl group which contains 6, 10, 12, or 14 carbon atoms and between 1 and 3 rings and an aromatic heterocycle group selected from the group consisting of pyrimidinyl, tetrahydroquinolyl, tetrahydroisoguinonlinyl, purinyl, pyrimidyl, indolinyl, benzimidazolyl, imidazolyl, imidazolinoyl, quinolyl, isoquinolyl, indolyl, pyridyl, pyrrolyl, pyrazolyl, pyrazinyl, quinoxolyl, furyl, thienyl, triazolyl, thiazolyl, β-carbolinyl, tetrazolyl, benzofuranyl, benzoxazolyl, isoxazolyl, thiadiazolyl, benzodioxolyl, benzothienyl, naphthyridinyl, pyridazinyl, phthalazinyl, pyridodiazinyl, triazinyl, thienothiophenyl, thienopyridinyl, oxadiazolyl, benzothiazolyl, benzotriazoyl, isoxazolopyridinyl, isothiazolyl, benzoisoxazolyl, benzoisothiazoyl, isothiazopyridyl, benzothiazolyl, benzofuranyl, carbazoyl, phenothiazinyl, phenanthridinyl, acridinyl, dibenzothiophenyl, oxazole, indolizinyl, isoindolyl, indazolyl, quinolizinyl, cinnolinyl, quinazolinyl, pteridinyl, phenazinyl, and phenoxazinyl, and said cyclic group optionally being singly or multiply substituted by —Q$_1$;

each Ar$_4$ is a cyclic group independently selected from the set consisting of an aryl group which contains 6, 10, 12, or 14 carbon atoms and between 1 and 3 rings, and a heterocycle group selected from the aroup consisting of pyrimidinyl, tetrahydroquinolyl, tetrahydroisoquinonlinyl, purinyl, pyrimidyl, indolinyl, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranyl, thiamorpholinyl sulfone, benzoxazolyl, oxopiperidinyl, oxopyrrolidinyl, oxazepinyl, azepinyl, isoxazolyl, tetrahydropyranyl, tetrahydrofuranyl, thiadiazolyl, benzodioxolyl, benzothienyl, tetrahydrothiophenyl, naphthyridinyl, pyridazinyl, phthalazinyl, pyridodiazinyl, triazinyl, thienothiophenyl, thienopyridinyl, oxadiazolyl, benzothiazolyl, benzotriazoyl, isoxazolopyridinyl, isothiazolyl, benzoisoxazolyl, benzoisothiazoyl, isothiazopyridyl, benzothiazolyl, benzofuranyl, carbazoyl, phenothiazinyl, phenanthridinyl, acridinyl, dibenzothiophenyl, pyranyl, thiopyranyl, oxazinyl thiazinyl, oxadiazinyl, thiadiazinyl, pyrrolidinyl, oxepanyl, theipanyl, diazepinyl, thiazepinyl, diazepanyl, oxazepanyl, thiazepanyl, pyrazolidinyl, oxazole, indolizinyl, isoindolyl, indazolyl, quinolizinyl, cinnolinyl, quinazolinyl, pteridinyl, phenazinyl, and phenoxazinyl, and said cyclic group optionally being singly or multiply substituted by —$Q_1$;

each $Q_1$ is independently selected from the group consisting of —$NH_2$, —$CO_2H$, —Cl, —F, —Br, —I, —$NO_2$, —CN, =O, —OH, -perfluoro $C_{1-3}$ alkyl, $R_5$, —$OR_5$, —$NHR_5$, $OR_9$, —$N(R_9)(R_{10})$, $R_9$, —C(O)—$R_{10}$, and

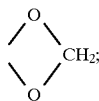

provided that when —$Ar_3$ is substituted with a $Q_1$ group which comprises one or more additional —$Ar_3$ groups, said additional —$Ar_3$ groups are not substituted with another —$Ar_3$.

2. The compound according to claim 1, wherein $R_3$ is —C(O)—H.

3. The compound according to claim 2, wherein the compound is:

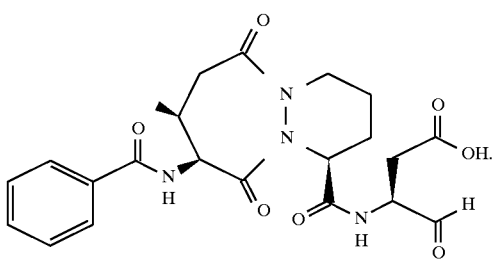

4. A pharmaceutical composition for treating an IL-1 mediated or an apoptosis mediated disease comprising a therapeutically effective amount of a compound according to claim 1, 2, or 3 and a pharmaceutically acceptable carrier.

5. A pharmaceutical composition for treating a disease selected from osteoarthritis, acute pancreatitis, chronic pancreatitis, asthma, rheumatoid arthritis, inflammatory bowel disease, Crohn's disease, graft vs. host disease, septic shock, cerebral ischemia and neurological damage due to stroke comprising a therapeutically effective amount of a compound according to claim 1, 2 or 3 and a pharmaceutically acceptable carrier.

6. A method for treating an IL-1 mediated or an apoptosis mediated disease comprising administering to a patient in need thereof a therapeutically effective amount of a compound according to claim 1, 2 or 3.

7. A method for treating a disease selected from osteoarthritis, acute pancreatitis, chronic pancreatitis, asthma, rheumatoid arthritis, inflammatory bowel disease, Crohn's disease, graft vs. host disease, septic shock, cerebral ischemia and neurological damage due to stroke comprising administering to a patient in need thereof a therapeutically effective amount of a compound according to claim 1, 2 or 3.

* * * * *